(12) United States Patent
Lee et al.

(10) Patent No.: US 8,586,550 B2
(45) Date of Patent: Nov. 19, 2013

(54) THIAZOLE DERIVATIVES AS SGLT2 INHIBITORS AND PHARMACEUTICAL COMPOSITION COMPRISING SAME

(75) Inventors: Jinhwa Lee, Yongin-si (KR); Jeongmin Kim, Yongin-si (KR); Suk Ho Lee, Yongin-si (KR); Junwon Lee, Yongin-si (KR); Kwang-Seop Song, Yongin-si (KR); Eun-Jung Park, Yongin-si (KR); Min Ju Kim, Yongin-si (KR); Hee Jeong Seo, Yongin-si (KR); Sung-Han Lee, Yongin-si (KR); Eun Jung Son, Yongin-si (KR); Jong Yup Kim, Yongin-si (KR); Suk Youn Kang, Yongin-si (KR); Younggyu Kong, Yongin-si (KR)

(73) Assignee: Green Cross Corporation, Yongin-Si, Gyeonggi-Do (KR)

( * ) Notice: Subject to any disclaimer, the term of this patent is extended or adjusted under 35 U.S.C. 154(b) by 0 days.

(21) Appl. No.: 13/704,081

(22) PCT Filed: Jun. 10, 2011

(86) PCT No.: PCT/KR2011/004273
§ 371 (c)(1),
(2), (4) Date: Dec. 13, 2012

(87) PCT Pub. No.: WO2011/159067
PCT Pub. Date: Dec. 22, 2011

(65) Prior Publication Data
US 2013/0090298 A1    Apr. 11, 2013

Related U.S. Application Data

(60) Provisional application No. 61/356,405, filed on Jun. 18, 2010.

(51) Int. Cl.
*A61K 31/70* (2006.01)
*A61K 31/425* (2006.01)
*C07H 5/04* (2006.01)
*C07H 5/06* (2006.01)
*C07D 277/60* (2006.01)

(52) U.S. Cl.
USPC ............. 514/23; 514/366; 536/54; 536/55.3; 548/148

(58) Field of Classification Search
None
See application file for complete search history.

(56) References Cited

U.S. PATENT DOCUMENTS 6,683,056 B2    1/2004    Washburn

OTHER PUBLICATIONS

Wolff, Manfred E. "Burger's Medicinal Chemistry, 5ed, Part I", John Wiley & Sons, 1995, pp. 975-977.*
Banker, G.S. et al, "Modern Pharmaceutics, 3ed.", Marcel Dekker, New York, 1996, p. 596.*
Adachi et al., Metabolism, vol. 49 (8), 2000, 990-995.*
Lee, J. et al., *Novel C-aryl Glucoside SGLT2 Inhibitors as Potential Antidiabetic agents: 1,3,4-Thiadiazolylmethylphenyl Glucoside Cogeners*, Bioorganic & Medicinal Chemistry vol. 18, (2010) pp. 2178-2194.
Meng, W. et al., *Discovery of Dapagliflozin: A Potent, Selective Renal Sodium-Dependent Glucose Cotransporter 2 (SGLT2) Inhibitor for the Treatment of Type 2 Diabetes*, Journal of Medicinal Chemistry vol. 51 (2008) pp. 1145-1149.
Zhou, H. et al., *Synthesis and SAR of Benzisothiazole- and Indolizine-beta-D-Glucopyranoside Inhibitors of SGLT2*, Medicinal Chemistry Letters vol. 1 (2010) pp. 19-23.
International Search Report and Written Opinion for Application No. PCT/KR2011/004273, dated Feb. 10, 2012.

* cited by examiner

*Primary Examiner* — Traviss C McIntosh, III
(74) *Attorney, Agent, or Firm* — Alston & Bird LLP

(57) ABSTRACT

The present invention relates to a novel compound with thiazole ring having an inhibitory activity against sodium-dependent glucose cotransporter 2 (SGLT2) being present in the intestine and kidney, and a pharmaceutical composition comprising the same as an active ingredient, which is useful for preventing or treating metabolic disorders, particularly diabetes.

10 Claims, 1 Drawing Sheet

THIAZOLE DERIVATIVES AS SGLT2 INHIBITORS AND PHARMACEUTICAL COMPOSITION COMPRISING SAME

FIELD OF THE INVENTION

The present invention relates to a novel compound with thiazole ring having an inhibitory activity against sodium-dependent glucose cotransporter 2 (SGLT2) being present in the intestine and kidney, and a pharmaceutical composition comprising the same as an active ingredient, which is useful for preventing or treating diabetes.

BACKGROUND OF THE INVENTION

The prevalence of diabetes has become an increasing concern to the world's population. An estimated 285 million people, corresponding to 6.4% of the world's adult population, will live with diabetes in 2010. The number is expected to grow to 438 million by 2030, corresponding to 7.8% of the adult population. Diabetes is characterized by a chronic metabolic disorder that is caused by failure of the body to produce insulin and/or an inability of the body to respond adequately to circulating insulin. Secreted by the pancreas, insulin increases the ability of tissue to absorb blood glucose. Accordingly, disruption of insulin function results in the high level of blood glucose that is commonly associated with diabetic patients. There are two generally recognized form of diabetes: Type 1 diabetes, or insulin-dependent diabetes mellitus (IDDM), is characterized as an autoimmune disease involving pancreatic β-cells, while type 2 diabetes, or noninsulin-dependent diabetes mellitus (NIDDM), is characterized by β-cell dysfunction and insulin resistance. Type 2 diabetes is the most prevalent abnormality of glucose homeostasis, accounting for approximately 90-95% of all cases of diabetes. The diabetes has been widespread throughout the whole world due to ageing populations and rapid cultural changes such as increasing urbanization, dietary change, decreased physical activity and other unhealthy behavioral patterns.

The burden of diabetes is driven by vascular complications such as cardiovascular disease, stroke, nephropathy, retinopathy, renal failure, and lower limb infection and gangrene. Although these complications result from multiple metanolic disorders, hyperglycemia is considered as the main cause of both the vascular consequences of the disease and the progressive nature of diabetes itself. Most harmful of all is that high glucose levels aggravate insulin resistance, impair β-cell function and finally contribute to β-cell apoptosis. The loss of β-cell function deteriorates hyperglycemia, resulting in a vicious cycle that culminates in the abject destruction of the β-cells. The United Kingdom Prevention of Diabetes Study (UKPDS) showed that incremental reductions in glycosylated hemoglobin (HbAlC) lowered the risk of diabetes-related events [Stratton, I. M. et al. *Br. Med. J.* 2000, 321, 405-412]. Thus, it is recommended that patients with type 2 diabetes should reduce HbAlC values to 7% and less.

The most important strategy for treatment of type 2 diabetes involves lifestyle interventions that promote body weight loss, leading to an improvement in glycemic control. In case lifestyle interventions are not enough for the management of diabetes, an extensive range of antidiabetic drugs might be considered for the treatment of the condition (monotherapies and combination therapies). These therapies target the liver to reduce glucose output, small intestine to decrease glucose absorption, adipose deposits or muscle to elevate glucose cellular uptake or to promote glucose metabolism, serum proteases to prolong incretin action, and the pancreas to enhance insulin release. Despite the wide range of antihyperglycemic agent, it is difficult for many patients to achieve HbAlC target level. In a study reviewing diabetic patients for control of vascular risk factors, only 37.0% of participants achieved the target goal of HbAlC level of less than 7.0% [Saydah, S. H. et al. *J. Am. Med. Assoc.* 2004, 291, 335-342. In addition, current therapies have limited durability and/or are associated with significant side effects such as gastrointestinal intolerance, hypoglycemia, weight gain, lactic acidiosis and edema. Thus, significant unmet medical needs still remain for the treatment of diabetes. In particular, safer, better tolerated medications which provide increased efficacy and long-term durability are desired.

The obvious need for new approaches to treat patients with uncontrolled type 2 diabetes has promoted continuous exploration of alternative targets in organs involved in maintenance of glucose homeostasis. In the context of type 2 diabetes, renal glucose reabsorption contributes to plasma glucose levels and the concomitant microvascular complications. Evaluation of molecular targets available in the kidney (a major unexploited contributor to glucose homeostasis) stimulated interest in the development of a new class of antihyperglycemic agents that promote urinary glucose excertion. Inhibitors of the SGLT2 prevent renal glucose reabsorption from the glomerular filtrate and provide an insulin-independent way of controlling hyperglycemia.

Sodium-dependent glucose cotransporters (SGLTs) couple the transport of glucose against a concentration gradient with the simultaneous transport of $Na^+$ down a concentration gradient. Two important SGLT isoforms have been cloned and identified as SGLT1 and SGLT2. SGLT1 is located in the gut, kidney, and heart where its expression regulates cardiac glucose transport. SGLT1 is a high-affinity, low-capacity transporter and therefore accounts for only a small fraction of renal glucose reabsorption. In contrast, SGLT2 is a low-affinity, high-capacity transporter located exclusively at the apica domain of the epithelial cells in the early proximal convoluted tublule. In healthy individuals, greater than 99% of the plasma glucose that filtered in the kidney glomerulus is reabsorbed, resulting in less than 1% of the total filtered glucose being excerted in urine. It is estimated that 90% of renal glucose reabsorption is facilitated by SGLT2; the remaining 10% is likely mediated by SGLT1 in the late proximal straight tubule. Genetic mutations in SGLT2 lead to increased renal glucose excretion of as much as 140 g/day depending on the mutation with no apparent adverse effects on carbohydrate metabolism. Since SGLT2 appears to be responsible for the majority of renal glucose reabsorption based on human mutation studies, it has become target of therapeutic interest [Lee, J. et al. *Bioorg. Med. Chem.* 2010, 18, 2178-2194; van den Heuvel, L. P. et al. *Hum. Genet.* 2020, 111, 544-547].

Phlorizon was isolated from the root bark of the apple tree and evaluated as the first SGLT inhibitor. Despite antidiabetic potency of phlorizin, its metabolic instability due to β-glucosidase cleavage in the intestinal tract has prevented its development as a drug for the treatment of diabetes. Subsequently, T-1095, by Tanabe Seiyaku, was reported as the first orally absorbable SGLT2 inhibitor, overcoming the disadvantage of phlorizin. T-1095 was absorbed in the intestine and converted to an active form, T-1095A. Following the discovery of T-1095, O-aryl glucosides such as sergliflozin and remogliflozin advanced furthest in clinical trials. Again, concern regarding gut β-glucosidase-mediated degradation, resulted in developing sergliflozin A and remogliflozin A being administered as the ethyl carbonate prodrugs sergliflozin and remogliflozin, respectively. Subsequent endeavors to identify SGLT2 inhibitors suitable for oral administration without the need for a prodrug led to the discovery of C-aryl glucoside-derived SGLT2 inhibitors. C-aryl glucoside appear to have drug-like properties with enhanced chemical stability of the glucosidic bond. Extensive SAR studies by Bristol-Myers Squibb identified dapagliflozin, a potent, selective SGLT2 inhibitor for the treatment of type 2 diabetes. At present, dapagliflozin is the most advanced SGLT2 inhibitor in clinical trials and is believed to be the first SGLT2 inhibitor to go to market [Meng, W. et al. *J. Med. Chem.* 2008, 51, 1145-1149]. On the other hand, Mitsubishi Tanabe Pharma, in collaboration with Johnson & Johnson, is developing canagliflozin, another novel C-aryl glucoside-derived SGLT2 inhibitor [Tanabe Seiyaku, WO2008013321].

Considering the important impact of diabetes on public health and unmet medical needs of current therapy, it is no surprise that SGLT2 inhibitors are currently interesting topics of studies, which were published in the following review articles [Washburn, W. N. *Expert Opin. Ther. Patents,* 2009, 19, 1485-1499; Washburn, W. N. *J. Med. Chem.* 2009, 52, 1785-1794].

SUMMARY OF THE INVENTION

It is a primary object of the present invention to provide a novel compound, or a pharmaceutically acceptable salt, or a prodrug thereof, which is effective as a SGLT2 inhibitor, and useful for the prevention and/or treatment of metabolic disorders, particularly diabetes.

It is another object of the present invention to provide a method for preparing the compound.

It is another object of the present invention to provide a pharmaceutical composition comprising the compound for preventing or treating metabolic disorders, particularly diabetes.

According to one aspect of the present invention, there is provided a compound of formula I, or a pharmaceutically acceptable salt or a prodrug thereof:

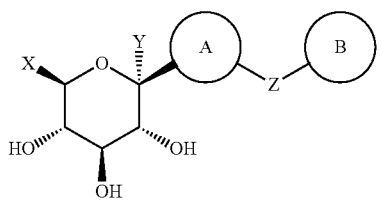

I wherein, ring A, ring B, X, Y, and Z have the meanings as defined in the following description.

According to another aspect of the present invention, there is provided a method for preparing the compound of formula I.

According to a further aspect of the present invention, there is provided a pharmaceutical composition for treating or preventing a metabolic disorder, comprising the compound of formula I, or a pharmaceutically acceptable salt or a prodrug thereof, as an active ingredient, and a pharmaceutically acceptable carrier.

BRIEF DESCRIPTION OF THE DRAWINGS

The above and other objects and features of the present invention will become apparent from the following description of the invention, when taken in conjunction with the accompanying drawings, which respectively show.

DETAILED DESCRIPTION OF THE INVENTION

Figure 1:
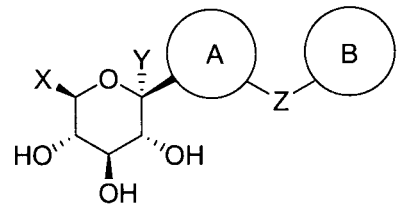
FIG. 1 represents the compound of formula I according to the present invention.

Hereinafter, the present invention is described in detail.

As used herein, the term "alkyl" refers to a straight or branched chain saturated hydrocarbon radical. Examples of "alkyl" as used herein include, but are not limited to, methyl, ethyl, n-propyl, isopropyl, n-butyl, isobutyl, t-butyl, n-pentyl, isopentyl and hexyl.

As used herein, the term "substituted alkyl" refers to a straight or branched chain saturated hydrocarbon radical, which is optionally substituted by one or more substituents selected from the group consisting of $C_{1-3}$ alkyl optionally having one to three fluorine substituents, $C_{2-3}$ alkenyl, $C_{2-3}$ alkynyl, $C_{1-2}$ alkoxy optionally having one to three fluorine substituents, sulfanyl, sulfinyl, sulfonyl, oxo, hydroxy, mercapto, amino, guanidino, carboxy, aminocarbonyl, aryl, aryloxy, heteroaryl, heteroaryloxy, heterocyclic, aminosulfonyl, sulfonylamino, carboxyamide, ureido, nitro, cyano and halogen.

As used herein, the term "alkenyl" refers to a straight or branched chain hydrocarbon radical having at least one carbon-carbon double bond. Examples of "alkenyl" as used herein include, but are not limited to, ethenyl and propenyl.

As used herein, the term "substituted alkenyl" refers to a straight or branched chain hydrocarbon radical having at least one carbon-carbon double bond, which has optional substituents selected from the group consisting of $C_{1-3}$ alkyl optionally having one to three fluorine substituents, amino, aryl, cyano and halogen.

As used herein, the term "alkynyl" refers to a straight or branched chain hydrocarbon radical having at least one carbon-carbon triple bond. Examples of "alkynyl" as used herein include, but are not limited to, acetylenyl and 1-propynyl.

As used herein, the term "substituted alkynyl" refers to a straight or branched chain hydrocarbon radical having at least one carbon-carbon triple bond, optionally having one or more substituents selected from the group consisting of $C_{1-3}$ alkyl optionally having one to three fluorine substituents, amino, aryl and halogen.

As used herein, the term "halogen" refers to fluorine (F), chlorine (Cl), bromine (Br), or iodine (I).

As used herein, the term "carbocycle" refers to a non-aromatic cyclic hydrocarbon radical composed of three to seven carbon atoms. Five- to seven-membered rings may contain a double bond in the ring structure. Exemplary "carbocycle" groups include, but are not limited to, cyclopropyl, cyclobutyl, cyclopentyl, cyclopentenyl, cyclohexyl and cycloheptyl.

As used herein, the term "substituted carbocycle" refers to a non-aromatic cyclic hydrocarbon radical composed by three to seven carbon atoms, which is optionally substituted with one or more substituents selected from the group consisting of $C_{1-3}$ alkyl optionally having one to three fluorine substituents, $C_{2-3}$ alkenyl, $C_{2-3}$ alkynyl, $C_{1-2}$ alkoxy optionally having one to three fluorine substituents, sulfanyl, sulfinyl, sulfonyl, oxo, hydroxy, mercapto, amino, guanidino, carboxy, aminocarbonyl, aryl, aryloxy, heteroaryl, heterocyclic, aminosulfonyl, sulfonylamino, carboxyamide, nitro, ureido, cyano and halogen.

As used herein, the term "aryl" refers to an optionally substituted benzene ring or refers to a ring system which may result by fusing one or more optional substituents. Exemplary optional substituents include substituted $C_{1-3}$ alkyl, substituted $C_{2-3}$ alkenyl, substituted $C_{2-3}$ alkynyl, heteroaryl, heterocyclic, aryl, alkoxy optionally having one to three fluorine substituents, aryloxy, aralkoxy, acyl, aroyl, heteroaroyl, acyloxy, aroyloxy, heteroaroyloxy, sulfanyl, sulfinyl, sulfonyl, aminosulfonyl, sulfonylamino, carboxyamide, aminocarbonyl, carboxy, oxo, hydroxy, mercapto, amino, nitro, cyano, halogen, or ureido. Such a ring or ring system may be optionally fused to aryl rings (including benzene rings) optionally having one or more substituents, carbocycle rings or heterocyclic rings. Examples of "aryl" groups include, but are not limited to, phenyl, naphthyl, tetrahydronaphthyl, biphenyl, indanyl, anthracyl or phenanthryl, as well as substituted derivatives thereof.

As used herein, the term "heteroaryl" refers to an optionally substituted monocyclic five to six-membered aromatic ring containing one or more heteroatomic substitutions selected from S, SO, $SO_2$, O, N, or N-oxide, or refers to such an aromatic ring fused to one or more rings such as heteroaryl rings, aryl rings, heterocyclic rings, or carbocycle rings (e.g., a bicyclic or tricyclic ring system), each having optional substituents.

Examples of optional substituents are selected from the group consisting of substituted $C_{1-3}$ alkyl, substituted $C_{2-3}$ alkenyl, substituted $C_{2-3}$ alkynyl, heteroaryl, heterocyclic, aryl, $C_{1-3}$ alkoxy optionally having one to three fluorine substituents, aryloxy, aralkoxy, acyl, aroyl, heteroaroyl, acyloxy, aroyloxy, heteroaroyloxy, sulfanyl, sulfinyl, sulfonyl, aminosulfonyl, sulfonylamino, carboxyamide, aminocarbonyl, carboxy, oxo, hydroxy, mercapto, amino, nitro, cyano, halogen or ureido. Examples of "heteroaryl" groups used herein include, but are not limited to, benzoimidazolyl, benzothiazolyl, benzoisothiazolyl, benzothiophenyl, benzopyrazinyl, benzotriazolyl, benzo[1,4]dioxanyl, benzofuranyl, 9H-a-carbolinyl, cinnolinyl, furanyl, furo[2,3-b]pyridinyl, imidazolyl, imidazolidinyl, imidazopyridinyl, isoxazolyl, isothiazolyl, isoquinolinyl, indolyl, indazolyl, indolizinyl, naphthyridinyl, oxazolyl, oxothiadiazolyl, oxadiazolyl, phthalazinyl, pyridyl, pyrrolyl, purinyl, pteridinyl, phenazinyl, pyrazolyl, pyridyl, pyrazolopyrimidinyl, pyrrolizinyl, pyridazyl, pyrazinyl, pyrimidyl, 4-oxo-1,2-dihydro-4H-pyrrolo[3,2,1-ij]-quinolin-4-yl, quinoxalinyl, quinazolinyl, quinolinyl, quinolizinyl, thiophenyl, triazolyl, triazinyl, tetrazolopyrimidinyl, triazolopyrimidinyl, tetrazolyl, thiazolyl, thiazolidinyl, and substituted versions thereof.

As used herein, the term "heterocyclic alkyl" refers to a three to seven-membered ring containing one or more heteroatomic moieties selected from S, SO, $SO_2$, O, N, or N-oxide, optionally substituted with one or more substituents selected from the group which includes substituted $C_{1-3}$ alkyl, substituted $C_{2-3}$ alkenyl, substituted $C_{2-3}$ alkynyl, heteroaryl, heterocyclic, aryl, $C_{1-3}$ alkoxy optionally having one to three fluorine substituents, aryloxy, aralkoxy, acyl, aroyl, heteroaroyl, acyloxy, aroyloxy, heteroaroyloxy, sulfanyl, sulfinyl, sulfonyl, aminosulfonyl, sulfonylamino, carboxyamide, aminocarbonyl, carboxy, oxo, hydroxy, mercapto, amino, nitro, cyano, halogen, and ureido. Such a ring can be saturated or have one or more degrees of unsaturation. Such a ring may be optionally fused to one or more "heterocyclic" ring(s), aryl ring(s), heteroaryl ring(s) or carbocycle ring(s), each having optional substituents.

Examples of "heterocyclic" moieties include, but are not limited to, 1,4-dioxanyl, 1,3-dioxanyl, pyrrolidinyl, pyrrolidin-2-onyl, piperidinyl, imidazolidine-2,4-dionepiperidinyl, piperazinyl, piperazine-2,5-dionyl, morpholinyl, dihydropyranyl, dihydrocinnolinyl, 2,3-dihydrobenzo[1,4]dioxinyl, 3,4-dihydro-2H-benzo[b][1,4]-dioxepinyl, tetrahydropyranyl, 2,3-dihydrofuranyl, 2,3-dihydrobenzo furanyl, dihydroisoxazolyl, tetrahydrobenzodiazepinyl, tetrahydroquinolinyl, tetrahydrofuranyl, tetrahydronaphthyridinyl, tetrahydropurinyl, tetrahydrothiopyranyl, tetrahydrothiophenyl, tetrahydroquinoxalinyl, tetrahydropyridinyl, tetrahydrocarbolinyl, 4H-benzo[1,3]-dioxinyl, benzo[1,3]dioxonyl, 2,2-difluorobenzo-[1,3]-dioxonyl, 2,3-dihydro-phthalazine-1,4-dionyl, and isoindole-1,3-dionyl.

As used herein, the term "alkoxy" refers to the group —$OR_a$, where $R_a$ is alkyl as defined above. Exemplary alkoxy groups useful in the present invention include, but are not limited to, methoxy, difluoromethoxy, trifluoromethoxy, ethoxy, n-propoxy, isopropoxy, n-butoxy and t-butoxy.

As used herein the term "aralkoxy" refers to the group —$OR_aR_b$, wherein $R_a$ is alkyl and $R_b$ is aryl as defined above.

As used herein the term "aryloxy" refers to the group —$OR_b$, wherein $R_b$ is aryl as defined above.

As used herein, the term "mercapto" refers to the group —SH.

As used herein, the term "sulfanyl" refers to the group —$SR_c$, wherein $R_c$ is substituted alkyl, substituted carbocycle, aryl, heteroaryl or heterocyclic, as defined above.

As used herein, the term "sulfinyl" refers to the group —S—(O)$R_c$, wherein $R_c$ is substituted alkyl, substituted carbocycle, aryl, heteroaryl or heterocyclic, as defined above.

As used herein, the term "sulfonyl" refers to the group —$S(O)_2R_c$, wherein $R_c$ is substituted alkyl, substituted carbocycle, aryl, heteroaryl or heterocyclic, as defined above.

As used herein, the term "oxo" refers to the group =O.

As used herein, the term "hydroxy" refers to the group —OH.

As used herein, the term "amino" refers to the group —$NH_2$. The amino group is optionally substituted by substituted alkyl, substituted carbocycle, aryl, heteroaryl or heterocyclic, as defined above.

As used herein, the term "cyano" refers to the group —CN.

As used herein, the term "aminosulfonyl" refers to the group —$S(O)_2NH_2$. The aminosulfonyl group is optionally substituted by substituted alkyl, substituted carbocycle, aryl, heteroaryl or heterocyclic, as defined above.

As used herein, the term "sulfonylamino" refers to the group —$NHS(O)_2R_c$ wherein $R_c$ is substituted alkyl, substituted carbocycle, aryl, heteroaryl or heterocyclic, as defined above.

As used herein, the term "carboxyamide" refers to the group —$NHC(O)R_c$, wherein $R_c$ is substituted alkyl, substituted carbocycle, aryl, heteroaryl or heterocyclic, as defined above.

As used herein, the term "carboxy" refers to the group —C(O)OH. The carboxy group is optionally substituted by substituted alkyl, substituted carbocycle, aryl, heteroaryl or heterocyclic, as defined above.

As used herein, the term "aminocarbonyl" refers to the group —$C(O)NH_2$. The aminocarbonyl group is optionally substituted by substituted alkyl, substituted carbocycle, aryl, heteroaryl or heterocyclic, as defined above.

As used herein, the term "ureido" refers to the group —$NHC(O)NHR_d$ wherein $R_d$ is hydrogen, alkyl, carbocycle or aryl as defined above.

As used herein, the term "guanidino" refers to the group —NHC(=NH)$NH_2$.

As used herein, the term "acyl" refers to the group —C(O)R$_e$, wherein R$_e$ is alkyl, carbocycle, or heterocyclic as defined herein.

As used herein, the term "aroyl" refers to the group —C(O)R$_b$, wherein R$_b$ is aryl as defined herein.

As used herein, the term "heteroaroyl" refers to the group —C(O)R$_f$, wherein R$_f$ is heteroaryl as defined herein.

As used herein, the term "acyloxy" refers to the group —OC(O)R$_e$, wherein R$_e$ is alkyl, carbocycle, or heterocyclic as defined herein.

As used herein, the term "aroyloxy" refers to the group —OC(O)R$_b$, wherein R$_b$ is aryl as defined herein.

As used herein, the term "heteroaroyloxy" refers to the group —OC(O)R$_f$, wherein R$_f$ is heteroaryl as defined herein.

It is to be understood that the present invention also includes a pharmaceutically acceptable salts of the inventive compound. Examples of such salts include acid addition salts such as a hydrochloric acid, trifluoroacetic acid, formic acid, citric acid, fumaric acid, fumarate mono-sodium, p-toluenesulfonic acid, stearic acid, citrate di-sodium, tartaric acid, malic acid, lactic acid, succinic acid, and salicylic acid addition salts; and salts with an alkaline earth metal such as sodium, potassium and magnesium salts.

Further, the present invention also includes a prodrug form of the inventive compound. A prodrug is an active or inactive compound that is modified chemically through in vivo physiological action, such as hydrolysis, metabolism and the like, into a compound of the present invention following administration of the prodrug to a patient.

Preferably, the prodrug is carboxylate or aminoacetate of the compound of formula I, the carboxylate or aminoacetate being optionally substituted with at least one substituent selected from the group consisting of C$_{1-7}$ alkyl, C$_{1-7}$ alkoxy, C$_{2-7}$ alkenyl, C$_{2-7}$ alkenyloxy, C$_{6-10}$ aryl, C$_{6-10}$ aryloxy, C$_{6-10}$ aryl-C$_{1-4}$ alkyl, C$_{6-10}$ aryl-C$_{1-4}$ alkoxy, and C$_{6-10}$ aryl substituted with at least one C$_{1-4}$ alkoxy.

In accordance with one aspect of the present invention, there is provided a compound of formula I, or a pharmaceutically acceptable salt or a prodrug thereof:

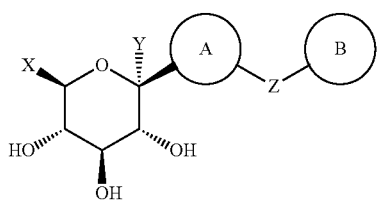

I wherein,
ring A is benzene, naphthalene, or indole;
ring B is thiazole;
X is methyl or cyclopropyl;
Y is H, C$_{1-4}$ alkoxy, or fused with a substituent of ring A to form 3 to 7-membered heterocyclic alkyl or 5 to 14-membered heteroaryl; and
Z is methylene or cyclopropane, and
optionally, said ring A, ring B, X, Y, and Z are each independently substituted with at least one substituent selected from the group consisting of halogen, hydroxy, cyano, nitro, amino, mercapto, carboxyl, carbamoyl, tosyl, —CF$_3$, C$_{1-7}$ alkyl, C$_{2-7}$ alkenyl, C$_{2-7}$ alkynyl, C$_{1-4}$ alkoxy-C$_{1-4}$ alkyl, C$_{1-7}$ alkoxy, C$_{1-7}$ alkenyloxy, C$_{1-7}$ alkynyloxy, C$_{3-7}$ cycloalkyloxy, phenyl-C$_{1-4}$ alkoxy, C$_{1-4}$ alkenyloxy-C$_{1-4}$ alkyl, C$_{1-4}$ alkoxy-C$_{1-4}$ alkoxy, C$_{6-10}$ aryloxy, 5 to 14-membered heteroaryl-C$_{1-4}$ alkoxy, C$_{3-7}$ cycloalkyl, C$_{3-7}$ cycloalkenyl, 3 to 7-membered heterocyclic alkyl, C$_{6-10}$ aryl, 5 to 14-membered heteroaryl, C$_{1-4}$ alkylsulfanyl, C$_{1-4}$ alkylsulfinyl, C$_{1-4}$ alkylsulfonyl, C$_{6-10}$ arylsulfanyl, C$_{6-10}$ arylsulfinyl, C$_{6-10}$ arylsulfonyl, mono- or di-C$_{1-4}$ alkylamino, C$_{1-4}$ alkanoylamino, C$_{1-4}$ alkoxycarbonyl, mono- or di-C$_{1-4}$ alkylcarbamoyl, C$_{1-4}$ alkanoyl, C$_{1-4}$ alkylsulfonylamino, and C$_{6-10}$ aryl sulfonylamino; and said alkyl, alkenyl, or alkoxy is optionally substituted with a substituent selected from the group consisting of halogen, hydroxy, cyano, nitro, amino, and mercapto; and said cycloalkyl, heterocyclic alkyl, aryl, or heteroaryl is optionally substituted with a substituent selected from the group consisting of halogen, hydroxy, cyano, nitro, amino, mercapto, C$_{1-4}$ alkyl, and C$_{1-4}$ alkoxy; and said heterocyclic alkyl and heteroaryl each independently contains at least one heteroatom selected from N, O and S; and when X, Y, Z and ring A are respectively hydroxymethyl, H, methylene and chlorobenzene, ring B is neither 2-thiazolyl nor 5-phenylthiazol-2-yl.

Preferably, ring A is selected from the group consisting of:

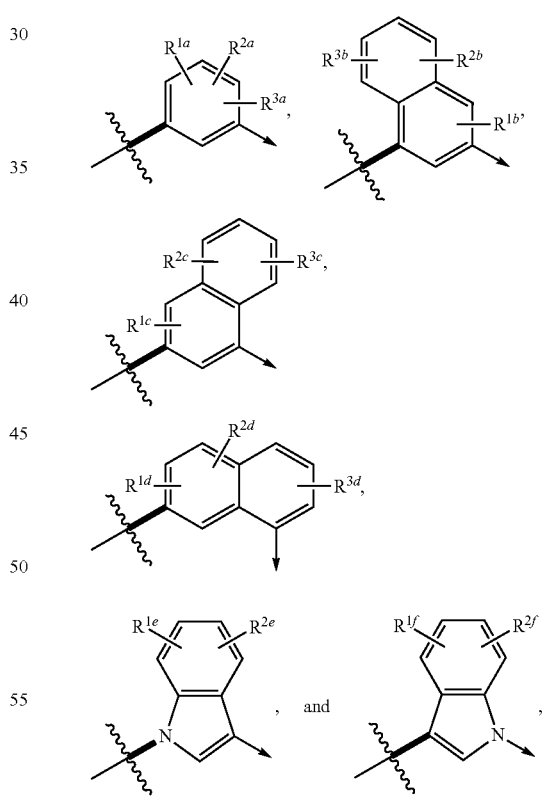

wherein, R$^{1a}$, R$^{2a}$, R$^{3a}$, R$^{1b}$, R$^{2b}$, R$^{3b}$, R$^{1c}$, R$^{2c}$, R$^{3c}$, R$^{1d}$, R$^{2d}$, R$^{3d}$, R$^{1e}$, R$^{2e}$, R$^{1f}$, and R$^{2f}$ are each independently H, halogen, hydroxy, cyano, —CF$_3$, C$_{1-7}$ alkyl, C$_{3-7}$ cycloalkyl, C$_{1-7}$ alkoxy, C$_{1-7}$ alkenyloxy, C$_{1-7}$ alkynyloxy, C$_{1-4}$ alkenyloxy-C$_{1-4}$ alkyl, C$_{1-4}$ alkoxy-C$_{1-4}$ alkoxy, or 5 to 14-membered heteroaryl-C$_{1-4}$ alkoxy;

ring B is

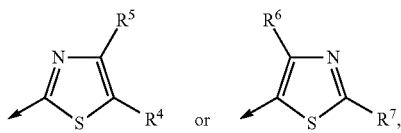

wherein, $R^4$, $R^5$, $R^6$ and $R^7$ are each independently H, $C_{1-7}$ alkyl, $C_{2-7}$ alkenyl, $C_{2-7}$ alkynyl, $C_{1-7}$ alkoxy, $C_{6-10}$ aryloxy, $C_{1-7}$ alkoxycarbonyl, $C_{3-7}$ cycloalkyl, $C_{1-4}$ alkylsulfanyl, $C_{6-10}$ aryl, or 5 to 14-membered heteroaryl;

X is

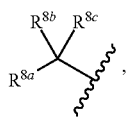

wherein, $R^{8a}$, $R^{8b}$, and $R^{8c}$ are each independently H, halogen, hydroxy, $C_{1-7}$ alkyl, $C_{2-7}$ alkenyl, $C_{1-7}$ alkoxy, $C_{1-4}$ alkylsulfanyl, $C_{1-4}$ alkylsulfonyl, $C_{6-10}$ arylsulfonyl, $C_{6-10}$ aryl, $C_{6-10}$ aryloxy, and 5 to 14-membered heteroaryl;

Y is H or $C_{1-2}$ alkoxy, or fused with $R^{1a}$, $R^{2a}$ or $R^{3a}$ to form 3 to 7-membered heterocyclic alkyl or 5 to 14-membered heteroaryl; and Z is methylene or

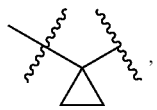 [SMILES: *C1(*)CC1]

said alkyl, alkenyl, or alkoxy being optionally substituted with a substituent selected from the group consisting of halogen, hydroxy, cyano, nitro, amino, and mercapto; and said cycloalkyl, heterocyclic alkyl, aryl, or heteroaryl being optionally substituted with a substituent selected from the group consisting of halogen, hydroxy, cyano, nitro, amino, mercapto, $C_{1-4}$ alkyl, and $C_{1-4}$ alkoxy; and said heterocyclic alkyl and heteroaryl each independently contains at least one heteroatom selected from N, O and S; and when X, Y, Z and ring A are respectively hydroxymethyl, H, methylene and chlorobenzene, ring B is neither 2-thiazolyl nor 5-phenylthiazol-2-yl.

More preferably, $R^{1a}$, $R^{2a}$, $R^{3a}$, $R^{1b}$, $R^{2b}$, $R^{3b}$, $R^{1c}$, $R^{2c}$, $R^{3c}$, $R^{1d}$, $R^{2d}$, $R^{3d}$, $R^{1e}$, $R^{2e}$, $R^{1f}$, and $R^{2f}$ are each independently H, Cl, F, Br, trifluoromethyl, cyano, hydroxy, methyl, hydroxymethyl, methoxy, ethoxy, hydroxyethoxy, propoxy, allyloxy, butenyloxy, propynyloxy, triazolylethoxy, tetrahydrofuranylmethoxy, allyloxymethyl, or methoxyethoxy;

$R^4$ and $R^7$ are each independently H, methyl, ethyl, n-propyl, i-propyl, n-butyl, n-pentyl, n-hexyl, n-heptyl, allyl, butenyl, ethoxy, propoxy, pentoxy, cyclopentyl, cyclohexyl, cyclopentenyl, methylsulfanyl, ethylsulfanyl, propylsulfanyl, butylsulfanyl, pentylsulfanyl, phenyl, benzyl, thiophenyl, furanyl, thiazolyl, pyridinyl, thiadiazolyl, benzofuranyl, oxazolyl, i-oxazolyl, or pyrazinyl, wherein phenyl or thiophenyl is optionally substituted with halogen or methyl;

$R^5$ and $R^6$ are H;

$R^{8a}$, $R^{8b}$ t and $R^{8c}$ are each independently H, fluoro, hydroxy, methyl, allyl, butenyl, mesyl, tosyloxy, methoxy, ethoxy, hydroxyethoxy, methylsulfanyl, ethylsulfanyl, triazolyl, or tetrazolyl;

Y is H, or fused with $R^{1a}$, $R^{2a}$ or $R^{3a}$ to form tetrahydrofuran; and Z is methylene or

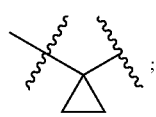 [SMILES: *C1(*)CC1]

and when X, Y, Z and ring A are respectively hydroxymethyl, H, methylene and chlorobenzene, ring B is neither 2-thiazolyl nor 5-phenylthiazol-2-yl.

Compounds especially useful in the present invention are selected from the group consisting of:

(1) (2S,3R,4R,5S,6R)-2-(4-Chloro-3-((5-(thiophen-3-yl)thiazol-2-yl)methyl)phenyl)-6-(hydroxymethyl)-tetrahydro-2H-pyran-3,4,5-triol (2) (2S,3R,4R,5S,6R)-2-(3-((5-(4-Fluorophenyl)thiazol-2-yl)methyl)-4-methoxynaphthalen-1-yl)-6-(hydroxymethyl)-tetrahydro-2H-pyran-3,4,5-triol (3) (2S,3R,4R,5S,6R)-2-(4-Chloro-3-(1-(5-(furan-2-yl)thiazol-2-yl)cyclopropyl)phenyl)-6-(hydroxymethyl)-tetrahydro-2H-pyran-3,4,5-triol (4) (2S,3R,4R,5S,6R)-2-(3-((5-(Furan-2-yl)thiazol-2-yl)methyl)-4-(trifluoromethyl)phenyl)-6-(hydroxymethyl)-tetrahydro-2H-pyran-3,4,5-triol (5) (2S,3R,4R,5S,6R)-2-(4-Chloro-3-((5-(furan-2-yl)thiazol-2-yl)methyl)phenyl)-6-(hydroxymethyl)-tetrahydro-2H-pyran-3,4,5-triol (6) (2S,3R,4R,5S,6R)-2-(4-Chloro-3-((5-(furan-3-yl)thiazol-2-yl)methyl)phenyl)-6-(hydroxymethyl)-tetrahydro-2H-pyran-3,4,5-triol (7) (2S,3R,4R,5S,6R)-2-(4-Chloro-3-((5-(thiophen-2-yl)thiazol-2-yl)methyl)phenyl)-6-(hydroxymethyl)tetrahydro-2H-pyran-3,4,5-triol (8) (2S,3R,4R,5S,6R)-2-(4-Chloro-3-((5-(5-chlorothiophen-2-yl)thiazol-2-yl)methyl)phenyl)-6-(hydroxymethyl)tetrahydro-2H-pyran-3,4,5-triol (9) (2S,3R,4R,5S,6R)-2-(3-(2,5'-Bithiazol-2'-ylmethyl)-4-chlorophenyl)-6-(hydroxymethyl)-tetrahydro-2H-pyran-3,4,5-triol

(10) (2S,3R,4R,5S,6R)-2-(4-Chloro-3-((5-(pyridin-2-yl)thiazol-2-yl)methyl)phenyl)-6-(hydroxymethyl)-tetrahydro-2H-pyran-3,4,5-triol

(11) (2S,3R,4R,5S,6R)-2-(4-Chloro-3-((5-(4-fluorophenyl)thiazol-2-yl)methyl)phenyl)-6-(hydroxymethyl)-tetrahydro-2H-pyran-3,4,5-triol

(12) (2S,3R,4R,5S,6R)-2-(4-chloro-3-((5-ethylthiazol-2-yl)methyl)phenyl)-6-(hydroxymethyl)-tetrahydro-2H-pyran-3,4,5-triol

(13) (2S,3R,4R,5S,6R)-2-(3-((5-Butylthiazol-2-yl)methyl)-4-chlorophenyl)-6-(hydroxymethyl)-tetrahydro-2H-pyran-3,4,5-triol

(14) (2S,3R,4R,5S,6R)-2-(4-Chloro-3-((5-pentylthiazol-2-yl)methyl)phenyl)-6-(hydroxymethyl)-tetrahydro-2H-pyran-3,4,5-triol

(15) (2S,3R,4R,5S,6R)-2-(4-Chloro-3-((5-hexylthiazol-2-yl)methyl)phenyl)-6-(hydroxymethyl)-tetrahydro-2H-pyran-3,4,5-triol

(16) (2S,3R,4R,5S,6R)-2-(4-Chloro-3-((5-isopropylthiazol-2-yl)methyl)phenyl)-6-(hydroxymethyl)-tetrahydro-2H-pyran-3,4,5-triol

(17) (2S,3R,4R,5S,6R)-2-(3-((5-Allylthiazol-2-yl)methyl)-4-chlorophenyl)-6-(hydroxymethyl)-tetrahydro-2H-pyran-3,4,5-triol

(18) 2S,3R,4R,5S,6R,E)-2-(3-((5-(but-2-en-2-yl)thiazol-2-yl)methyl)-4-chlorophenyl)-6-(hydroxymethyl)-tetrahydro-2H-pyran-3,4,5-triol

(19) (2S,3R,4R,5S,6R)-2-(4-Chloro-3-((5-cyclopentylthiazol-2-yl)methyl)phenyl)-6-(hydroxymethyl)-tetrahydro-2H-pyran-3,4,5-triol

(20) (2S,3R,4R,5S,6R)-2-(4-Chloro-3-((5-cyclohexylthiazol-2-yl)methyl)phenyl)-6-(hydroxymethyl)-tetrahydro-2H-pyran-3,4,5-triol

(21) (2S,3R,4R,5S,6R)-2-(4-Chloro-3-((5-ethoxythiazol-2-yl)methyl)phenyl)-6-(hydroxymethyl)-tetrahydro-2H-pyran-3,4,5-triol

(22) (2S,3R,4R,5S,6R)-2-(4-Chloro-3-((5-propoxythiazol-2-yl)methyl)phenyl)-6-(hydroxymethyl)-tetrahydro-2H-pyran-3,4,5-triol

(23) (2S,3R,4R,5S,6R)-2-(4-Chloro-3-((5-(pentyloxy)thiazol-2-yl)methyl)phenyl)-6-(hydroxymethyl)-tetrahydro-2H-pyran-3,4,5-triol

(24) (2S,3R,4R,5S,6R)-2-(4-Chloro-3-((5-(ethylthio)thiazol-2-yl)methyl)phenyl)-6-(hydroxymethyl)-tetrahydro-2H-pyran-3,4,5-triol

(25) (2S,3R,4R,5S,6R)-2-(4-Chloro-3-((5-(propylthio)thiazol-2-yl)methyl)phenyl)-6-(hydroxymethyl)-tetrahydro-2H-pyran-3,4,5-triol

(26) (2S,3R,4R,5S,6R)-2-(3-((5-(Butylthio)thiazol-2-yl)methyl)-4-chlorophenyl)-6-(hydroxymethyl)-tetrahydro-2H-pyran-3,4,5-triol

(27) (2S,3R,4R,5S,6R)-2-(3-((5-(Butylthio)thiazol-2-yl)methyl)-4-chlorophenyl)-6-(hydroxymethyl)-tetrahydro-2H-pyran-3,4,5-triol

(28) (2S,3R,4R,5S,6R)-2-(4-Chloro-3-(1-(5-(furan-3-yl)thiazol-2-yl)cyclopropyl)phenyl)-6-(hydroxymethyl)tetrahydro-2H-pyran-3,4,5-triol

(29) (2S,3R,4R,5S,6R)-2-(4-Chloro-3-(1-(5-(thiophen-2-yl)thiazol-2-yl)cyclopropyl)phenyl)-6-(hydroxymethyl)tetrahydro-2H-pyran-3,4,5-triol

(30) (2S,3R,4R,5S,6R)-2-(3-((5-(Furan-2-yl)thiazol-2-yl)methyl)-4-methylphenyl)-6-(hydroxymethyl)tetrahydro-2H-pyran-3,4,5-triol

(31) (2S,3R,4R,5S,6R)-2-(4-Chloro-2-ethoxy-5-((5-(furan-3-yl)thiazol-2-yl)methyl)phenyl)-6-(hydroxymethyl)tetrahydro-2H-pyran-3,4,5-triol

(32) (2R,3S,4R,5R,6S)-2-(Hydroxymethyl)-6-(4-methyl-3-((5-(thiophen-2-yl)thiazol-2-yl)methyl)phenyl)tetrahydro-2H-pyran-3,4,5-triol

(33) (2R,3S,4R,5R,6S)-2-(Hydroxymethyl)-6-(4-methyl-3-((5-(thiophen-3-yl)thiazol-2-yl)methyl)phenyl)tetrahydro-2H-pyran-3,4,5-triol

(34) (2S,3R,4R,5S,6R)-2-(3-(2,5'-Bithiazol-2'-ylmethyl)-4-methylphenyl)-6-(hydroxymethyl)tetrahydro-2H-pyran-3,4,5-triol

(35) (2R,3S,4R,5R,6S)-2-(Hydroxymethyl)-6-(4-methyl-3-((5-phenylthiazol-2-yl)methyl)phenyl)tetrahydro-2H-pyran-3,4,5-triol

(36) (2R,3S,4R,5R,6S)-2-(Hydroxymethyl)-6-(4-methyl-3-((5-p-tolylthiazol-2-yl)methyl)phenyl)tetrahydro-2H-pyran-3,4,5-triol

(37) (2S,3R,4R,5S,6R)-2-(3-((5-(4-Fluorophenyl)thiazol-2-yl)methyl)-4-methylphenyl)-6-(hydroxymethyl)tetrahydro-2H-pyran-3,4,5-triol

(38) (2S,3R,4R,5S,6R)-2-(3-((5-(4-Chlorophenyl)thiazol-2-yl)methyl)-4-methylphenyl)-6-(hydroxymethyl)tetrahydro-2H-pyran-3,4,5-triol

(39) (2S,3R,4R,5S,6R)-2-(3-((5-Benzylthiazol-2-yl)methyl)-4-methylphenyl)-6-(hydroxymethyl)tetrahydro-2H-pyran-3,4,5-triol

(40) (2S,3R,4R,5S,6R)-2-(4-Fluoro-3-((5-(furan-2-yl)thiazol-2-yl)methyl)phenyl)-6-(hydroxymethyl)tetrahydro-2H-pyran-3,4,5-triol

(41) (2S,3R,4R,5S,6R)-2-(4-Fluoro-3-((5-(furan-3-yl)thiazol-2-yl)methyl)phenyl)-6-(hydroxymethyl)tetrahydro-2H-pyran-3,4,5-triol

(42) (2S,3R,4R,5S,6R)-2-(4-Fluoro-3-((5-(thiophen-2-yl)thiazol-2-yl)methyl)phenyl)-6-(hydroxymethyl)tetrahydro-2H-pyran-3,4,5-triol

(43) (2S,3R,4R,5S,6R)-2-(4-Fluoro-3-((5-(thiazol-3-yl)thiazol-2-yl)methyl)phenyl)-6-(hydroxymethyl)tetrahydro-2H-pyran-3,4,5-triol

(44) (2S,3R,4R,5S,6R)-2-(4-Fluoro-3-((5-phenylthiazol-2-yl)methyl)phenyl)-6-(hydroxymethyl)tetrahydro-2H-pyran-3,4,5-triol

(45) (2S,3R,4R,5S,6R)-2-(4-Fluoro-3-((5-(4-fluorophenyl)thiazol-2-yl)methyl)phenyl)-6-(hydroxymethyl)tetrahydro-2H-pyran-3,4,5-triol

(46) (2S,3R,4R,5S,6R)-2-(4-Bromo-3-((5-(furan-2-yl)thiazol-2-yl)methyl)phenyl)-6-(hydroxymethyl)-tetrahydro-2H-pyran-3,4,5-triol

(47) (2S,3R,4R,5S,6R)-2-(4-Bromo-3-((5-(thiophen-3-yl)thiazol-2-yl)methyl)phenyl)-6-(hydroxymethyl)-tetrahydro-2H-pyran-3,4,5-triol

(48) (2S,3R,4R,5S,6R)-2-(3-((5-(Furan-3-yl)thiazol-2-yl)methyl)-4-(trifluoromethyl)phenyl)-6-(hydroxymethyl)tetrahydro-2H-pyran-3,4,5-triol

(49) (2R,3S,4R,5R,6S)-2-(Hydroxymethyl)-6-(3-((5-(thiophen-2-yl)thiazol-2-yl)methyl)-4-(trifluoromethyl)phenyl)tetrahydro-2H-pyran-3,4,5-triol

(50) (2R,3S,4R,5R,6S)-2-(Hydroxymethyl)-6-(3-((5-(thiophen-3-yl)thiazol-2-yl)methyl)-4-(trifluoromethyl)phenyl)tetrahydro-2H-pyran-3,4,5-triol

(51) (2R,3S,4R,5R,6S)-2-(Hydroxymethyl)-6-(3-((5-phenylthiazol-2-yl)methyl)-4-(trifluoromethyl)phenyl)tetrahydro-2H-pyran-3,4,5-triol

(52) (2S,3R,4R,5S,6R)-2-(3-((5-(4-Fluorophenyl)thiazol-2-yl)methyl)-4-(trifluoromethyl)phenyl)-6-(hydroxymethyl)tetrahydro-2H-pyran-3,4,5-triol

(53) (2S,3R,4R,5S,6R)-2-(4-Chloro-2-fluoro-5-((5-(furan-2-yl)thiazol-2-yl)methyl)phenyl)-6-(hydroxymethyl)tetrahydro-2H-pyran-3,4,5-triol

(54) (2S,3R,4R,5S,6R)-2-(4-Chloro-2-fluoro-5-((5-(furan-3-yl)thiazol-2-yl)methyl)phenyl)-6-(hydroxymethyl)tetrahydro-2H-pyran-3,4,5-triol

(55) (2S,3R,4R,5S,6R)-2-(4-Chloro-2-fluoro-5-((5-(thiophen-2-yl)thiazol-2-yl)methyl)phenyl)-6-(hydroxymethyl)tetrahydro-2H-pyran-3,4,5-triol

(56) (2S,3R,4R,5S,6R)-2-(4-Chloro-2-fluoro-5-((5-(thiophen-3-yl)thiazol-2-yl)methyl)phenyl)-6-(hydroxymethyl)tetrahydro-2H-pyran-3,4,5-triol

(57) (2S,3R,4R,5S,6R)-2-(4-Chloro-2-fluoro-5-((5-phenylthiazol-2-yl)methyl)phenyl)-6-(hydroxymethyl)tetrahydro-2H-pyran-3,4,5-triol

(58) (2S,3R,4R,5S,6R)-2-(4-Chloro-2-fluoro-5-((5-(4-fluorophenyl)thiazol-2-yl)methyl)phenyl)-6-(hydroxymethyl)tetrahydro-2H-pyran-3,4,5-triol

(59) (2S,3R,4R,5S,6R)-2-(2,4-Dichloro-5-((5-(furan-2-yl)thiazol-2-yl)methyl)phenyl)-6-(hydroxymethyl)tetrahydro-2H-pyran-3,4,5-triol

(61) (2S,3R,4R,5S,6R)-2-(2,4-Dichloro-5-((5-(thiophen-2-yl)thiazol-2-yl)methyl)phenyl)-6-(hydroxymethyl)tetrahydro-2H-pyran-3,4,5-triol
(62) (2S,3R,4R,5S,6R)-2-(2,4-Dichloro-5-((5-(thiophen-3-yl)thiazol-2-yl)methyl)phenyl)-6-(hydroxymethyl)tetrahydro-2H-pyran-3,4,5-triol
(63) (2S,3R,4R,5S,6R)-2-(2,4-Dichloro-5-((5-methylthiazol-2-yl)methyl)phenyl)-6-(hydroxymethyl)tetrahydro-2H-pyran-3,4,5-triol
(64) (2S,3R,4R,5S,6R)-2-(2,4-Dichloro-5-((5-ethylthiazol-2-yl)methyl)phenyl)-6-(hydroxymethyl)tetrahydro-2H-pyran-3,4,5-triol
(65) (2S,3R,4R,5S,6R)-2-(2,4-Dichloro-5-((5-propylthiazol-2-yl)methyl)phenyl)-6-(hydroxymethyl)tetrahydro-2H-pyran-3,4,5-triol
(66) (2S,3R,4R,5S,6R)-2-(5-((5-Butylthiazol-2-yl)methyl)-2,4-dichlorophenyl)-6-(hydroxymethyl)tetrahydro-2H-pyran-3,4,5-triol
(67) (2S,3R,4R,5S,6R)-2-(2,4-Dichloro-5-((5-hexylthiazol-2-yl)methyl)phenyl)-6-(hydroxymethyl)tetrahydro-2H-pyran-3,4,5-triol
(68) (2S,3R,4R,5S,6R)-2-(2,4-Dichloro-5-((5-cyclopentylthiazol-2-yl)methyl)phenyl)-6-(hydroxymethyl)tetrahydro-2H-pyran-3,4,5-triol
(69) (2S,3R,4R,5S,6R)-2-(4-Chloro-5-((5-(furan-2-yl)thiazol-2-yl)methyl)-2-methoxyphenyl)-6-(hydroxymethyl)tetrahydro-2H-pyran-3,4,5-triol
(70) (2S,3R,4R,5S,6R)-2-(4-Chloro-5-((5-(furan-3-yl)thiazol-2-yl)methyl)-2-methoxyphenyl)-6-(hydroxymethyl)tetrahydro-2H-pyran-3,4,5-triol
(71) (2S,3R,4R,5S,6R)-2-(4-Chloro-3-((4-phenylthiazol-2-yl)methyl)phenyl)-6-(hydroxymethyl)tetrahydro-2H-pyran-3,4,5-triol
(72) (2S,3R,4R,5S,6R)-2-(4-Chloro-2-methoxy-5-((5-(thiophen-3-yl)thiazol-2-yl)methyl)phenyl)-6-(hydroxymethyl)tetrahydro-2H-pyran-3,4,5-triol
(73) (2S,3R,4R,5S,6R)-2-(4-Chloro-2-methoxy-5-((5-phenylthiazol-2-yl)methyl)phenyl)-6-(hydroxymethyl)tetrahydro-2H-pyran-3,4,5-triol
(74) (2S,3R,4R,5S,6R)-2-(4-Chloro-5-((5-(4-fluorophenyl)thiazol-2-yl)methyl)-2-methoxyphenyl)-6-(hydroxymethyl)tetrahydro-2H-pyran-3,4,5-triol
(75) (2S,3R,4R,5S,6R)-2-(4-Chloro-5-((5-hexylthiazol-2-yl)methyl)-2-methoxyphenyl)-6-(hydroxymethyl)tetrahydro-2H-pyran-3,4,5-triol
(76) (2S,3R,4R,5S,6R)-2-(4-Chloro-5-((5-cyclopentylthiazol-2-yl)methyl)-2-methoxyphenyl)-6-(hydroxymethyl)tetrahydro-2H-pyran-3,4,5-triol
(77) (2S,3R,4R,5S,6R)-2-(4-Chloro-2-ethoxy-5-((5-(furan-2-yl)thiazol-2-yl)methyl)phenyl)-6-(hydroxymethyl)tetrahydro-2H-pyran-3,4,5-triol
(78) (2S,3R,4R,5S,6R)-2-(4-Chloro-2-ethoxy-5-((5-(furan-3-yl)thiazol-2-yl)methyl)phenyl)-6-(hydroxymethyl)-tetrahydro-2H-pyran-3,4,5-triol
(79) (2S,3R,4R,5S,6R)-2-(4-Chloro-2-ethoxy-5-((5-(thiophen-2-yl)thiazol-2-yl)methyl)phenyl)-6-(hydroxymethyl)tetrahydro-2H-pyran-3,4,5-triol
(80) (2S,3R,4R,5S,6R)-2-(4-Chloro-2-ethoxy-5-((5-(thiophen-3-yl)thiazol-2-yl)methyl)phenyl)-6-(hydroxymethyl)tetrahydro-2H-pyran-3,4,5-triol
(81) (2S,3R,4R,5S,6R)-2-(4-Chloro-2-ethoxy-5-((5-phenylthiazol-2-yl)methyl)phenyl)-6-(hydroxymethyl)tetrahydro-2H-pyran-3,4,5-triol
(82) (2S,3R,4R,5S,6R)-2-(4-Chloro-2-ethoxy-5-((5-(4-fluorophenyl)thiazol-2-yl)methyl)phenyl)-6-(hydroxymethyl)tetrahydro-2H-pyran-3,4,5-triol
(83) (2S,3R,4R,5S,6R)-2-(2-(Allyloxy)-4-chloro-5-((5-(furan-2-yl)thiazol-2-yl)methyl)phenyl)-6-(hydroxymethyl)tetrahydro-2H-pyran-3,4,5-triol
(84) (2S,3R,4R,5S,6R)-2-(2-(Allyloxy)-4-chloro-5-((5-(furan-3-yl)thiazol-2-yl)methyl)phenyl)-6-(hydroxymethyl)tetrahydro-2H-pyran-3,4,5-triol
(85) (2S,3R,4R,5S,6R)-2-(2-(Allyloxy)-4-chloro-5-((5-(thiophen-2-yl)thiazol-2-yl)methyl)phenyl)-6-(hydroxymethyl)tetrahydro-2H-pyran-3,4,5-triol
(86) (2S,3R,4R,5S,6R)-2-(2-(Allyloxy)-4-chloro-5-((5-(thiophen-3-yl)thiazol-2-yl)methyl)phenyl)-6-(hydroxymethyl)tetrahydro-2H-pyran-3,4,5-triol
(87) (2S,3R,4R,5S,6R)-2-(2-(Allyloxy)-4-chloro-5-((5-phenylthiazol-2-yl)methyl)phenyl)-6-(hydroxymethyl)tetrahydro-2H-pyran-3,4,5-triol
(88) (2S,3R,4R,5S,6R)-2-(2-(Allyloxy)-4-chloro-5-((5-(4-fluorophenyl)thiazol-2-yl)methyl)phenyl)-6-(hydroxymethyl)tetrahydro-2H-pyran-3,4,5-triol
(89) (2S,3R,4R,5S,6R)-2-(2-(Allyloxymethyl)-4-chloro-5-((5-(furan-2-yl)thiazol-2-yl)methyl)phenyl)-6-(hydroxymethyl)-tetrahydro-2H-pyran-3,4,5-triol
(90) (2S,3R,4R,5S,6R)-2-(2-(Allyloxymethyl)-4-chloro-5-((5-(furan-3-yl)thiazol-2-yl)methyl)phenyl)-6-(hydroxymethyl)-tetrahydro-2H-pyran-3,4,5-triol
(91) (2S,3R,4R,5S,6R)-2-(2-(Allyloxymethyl)-4-chloro-5-((5-(thiophen-2-yl)thiazol-2-yl)methyl)phenyl)-6-(hydroxymethyl)-tetrahydro-2H-pyran-3,4,5-triol
(92) (2S,3R,4R,5S,6R)-2-(2-(Allyloxymethyl)-4-chloro-5-((5-(thiophen-3-yl)thiazol-2-yl)methyl)phenyl)-6-(hydroxymethyl)-tetrahydro-2H-pyran-3,4,5-triol
(93) (2S,3R,4R,5S,6R)-2-(3-((5-(Furan-2-yl)thiazol-2-yl)methyl)naphthalen-1-yl)-6-(hydroxymethyl)tetrahydro-2H-pyran-3,4,5-triol
(94) (2R,3S,4R,5R,6S)-2-(Hydroxymethyl)-6-(3-((5-(thiophen-2-yl)thiazol-2-yl)methyl)naphthalen-1-yl)tetrahydro-2H-pyran-3,4,5-triol
(95) (2S,3R,4R,5S,6R)-2-(3-((5-(Furan-2-yl)thiazol-2-yl)methyl)-4-methoxynaphthalen-1-yl)-6-(hydroxymethyl)-tetrahydro-2H-pyran-3,4,5-triol
(96) (2R,3S,4R,5R,6S)-2-(Hydroxymethyl)-6-(4-methoxy-3-((5-(thiophen-2-yl)thiazol-2-yl)methyl)naphthalen-1-yl)-tetrahydro-2H-pyran-3,4,5-triol
(97) (2R,3S,4R,5R,6S)-2-(Hydroxymethyl)-6-(4-methoxy-3-((5-phenylthiazol-2-yl)methyl)naphthalen-1-yl)-tetrahydro-2H-pyran-3,4,5-triol
(98) (2R,3S,4R,5R,6S)-2-(Hydroxymethyl)-6-(4-methoxy-3-((5-methylthiazol-2-yl)methyl)naphthalen-1-yl)-tetrahydro-2H-pyran-3,4,5-triol
(99) (2R,3S,4R,5R,6S)-2-(Hydroxymethyl)-6-(4-methoxy-3-((5-propylthiazol-2-yl)methyl)naphthalen-1-yl)-tetrahydro-2H-pyran-3,4,5-triol
(100) (2S,3R,4R,5S,6R)-2-(3-((5-Heptylthiazol-2-yl)methyl)-4-methoxynaphthalen-1-yl)-6-(hydroxymethyl)-tetrahydro-2H-pyran-3,4,5-triol
(101) (2S,3R,4R,5S,6R)-2-(3-((5-Cyclopentylthiazol-2-yl)methyl)-4-methoxynaphthalen-1-yl)-6-(hydroxymethyl)-tetrahydro-2H-pyran-3,4,5-triol
(102) (2S,3R,4R,5S,6R)-2-(4-Cyclopropyl-3-((5-(furan-2-yl)thiazol-2-yl)methyl)phenyl)-6-(hydroxymethyl)-tetrahydro-2H-pyran-3,4,5-triol
(103) (2S,3R,4R,5S,6R)-2-(3-((5-Ethoxythiazol-2-yl)methyl)-4-methoxynaphthalen-1-yl)-6-(hydroxymethyl)-tetrahydro-2H-pyran-3,4,5-triol
(104) (2S,3R,4R,5S,6R)-2-(4-((5-(Furan-2-yl)thiazol-2-yl)methyl)naphthalen-2-yl)-6-(hydroxymethyl)-tetrahydro-2H-pyran-3,4,5-triol (105) (2S,3R,4R,5S,6R)-2-(4-((5-Ethylthiazol-2-yl)methyl)naphthalen-2-yl)-6-(hydroxymethyl)-tetrahydro-2H-pyran-3,4,5-triol
(106) Ethyl 2-(2-chloro-5-((2S,3R,4R,5S,6R)-3,4,5-trihydroxy-6-(hydroxymethyl)-tetrahydro-2H-pyran-2-yl)benzyl)thiazole-5-carboxylate
(107) (2S,3R,4R,5S,6R)-2-(3-((5-(1,3,4-Thiadiazol-2-yl)thiazol-2-yl)methyl)-4-chlorophenyl)-6-(hydroxymethyl)-tetrahydro-2H-pyran-3,4,5-triol
(108) (2S,3R,4R,5S,6R)-2-(3-((5-(1,3,4-Thiadiazol-2-yl)thiazol-2-yl)methyl)-4-chlorophenyl)-6-(hydroxymethyl)-tetrahydro-2H-pyran-3,4,5-triol
(109) 2-((5-(Thiophen-3-yl)thiazol-2-yl)methyl)-4-((2S,3R,4R,5S,6R)-3,4,5-trihydroxy-6-(hydroxymethyl)-tetrahydro-2H-pyran-2-yl)benzonitrile
(110) (2S,3R,4R,5S,6R)-2-(4-Cyclopropyl-3-((5-(furan-2-yl)thiazol-2-yl)methyl)phenyl)-6-(hydroxymethyl)-tetrahydro-2H-pyran-3,4,5-triol
(111) (2S,3R,4R,5S,6R)-2-(3-((5-(Furan-2-yl)thiazol-2-yl)methyl)phenyl)-6-(hydroxymethyl)-tetrahydro-2H-pyran-3,4,5-triol
(112) (2S,3R,4R,5S,6R)-2-(4-Chloro-5-((5-(furan-2-yl)thiazol-2-yl)methyl)-2-hydroxyphenyl)-6-(hydroxymethyl)-tetrahydro-2H-pyran-3,4,5-triol
(113) (2S,3R,4R,5S,6R)-2-(4-Chloro-5-((5-(furan-2-yl)thiazol-2-yl)methyl)-2-(hydroxymethyl)phenyl)-6-(hydroxymethyl)-tetrahydro-2H-pyran-3,4,5-triol
(114) (2S,3R,4R,5S,6R)-2-(4-Chloro-5-((5-(furan-3-yl)thiazol-2-yl)methyl)-2-(hydroxymethyl)phenyl)-6-(hydroxymethyl)-tetrahydro-2H-pyran-3,4,5-triol
(115) (2S,3R,4R,5S,6R)-2-(4-Chloro-2-(hydroxymethyl)-5-((5-(thiophen-2-yl)thiazol-2-yl)methyl)phenyl)-6-(hydroxymethyl)-tetrahydro-2H-pyran-3,4,5-triol
(116) (2S,3R,4R,5S,6R)-2-(4-Chloro-2-(hydroxymethyl)-5-((5-(thiophen-3-yl)thiazol-2-yl)methyl)phenyl)-6-(hydroxymethyl)-tetrahydro-2H-pyran-3,4,5-triol
(117) (2S,3R,4R,5S,6R)-2-(4-Chloro-5-((5-(furan-2-yl)thiazol-2-yl)methyl)-2-(2-methoxyethoxy)phenyl)-6-(hydroxymethyl)-tetrahydro-2H-pyran-3,4,5-triol
(118) (2S,3R,4R,5S,6R)-2-(4-Chloro-5-((5-(furan-2-yl)thiazol-2-yl)methyl)-2-propoxyphenyl)-6-(hydroxymethyl)tetrahydro-2H-pyran-3,4,5-triol
(119) (2S,3R,4R,5S,6R)-2-(2-(But-3-enyloxy)-4-chloro-5-((5-(furan-2-yl)thiazol-2-yl)methyl)phenyl)-6-(hydroxymethyl)tetrahydro-2H-pyran-3,4,5-triol
(120) (2S,3R,4R,5S,6R)-2-(4-Chloro-5-((5-(furan-2-yl)thiazol-2-yl)methyl)-2-(prop-2-ynyloxy)phenyl)-6-(hydroxymethyl)-tetrahydro-2H-pyran-3,4,5-triol
(121) (2S,3R,4R,5S,6R)-2-(4-Chloro-5-((5-(furan-2-yl)thiazol-2-yl)methyl)-2-(2-hydroxyethoxy)phenyl)-6-(hydroxymethyl)tetrahydro-2H-pyran-3,4,5-triol
(122) (2S,3R,4R,5S,6R)-2-(2-(2-(1H-1,2,4-Triazol-1-yl)ethoxy)-4-chloro-5-((5-(furan-2-yl)thiazol-2-yl)methyl)phenyl)-6-(hydroxymethyl)-tetrahydro-2H-pyran-3,4,5-triol
(123) (2S,3R,4R,5S,6R)-2-(3-((5-(4-Fluorophenyl)thiazol-2-yl)methyl)-4-hydroxynaphthalen-1-yl)-6-(hydroxymethyl)-tetrahydro-2H-pyran-3,4,5-triol
(124) (2S,3R,4R,5S,6R)-2-(4-Hydroxy-3-((5-(thiophen-2-yl)thiazol-2-yl)methyl)naphthalen-1-yl)-6-(hydroxymethyl)-tetrahydro-2H-pyran-3,4,5-triol
(125) (2S,3R,4R,5S,6R)-2-(4-Hydroxy-3-((5-phenylthiazol-2-yl)methyl)naphthalen-1-yl)-6-(hydroxymethyl)-tetrahydro-2H-pyran-3,4,5-triol
(126) (2S,3R,4R,5S,6R)-2-(4-Hydroxy-3-((5-propylthiazol-2-yl)methyl)naphthalen-1-yl)-6-(hydroxymethyl)-tetrahydro-2H-pyran-3,4,5-triol
(127) (2S,3R,4R,5S,6R)-2-(3-((5-Heptylthiazol-2-yl)methyl)-4-hydroxynaphthalen-1-yl)-6-(hydroxymethyl)-tetrahydro-2H-pyran-3,4,5-triol
(128) (2S,3R,4R,5S,6R)-2-(3-((5-Ethoxythiazol-2-yl)methyl)-4-hydroxynaphthalen-1-yl)-6-(hydroxymethyl)-tetrahydro-2H-pyran-3,4,5-triol
(129) (1S,3',4'S,5'S,6'R)-5-Chloro-6'-(hydroxymethyl)-6-(1-(5-(thiophen-2-yl)thiazole-2-yl)cyclopropyl)-3',4',5',6'-tetrahydro-3H-spiro[isobenzofuran-1,2'-pyran]-3',4',5'-triol
(130) (2R,3R,4S,5S,6R)-2-(3-((5-(Furan-2-yl)thiazol-2-yl)methyl)-1H-indol-1-yl)-6-(hydroxymethyl)-tetrahydro-2H-pyran-3,4,5-triol
(131) (2R,3S,4S,5R,6R)-2-(Hydroxymethyl)-6-(3-((5-(thiophen-2-yl)thiazol-2-yl)methyl)-1H-indol-1-yl)tetrahydro-2H-pyran-3,4,5-triol
(132) (2R,3S,4S,5R,6R)-2-(Hydroxymethyl)-6-(3-((5-methylthiazol-2-yl)methyl)-1H-indol-1-yl)tetrahydro-2H-pyran-3,4,5-triol
(133) (2R,3R,4S,5S,6R)-2-(3-((5-Ethylthiazol-2-yl)methyl)-1H-indol-1-yl)-6-(hydroxymethyl)tetrahydro-2H-pyran-3,4,5-triol
(134) (2R,3S,4S,5R,6R)-2-(Hydroxymethyl)-6-(3-((5-propylthiazol-2-yl)methyl)-1H-indol-1-yl)tetrahydro-2H-pyran-3,4,5-triol
(135) (2R,3R,4S,5S,6R)-2-(3-((5-Butylthiazol-2-yl)methyl)-1H-indol-1-yl)-6-(hydroxymethyl)tetrahydro-2H-pyran-3,4,5-triol
(136) (2R,3S,4S,5R,6R)-2-(Hydroxymethyl)-6-(3-((5-pentylthiazol-2-yl)methyl)-1H-indol-1-yl)tetrahydro-2H-pyran-3,4,5-triol
(137) (2R,3S,4R,5R,6S)-2-(Hydroxymethyl)-6-(1-((5-phenylthiazol-2-yl)methyl)-1H-indol-3-yl)-tetrahydro-2H-pyran-3,4,5-triol
(138) ((2R,3S,4R,5R,6S)-6-(4-Chloro-3-((5-(furan-2-yl)thiazol-2-yl)methyl)phenyl)-3,4,5-trihydroxy-tetrahydro-2H-pyran-2-yl)methyl 4-methylbenzenesulfonate
(139) (2S,3R,4R,5S,6R)-2-(4-Chloro-3-((5-(furan-2-yl)thiazol-2-yl)methyl)phenyl)-6-(methoxymethyl)-tetrahydro-2H-pyran-3,4,5-triol
(140) (2S,3R,4R,5S,6R)-2-(4-Chloro-3-((5-(furan-2-yl)thiazol-2-yl)methyl)phenyl)-6-(ethoxymethyl)tetrahydro-2H-pyran-3,4,5-triol
(141) (2S,3R,4R,5S,6R)-2-(4-Chloro-3-((5-(furan-2-yl)thiazol-2-yl)methyl)phenyl)-6-((2-hydroxyethoxy)methyl)tetrahydro-2H-pyran-3,4,5-triol
(142) (2S,3R,4S,5S,6S)-2-(4-Chloro-3-((5-(furan-2-yl)thiazol-2-yl)methyl)phenyl)-6-(methylthiomethyl)-tetrahydro-2H-pyran-3,4,5-triol
(143) (2S,3R,4S,5S,6S)-2-(4-Chloro-3-((5-(furan-2-yl)thiazol-2-yl)methyl)phenyl)-6-(ethylthiomethyl)tetrahydro-2H-pyran-3,4,5-triol
(144) (2S,3R,4S,5S,6S)-2-(4-Chloro-3-((5-(furan-2-yl)thiazol-2-yl)methyl)phenyl)-6-(methylsulfonylmethyl)-tetrahydro-2H-pyran-3,4,5-triol
(145) (2S,3R,4S,5S,6S)-2-(4-Chloro-3-((5-(furan-2-yl)thiazol-2-yl)methyl)phenyl)-6-(fluoromethyl)-tetrahydro-2H-pyran-3,4,5-triol
(146) (2S,3R,4S,5S,6R)-2-(4-Chloro-3-((5-(furan-2-yl)thiazol-2-yl)methyl)phenyl)-6-methyl-tetrahydro-2H-pyran-3,4,5-triol
(147) (2R,3S,4R,5R,6S)-2-((1H-1,2,4-Triazol-1-yl)methyl)-6-(4-chloro-3-((5-(furan-2-yl)thiazol-2-yl)methyl)phenyl)-tetrahydro-2H-pyran-3,4,5-triol
(148) (2R,3S,4R,5R,6S)-2-((2H-Tetrazol-2-yl)methyl)-6-(4-chloro-3-((5-(furan-2-yl)thiazol-2-yl)methyl)phenyl)-tetrahydro-2H-pyran-3,4,5-triol (149) (2R,3S,4R,5R,6S)-2-((1H-Tetrazol-1-yl)methyl)-6-(4-chloro-3-((5-(furan-2-yl)thiazol-2-yl)methyl)phenyl)tetrahydro-2H-pyran-3,4,5-triol (150) (2S,3R,4R,5S,6S)-2-(4-Chloro-3-((5-(furan-2-yl)thiazol-2-yl)methyl)phenyl)-6-(difluoromethyl)-tetrahydro-2H-pyran-3,4,5-triol (151) (2S,3R,4R,5S,6R)-2-(4-Chloro-3-((5-(furan-2-yl)thiazol-2-yl)methyl)phenyl)-6-(1-hydroxyethyl)-tetrahydro-2H-pyran-3,4,5-triol (152) (2S,3R,4R,5S,6R)-2-(4-Chloro-3-((5-(furan-2-yl)thiazol-2-yl)methyl)phenyl)-6-(1-hydroxyallyl)-tetrahydro-2H-pyran-3,4,5-triol (153) (2S,3R,4R,5S,6R)-2-(4-Chloro-3-((5-(furan-2-yl)thiazol-2-yl)methyl)phenyl)-6-(1-hydroxybut-3-enyl)-tetrahydro-2H-pyran-3,4,5-triol (154) (2S,3R,4R,5S,6R)-2-(4-chloro-3-((5-(thiophen-3-yl)thiazol-2-yl)methyl)phenyl)-6-(1-hydroxyethyl)tetrahydro-2H-pyran-3,4,5-triol (156) (2S,3R,4R,5S,6S)-2-(4-Chloro-3-((5-(furan-2-yl)thiazol-2-yl)methyl)phenyl)-6-(2-hydroxypropan-2-yl)-tetrahydro-2H-pyran-3,4,5-triol (157) (2S,3R,4R,5S,6S)-2-(4-Chloro-3-((5-(furan-2-yl)thiazol-2-yl)methyl)phenyl)-6-(1-hydroxycyclopropyl)-tetrahydro-2H-pyran-3,4,5-triol (159) Butyl ((2R,3S,4R,5R,6S)-6-(4-chloro-3-((5-(thiophen-3-yl)thiazol-2-yl)methyl)phenyl)-3,4,5-trihydroxy-tetrahydro-2H-pyran-2-yl)methyl carbonate (160) ((2R,3S,4R,5R,6S)-6-(4-Chloro-3-((5-(furan-2-yl)thiazol-2-yl)methyl)phenyl)-3,4,5-trihydroxytetrahydro-2H-pyran-2-yl)methyl ethyl carbonate (161) Butyl ((2R,3S,4R,5R,6S)-6-(4-chloro-3-((5-(furan-2-yl)thiazol-2-yl)methyl)phenyl)-3,4,5-trihydroxytetrahydro-2H-pyran-2-yl)methyl carbonate (162) tert-Butyl ((2R,3S,4R,5R,6S)-6-(4-chloro-3-((5-(furan-2-yl)thiazol-2-yl)methyl)phenyl)-3,4,5-trihydroxytetrahydro-2H-pyran-2-yl)methyl carbonate (163) Allyl((2R,3S,4R,5R,6S)-6-(4-chloro-3-((5-(furan-2-yl)thiazol-2-yl)methyl)phenyl)-3,4,5-trihydroxytetrahydro-2H-pyran-2-yl)methyl carbonate (164) Benzyl ((2R,3S,4R,5R,6S)-6-(4-chloro-3-((5-(furan-2-yl)thiazol-2-yl)methyl)phenyl)-3,4,5-trihydroxytetrahydro-2H-pyran-2-yl)methyl carbonate (165) ((2R,3S,4R,5R,6S)-6-(4-Chloro-3-((5-(thiophen-3-yl)thiazol-2-yl)methyl)phenyl)-3,4,5-trihydroxytetrahydro-2H-pyran-2-yl)methyl ethyl carbonate (166) Allyl (((2R,3S,4R,5R,6S)-6-(4-chloro-3-((5-(thiophen-3-yl)thiazol-2-yl)methyl)phenyl)-3,4,5-trihydroxytetrahydro-2H-pyran-2-yl)methyl) carbonate (167) Benzyl (((2R,3S,4R,5R,6S)-6-(4-chloro-3-((5-(thiophen-3-yl)thiazol-2-yl)methyl)phenyl)-3,4,5-trihydroxytetrahydro-2H-pyran-2-yl)methyl) carbonate (168) ((2R,3S,4R,5R,6S)-6-(4-Chloro-3-((2-(thiophen-3-yl)thiazol-5-yl)methyl)phenyl)-3,4,5-trihydroxy-tetrahydro-2H-pyran-2-yl)methyl ethyl carbonate (169) ((2R,3S,4R,5R,6S)-6-(4-Chloro-3-((5-(furan-2-yl)thiazol-2-yl)methyl)phenyl)-3,4,5-trihydroxytetrahydro-2H-pyran-2-yl)methyl isobutyrate (170) ((2R,3S,4R,5R,6S)-6-(4-Chloro-3-((5-(furan-2-yl)thiazol-2-yl)methyl)phenyl)-3,4,5-trihydroxytetrahydro-2H-pyran-2-yl)methyl pivalate (171) ((2R,3S,4R,5R,6S)-6-(4-Chloro-3-((5-(thiophen-3-yl)thiazol-2-yl)methyl)phenyl)-3,4,5-trihydroxy-tetrahydro-2H-pyran-2-yl)methyl pivalate (172) ((2R,3S,4R,5R,6S)-6-(4-Chloro-3-((5-(thiophen-3-yl)thiazol-2-yl)methyl)phenyl)-3,4,5-trihydroxytetrahydro-2H-pyran-2-yl)methyl isobutyrate (173) ((2R,3S,4R,5R,6S)-6-(4-Chloro-3-((5-(thiophen-3-yl)thiazol-2-yl)methyl)phenyl)-3,4,5-trihydroxy-tetrahydro-2H-pyran-2-yl)methyl 3,4-dimethoxybenzoate (174) ((2R,3S,4R,5R,6S)-6-(4-Chloro-3-((5-(furan-2-yl)thiazol-2-yl)methyl)phenyl)-3,4,5-trihydroxytetrahydro-2H-pyran-2-yl)methyl 3,4-dimethoxybenzoate (175) ((2R,3S,4R,5R,6S)-6-(4-Chloro-3-((5-(furan-2-yl)thiazol-2-yl)methyl)phenyl)-3,4,5-trihydroxytetrahydro-2H-pyran-2-yl)methyl 3,4,5-trimethoxybenzoate (176) (2S,3S)-((2R,3S,4R,5R,6S)-6-(4-Chloro-3-((5-(furan-2-yl)thiazol-2-yl)methyl)phenyl)-3,4,5-trihydroxy-tetrahydro-2H-pyran-2-yl)methyl 2-amino-3-methylpentanoate (177) (S)-((2R,3S,4R,5R,6S)-6-(4-Chloro-3-((5-(furan-2-yl)thiazol-2-yl)methyl)phenyl)-3,4,5-trihydroxytetrahydro-2H-pyran-2-yl)methyl 2-aminopropanoate (178) (S)-((2R,3S,4R,5R,6S)-6-(4-Chloro-3-((5-(furan-2-yl)thiazol-2-yl)methyl)phenyl)-3,4,5-trihydroxytetrahydro-2H-pyran-2-yl)methyl 2-amino-3-methylbutanoate (179) (S)-((2R,3S,4R,5R,6S)-6-(4-Chloro-3-((5-(furan-2-yl)thiazol-2-yl)methyl)phenyl)-3,4,5-trihydroxytetrahydro-2H-pyran-2-yl)methyl 2-amino-4-methylpentanoate (180) (S)-((2R,3S,4R,5R,6S)-6-(4-Chloro-3-((5-(furan-2-yl)thiazol-2-yl)methyl)phenyl)-3,4,5-trihydroxytetrahydro-2H-pyran-2-yl)methyl 2-amino-3-phenylpropanoate (181) (2S,3S)-((2R,3S,4R,5R,6S)-6-(4-Chloro-3-((5-(thiophen-3-yl)thiazol-2-yl)methyl)phenyl)-3,4,5-trihydroxytetrahydro-2H-pyran-2-yl)methyl 2-amino-3-methylpentanoate (182) (2R,3R,4R,5S,6S)-2-((2-Aminoacetoxy)methyl)-6-(4-chloro-3-((5-(furan-2-yl)thiazol-2-yl)methyl)phenyl)-tetrahydro-2H-pyran-3,4,5-triyltris(2-aminoacetate)

(183) (2S,3R,4R,5S,6R)-2-(4-Chloro-3-((2-phenylthiazol-5-yl)methyl)phenyl)-6-(hydroxymethyl)-tetrahydro-2H-pyran-3,4,5-triol (184) (2S,3R,4R,5S,6R)-2-(4-Chloro-3-((2-(furan-2-yl)thiazol-5-yl)methyl)phenyl)-6-(hydroxymethyl)tetrahydro-2H-pyran-3,4,5-triol (185) (2S,3R,4R,5S,6R)-2-(3-((2-(Benzo furan-2-yl)thiazol-5-yl)methyl)-4-chlorophenyl)-6-(hydroxymethyl)tetrahydro-2H-pyran-3,4,5-triol (186) (2S,3R,4R,5S,6R)-2-(4-Chloro-3-((2-(furan-3-yl)thiazol-5-yl)methyl)phenyl)-6-(hydroxymethyl)tetrahydro-2H-pyran-3,4,5-triol (187) (2S,3R,4R,5S,6R)-2-(4-Chloro-3-((2-(thiophen-2-yl)thiazol-5-yl)methyl)phenyl)-6-(hydroxymethyl)tetrahydro-2H-pyran-3,4,5-triol (188) (2S,3R,4R,5S,6R)-2-(4-Chloro-3-((2-(5-methylthiophen-2-yl)thiazol-5-yl)methyl)phenyl)-6-(hydroxymethyl)tetrahydro-2H-pyran-3,4,5-triol (189) (2S,3R,4R,5S,6R)-2-(4-Chloro-3-((2-(5-chlorothiophen-2-yl)thiazol-5-yl)methyl)phenyl)-6-(hydroxymethyl)tetrahydro-2H-pyran-3,4,5-triol (190) (2S,3R,4R,5S,6R)-2-(4-Chloro-3-((2-(thiophen-3-yl)thiazol-5-yl)methyl)phenyl)-6-(hydroxymethyl)tetrahydro-2H-pyran-3,4,5-triol (191) (2S,3R,4R,5S,6R)-2-(4-Chloro-3-((2-(oxazol-4-yl)thiazol-5-yl)methyl)phenyl)-6-(hydroxymethyl)tetrahydro-2H-pyran-3,4,5-triol (192) (2S,3R,4R,5S,6R)-2-(4-Chloro-3-((2-(isoxazol-5-yl)thiazol-5-yl)methyl)phenyl)-6-(hydroxymethyl)tetrahydro-2H-pyran-3,4,5-triol (193) (2S,3R,4R,5S,6R)-2-(3-(2,4'-Bithiazol-5-ylmethyl)-4-chlorophenyl)-6-(hydroxymethyl)tetrahydro-2H-pyran-3,4,5-triol (194) (2S,3R,4R,5S,6R)-2-(4-Chloro-3-((2-(4-fluorophenyl)thiazol-5-yl)methyl)phenyl)-6-(hydroxymethyl)tetrahydro-2H-pyran-3,4,5-triol
(195) (2S,3R,4R,5S,6R)-2-(4-Chloro-3-((2-(pyrazin-2-yl)thiazol-5-yl)methyl)phenyl)-6-(hydroxymethyl)tetrahydro-2H-pyran-3,4,5-triol
(196) (2S,3R,4R,5S,6R)-2-(4-Chloro-3-((2-(cyclopent-3-enyl)thiazol-5-yl)methyl)phenyl)-6-(hydroxymethyl)tetrahydro-2H-pyran-3,4,5-triol
(197) (2S,3R,4R,5S,6R)-2-(4-Chloro-3-((2-(methylthio)thiazol-5-yl)methyl)phenyl)-6-(hydroxymethyl)tetrahydro-2H-pyran-3,4,5-triol
(198) (2S,3R,4R,5S,6R)-2-(4-Chloro-3-((2-(propylthio)thiazol-5-yl)methyl)phenyl)-6-(hydroxymethyl)tetrahydro-2H-pyran-3,4,5-triol
(199) (2S,3R,4R,5S,6R)-2-(3-((2-(Furan-2-yl)thiazol-5-yl)methyl)-4-methylphenyl)-6-(hydroxymethyl)tetrahydro-2H-pyran-3,4,5-triol
(200) (2R,3S,4R,5R,6S)-2-(Hydroxymethyl)-6-(4-methyl-3-((2-(thiophen-3-yl)thiazol-5-yl)methyl)phenyl)tetrahydro-2H-pyran-3,4,5-triol
(201) (2S,3R,4R,5S,6R)-2-(4-Chloro-2-fluoro-5-((2-(furan-2-yl)thiazol-5-yl)methyl)phenyl)-6-(hydroxymethyl)tetrahydro-2H-pyran-3,4,5-triol
(202) (2S,3R,4R,5S,6R)-2-(4-Chloro-2-fluoro-5-((2-(thiophen-2-yl)thiazol-5-yl)methyl)phenyl)-6-(hydroxymethyl)tetrahydro-2H-pyran-3,4,5-triol
(203) (2S,3R,4R,5S,6R)-2-(4-Chloro-2-fluoro-5-((2-(thiophen-3-yl)thiazol-5-yl)methyl)phenyl)-6-(hydroxymethyl)tetrahydro-2H-pyran-3,4,5-triol
(204) (2S,3R,4R,5S,6R)-2-(4-bromo-3-((5-(thiophen-3-yl)thiazol-2-yl)methyl)phenyl)-6-(hydroxymethyl)tetrahydro-2H-pyran-3,4,5-triol
(205) ((2R,3S,4R,5R,6S)-6-(4-chloro-3-((2-(thiophen-3-yl)thiazol-5-yl)methyl)phenyl)-3,4,5-trihydroxytetrahydro-2H-pyran-2-yl)methyl ethyl carbonate The present invention also provides a method for preparing the compound of formula XV, comprising (a) reacting the compound of formula II sequentially with an organometallic compound and the compound of formula I, followed by reduction, cyanization and hydrolysis to obtain the compound of formula XI; and (b) reacting the compound of formula XI with the compound of formula XII, followed by thionation-cyclization of the resulting product and deprotection of the four benzyl groups:

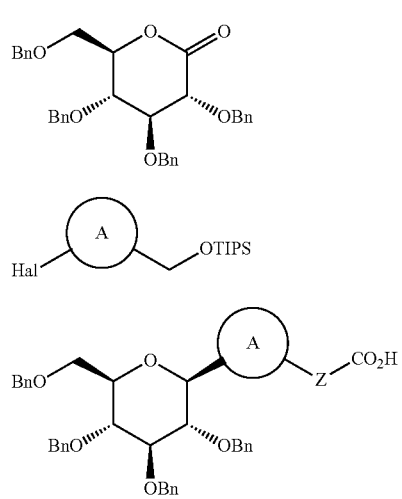

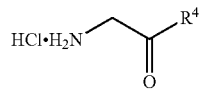

XII

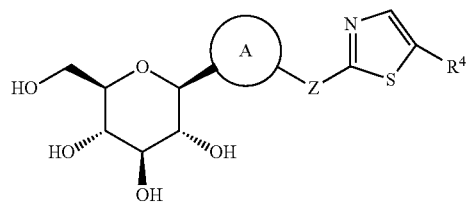

XV wherein, Hal is halogen, Bn is benzyl, TIPS is triisopropylsilyl, Z is methylene, and ring A and $R^4$ are as defined above.

The present invention further provides a method for preparing the compound of formula XXIX, comprising (a) reacting the compound of formula II sequentially with an organometallic compound and the compound of formula 1, followed by reduction, cyanization and hydrolysis to obtain the compound of formula XI; (b) (b-1) reacting the compound of formula XI sequentially with (trimethylsilyl)diazomethane, HBr, and hexamethylenetetramine, or (b-2) reacting the compound of formula XI with nitromethane followed by reduction, to obtain the compound of formula XXV; and (c) reacting the compound of formula XXV with $HO_2C-R^7$, followed by thionation-cyclization of the resulting product and deprotection of the four benzyl groups:

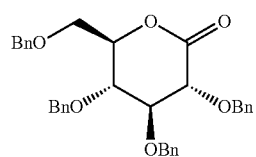

1

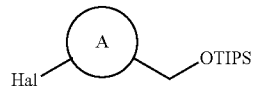

II

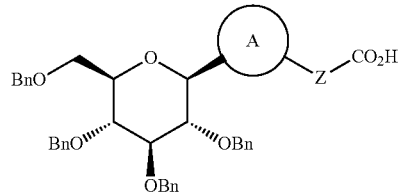

XI

XXV

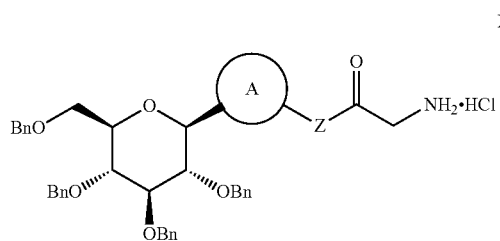

XXIX wherein, Hal is halogen, Bn is benzyl, TIPS is triisopropylsilyl, Z is methylene, and ring A and R⁷ are as defined above.

The compounds of the present invention and the preparation thereof will be better understood in connection with the following synthetic schemes, which are merely illustrative of the methods by which the compounds of the invention may be prepared and are not intended to limit the scope of the invention as defined in the appended claims.

General Synthetic Sequence

Scheme 1

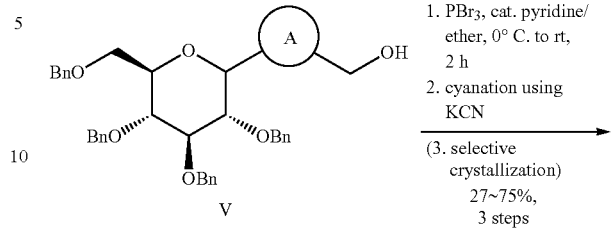

The carboxylic acid VII used as a key intermediate in preparing the thiazole-containing C-aryl glucoside can be prepared by a method as shown in Scheme 1. Metal-halogen exchange of halogenated compound II (TIPSCl: triisopropylsilyl chloride), followed by addition of the nascent organo metallic compound III to perbenzylated gluconolactone 1, produce a mixture of the corresponding lactols IV, which are reduced using triethylsilane and boron trifluoride diethyl etherate, followed by desilylation, afford alcohol V in 49-98% yield for three steps. The alcohol V is converted to bromide using phosphorus tribromide in the presence of pyridine, which is cyanated with potassium cyanide. If necessary, a mixture of α,β-isomers is resolved after selective crystallization from ethanol to produce the required β-isomer VI in high separation yield. Hydrolysis of cyanide VI with sodium hydroxide in aqueous ethanol generates the carboxylic acid VII in high yield.

Scheme 2

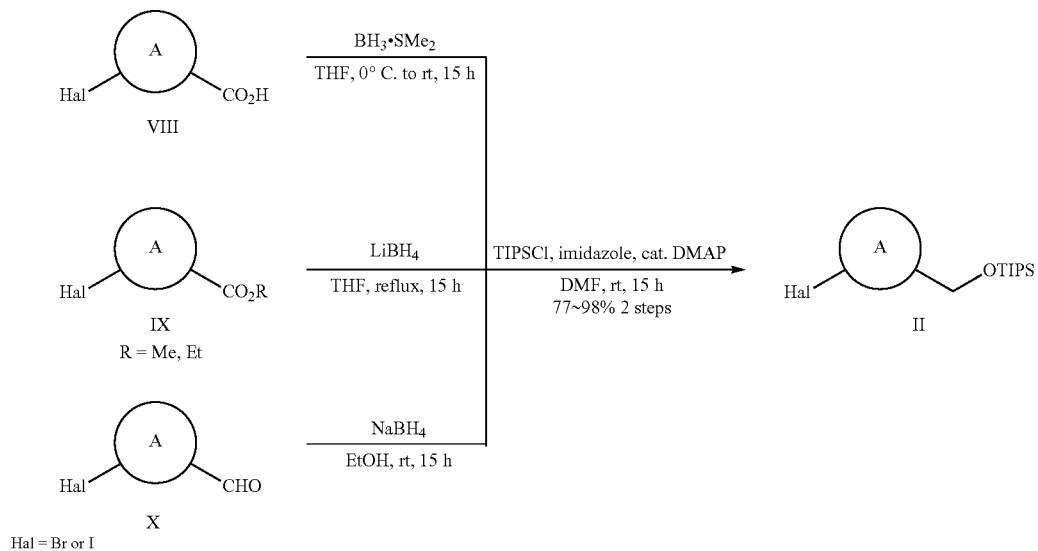

The silyl-protected alcohol II can be prepared smoothly by reduction of the corresponding acid, ester, and aldehyde with borane dimethylsulfide complex, lithium borohydride, and sodium borohydride respectively, and subsequent silylation of the corresponding alcohol with triisopropyl chloride in the presence of imidazole and DMAP, as shown in Scheme 2.

Scheme 3

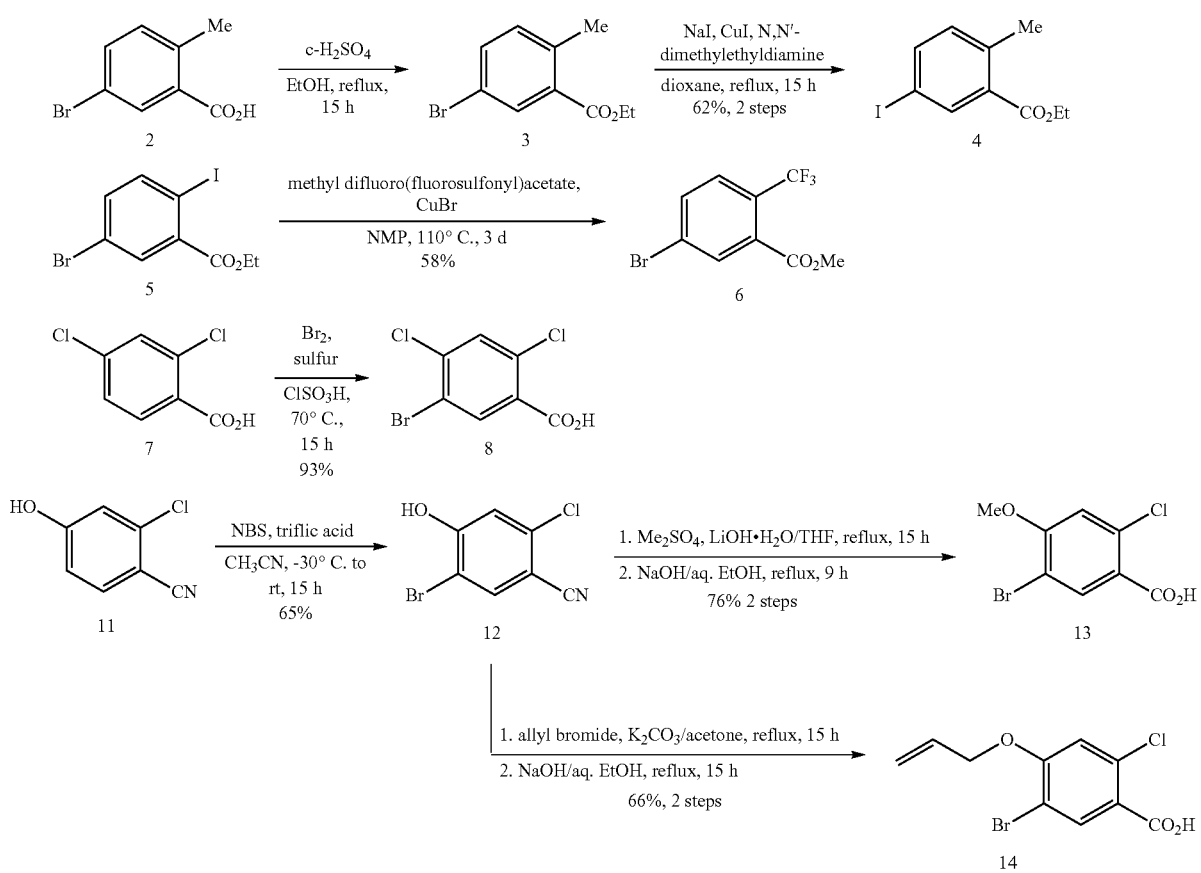

Preparation of the starting material in case of benzenes at ring A is described in Scheme 3. Thus, the carboxylic acid 2 is converted to the ester 3 using sulfuric acid in refluxed ethanol, which is treated with sodium iodide in the presence of copper(I) iodide and N,N'-dimethylethyldiamine to generate iodide 4 in 62% yield for the two steps. Treatment of iodobenzoate 5 with methyl difluoro(fluorosulfonyl)acetate and copper(I) bromide produces the corresponding trifluoromethylbenzoate 6 in 58% yield [Signal pharmaceuticals, WO2009089042]. 2,4-Dichorobenzoic acid 7 is brominated at the 5-position with bromine in the presence of sulfur and chlorobenzoic acid in 93% yield [Ródriguez-Dóminguez, J. C. et al. *J. Het. Chem.* 2007, 44, 273-275]. A similar bromination approach that is described for synthesis of bromide 8 is involved to give rise to 5-bromo-2-chloro-4-fluorobenzoic acid. The bromination at the 5-position of 2-chloro-4-hydroxybenzonitrile 11 using NBS and triflic acid yields bromide 12 in 65% yield. 5-Bromo-2-chloro-4-hydroxybenzonitrile 12 is converted to methyl ether using dimethyl sulfate in the presence of lithium hydroxide monohydrate, which is hydrolysed with sodium hydroxide in aqueous ethanol to generate 5-bromo-2-chloro-4-methoxybenzoic acid 13 in 76% yield for the two steps. Alternatively, allylation of hydroxybenzonitrile 12 with allyl bromide and potassium carbonate, and subsequent hydrolysis of the cyanide with sodium hydroxide generate allyloxybenzoic acid 14 in 66% yield for two steps. With hydroxybenzonirile 12 in hands, 5-bromo-2-chloro-4-ethoxybenzoic acid is synthesized in an analogous manner as described to generate compound 14.

Scheme 4

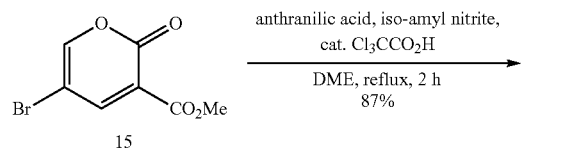

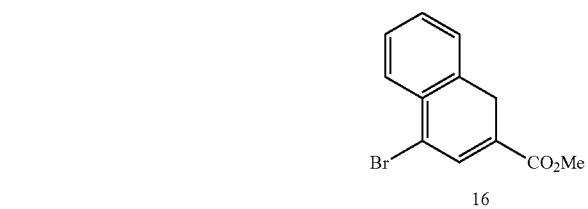

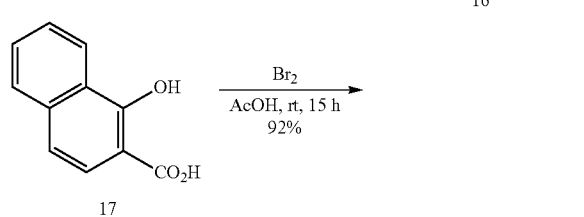

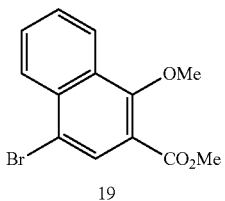

19

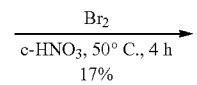

20

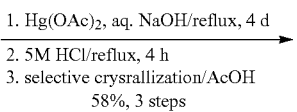

21

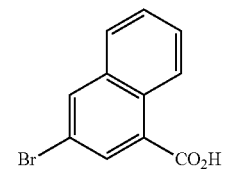

22

Preparation of the starting material in case of naphthalenes at ring A is described in Scheme 4. One isomer of naphthalene may be prepared by adopting the procedure shown in the literature [Ashworth, I. W. et al. *Org. Process Res. Dev.* 2003, 7, 74-81; Huan, Y. et al. *J. Med. Chem.* 2001, 44, 1815-1826]. Thus, 4-bromo-2-naphthoate 16 is obtained by the Diels-Alder addition of 3-bromocoumalate 15 to in situ-generated benzyne in 87% yield and 4-bromo-1-methoxy-2-naphthoate 19 is obtained by the bromination at the 4-position of 1-hydroxy-2-naphthoic acid 17 using bromine in glacial acetic acid and then methylation of both phenol and carboxylic acid with dimethyl sulfate under basic conditions in 72% yield for the two steps. The other isomer of naphthalene is prepared by adopting AstraZeneca's procedure [Moseley, J. D. et al, *Org. Process Res. Dev.* 2003, 7, 58-66]. Thus, 1,8-naphthalic anhydride 20 is brominated at the 3-position with bromine in concentrated nitric acid in low yield, and mercury(II) acetate-mediated decarboxylation proceeds by digestion. Acidic hydrolysis of a mixture of organo-Hg intermediates, and subsequent selective crystallization from acetic acid give 3-bromo-1-naphthoic acid 22 in 58% yield for the three steps.

Scheme 5

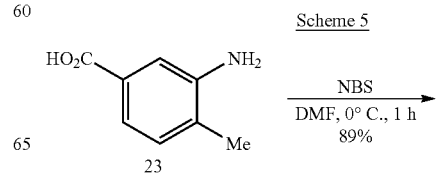

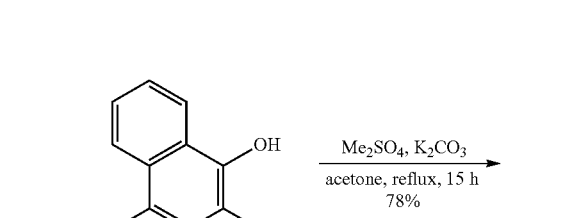

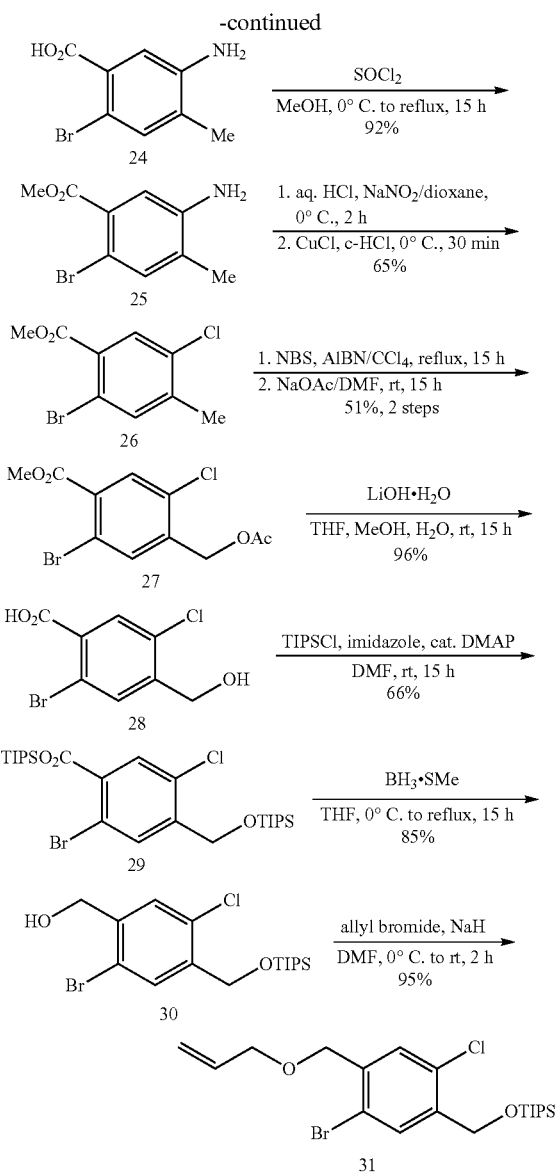
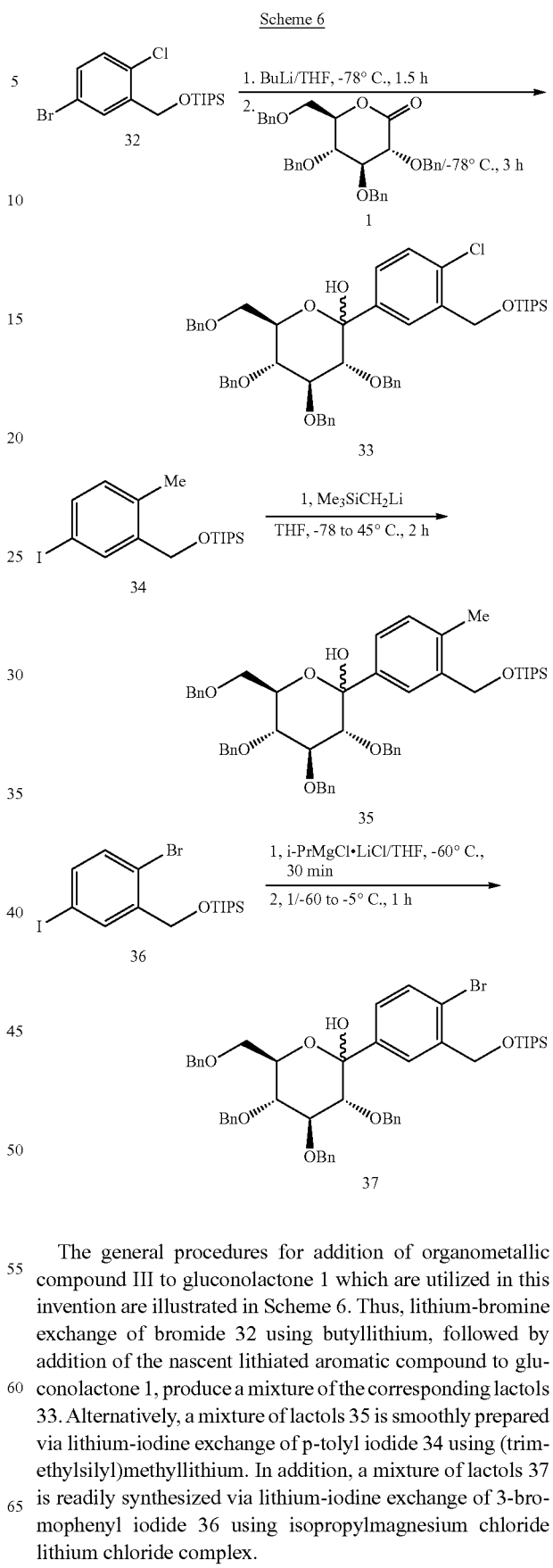

Preparation of the starting material in case of (4-(allyoxymethyl)-5-bromo-2-chlorobenzyloxy)triisopropylsilane 31 is described in Scheme 5. In this event, 2-bromo-5-chlorobenzoate 26 may be prepared by adopting the reported procedure [Theracos, US2008242596]. Thus, the bromination at the 6-position of 3-amino-4-methylbenzoic acid 23 using NBS yields bromide 24 in 89% yield. Subsequent esterification under acidic conditions yields ester 25 in 92% yield. A Sandmeyer reaction is used to introduce the chlorine substituent in 65% yield. Bromination of benzylic position using NBS and AIBN, followed by treatment with sodium acetate afford benzyl acetate 27 in 51% yield for the two steps. Hydrolysis of two esters with sodium hydroxide, and subsequent silylation of both alcohol and carboxylic acid with TIPSCl in the presence of imidazole and DMAP generate silyl ether 29 in 63% yield for the two steps. Silyl ester 29 is reduced to the corresponding alcohol 30 by using borane dimethylsulfide complex in 85% yield. Subsequently, allylation of alcohol with allyl bromide under basic conditions generates the requisite bromide 31 in high yield.

The general procedures for addition of organometallic compound III to gluconolactone 1 which are utilized in this invention are illustrated in Scheme 6. Thus, lithium-bromine exchange of bromide 32 using butyllithium, followed by addition of the nascent lithiated aromatic compound to gluconolactone 1, produce a mixture of the corresponding lactols 33. Alternatively, a mixture of lactols 35 is smoothly prepared via lithium-iodine exchange of p-tolyl iodide 34 using (trimethylsilyl)methyllithium. In addition, a mixture of lactols 37 is readily synthesized via lithium-iodine exchange of 3-bromophenyl iodide 36 using isopropylmagnesium chloride lithium chloride complex.

Scheme 7

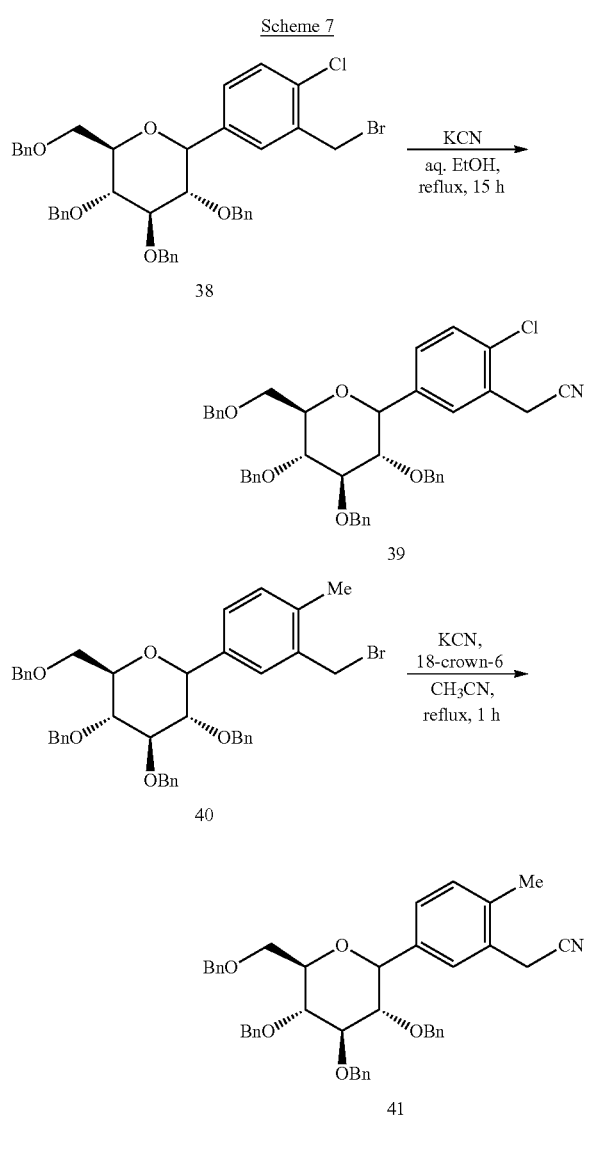

Scheme 8

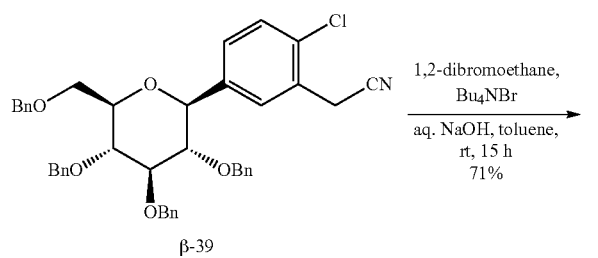

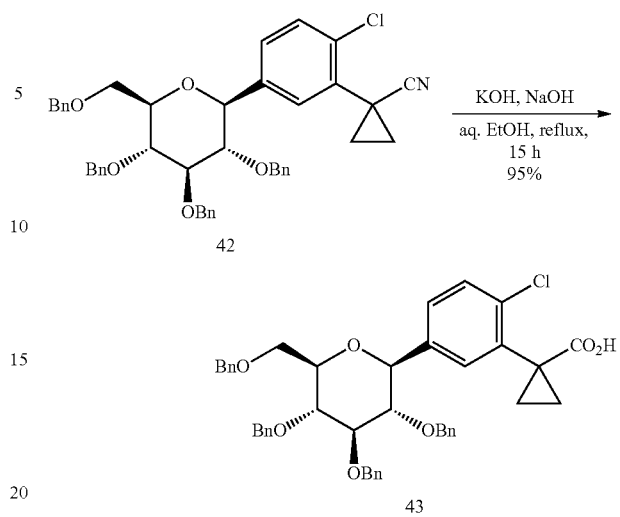

The general procedures for cyanation using potassium cyanide which are utilized in this invention are illustrated in Scheme 7. Thus, the bromide 38 is treated with potassium cyanide in refluxed aqueous ethanol to provide cyanide 39. Alternatively, the cyanide 41 is synthesized by treating a bromide compound 40 with potassium cyanide in the presence of 18-crown-6 in refluxed acetonitrile.

The phenylcyclopropanecarboxylic acid 43 used as a intermediate in preparing the thiazole containing C-aryl glucoside can be prepared by a method as shown in Scheme 8. The phenylacetonitrile β-39 is reacted with 1,2-dibromoethane in the presence of sodium hydroxide and a phase-transfer catalyst in toluene and water to provide a corresponding phenylcyclopropanecarbonitrile 42 in 71% yield. This carbonitrile 42 is treated with potassium hydroxide and sodium hydroxide in refluxed aqueous ethanol to provide cyclopropanecarboxylic acid 43 in 95% yield.

Scheme 9

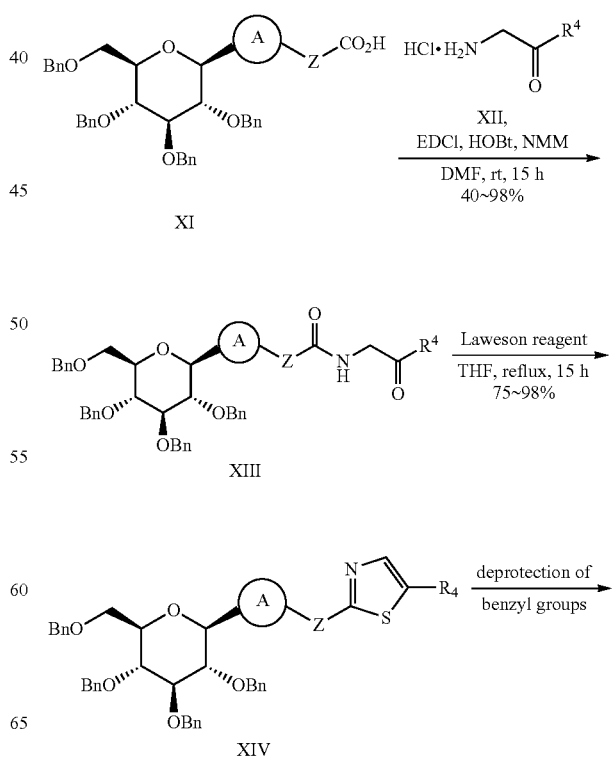

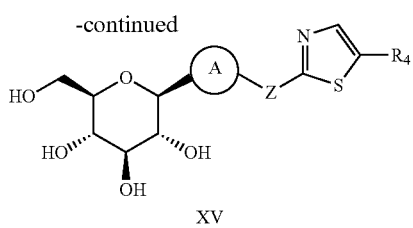

The synthesis of the thiazoles at ring B XV (one isomer of thiazole) may commence with the carboxylic acid XI. Compounds of general structure XV are prepared by (i) reacting a carboxylic acid XI with a amine compound XII in the presence of coupling reagent, e.g., EDCI, HOBt, and NMM, (ii) thionation-cyclization of the resulting amide XIII using Lawesson's reagent under heating conditions, and (iii) deprotection of the four benzyl groups under Lewis acidic or nucleophilic conditions to obtain the target C-aryl glucoside XV as shown in Scheme 9.

The requisite amine XII used in Scheme 9 may be prepared as shown in Scheme 10. The Weinreb amide 45 is available though the coupling of N-Boc-glycine 44 with N,O-dimethylhydroxylamine mediated by coupling reagents such as EDCI, HOBt, and NMM in 82% yield. The Weinreb amide 45 is subjected to a Grignard reagent or lithiated aromatic to afford the corresponding ketone XVI in 30-80% yield. Additionally, the carboxylic acid 44 is converted to the thioester XVII using a thiol in the presence of EDCI, HOBt, and diisopropylethylamine in moderate yield. Subsequent deprotection of XVI and XVII with hydrogen chloride solution yields the requisite XII. The amino ester XII was synthesized by esterification under acidic conditions in moderate yield.

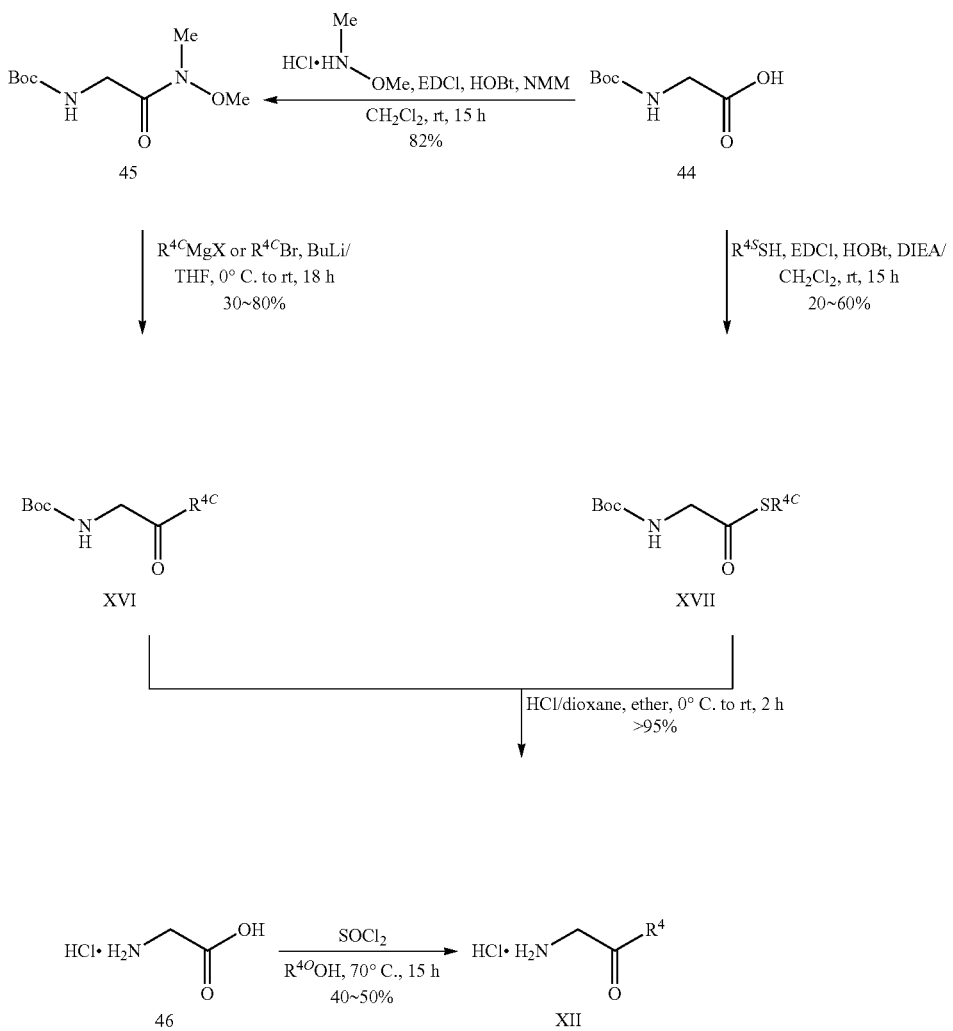

Scheme 11
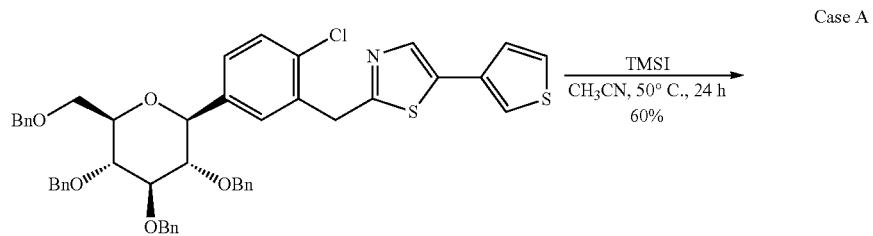
Case A
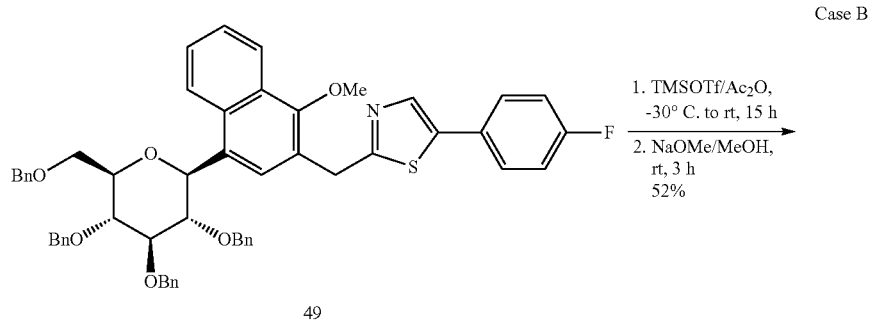
Case B
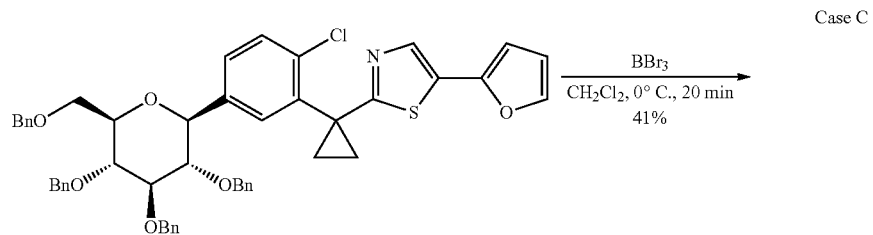
Case C

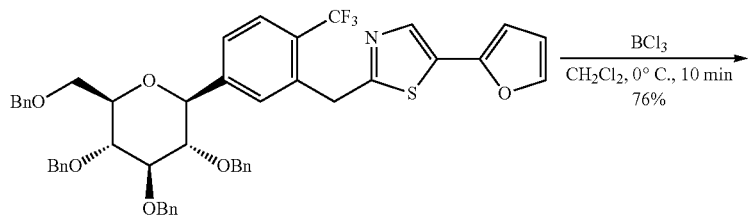

53

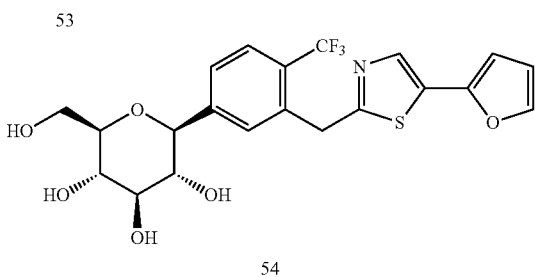

54

The general procedures for deprotection of the four benzyl groups which are utilized in this invention are illustrated in Scheme 11. Several of the Lewis acidic or nucleophilic conditions are used: i.e. (i) debenzylation using iodotrimethylsilane in acetonitrile or neat iodomethylsilane under heating conditions as shown in Case A; (ii) debenzylation and concurrent acetylation using TMSOTf in combination with acetic anhydride under cooling conditions, followed by deacetylation using sodium methoxide as shown in Case B; (iii) debenzylation using boron tribromide at 0° C. for 20 min as shown in Case C; (iv) debenzylation using boron trichloride at 0° C. for 10 min as shown in Case D.

Scheme 12

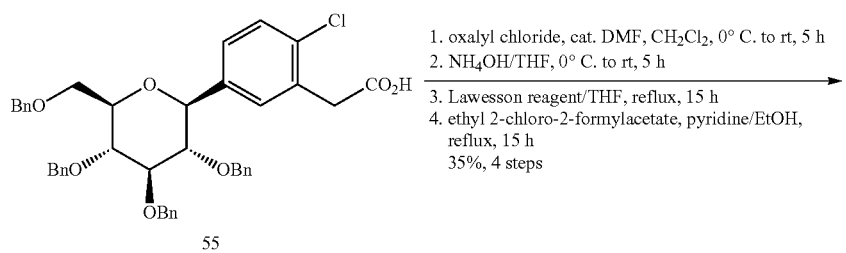

55

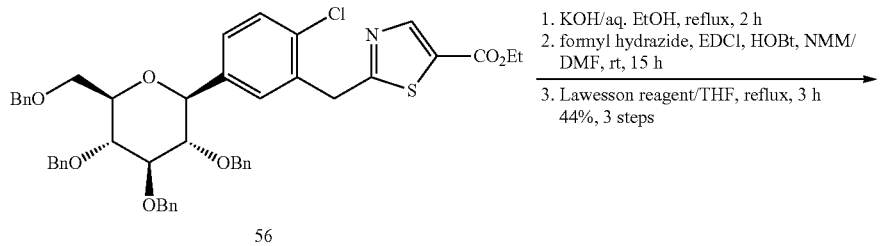

56

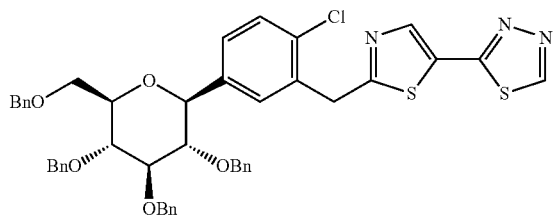

57

The ester or 1,3,4-thiadiazole substituted thiazoles at ring B may be prepared as shown in Scheme 12. Typical conversion of the carboxylic acid 55 to amide functionality via acyl chloride and the following thionation using Lawesson's reagent produce the corresponding thioamide, which is treated with ethyl 2-chloro-2-formylacetate and pyridine in refluxed ethanol to provide the corresponding thiazole-5-carboxylic acid 56 in 35% over four steps. The ester 56 is hydrolysed under basic conditions to generate the corresponding acid. Next, this acid is coupled with formyl hydrazide under conditions of EDCI, HOBt, and NMM. Following cyclization using Lawesson's reagent produced 5-(1,3,4-thiadiazol-2-yl)-thiazole 57 in 44% yield for the four steps.

Scheme 13

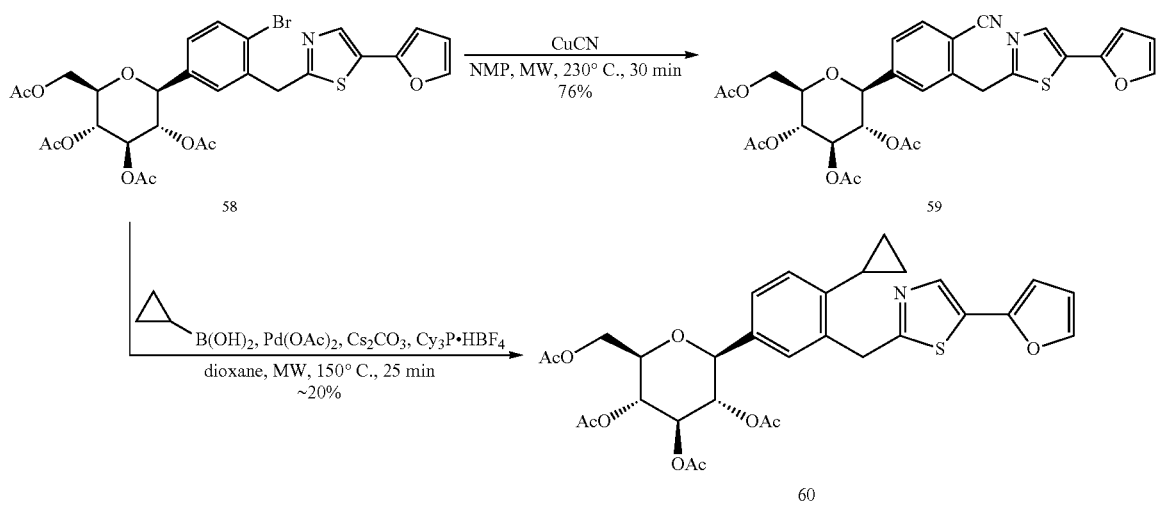

Further derivatization of benzene at ring A is described in Scheme 13. The bromide 58 is cyanated with copper(I) cyanide under microwave irradiation to provide cyanobenzene 59 in 76% yield. In addition, the bromide 58 is coupled with a cyclopropylboronic acid under Suzuki-Miyamura cross-coupling conditions to afford a cyclopropylbenzene 60 in low yield.

Scheme 14

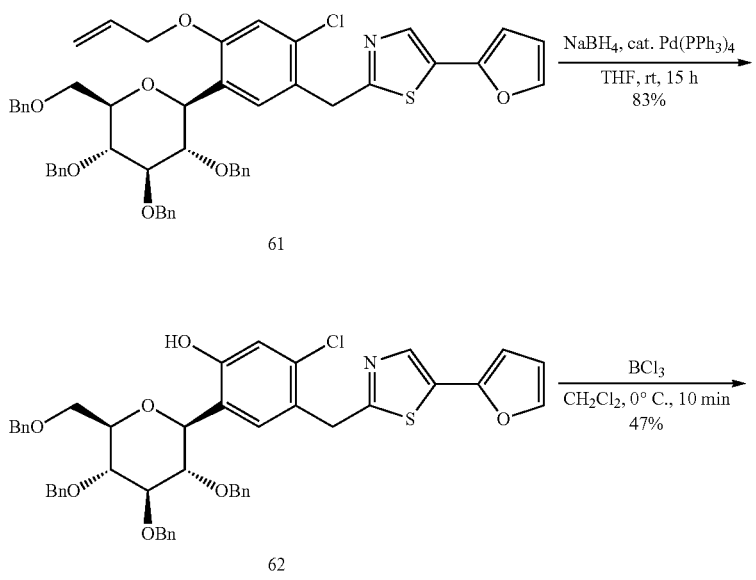

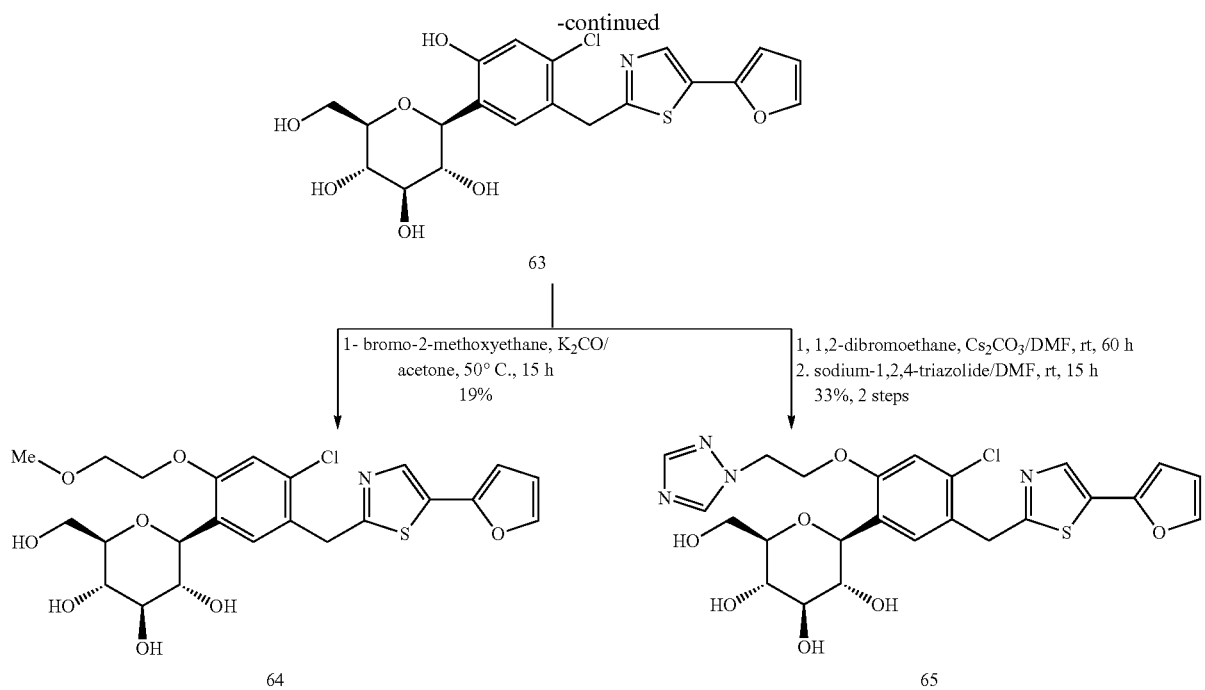

Another derivatization of benzene at ring A is described in Scheme 14. Deprotection of the allyl group with sodium borohydride in the presence of tetrakis(triphenylphosphine)palladium(0), followed by debenzylation using boron trichloride generate the corresponding phenol 63 in 39% yield for the two steps. The phenol 63 is alkylated with 1-bromo-2-methoxyethane under basic conditions to provide 2-methoxyethyl ether 64 in low yield. Additionally, alkylation of phenol 63 with 1,2-dibromoethane in the presence of cesium carbonate, followed by reaction with sodium-1,2,4-triazolide, then affords the compound 65 containing 1,2,4-triazole in 33% yield over two steps.

Scheme 15

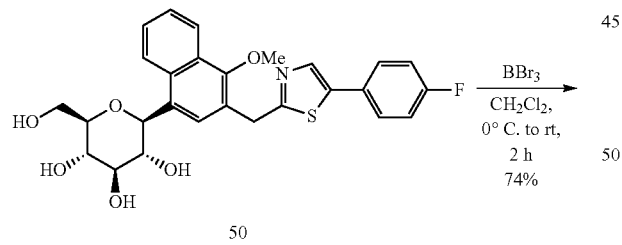

-continued

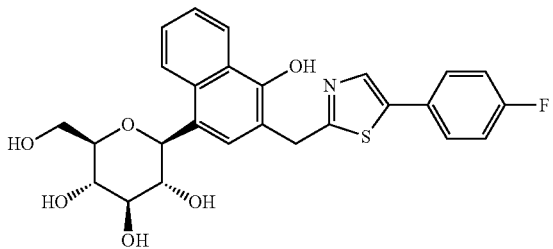

The hydroxynaphthalene at ring A is prepared as shown in Scheme 15. Thus, demethylation of methyl ether 50 with boron tribromide generates hydroxide 66 in 74% yield.

Scheme 16

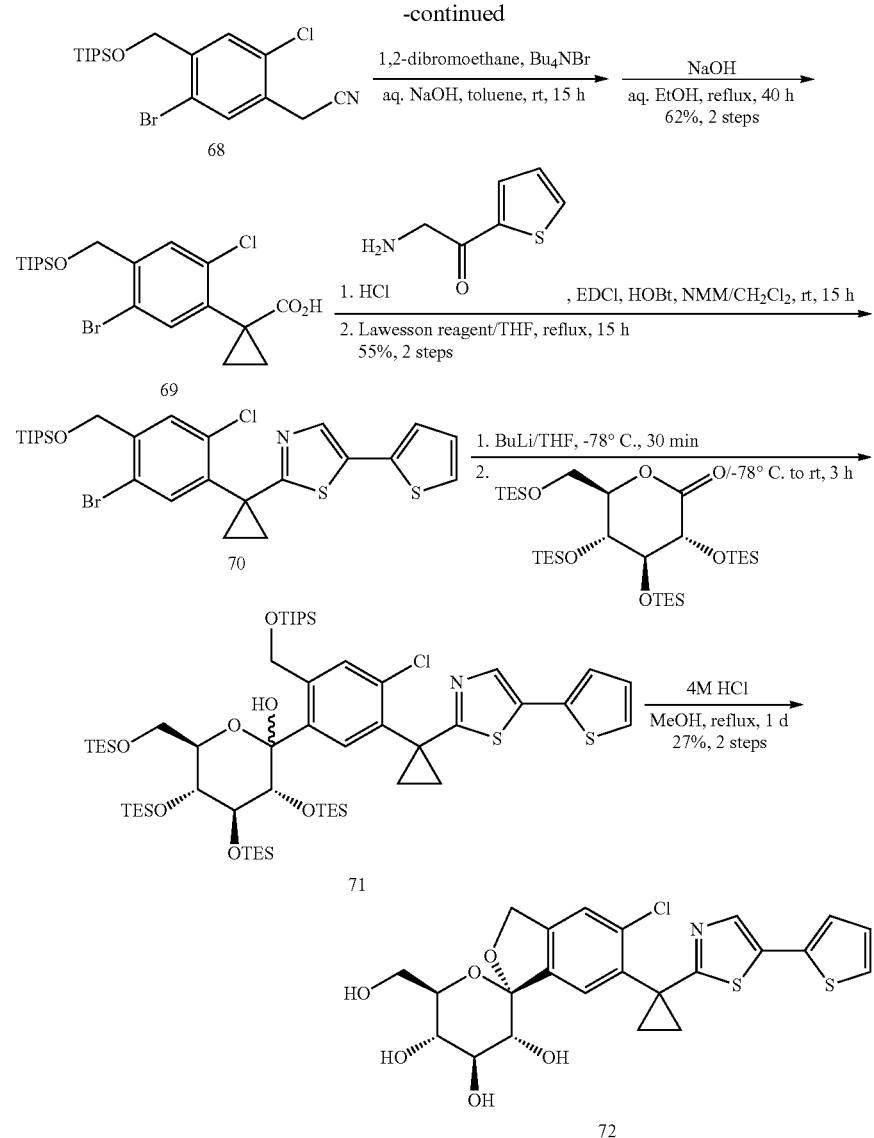

The O-spiro target compound may be synthesized as in Scheme 16. Bromication of the toyl compound 67, prepared by following a generic procedure from methyl 2-bromo-5-chloro-4-methylbenzoate, using NBS and AIBN, followed by treatment with sodium cyanide afford phenylacetonitrile 68 in 64% yield for the two steps. As in Scheme 8, the benzylic position dialkylation and the following hydrolysis using sodium hydroxide produce cyclopropanecarboxylic acid 69 in 62% yield for two steps. As in Scheme 9, usual coupling between acid 69 and 2-amino-1-(thiophen-2-yl)ethanone in the presence of EDCI, HOBt, and NMM and cyclization using Lawesson's reagent produce thiazole 70. As in Scheme 6, lithium-halogen exchange of bromide 70, followed by addition of the nascent lithiated aromatic to persilylated gluconolactone, produce a mixture of the corresponding lactols 71, which finally undergoes deprotection and cyclization in one-pot with hydrogen chloride to provide the desired O-spiro C-aryl glucoside 72 as a single anomer in moderate yield.

Scheme 17

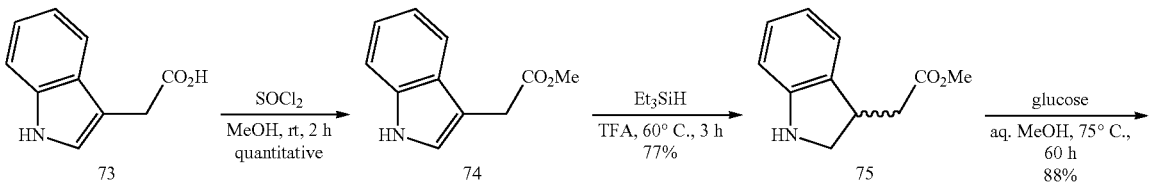

-continued
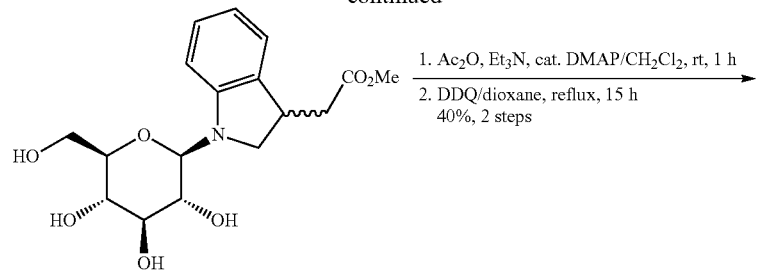
76
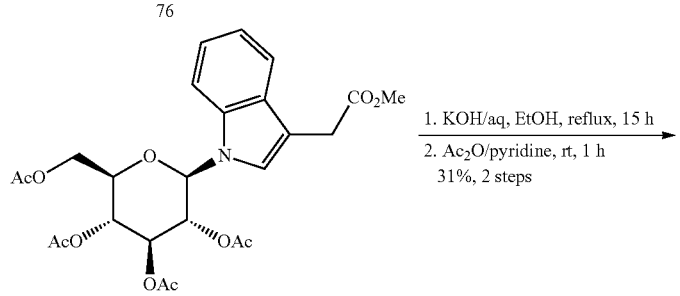
77
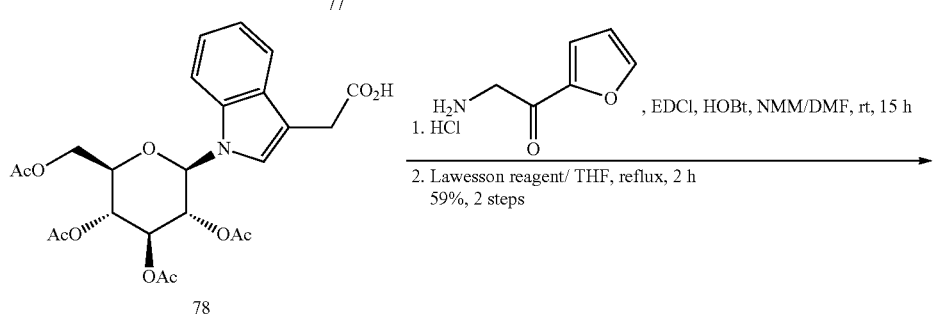
78
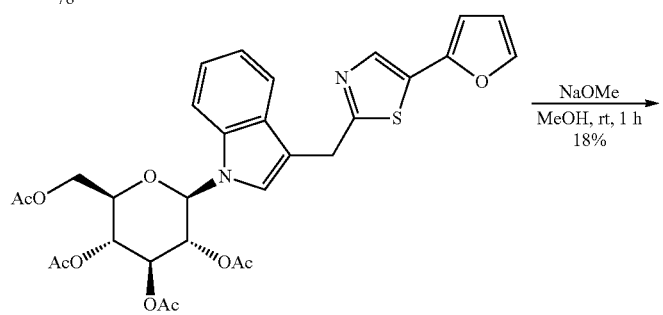
79
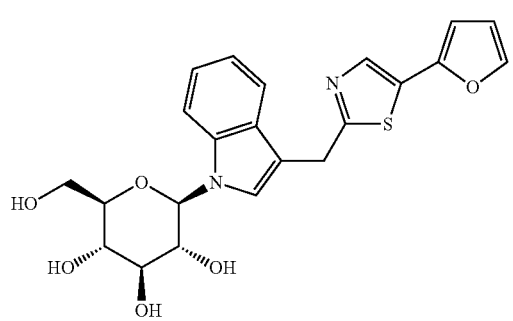
80
In order to accommodate need for SAR optimization of the thiazole derivatives, indoles at A ring may be synthesized and evaluated. One isomer of indole may be prepared by adopting the reported procedure [Kai, K. et al. *Phytochemistry*, 2007, 68, 2512-2522]. First, commercially available indole-3-acetic acid 73 is esterified under acidic conditions. Next, the indole ring of 74 is partially reduced to indoline 75 using triethylsilane and TFA in 77% yield. Condensation of 75 with D-glucose is accomplished in refluxed aqueous methanol in 88% yield. The product 76 is then acylated and oxidized to regenerate the indole ring in 40% over two steps (product 77). After hydrolysis, peracetylation of the tetrahydroxy groups using acetic anhydride and pyridine yields N-β-D-glucopyranosyl indole-3-acetic acid 78 in 40% yield for the two steps.

As in Scheme 9, usual coupling between acid 78 and 2-amino-1-(furan-2-yl)ethanone in the presence of EDCI, HOBt, and NMM and then cyclization using Lawesson's reagent produce thiazole 79 in 59% yield for the two steps. Finally, treatment of the tetraacetate 79 with sodium methoxide generates the target compound 80 in 18% yield as shown in Scheme 17.

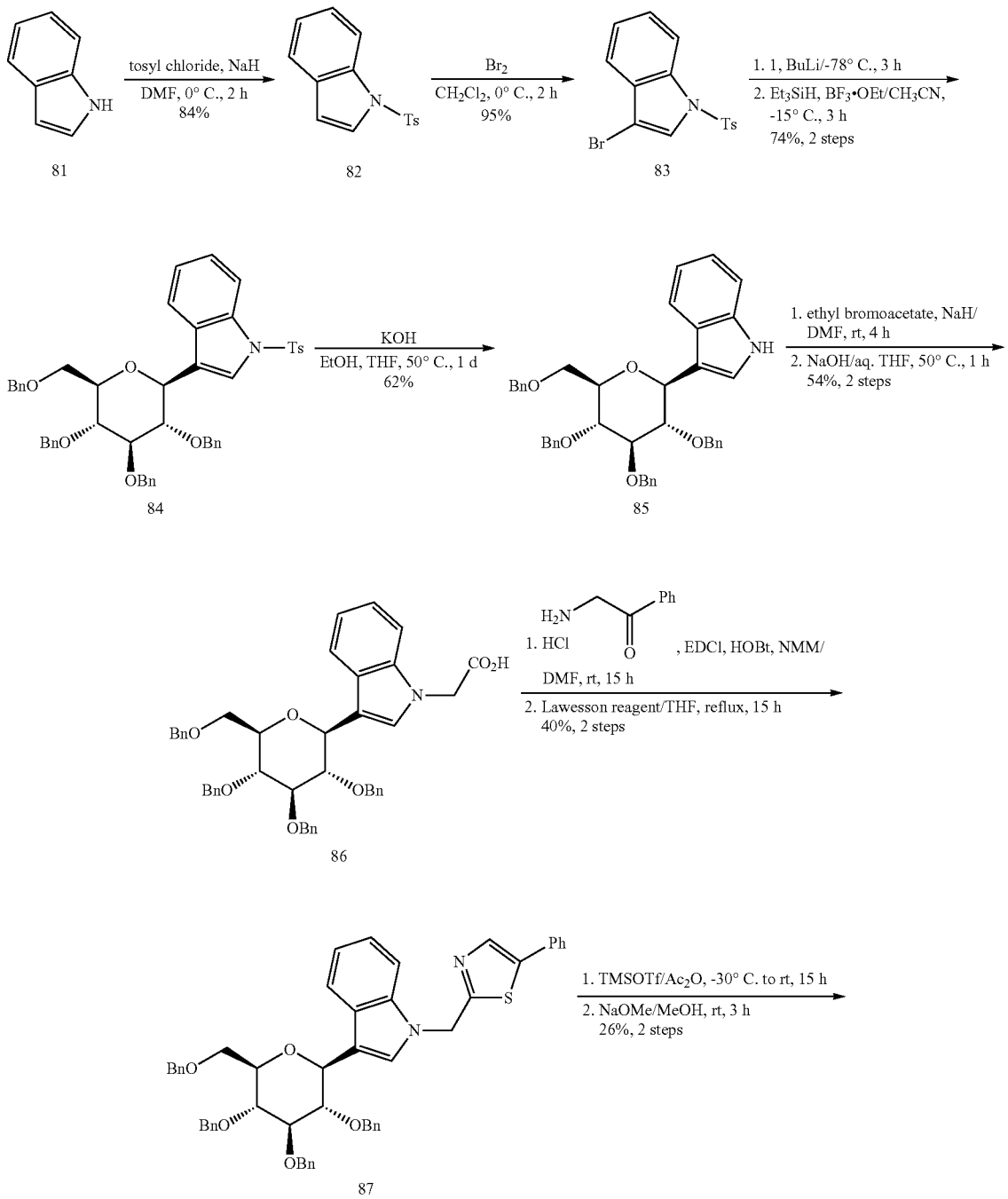

Scheme 18

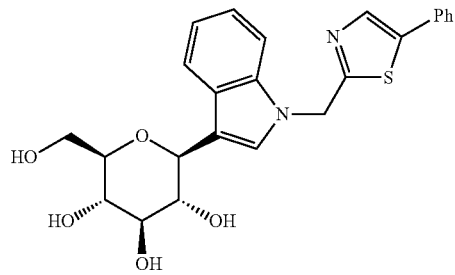

88

The other isomer of indole at ring A is synthesized by adopting Kissei's procedure [Kissei Pharmaceutical, EP1813611]. First, N-tosylation and bromination at the 3-position of indole 81 yield 3-bromo-N-tosylindole 83 in high yield. As in scheme 1, lithium-halogen exchange, followed by addition of the lithiated indole to gluconolactone 1, produce the corresponding lactol, which is reduced using triethylsilane and boron trifluoride diethyl etherate to generate indole-C-glucoside 84 in 74% yield for the two steps. After deprotection, condensation of 1H-indole 85 with ethyl bromoacetate under basic conditions, and subsequent hydrolysis generate acid 86 in moderate yield. As in Scheme 9, usual coupling between acid 86 and 2-amino-1-phenylethanone in the presence of EDCI, HOBt, and NMM and the cyclization using Lawesson's reagent produce thiazole 87 in 40% yield for the two steps. Finally, peracetylation using TMSOTf and acetic anhydride, followed by hydrolysis using sodium methoxide yield the target compound 88 in 26% yield for the two steps.

Scheme 19
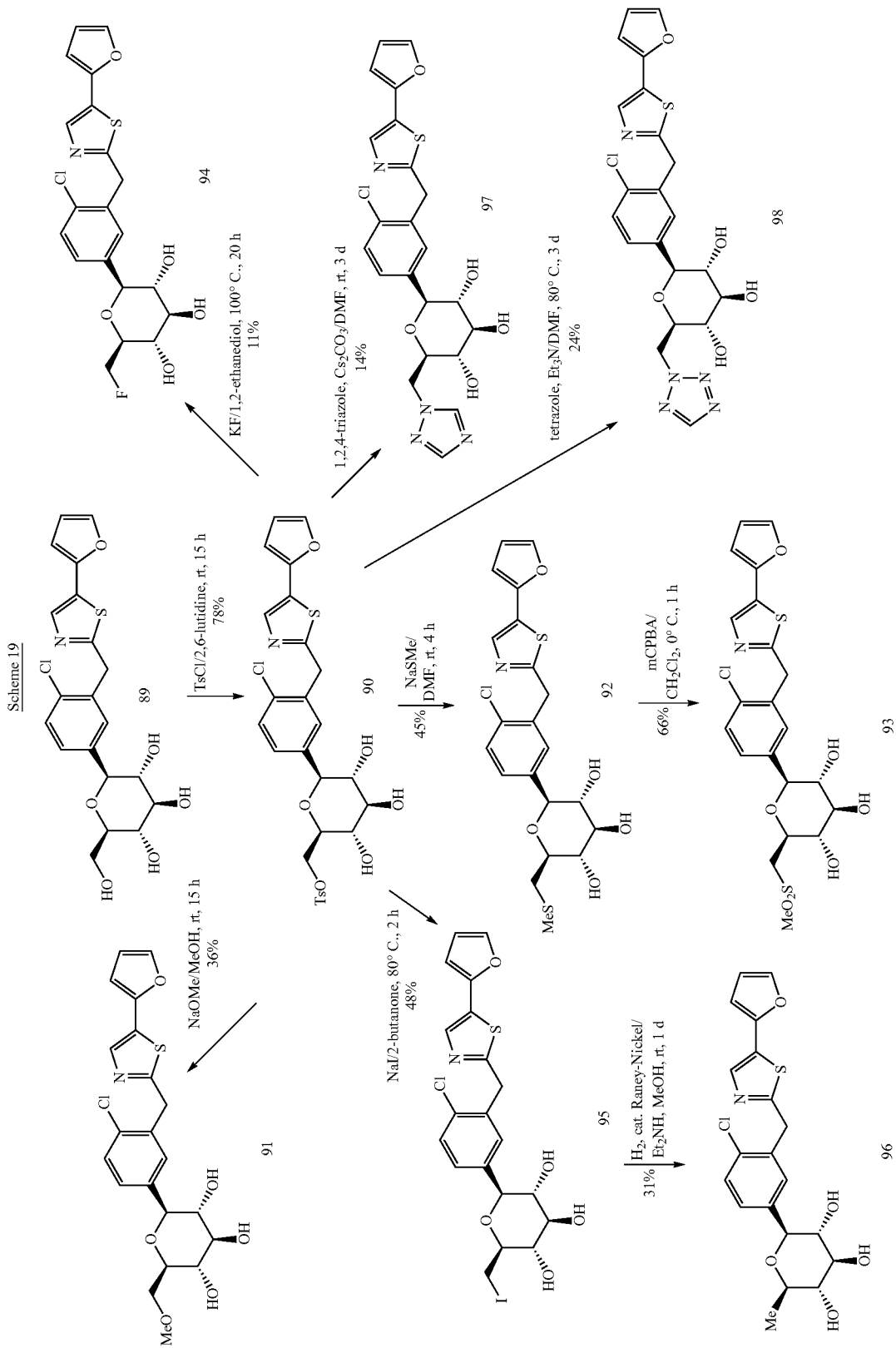

Modification at the C-5 position of the pyranose ring may be performed as shown in Scheme 19. In this event, resioselective tosylation of a tetra-ol 89 generates the C-6 activated C-aryl glucoside 90, which proves to be a versatile intermediate. Treatment of tosylate 90 with sodium alkoxide provides the corresponding ether 91. Likewise, treatment on tosylate 90 with sodium thioalkoxide yields alkyl sulfide 92. Subsequent oxidation with mCPBA affords the corresponding sulfonyl compound 93. Fluorination is conducted on tosylate 90 using potassium fluoride to afford fluoride 94. Similarly, iodination is conducted on tosylate 90 using sodium iodide to afford iodide 95. Subsequent hydrogenolysis in the presence of Raney-Nickel affords the corresponding 96 [Hanessian, S. et al. *Tetrahedron*, 2009, 65, 6656-6669]. In another variation, tosylate 90 can be reacted with 1,2,4-triazole and tetrazole in the presence of a base to provide 97 and 98 (and regioisomer of 98), respectively.

Scheme 20

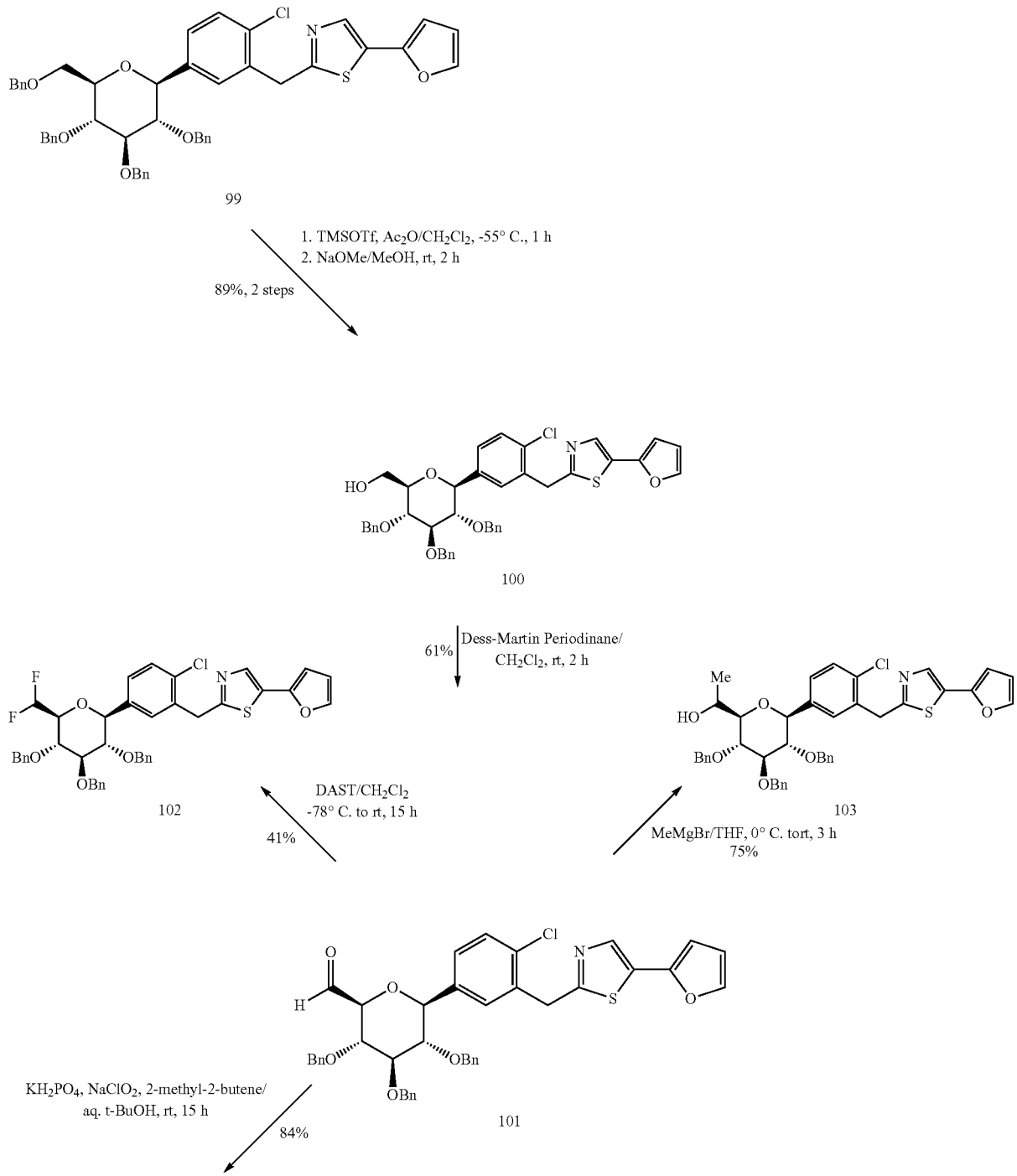

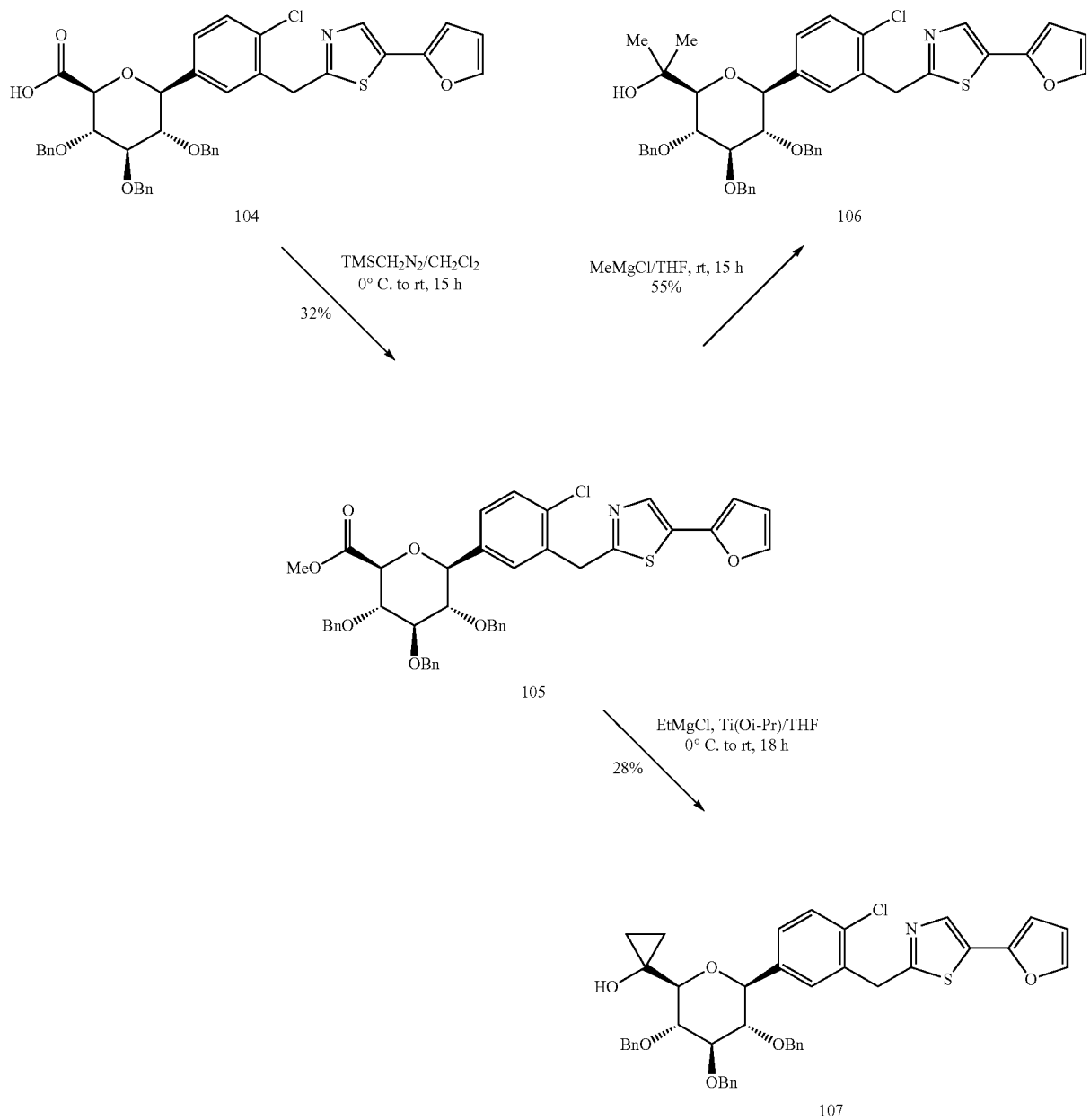

Another modification at the C-5 position of the pyranose ring may be performed as shown in Scheme 20. First, Selective debenzylation and concurrent acetylation of tetrabenzyl compound 99 using TMSOTf and acetic anhydride at −55° C., followed by deacetylation using sodium methoxide produce the primary alcohol 100, which is oxidized through the use of Dess-Martin periodinane to generate aldehyde 101 in 54% over three steps. Aldehyde 101 can be converted into the corresponding difluoride 102 through the use of a fluorinating agent such as diethylaminosulfur trifluoride (DAST) in 41% yield. Alternatively, aldehyde 101 can be treated with a Grignard reagent such as methylmagnesium bromide to afford the corresponding secondary alcohol 103 in 75% yield. In another variation, aldehyde 101 can be further oxidized to acid 104 by use of sodium chlorite, potassium phosphate monobasic, and 2-methyl-2-butene in aqueous t-BuOH in 84% yield. Subsequent methylation with trimethylsilyl diazomethane affords the corresponding methyl ester 105 in 32% yield, which is then treated with methylmagnesium chloride to appord the corresponding tertiary alcohol 106 in 55% yield. Additionally, the Kulinkovich reaction allows the preparation of the cyclopropanol 107 by the reaction of Grignard reagent with the ester 105 in the presence of titanium(IV) isopropoxide as catalyst in moderate yield.

Scheme 21

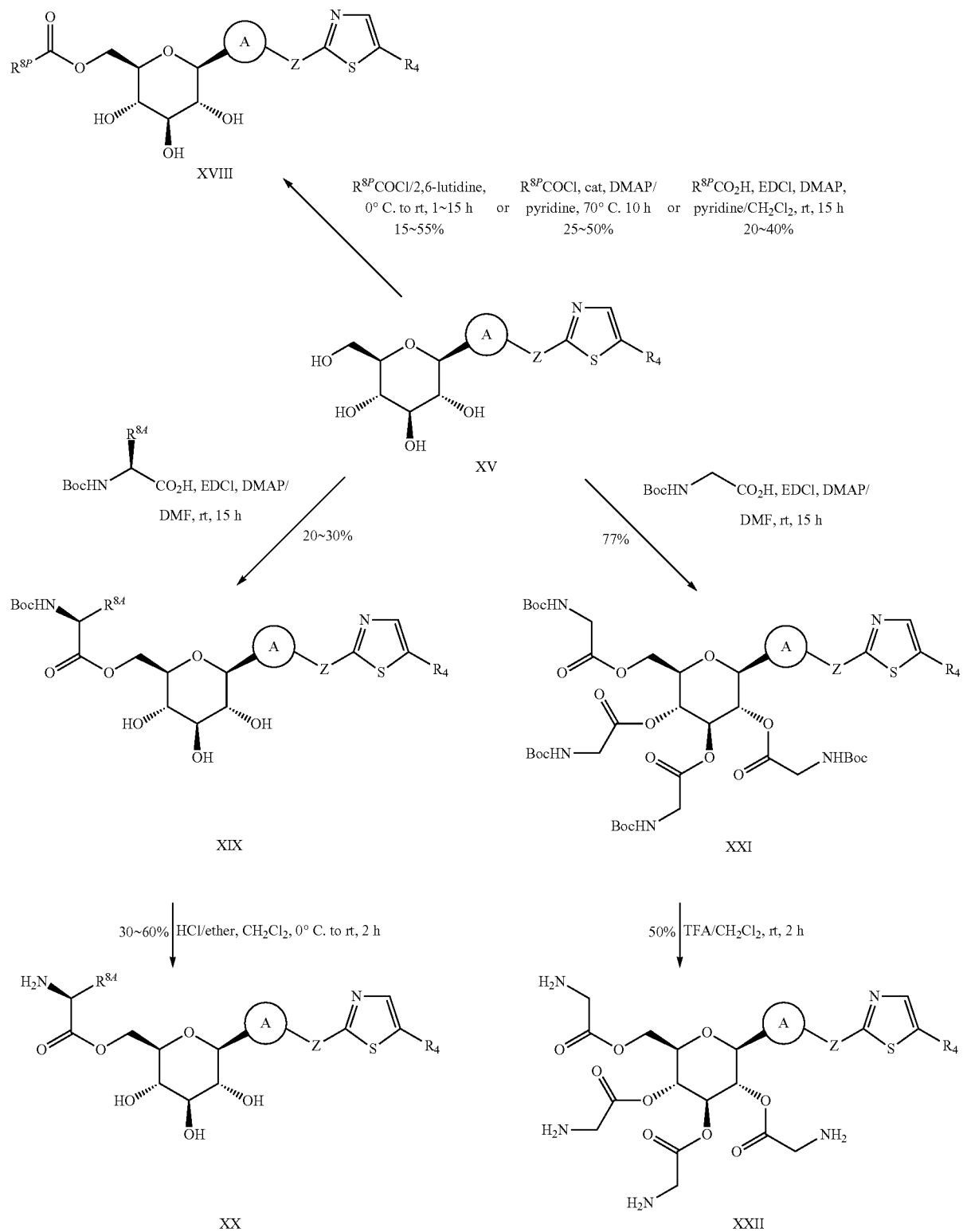

Preparation of prodrugs of thiazole derivatives may be performed as shown in Scheme 21. The mono-ester/-carbonate functionality of XVIII is introduced by treating the active form XV with $R^{8P}COCl$ in the presence of 2,6-lutidine or DMAP and pyridine in moderate yield, wherein $R^{8P}$ denotes alkyl, aryl, and alkoxy. Alternatively, the mono-ester/-carbonate XVIII is also available through the coupling between XV and $R^{8P}CO_2H$ in the presence of EDCI, DMAP, and pyridine. Additionally, the mono-α-aminoester containing prodrugs XX is produced through the coupling of the active form XV with N-Boc-protected α-aminoacid mediated by coupling reagents such as EDCI and DMAP, followed by deprotection under acidic conditions, wherein $R^{8A}$ denotes substituents of commercially available α-aminoacids. In another variation, the peresterified prodrugs XXIII is generated through a series of reactions as previously described to generate XXI using excessive N-Boc-glycine.

For SAR investigations, reversed thiazoles at ring B is synthesized and evaluated. Preparation of the key intermediate, α-aminoketone XXV, is described in Scheme 22. First, the α-diazoketone XXIII is formed from the acid chloride with (trimethylsilyl)diazomethane in moderate yield. Treatment of the α-diazoketone XXIII with aqueous HBr affords the α-bromoketone XXIV, which is treated with hexamethylenetetramine to produce the corresponding quaternary ammonium salt. By refluxing in concentrated ethanolic hydrochloric acid solution, this salt is converted to the α-aminoketone XXV (Route A). Alternatively, the α-aminoketone XXV is also smoothly prepared from the carboxylic acid XI via a three-step sequence: i.e. (i) activation of carboxylic acid group using CDI; (ii) addition of nitromethane under basic conditions; (iii) Reduction of nitroketone XXVI using stannous chloride (Route B).

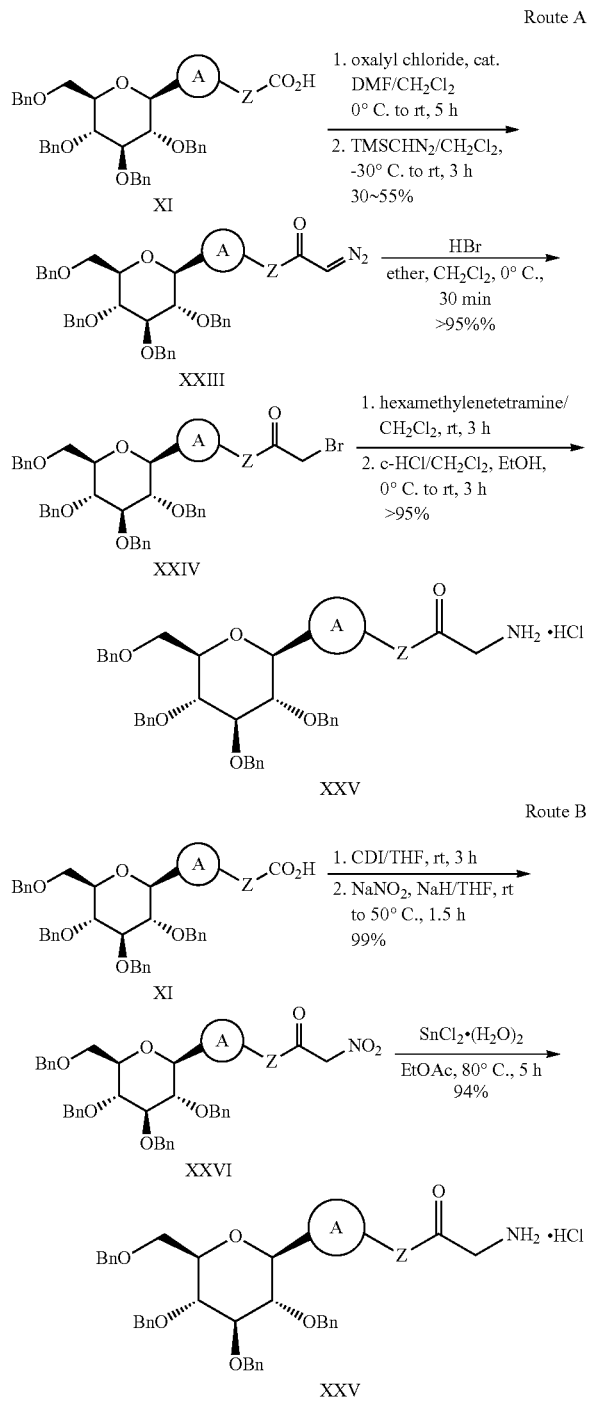

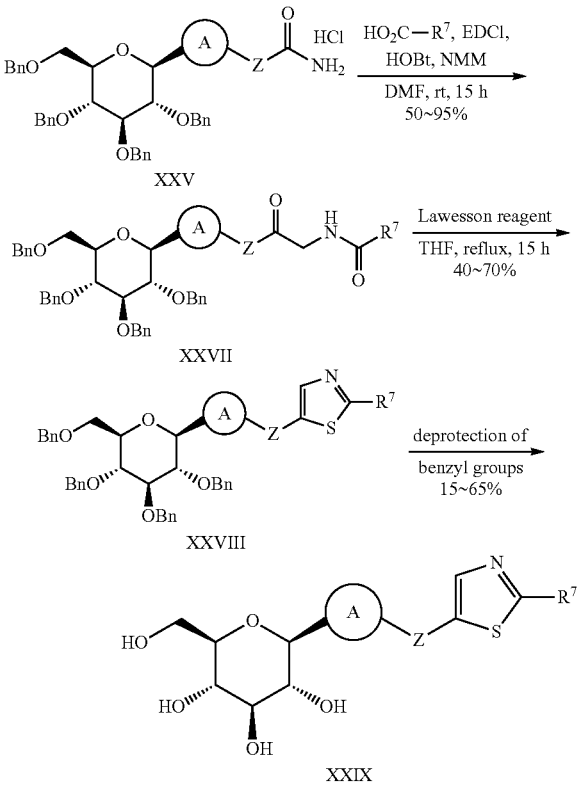

Reversed thiazole at ring B of XXIX (the other isomer of thiazole) may be synthesized as shown in Scheme 23. Thus, the three steps are involved to give rise to the target compound XXIX in an analogous manner as previously described in Scheme 9: i.e. (i) coupling of the amine XXV with the corresponding carboxylic acid mediated by coupling reagents such as EDCI, HOBt and NMM; (ii) thionation-cyclization using Lawesson's reagent; (iii) deprotection of the four benzyl groups under acidic or nucleophilic conditions.

The inventive thiazole derivative of formula (I) or a pharmaceutically acceptable salt or a prodrug thereof is effective as an inhibitor against sodium-dependent glucose cotransporter (SGLT2), thereby preventing or treating diabetes.

Accordingly, the present invention provides a pharmaceutical composition for preventing or treating a metabolic disorder, particularly diabetes, which comprises the compound of formula (I), or a pharmaceutically acceptable salt or a prodrug thereof as an active ingredient and a pharmaceutically acceptable carrier.

Further, the present invention provides a method for preventing or treating a metabolic disorder, particularly diabetes, in a mammal, which comprises administering the compound of formula (I) or a pharmaceutically acceptable salt or a prodrug thereof to the mammal.

Also, the present invention provides a method for inhibiting SGLT2 in a mammal, which comprises administering the compound of formula (I) or a pharmaceutically acceptable salt or a prodrug thereof to the mammal.

The pharmaceutical composition may be administered orally or parenterally, e.g., intramuscularly or subcutaneously. The formulation for oral administration may take various forms such as a syrup, tablet, capsule, cream and lozenge. A syrup formulation will generally contain a suspension or solution of the compound or its salt in a liquid carrier, e.g., ethanol, peanut oil, olive oil, glycerine or water, optionally with a flavoring or coloring agent. When the composition is in the form of a tablet, any one of pharmaceutical carriers routinely used for preparing solid formulations may be used. Examples of such carriers include magnesium stearate, terra alba, talc, gelatin, acacia, stearic acid, starch, lactose and sucrose. When the composition is in the form of a capsule, any of the routine encapsulation procedures may be employed, e.g., using the aforementioned carriers in a hard gelatin capsule shell. When the composition is formulated in the form of a soft gelatin shell capsule, any of the pharmaceutical carrier routinely used for preparing dispersions or suspensions may be prepared using an aqueous gum, cellulose, silicate or oil. The formulation for intramuscular or subcutaneous administration may take a liquid form such as a solution, suspension and emulsion which includes aqueous solvents such as water, physiological saline and Ringer's solution; or lipophilic solvents such as fatty oil, sesame oil, corn oil and synthetic fatty acid ester.

Preferably the composition is formulated in a specific dosage form for a particular patient.

Each dosage unit for oral administration contains suitably from 0.1 mg to 500 mg, and preferably from 1 mg to 100 mg of the compound of formula (I) or its pharmaceutically acceptable salt or prodrug.

The suitable daily dosage for oral administration is about 0.01 mg/kg body weight to 40 mg/kg body weight of the compound of formula (I) or its pharmaceutically acceptable salt or prodrug, and may be administered 1 to 6 times a day, depending on the patient's condition.

The present invention further provides a use of the inventive compound for the manufacture of a medicament for preventing or treating a metabolic disorder, particularly diabetes.

The present invention is further described and illustrated in Examples provided below, which are, however, not intended to limit the scope of the present invention.

EXPERIMENTAL SECTION

As used herein the symbols and conventions used describing the processes, schemes and examples of the present invention are consistent with those used in the contemporary scientific literature, for example, the *Journal of the American Chemical Society* or the *Journal of Biological Chemistry*.

| | |
|---|---|
| Hz (Hertz) | TLC (thin layer chromatography) |
| $T_r$ (retention time) | RP (reverse phase) |
| MeOH (methanol) | i-PrOH (isopropanol) |
| TFA (trifluoroacetic acid) | TEA (triethylamine) |
| EtOH (ethanol) | THF (tetrahydrofuran) |
| DMSO (dimethylsulfoxide) | EtOAc (ethyl acetate) |
| DCM (dichlromethane) | HOAc (acetic acid) |
| DMF (N,N-dimethylformamide) | Ac (acetyl) |
| CDI (1,1-carbnyldiimidazole) | Bn (benzyl) |
| TES (Triethylsilyl) | NBS (N-Bromosuccinimide) |
| HOBt (1-hydroxybenzotriazole) | TIPSCl (triisopropylsilyl chloride) |
| Boc (tert-butyloxycarbonyl) | |
| mCPBA (meta-chloroperbenzoic acid) | |
| NMM (N-methyl morpholine) | |
| TBAF (tetra-n-butylammonium fluoride) | |
| DMAP (4-dimethylaminopyridine) | |
| HPLC (high pressure liquid chromatography) | |
| EDCI (1-ethyl-3-[3-dimethyl-aminopropyl]carbodiimide hydrochloride) | |
| DME (1,2-dimethoxyethane) | |
| AIBN (2,2'-azobis(2-methylpropionitrile)) | |
| DIEA (N,N'-diisopropylethylamine) | |
| TMSI (iodotrimethylsilane) | |
| TMSOTf (trimethylsilyl trifluoromethanesulfonate) | |
| DDQ (2,3-dichloro-5,6-dicyano-p-benzoquinone) | |
| DAST (diethylaminosulfur trifluoride) | |
| NMP (1-methyl-2-pyrrolidinone) | |
| MW (micrwave irradiation) | |

All reactions are conducted under an inert atmosphere at room temperature, unless otherwise noted. n-Butyllithium (Aldrich) was titrated with N-benzylbenzamide as indicator. All reagents were purchased at the highest commercial quality and used without further purification, unless otherwise indicated. All experiment involving moisture- and/or air-sensitive compounds were performed in oven- and/or flame-dried glassware with rubber septa under a positive pressure of nitrogen using standard Schlenck technique. Microwave reaction was conducted with a Biotage Initiator microwave reactor. NMR spectra were obtained on a Varian 400-MR (400 MHz $^1$H, 100 MHz $^{13}$C) spectrometer. NMR spectra were recorded in ppm (δ) relative to tetramethylsilane (δ=0.00) as an internal standard unless stated otherwise and are reported as follows: chemical shift, multiplicity (s=singlet, d=doublet, t=triplet, q=quartet, quint=quintet, sext=sextet, m=multiplet, and br=broad), coupling constant, and integration. $^{13}$C NMR spectra were referenced to the residual chloroform-d$_1$ (δ=77.0) or DMSO-d$_6$ (δ=39.7). Mass spectra were obtained with an Agilent 6110 quadruple LC-MSD (ESI+). High resolution mass spectra were obtained on a Jeol JMS-700 Mstation (10 kV, HFAB). Optical rotations were obtained on a Rudolph Autopol III digital polarimeter. Preparative HPLC purifications were performed on a Gilson purification system. For preparative HPLC, ca. 100 mg of a product was injected in 1 mL of methanol onto a SunFire Prep C18 OBD 5 μm 30×100 mm Column with a 30 min gradient from 5 to 90% acetonitrile in water and a 45 mL/min flow rate. Biotage SP1 and Isolera purification systems were used for normal phase column chromatography with ethyl acetate and hexane. Flash chromatography was performed using E. Merck 230-400 mesh silica gel according to the procedure of Still et al. Reactions were monitored by either thin-layer chromatography (TLC) on 0.25 mm E. Merck silica gel plates (60E-254) using UV light and p-anisaldehyde solution as visualizing agents or HPLC analysis on an Agilent 1200 series system.

The following synthetic schemes are merely illustrative of the methods by which the compounds of the invention may be prepared and are not intended to limit the scope of the invention as defined in the appended claims.

Unless otherwise noted, all starting materials were obtained from commercial suppliers and used without further purification.

Preparation of the Intermediates

Preparation Example 1

2-(2-Chloro-5-((2S,3S,4R,5R,6R)-3,4,5-tris(benzyloxy)-6-(benzyloxymethyl)-tetrahydro-2H-pyran-2-yl)phenyl)acetic acid (55)

Step 1: (2-Chloro-5-((3S,4R,5R,6R)-3,4,5-tris(benzyloxy)-6-(benzyloxy-methyl)-tetrahydro-2H-pyran-2-yl)phenyl)methanol To a solution of bromide 32 (97 g, 257 mmol) in THF (1 L) at −78° C. under an atmosphere of nitrogen was added dropwise n-butyllithium (2.5 M in hexanes, 103 mL, 257 mmol), and the mixture was stirred for 1.5 h at the same temperature. Then a solution of lacone 1 (106 g, 198 mmol) in THF (500 mL) was added dropwise, and the mixture was stirred for 3 h at the same temperature. The reaction mixture was quenched by addition of saturated ammonium chloride. After complete addition, the solution was gradually raised to room temperature. The organic layer was separated and the aqueous layer was extracted with EtOAc. The combined organic layers were washed with brine, dried over anhydrous $MgSO_4$, filtered and concentrated in vacuo to yield a yellow oil, which was carried on to the next step without further purification.

To a stirred −50° C. solution of the lactols 33 in dichloromethane (500 mL) was added triethylsilane (63 mL, 396 mmol) followed by boron trifluoride diethyl etherate (50 mL, 396 mmol) at a rate such that the reaction temperature was maintained between −40 and −50° C. The solution was allowed to warm to −10° C. over 2 h prior to quenching with saturated potassium carbonate. After removal of organic volatiles under reduced pressure, the residue was partitioned between EtOAc and water. Following extraction of the aqueous layer with EtOAc, the combined organic layers were washed with water prior to drying over anhydrous $MgSO_4$. Filtration and concentration under reduced pressure yielded a yellow oil, which was carried on to the next step without further purification.

To a solution of (2-chloro-5-((3S,4R,5R,6R)-3,4,5-tris(benzyloxy)-6-(benzyloxymethyl)-tetrahydro-2H-pyran-2-yl)benzyloxy)triisopropylsilane in THF (500 mL) was added tetrabutylammonium fluoride (1.0 M in THF, 594 mL, 594 mmol) and the reaction mixture stirred at ambient temperature for 2 h. After removal of organic volatiles under reduced pressure, the residue was partitioned between EtOAc and saturated ammonium chloride. The organic layer was separated and the aqueous layer was extracted with EtOAc. The combined organic layers were washed with brine, dried over anhydrous $MgSO_4$, filtered and concentrated in vacuo. The crude residue was purified on column chromatography to provide the titled compound (168 g, 98%, ca. 2:1 mixture of anomers (β:α)) as a white solid.

$^1$H NMR (400 MHz, $CDCl_3$) β-anomer: δ 7.50 (s, 1H), 7.38-7.17 (m, 20H), 6.94-6.92 (m, 2H), 4.96-4.46 (m, 9H), 4.23 (d, J=9.2 Hz, 1H), 3.86 (d, J=10.4 Hz, 1H), 3.81-3.67 (m, 4H), 3.61-3.59 (m, 1H), 3.44 (t, J=9.2 Hz, 1H); α-anomer: δ 7.78 (s, 1H), 7.63 (dd, J=8.4, 1.6 Hz, 1H), 7.38-7.17 (m, 19H), 7.13-7.10 (m, 2H), 5.15 (d, J=3.6 Hz, 1H), 4.96-4.46 (m, 8H), 4.01-3.95 (m, 2H), 3.83-3.64 (m, 5H), 3.55-3.51 (m, 1H); MNa+687.

Step 2: 2-(2-Chloro-5-((3S,4R,5R,6R)-3,4,5-tris(benzyloxy)-6-(benzyloxymethyl)-tetrahydro-2H-pyran-2-yl)phenyl)acetonitrile (39)

To a solution of (2-chloro-5-((3S,4R,5R,6R)-3,4,5-tris(benzyloxy)-6-(benzyloxy-methyl)-tetrahydro-2H-pyran-2-yl)phenyl)methanol (130 g, 195 mmol) in ether (600 mL) at 0° C. was added pyridine (0.79 mL, 9.8 mmol) and phosphorus tribromide (6.4 mL, 68 mmol). The reaction was allowed to slowly warm to room temperature over 15 h and refluxed 1 h. After cooling to room temperature, the reaction mixture was diluted with EtOAc and washed with water then brine. The organic extract was dried over anhydrous $MgSO_4$, filtered, and evaporated in vacuo to yield a yellow solid, which was carried on to the next step without further purification.

To a solution of the (2R,3R,4R,5S)-3,4,5-tris(benzyloxy)-2-(benzyloxymethyl)-6-(3-(bromomethyl)-4-chlorophenyl)-tetrahydro-2H-pyran in ethanol (260 mL) and water (130 mL) was added potassium cyanide (31.8 g, 488 mmol). The reaction mixture was refluxed overnight. After cooling to room temperature, the mixture was diluted with water and extracted with EtOAc. The organic layer was washed with brine, dried over anhydrous $MgSO_4$, filtered and evaporated in vacuo. Purification was accomplished by chromatography to provide the titled compound 39 (105 g, 80%, ca. 2:1 mixture of anomers β:α).

$^1$H NMR (400 MHz, $CDCl_3$) β-anomer: δ 7.48 (s, 1H), 7.37-7.17 (m, 20H), 6.93-6.91 (m, 2H), 4.93 (s, 2H), 4.86 (d, J=10.8 Hz, 1H), 4.63 (d, J=10.8 Hz, 1H), 4.62 (d, J=12.4 Hz, 1H), 4.56 (d, J=12.4 Hz, 1H), 4.52 (d, J=10.8 Hz, 1H), 4.22 (d, J=9.6 Hz, 1H), 3.93 (d, J=10.8 Hz, 1H), 3.84-3.68 (m, 6H), 3.62-3.58 (m, 1H), 3.43 (t, J=8.8 Hz, 1H); α-anomer: δ 7.83 (d, J=1.6 Hz, 1H), 7.64 (dd, J=8.4, 1.6 Hz, 1H), 7.37-7.19 (m, 19H), 7.13-7.10 (m, 2H), 5.11 (d, J=2.8 Hz, 1H), 4.93-4.46 (m, 8H), 3.96-3.92 (m, 2H), 3.79-3.71 (m, 3H), 3.70-3.62 (m, 2H), 3.55-3.51 (m, 1H); MNa+696.

Step 3: 2-(2-Chloro-5-((2S,3S,4R,5R,6R)-3,4,5-tris(benzyloxy)-6-(benzyloxymethyl)-tetrahydro-2H-pyran-2-yl)phenyl)acetonitrile (β-39)

The mixture of cyanides 39 (105 g, 156 mmol, ca. 2:1 β:α) was slurried in ethanol (1 L) and heated to reflux with stirring. The reaction mixture was held at reflux for 1 h to ensure that all of solution had homogenized. It was then cooled evenly at 15° C./h to ambient temperature and stirred overnight at this temperature. The resulting solid was isolated by filtration and dried in vacuo to yield the titled compound β-39 (53 g, 51%) as a white solid.

$[\alpha]_D^{21}$ −10.6 (c 1.01, chloroform);

$^1$H NMR (400 MHz, $CDCl_3$) δ 7.48 (s, 1H), 7.37-7.17 (m, 20H), 6.93-6.91 (m, 2H), 4.93 (s, 2H), 4.86 (d, J=10.8 Hz, 1H), 4.63 (d, J=10.8 Hz, 1H), 4.62 (d, J=12.4 Hz, 1H), 4.56 (d, J=12.4 Hz, 1H), 4.52 (d, J=10.8 Hz, 1H), 4.22 (d, J=9.6 Hz, 1H), 3.93 (d, J=10.8 Hz, 1H), 3.84-3.68 (m, 6H), 3.62-3.58 (m, 1H), 3.43 (t, J=8.8 Hz, 1H); $^{13}$C NMR (100 MHz, $CDCl_3$) δ 129.49, 128.86, 128.45, 128.38, 128.26, 128.08, 128.01, 127.87, 127.82, 127.70, 127.68, 127.67, 127.64, 127.61, 139.09, 138.52, 138.23, 138.07, 137.41, 132.97, 129.49, 128.86, 128.45, 128.38, 128.26, 128.08, 128.01, 127.87, 127.82, 127.70, 127.68, 127.67, 127.64, 127.61, 116.57, 86.87, 83.59, 80.47, 79.41, 78.28, 75.67, 75.16, 74.96, 73.47, 69.07, 22.12; HRMS (FAB, 6 keV) calcd for $C_{42}H_{41}ClNO_5$ ([M+H]$^+$) 674.2673, found 674.2672; MNa+696.

Step 4: 2-(2-Chloro-5-((2S,3S,4R,5R,6R)-3,4,5-tris(benzyloxy)-6-(benzyloxymethyl)-tetrahydro-2H-pyran-2-yl)phenyl)acetic acid (55)

To a solution of cyanide β-39 (53 g, 79 mmol) in EtOH (300 mL) was added aq. NaOH solution (8.0 N, 300 mL, 2.4 mol). The reaction mixture was refluxed overnight. After cooling to room temperature, hydrochloric acid (3.0N) was added to neutralize the reaction mixture. The mixture was diluted with water and extracted with EtOAc. The organic layer was washed with water and brine prior to drying over anhydrous $MgSO_4$. Filtration and concentration under reduced pressure yielded the titled compound 55 (54 g, 98%) as a white solid.
$[\alpha]_D^{21}$ -4.7 (c 1.10, chloroform);
$^1$H NMR (400 MHz, CDCl$_3$) δ 7.37-7.14 (m, 21H), 6.93-6.90 (m, 2H), 4.94 (d, J=10.8 Hz, 1H), 4.90 (d, J=10.8 Hz, 1H), 4.86 (d, J=11.2 Hz, 1H), 4.63 (d, J=10.8 Hz, 1H), 4.62 (d, J=14.0 Hz, 1H), 4.55 (d, J=12.4 Hz, 1H), 4.43 (d, J=10.4 Hz, 1H), 4.20 (d, J=9.6 Hz, 1H), 3.88 (d, J=10.8 Hz, 1H). 3.81-3.70 (m, 6H), 3.59-3.56 (m, 1H), 3.43 (t, J=8.8 Hz, 1H); $^{13}$C NMR (100 MHz, DMSO-d$_6$) δ 171.84, 139.10, 138.69, 138.66, 138.17, 133.72, 133.49, 131.99, 129.18, 128.68, 128.66, 128.45, 128.26, 128.19, 128.10, 128.00, 127.92, 127.87, 127.84, 86.25, 83.53, 80.14, 78.77, 78.55, 74.97, 74.51, 74.30, 72.75, 69.39, 39.19; MNH$_4$+710 and MNa+715.

Preparation Example 2

(5-Bromo-2-chlorobenzyloxyl)triisopropylsilane (32)

Step 1: 5-Bromo-2-chlorobenzyl alcohol

To a solution 5-bromo-2-chlorobenzoic acid (100 g, 425 mmol) in tetrahydrofuran (500 mL) at 0 r was added borane dimethyl sulfide complex (170 mL, 170 mmol). The resulting mixture was stirred with gradual warming to ambient temperature over 15 h, re-cooled to 0° C., and quenched with MeOH. The mixture was diluted with water and extracted with EtOAc. The organic layer was washed with brine, dried over anhydrous $MgSO_4$, filtered and evaporated in vacuo to yield the titled compound as a white solid, which was used without further purification.
$^1$H NMR (400 MHz, CDCl$_3$) δ 7.67 (d, J=2.4 Hz, 1H), 7.36 (dd, J=8.4, 2.4 Hz, 1H), 7.22 (d, J=8.4 Hz, 1H), 7.76 (d, J=6.4 Hz, 2H), 1.93 (t, J=6.4 Hz, 1H); [M-OH$^-$]+203.

Step 2: (5-Bromo-2-chlorobenzyloxyl)triisopropylsilane (32)

To a solution of 5-bromo-2-chlorobenzyl alcohol (425 mmol) in DMF (400 mL) was added imidazle (58 g, 850 mmol), 4-(dimethylamino)pyridine (2.6 g, 21 mmol), and triisopropylsilyl chloride (136 mL, 638 mmol). The resulting solution was stirred at ambient temperature for 15 h, diluted with a saturated ammonium chloride and extracted with EtOAc. The organic layer was washed with water then brine, dried over anhydrous $MgSO_4$, filtered and concentrated in vacuo. The crude residue was purified by column chromatography to yield the titled compound 32 (152 g, 403 mmol, 95%) as a colorless oil.

$^1$H NMR (400 MHz, CDCl$_3$) δ 7.77 (d, J=2.4 Hz, 1H), 7.31 (dd, J=8.4, 2.4 Hz, 1H), 7.16 (d, J=8.4 Hz, 1H), 4.83 (s, 2H), 1.25-1.17 (m, 3H), 1.11 (d, J=6.8 Hz, 18H).

Preparation Example 3

(5-Iodo-2-methylphenyl)methanol

Step 1: Ethyl 5-bromo-2-methylbenzoate (3)

To a mixture of acid 2 (50.0 g, 233 mmol) in EtOH (700 mL) was added c-H$_2$SO$_4$ (50 mL) at 0° C. The mixture was warmed-up to room temperature and stirred at 100° C. for 15 h. The mixture was cooled to room temperature and evaporated in vacuo to remove EtOH. The residue was diluted with EtOAc and washed with H$_2$O, aq. saturated NaHCO$_3$ solution. The organic layer was dried over anhydrous MgSO$_4$, filtered, and concentrated in vacuo. The residue was purified by silica column chromatography to provide the intermediate 3 (39.0 g, 69%).
$^1$H NMR (400 MHz, CDCl$_3$) δ 8.02 (d, J=1.6 Hz, 1H), 7.71 (dd, J=8.0, 2.0 Hz, 1H), 6.99 (d, J=8.0 Hz, 1H), 4.32 (q, J=7.2 Hz, 2H), 2.55 (s, 3H), 1.40 (t, J=7.2 Hz, 2H); MH+243.

Step 2: Ethyl 5-iodo-2-methylbenzoate (4)

To a solution of bromide 3 (39.0 g, 161 mmol) in 1,4-dioxane (150 mL) were added NaI (48.2 g, 321 mmol), CuI (1.6 g, 8.03 mmol) and N,N'-dimethylethyldiamine (1.8 mL, 16.1 mmol). The mixture was evacuated and backfilled with N$_2$. The mixture was stirred at 110° C. for 15 h. The mixture was cooled to room temperature and filtered off through celite. The filtrated was evaporated under vacuum to remove solvent. The residue was diluted with EtOAc and washed with aq. 50% NH$_4$Cl solution. The organic layer was dried over anhydrous MgSO$_4$, filtered, and concentrated in vacuo. The residue was purified by silica column chromatography to provide the titled compound 4 (41.3 g, 89%).
$^1$H NMR (400 MHz, CDCl$_3$) δ 8.20 (d, J=1.6 Hz, 1H), 7.68 (dd, J=8.0, 2.0 Hz, 1H), 6.98 (d, J=8.0 Hz, 1H), 4.35 (q, J=7.2 Hz, 2H), 2.53 (s, 3H), 1.39 (t, J=7.2 Hz, 2H); MH+291.

Step 3: (5-Iodo-2-methylphenyl)methanol

To a solution of ester 4 (41.0 g, 141 mmol) in THF (300 mL) was added lithium borohydride (2.0 M in THF, 212 mL). The reaction mixture was refluxed overnight. After cooling to 0° C., the reaction was quenched by addition of aq. saturated NH$_4$Cl solution. The mixture was diluted with water and extracted with EtOAc. The organic layer was washed with brine, dried over anhydrous MgSO$_4$, filtered and evaporated in vacuo to yield the titled compound (34.0 g, 97%) as a white solid, which was carried on to the next step without further purification.
[M-OH$^-$]+231.

Preparation Example 4

(5-Bromo-2-fluorophenyl)methanol

To a solution of 5-bromo-2-fluorobenzaldehyde (30.0 g, 148 mmol) in EtOH was added sodium borohydride (8.39 g, 222 mmol) at 0° C. The resulting mixture was stirred with gradual warming to ambient temperature over 15 h, re-cooled to 0° C., and quenched with aq. saturated NH$_4$Cl solution. The mixture was extracted with EtOAc. The organic layer was washed with brine, dried over MgSO$_4$, filtered and evaporated in vacuo to yield the titled compound (30.3 g, quantitative) as a white solid, which was carried on to the next step without further purification.

[M-OH⁻]+187.

Preparation Example 5

5-Bromo-2-chloro-4-methoxybenzoic acid (13)

Step 1: 5-Bromo-2-chloro-4-hydroxybenzonitrile (12)

To a solution of 2-chloro-4-hydroxybenzonitrile 11 (10.0 g, 65.1 mmol) in $CH_3CN$ (200 mL) were added triflic acid (10 mL, 71.6 mmol), NBS (16.2 g, 91.2 mmol) at −30° C. The mixture was warmed-up to room temperature and stirred at room temperature for 15 h. The reaction was quenched by addition of aq. saturated $NaHSO_3$ solution. The mixture was extracted with EtOAc. The combined organic extract was dried over anhydrous $MgSO_4$, filtered and concentrated in vacuo. The residue was purified by silica column chromatography to provide the titled compound 12 (9.8 g, 65%).

$^1$H NMR (400 MHz, $CD_3OD$) δ 7.91 (s, 1H), 7.03 (s, 1H), 4.85 (s, 1H); MH+232.

Step 2: 5-Bromo-2-chloro-4-methoxybenzoic acid (13)

To a solution of benzonitrile 12 (35.2 g, 151 mmol) in THF (500 mL) were added lithium hydroxide monohydrate (9.0 g, 197 mmol) and dimethyl sulfate (20 mL, 197 mmol). The reaction mixture was stirred at 75° C. for 15 h. The mixture was cooled to room temperature and diluted with EtOAc. The mixture was washed with aq. 50% NaCl solution and dried over anhydrous $MgSO_4$, filtered and concentrated in vacuo. The residue was purified by silica column chromatography to provide the intermediate (30.7 g).

To a solution of intermediate (30.7 g) in EtOH (500 mL)/$H_2O$ (250 mL) was added NaOH (127 g, 3.11 mol). The mixture was stirred at 100° C. for 9 h. The mixture was cooled to room temperature and evaporated in vacuo to remove EtOH. The residue was diluted with $H_2O$, cooled to 0° C. and acidified with aq. 6 N HCl solution. The titled compound 13 was precipitated as a solid, filtered off and washed with $H_2O$. The solid was dried under vacuum at 50° C. for 16 h to obtain the product (33.7 g, 76%, 2 steps).

MH+265.

Preparation Example 6

4-(Allyloxy)-5-bromo-2-chlorobenzoic acid (14)

To a solution of benzonitrile 12 (35.0 g, 151 mmol) in acetone (500 mL) were added allyl bromide (20 mL, 226 mmol) and $K_2CO_3$ (42 g, 301 mmol). The reaction mixture was stirred at 65° C. for 15 h. The mixture was cooled to room temperature and evaporated in vacuo to remove acetone. The residue was diluted with EtOAc (2500 mL). The mixture was washed with aq. 50% NaCl solution (500 mL) and dried over anhydrous $MgSO_4$, filtered and concentrated in vacuo. The residue was purified by silica column chromatography to provide the intermediate (26.5 g).

To a solution of intermediate (26.5 g) in EtOH (400 mL)/$H_2O$ (200 mL) was added NaOH (137 g, 3.41 mol). The mixture was stirred at 100° C. for 15 h. The mixture was cooled to room temperature and evaporated in vacuo to remove EtOH. The residue was diluted with $H_2O$, cooled to 0° C. and acidified with c-HCl. The titled compound 14 was precipitated as a solid and dissolved with EtOAc (300 mL). The extracted organic layer was dried over anhydrous $MgSO_4$, filtered and concentrated in vacuo to obtain the product (28.4 g, 66%, 2 steps).

MH+291.

Preparation Example 7

Methyl 4-bromo-2-naphthoate (16)

A solution of isoamyl nitrite (26.5 mL, 202 mmol) in DME (80 mL) and a solution of anthranilic acid (27.7 g, 202 mmol) in DME (80 mL) were both added in separate streams at matching rate over 30 min to a refluxing solution of bromo coumalate 15 (15.7 g, 67.3 mmol) in DME (80 mL) in the presence of trichloroacetic acid (1.1 g, 6.7 mmol). The reaction mixture was heated under reflux for further 1.5 h after the end of addition. The mixture was cooled to ambient temperature and then diluted with toluene. The toluene solution was washed with aq. NaOH (2.0/V), 5% aq. sodium bisulfite, water, hydrochloric acid (2.0 N), and water prior to drying over anhydrous $MgSO_4$. Filtration and removal of the volatiles under reduced pressure left the crude product which was purified by silica column chromatography to provide the titled compound 16 (15.5 g, 87%) as a pale brown solid.

$^1$H NMR (400 MHz, $CDCl_3$) δ 8.57 (s, 1H), 8.37 (d, J=1.6 Hz, 1H), 8.27 (d, J=8.8 Hz, 1H), 7.95 (d, J=8.8 Hz, 1H), 7.71 (td, J=8.0, 1.6 Hz, 1H), 7.61 (td, J=8.0, 1.6 Hz, 1H), 3.99 (s, 3H); MH+265.

Preparation Example 8

Methyl 4-bromo-1-methoxy-2-naphthoate (19)

Step 1: 4-Bromo-1-hydroxy-2-naphthoic acid (18)

Bromine (6.1 mL, 120 mmol) was added to a solution of naphthoic acid 17 (18.9 g, 100 mmol) in glacial acetic acid (250 mL). The mixture was stirred at room temperature overnight. The resulting solid was filtered and dried in vacuo to provide the titled compound 18 (24.7 g, 92%) as a white solid.

$^1$H NMR (400 MHz, DMSO-$d_6$) δ 8.31 (d, J=8.4 Hz, 1H), 8.04 (d, J=8.4 Hz, 1H), 7.96 (s, 1H), 7.82 (t, J=7.2 Hz, 1H), 7.67 (t, J=7.2 Hz, 1H); MH+267.

Step 2: Methyl 4-bromo-1-methoxy-2-naphthoate (19)

A mixture of hydroxynaphthoic acid 18 (24.7 g, 92.2 mmol), dimethyl sulfate (21.8 mL, 231 mmol), and $K_2CO_3$ (31.9 g, 231 mmol) in acetone (200 mL) was refluxed overnight. The solid was filtered, and the filtrate was condensed to give a solid residue, which was recrystallized from EtOAc/hexanes to afford the titled compound 19 (21.2 g, 78%) as a white solid.

$^1$H NMR (400 MHz, DMSO-$d_6$) δ 8.27 (d, J=8.4 Hz, 1H), 8.14 (d, J=8.4 Hz, 1H), 8.07 (s, 1H), 7.86-7.82 (m, 1H), 7.77-7.72 (m, 1H), 3.96 (s, 3H), 3.89 (s, 3H); MH+295.

Preparation Example 9

3-Bromo-1-naphthoic acid (22)

Step 1: 3-Bromo-1,8-naphthalic anhydride (21)

Naphthalic anhydride 20 (100 g, 505 mmol) was slurried in c-nitric acid (70%, 2.0 L) and heated to 50° C. Bromine (19.4 mL, 379 mmol) was added evenly over 10 min, and the resulting solution was held at 50° C. for 4 h before cooling to 0° C. The resulting solid was isolated by filtration and dried in vacuo to provide the titled compound 21 (23.8 g, 17%) as a white solid.

$^1$H NMR (400 MHz, DMSO-$d_6$) δ 8.85 (s, 1H), 8.53 (d, J=7.6 Hz, 1H), 8.48 (d, J=7.6 Hz, 2H), 7.95 (t, J=7.8 Hz, 1H); $^{13}$C NMR (100 MHz, DMSO-$d_6$) δ 160.12, 159.57, 136.73, 134.31, 133.88, 132.65, 132.61, 128.68, 128.32, 121.33, 120.07, 119.38; MH+277.

Step 2: 3-Bromo-1-naphthoic acid (22)

To a mixture of bromo anhydride 21 (22.8 g, 82.4 mmol) and sodium hydroxide (13.2 g, 330 mmol) in water (500 mL) was added a solution of mercury(II) oxide (23.2 g, 107 mmol) in water (70 mL) and glacial acetic acid (24 mL). The reaction mixture was heated at reflux for 4 days and then cooled to room temperature. The resulting solid was filtered and dried in vacuo.

The organo-Hg intermediates were slurrified in hydrochloric acid (5.0 N, 650 mL) and the reaction mixture heated to reflux for a further 4 h and then cooled to ambient temperature. The resulting solid was filtered and dried in vacuo.

The crude bromo acid was recrystallized from glacial acetic acid with hot filtration to remove some insoluble material to afford the titled compound 22 (12.0 g, 58%, 3 steps) as a white solid.

$^1$H NMR (400 MHz, DMSO-$d_6$) δ 13.46 (br, 1H), 8.75 (d, J=8.4 Hz, 1H), 8.43 (d, J=2.0 Hz, 1H), 8.11 (d, J=2.0 Hz, 1H), 7.98 (d, J=7.6 Hz, 1H), 7.67-7.58 (m, 2H); $^{13}$C NMR (100 MHz, DMSO-$d_6$) δ 167.25, 134.78, 134.37, 131.96, 130.05, 129.13, 128.08, 127.88, 127.36, 125.58, 117.57; MH+251.

Preparation Example 10

(4-(Allyloxymethyl)-5-bromo-2-chlorobenzyloxy) triisopropylsilane (31)

Step 1: Methyl 4-(acetoxymethyl)-2-bromo-5-chlorobenzoate (27)

To a solution of ester 26 (60.4 g, 229 mmol) in CCl$_4$ (900 mL) were added NBS (49.0 g, 275 mmol) and AIBN (3.80 g, 22.9 mmol). The mixture was stirred at 85° C. for 15 h. The mixture was cooled to room temperature and filtered off through celite to remove insoluble solids. The filtrate was evaporated in vacuo to obtain the crude intermediate.

To a solution of crude bromide (93.6 g, 273 mmol) in DMF (500 mL) was added NaOAc (56 g, 683 mmol). The mixture was stirred at room temperature for 20 h and diluted with EtOAc. The organic layer was washed with aq. 50% NaCl solution and dried over anhydrous MgSO$_4$, filtered and concentrated in vacuo. The residue was triturated with MeOH and the titled compound was precipitated as a solid. The solid was filtered off, washed with MeOH, and dried under vacuum to obtain the product 27 (36 g, 51%, 2 steps).

$^1$H NMR (400 MHz, CDCl$_3$) δ 7.84 (s, 1H), 7.71 (s, 2H), 5.19 (s, 2H), 3.94 (s, 3H), 2.19 (s, 3H); MH+321.

Step 2: 2-Bromo-5-chloro-4-(hydroxymethyl)benzoic acid (28)

To a solution of acetate 27 (33.5 g, 104.1 mmol) in THF/MeOH/H$_2$O (250 mL/250 mL/90 mL) was added lithium hydroxide monohydrate (13.1 g, 312 mmol). The mixture was stirred at room temperature for 15 h. The mixture was evaporated in vacuo to remove organic solvents. The residue was diluted with H$_2$O, cooled to 0° C. and acidified with aq. 1 N HCl solution. The titled compound 28 was precipitated as a solid, filtered off and washed with H$_2$O. The solid was dried under vacuum at 50° C. for 15 h to obtain the product (27.2 g, 96%). MH+265.

Step 3: Triisopropylsilyl 2-bromo-5-chloro-4-((triisopropylsilyloxy)methyl)benzoate (29)

To a solution of alcohol 28 (23.2 g, 87.5 mmol) in DMF (250 mL) were added TIPSCl (77 mL, 358.5 mmol), imidazole (33 g, 481.3 mmol) and DMAP (4.1 g, 33.6 mmol). The mixture was stirred at room temperature for 15 h. After dilution with water, the mixture was extracted with EtOAc. The organic layer was dried over anhydrous MgSO$_4$, filtered and concentrated in vacuo. The residue was purified by silica column chromatography to provide the titled compound 29 (38 g, 66%).

$^1$H NMR (400 MHz, CDCl$_3$) δ 7.79 (s, 1H), 7.50 (s, 1H), 4.81 (s, 2H), 2.01 (m, 1H), 1.26-1.15 (m, 6H), 1.15 (d, J=6.8 Hz, 36H).

Step 4: (2-Bromo-5-chloro-4-((triisopropylsilyloxy) methyl)phenyl)methanol (30)

To a solution of silyl ester 29 (38.0 g, 65.8 mmol) in THF (300 mL) was added borane dimethylsulfide complex (1 M in THF, 13 mL) at 0° C. The mixture was stirred 0° C. for 15 min, at room temperature at 30 min, and at 75° C. for 15 h. The mixture was cooled to 0° C. MeOH and H$_2$O were added to the cooled mixture to quench the reaction. After dilution with water, the mixture was extracted with EtOAc. The organic layer was dried over anhydrous MgSO$_4$, filtered and concentrated in vacuo. The residue was purified by silica column chromatography to provide the titled compound 30 (22.9 g, 85%).

$^1$H NMR (400 MHz, CDCl$_3$) δ 7.80 (s, 1H), 7.44 (s, 1H), 4.78 (s, 2H), 4.71 (d, J=5.2 Hz, 2H), 2.01 (m, 1H), 1.26-1.16 (m, 3H), 1.12 (d, J=6.8 Hz, 18H).

Step 5: (4-(Allyloxymethyl)-5-bromo-2-chlorobenzyloxy)triisopropylsilane (31)

To a solution of alcohol 30 (31 g, 75.5 mmol) in DMF (300 mL) were added NaH (60% dispersion in mineral oil, 4.0 g, 98.2 mmol) at 0° C. The mixture was stirred at 0° C. for 15 min and allyl bromide (23 mL, 264 mmol) was added to the mixture at 0° C. The mixture was warmed up to room temperature and stirred at room temperature for 2 h. After dilution with water, the mixture was extracted with EtOAc. The organic layer was dried over anhydrous MgSO$_4$, filtered and concentrated in vacuo. The residue was purified by silica column chromatography to provide the titled compound 31 (32.1 g, 95%).

$^1$H NMR (400 MHz, CDCl$_3$) δ 7.79 (s, 1H), 7.45 (s, 1H), 6.05-5.91 (m, 1H), 5.35 (qd, J=17.2, 1.6 Hz, 1H), 5.24 (qd, J=10.4, 1.2 Hz, 1H), 4.82 (s, 2H), 4.53 (s, 2H), 4.11 (td, J=5.6, 1.2 Hz, 2H), 1.25-1.16 (m, 1H), 1.10 (d, J=7.2 Hz, 18H).

Preparation Example 11

(3R,4S,5R,6R)-3,4,5-Tris(benzyloxy)-6-(benzyloxymethyl)-2-(4-methyl-3-((triisopropylsilyloxy) methyl)phenyl)-tetrahydro-2H-pyran-2-ol (35)

A mixture of gluconolactone 1 (11.6 g, 21.5 mmol) and iodide 34 (6.7 g, 16.5 mmol) in THF (55 mL) was added trimethylsilylmethyl lithium (1.0 M in pentane, 35 mL) at −65° C. The mixture was allowed to slowly warm to −45° C. over 2 h. To a mixture was added aq. saturated NaHCO₃ solution to quench the reaction. After dilution with water, the mixture was stirred at room temperature for 30 min and extracted with EtOAc. The organic layer was dried over anhydrous MgSO₄, filtered and concentrated in vacuo. The crude titled compound 35 was carried on to the next step without further purification.

Preparation Example 12

(3R,4S,5R,6R)-3,4,5-Tris(benzyloxy)-6-(benzyloxymethyl)-2-(4-bromo-3-((triisopropylsilyloxy)methyl)phenyl)-tetrahydro-2H-pyran-2-ol (37)

To a solution of 4-bromo-1-iodobenzene 36 (18.1 g, 38.5 mmol) at −60° C. was added dropwise isopropylmagnesium chloride lithium chloride complex (1.0 M in THF, 50 mL), and the mixture was stirred for 30 min at the same temperature. Then a solution of lactone 1 (26.9 g, 50.0 mmol) in THF (30 mL) was added dropwise. The mixture was allowed to slowly warn to −5° C. over 1 h. To a mixture was added aq. saturated NH₄Cl solution to quench the reaction. After dilution with water, the mixture was extracted with EtOAc. The organic layer was washed with brine, dried over anhydrous MgSO₄, filtered and evaporated in vacuo to yield the crude titled compound 37, which was carried on to the next step without further purification.

Preparation Example 13

2-(2-Methyl-5-((3S,4R,5R,6R)-3,4,5-tris(benzyloxy)-6-(benzyloxymethyl)-tetrahydro-2H-pyran-2-yl)phenyl)acetonitrile (41)

To a solution of bromide 40 (7.11 g, 10.0 mmol) in CH₃CN (100 mL) were added potassium cyanide (1.0 g, 15.1 mmol) and 18-crown-6 (4.0 g, 15.1 mmol) at room temperature. The mixture was stirred at 85° C. for 1 h. The mixture was cooled to room temperature and concentrated in vacuo. After dilution with water, the mixture was extracted with EtOAc. The organic layer was dried over anhydrous MgSO₄, filtered and concentrated in vacuo. The residue was purified by silica column chromatography to provide beta and alpha anomeric mixture 41 (3.7 g, 57%).

¹H NMR (400 MHz, CDCl₃) β-anomer: δ 7.41-7.25 (m, 16H), 7.23-7.16 (m, 5H), 6.96-6.89 (m, 2H), 4.96-4.84 (m, 3H), 4.66-4.54 (m, 3H), 4.44 (d, J=10.4 Hz, 1H), 4.22 (d, J=9.6 Hz, 1H), 3.84 (d, J=10.4 Hz, 1H), 3.82-3.72 (m, 4H), 3.64-3.56 (m, 3H), 3.49 (t, J=9.2 Hz, 1H), 2.37 (s, 3H); MNa+676.

Preparation Example 14

1-(2-Chloro-5-((2S,3S,4R,5R,6R)-3,4,5-tris(benzyloxy)-6-(benzyloxymethyl)-tetrahydro-2H-pyran-2-yl)phenyl)cyclopropanecarboxylic acid (43)

Step 1: 1-(2-chloro-5-((2S,3S,4R,5R,6R)-3,4,5-tris (benzyloxy)-6-(benzyloxymethyl)-tetrahydro-2H-pyran-2-yl)phenyl)cyclopropanecarbonitrile (42)

To a solution of β-39 (4.0 g, 5.93 mmol) in toluene (40 mL) were added 1,2-dibromethane (0.8 mL, 8.90 mmol), tetrabutylammonium bromide (0.4 g, 1.19 mmol) and aq. 50% NaOH solution (40 mL). The mixture was stirred at room temperature for 15 h. After dilution with water, the mixture was extracted with EtOAc. The organic layer was dried over anhydrous MgSO₄, filtered and concentrated in vacuo. The residue was purified by silica column chromatography to provide the titled compound 42 (3.0 g, 71%).

¹H NMR (400 MHz, CDCl₃) β 7.42-7.25 (m, 16H), 7.23-7.17 (m, 5H), 6.92-6.86 (m, 2H), 4.95 (t, J=12.0 Hz, 2H), 4.86 (d, J=10.8 Hz, 1H), 4.67-4.51 (m, 4H), 4.19 (d, J=9.6 Hz, 1H), 3.88 (d, J=10.4 Hz, 1H), 3.84-3.72 (m, 4H), 3.62-3.55 (m, 1H), 3.41 (t, d, J 8.8 Hz, 1H), 1.73-1.64 (m, 2H), 1.29-1.23 (m, 1H), 1.21-1.15 (m, 1H); MNa+722.

Step 2: 1-(2-Chloro-5-((2S,3S,4R,5R,6R)-3,4,5-tris (benzyloxy)-6-(benzyloxymethyl)-tetrahydro-2H-pyran-2-yl)phenyl)cyclopropanecarboxylic acid (43)

To a solution of cyanide 42 (3.0 g, 4.25 mmol) in EtOH/H₂O (20 mL/20 mL) was added NaOH (20.5 g, 423 mmol). The mixture was stirred at 110° C. for 15 hours. The mixture was cooled to room temperature and evaporated in vacuo to remove EtOH. The residue was diluted with H₂O, cooled to 0° C. and acidified with c-HCl solution. The titled compound 43 was precipitated as a solid, dissolved with EtOAc and extracted. The organic layer was dried over anhydrous MgSO₄, filtered and concentrated in vacuo to provide the titled compound 43 (2.89 g, 99%).

¹H NMR (400 MHz, CDCl₃) δ 7.38-7.23 (m, 16H), 7.21-7.10 (m, 5H), 6.90-6.85 (m, 2H), 4.92 (q, J=11.2 Hz, 2H), 4.85 (d, J=10.8 Hz, 1H), 4.66-4.52 (m, 4H), 4.39 (d, J=10.4 Hz, 1H), 4.18 (d, J=9.6 Hz, 1H), 3.82-3.71 (m, 5H), 3.59-3.54 (m, 1H), 3.45-3.39 (m, 1H), 1.79-1.69 (m, 2H), 1.28-1.21 (m, 1H), 1.17-1.11 (m, 1H); MNa+741.

Preparation Example 15 tert-Butyl 2-(methoxy(methyl)amino)-2-oxoethylcarbamate (45)

To a mixture of N-Boc-glycine 44 (10.0 g, 57.1 mmol), N,O-dimethylhydroxylamine hydrochloride (6.68 g, 68.5 mmol), EDCI (13.1 g, 68.5 mmol), and HOBt (9.26 g, 68.5 mmol) in CH₂Cl₂ (200 mL) was added NMM (31.4 mL, 285 mmol). The resulting mixture was stirred at room temperature for 15 h. The reaction mixture was poured into 1.0 M HCl solution, and extracted with EtOAc. The organic phase was washed with a saturated NaHCO₃ solution and brine, and then dried over anhydrous MgSO₄. After evaporation of solvent, the residue was triturated with hexanes (100 mL) to provide the Weinreb amide 45 (10.2 g, 82%) as white solid.

Preparation Example 16

2-Amino-1-(thiophen-3-yl)ethanone hydrochloride

Step 1: tert-Butyl 2-oxo-2-(thiophen-3-yl)ethylcarbamate

To a solution of the Weinreb amide 45 (1.53 g, 7 mmol) in anhydrous THF (10 mL) was added dropwise (over a 10-min period) a solution of thiophen-3-ylmagnesium iodide (0.3 M in THF, 50 mL) under nitrogen atmosphere at 0° C. The reaction mixture was allowed to warm to room temperature and stirred for 18 h. The mixture was poured into a saturated NH₄Cl solution and extracted with EtOAc. The organic phase was dried over anhydrous MgSO₄, filtered and evaporated under vacuum. The residue was further purified by silica column chromatography to provide the titled compound (776 mg, 46%). MNa+264.

Step 2: 2-Amino-1-(thiophen-3-yl)ethanone hydrochloride

To a mixture of tert-butyl 2-oxo-2-(thiophen-3-yl)ethylcarbamate (776 mg, 3.21 mmol) in $Et_2O$ (3 mL) was added a HCl solution (4.0 M in dioxane, 6 mL) at 0° C. After stirring at 0° C. for 10 min, the resulting mixture was allowed warmed up to room temperature and stirred for 2 h. The reaction mixture was evaporated under vacuum to provide the titled compound (570 mg, quantitative) as a white solid. MH+142.

Preparation Example 17 tert-Butyl 2-(furan-3-yl)-2-oxoethylcarbamate

To a solution of n-BuLi (2.5 M in hexane, 7.68 mL) in anhydrous ether (10 mL) was added dropwise (over a 20-min period) a solution of 3-bromofuran (2.35 g, 16 mmol) in anhydrous THF (15 mL) under nitrogen atmosphere at −78° C. After stirring at −78° C. for 20 min, a solution of the Weinreb amide 45 (1.75 g, 8 mmol) in THF (15 mL) was added slowly to the mixture. The reaction mixture was allowed to warm to room temperature and stirred for 18 h. The mixture was poured into a saturated $NaHCO_3$ solution and extracted with EtOAc. The organic phase was dried over anhydrous $MgSO_4$, filtered and evaporated under vacuum. The residue was further purified by silica column chromatography to provide the titled compound (671 mg, 37%). MNa+ 248.

Preparation Example 18

S-Butyl 2-(tert-butoxycarbonylamino)ethanethioate

To a mixture of N-Boc-glycine 44 (3.50 g, 20 mmol), EDCI (4.22 g, 22 mmol), and HOBt (2.97 g, 22 mmol) in $CH_2Cl_2$ (100 mL) was added DIEA (8.71 mL, 50 mmol). After stirring at room temperature for 1 h, 1-buthanethiol (5.37 mL, 50 mmol) was added and the resulting mixture was stirred for 15 h. The reaction mixture was poured into 1.0 M HCl solution, and extracted with $CH_2Cl_2$. The organic phase was washed with a saturated $NaHCO_3$ solution, brine and dried over anhydrous $MgSO_4$. The solution was evaporated under vacuum to provide the titled compound (1.72 g, 35%), which was carried on to the next step without further purification. MNa+270.

Preparation Example 19

Propyl 2-aminoacetate hydrochloride

To a solution of glycine hydrochloride 46 (4.5 g, 40.3 mmol) in n-propanol (60 mL) was slowly added $SOCl_2$ (13.5 mL) at room temperature. The reaction mixture was stirred at 70° C. for 15 h. After cooling to room temperature, the mixture was evaporated under vacuum to provide the titled compound (6.1 g, 98%) as a white solid. MH+118.

Preparation Example 20

1-Amino-3-(2-chloro-5-((2S,3S,4R,5R,6R)-3,4,5-tris (benzyloxy)-6-(benzyloxymethyl)-tetrahydro-2H-pyran-2-yl)phenyl)propan-2-one hydrochloride (Route A)

Step 1: 1-(2-Chloro-5-((2S,3S,4R,5R,6R)-3,4,5-tris (benzyloxy)-6-(benzyloxymethyl)-tetrahydro-2H-pyran-2-yl)phenyl)-3-diazopropan-2-one To a solution of the carboxylic acid 55 (4.5 g, 6.49 mmol) in $CH_2Cl_2$ (25 mL) under nitrogen atmosphere was added oxalyl chloride (0.85 mL, 9.74 mmol) and DMF (0.2 mL) at 0° C. After an additional stirring at 0° C. for 15 min, the reaction mixture was stirred at room temperature for 5 h. The mixture was evaporated under vacuum to provide acyl chloride (4.70 g).

The residue was dissolved in $CH_2Cl_2$ (25 mL) and slowly added to a solution of (trimethylsilyl)diazomethane (2.0 M in ether, 6.49 mL) in anhydrous $CH_2Cl_2$ (27 mL) under nitrogen atmosphere at −30° C. The reaction mixture was gradually warmed to room temperature over a period of 3 h, and then quenched with MeOH. The mixture was evaporated under vacuum and the residue was further purified by silica column chromatography to provide the titled compound (2.09 g, 45%). MNa+739.

Step 2: 1-Amino-3-(2-chloro-5-((2S,3S,4R,5R,6R)-3,4,5-tris(benzyloxy)-6-(benzyloxymethyl)-tetrahydro-2H-pyran-2-yl)phenyl)propan-2-one hydrochloride To a solution of α-diazoketone compound (2.09 g, 2.91 mmol) from Step 1 in $Et_2O/CH_2Cl_2$ (4:1, 32 mL) was added c-HBr (1.15 mL) at 0° C. After stirring at 0° C. for 30 min, the mixture was quenched using a saturated $NaHCO_3$ solution and extracted with EtOAc. The organic phase was washed with brine, dried over anhydrous $MgSO_4$, filtered and evaporated under vacuum to afford α-bromoketone compound (2.19 g, 98%) as a yellow solid. MNa+793.

The crude α-bromoketone compound (2.19 g, 2.84 mmol) was dissolved in $CH_2Cl_2$ (12 mL), and hexamethylenetetramine (490 mg, 3.50 mmol) was added at room temperature. After stirring for 3 h, the white suspension was evaporated under vacuum to remove the voliatile solvent.

The crude quaternary ammonium salt was redissolved in $CH_2Cl_2$/EtOH (1:1, 35 mL) and stirred at 0° C. To a resulting solution was added c-HCl (4.4 mL) and stirred at 0° C. for 30 min. After an additional stirring at room temperature for 3 h, the mixture was poured into brine and extracted with $CH_2Cl_2$. The organic phase was dried over anhydrous $MgSO_4$, filtered and evaporated under vacuum to provide the titled compound (2.11 g, quantitative) as a pale brown solid.

$^1$H NMR (400 MHz, $CDCl_3$) δ 7.32-7.13 (m, 21H), 6.89-6.87 (m, 2H), 4.91-4.80 (m, 4H), 4.59-4.45 (m, 5H), 4.17 (d, J=9.6 Hz, 1H), 3.88-3.58 (m, 9H). MH+706.

Preparation Example 21

1-Amino-3-(2-chloro-5-((2S,3S,4R,5R,6R)-3,4,5-tris (benzyloxy)-6-(benzyloxymethyl)-tetrahydro-2H-pyran-2-yl)phenyl)propan-2-one hydrochloride (Route B)

Step 1: 1-(2-Chloro-5-((2S,3S,4R,5R,6R)-3,4,5-tris (benzyloxy)-6-(benzyloxymethyl)-tetrahydro-2H-pyran-2-yl)phenyl)-3-nitropropan-2-one To a anhydrous THF (22 mL) solution of the carboxylic acid 55 (2.97 g, 4.28 mmol) was added 1,1'-carbonyl diimidazole (800 mg, 4.93 mmol) at room temperature. In separate flask, nitromethane (0.92 mL, 17.12 mmol) was added to a THF (9 mL) solution of NaH (200 mg, 4.93 mmol). The resulting white suspension was stirred at room temperature for 3 h. Then the prepared acyl imidazole solution was added to the suspension through a cannula at room temperature. After the transfer, the mixture was heated to 50° C. for 1.5 h. It was cooled to room temperature and quenched with 1.0 M HCl. The organic layer was extracted with ethyl acetate, dried over anhydrous $MgSO_4$, filtered and concentrated in vacuo. The residue was purified by silica column chromatography to provide the titled compound (3.13 g, 99%).

$^1$H NMR (400 MHz, $CDCl_3$) δ 7.43-7.37 (m, 3H), 7.34-7.29 (m, 13H), 7.22-7.14 (m, 5H), 6.95-6.92 (m, 2H), 5.22 (s, 2H), 4.93 (s, 2H), 4.86 (d, J=10.8 Hz, 1H), 4.64-4.51 (m, 4H), 4.21 (d, J=9.6 Hz, 1H), 3.94-3.87 (m, 2H), 3.83-3.67 (m, 5H), 3.61-3.58 (m, 1H), 3.42 (t, d, J=8.8 Hz, 1H); MNa+758.

Step 2: 1-Amino-3-(2-chloro-5-((2S,3S,4R,5R,6R)-3,4,5-tris(benzyloxy)-6-(benzyloxymethyl)-tetrahydro-2H-pyran-2-yl)phenyl)propan-2-one hydrochloride (Route B)

To the ethyl acetate (23 mL) solution of the nitro ketone (1.7 g, 2.31 mmol) from step 1 was added Tin(II) chloride dehydrate (1.6 g, 6.93 mmo) under nitrogen atmosphere. The mixture was then heated to reflux for 5 h. It was cooled to room temperature and concentrated. The residue was purified by reverse-phase filtration on a C18 column using 0.1% TFA/MeOH and 0.1% TFA/water as solvents to give the pure amino ketone TFA salt. The amino ketone TFA salt was converted to the corresponding amino ketone HCl salt using 2.0 M HCl in ether solution at 0° C. and evaporated under vacuum to provide the titled compound HCl salt (1.55 g, 90%) as a white solid.

$^1$H NMR (400 MHz, $CD_3OD$) δ 7.40-7.36 (m, 3H), 7.34-7.29 (m, 3H), 7.29-7.22 (m, 10H), 7.18-7.14 (m, 5H), 6.93-6.90 (m, 2H), 4.89-4.85 (m, 2H), 4.83-4.79 (m, 1H), 4.61-4.55 (m, 2H), 4.48 (d, J=12.0 Hz, 1H), 4.40 (d, J=10.8 Hz, 1H), 4.23 (d, J=9.2 Hz, 1H), 4.07 (s, 2H), 4.01 (d, J=12.4 Hz, 1H), 3.90 (d, J=10.8 Hz, 1H), 3.78-3.66 (m, 5H), 3.58 (dt, J=9.6, 3.2 Hz, 1H), 3.46 (t, J=9.2 Hz, 1H); MH+706.

Preparation of the Thiazole Derivatives

Example 1

(2S,3R,4R,5S,6R)-2-(4-Chloro-3-((5-(thiophen-3-yl)thiazol-2-yl)methyl)phenyl)-6-(hydroxymethyl)-tetrahydro-2H-pyran-3,4,5-triol (48)

Step 1: 2-(2-Chloro-5-((2S,3S,4R,5R,6R)-3,4,5-tris(benzyloxy)-6-(benzyloxymethyl)-tetrahydro-2H-pyran-2-yl)phenyl)-N-(2-oxo-2-(thiophen-3-yl)ethyl)acetamide To a mixture of the carboxylic acid 55 (1.04 g, 1.5 mmol), 2-amino-1-(thiophen-3yl)ethanone hydrochloride (533 mg, 3.0 mmol), EDCI (575 mg, 3.0 mmol), and HOBt (507 mg, 3.75 mmol) in DMF (10 mL) was added NMM (0.83 mL, 7.5 mmol). The resulting mixture was stirred at room temperature for 15 h. The reaction mixture was poured into a HCl solution (1.0 M, 50 mL), and extracted with EtOAc. The organic phase was dried over anhydrous $MgSO_4$, filtered and evaporated under vacuum. The residue was further purified by silica column chromatography to provide the titled amide compound (529 mg, 0.65 mmol, 43%).

MH+816.

Step 2: 2-(2-Chloro-5-((2S,3S,4R,5R,6R)-3,4,5-tris(benzyloxy)-6-(benzyloxymethyl)-tetrahydro-2H-pyran-2-yl)benzyl)-5-(thiophen-3-yl)thiazole (47)

To a solution of the amide (529 mg, 0.65 mmol) from Step 1 in anhydrous THF (10 mL) was added Lawesson reagent (524 mg, 1.30 mmol). The reaction mixture was refluxed overnight. After cooling to room temperature, the reaction mixture was poured into a saturated $NaHCO_3$ solution, and extracted with EtOAc. The organic phase was dried over anhydrous $MgSO_4$, filtered and evaporated under vacuum. The residue was further purified by silica column chromatography to provide the titled thiaole compound 47 (482 mg, 91%).

MH+815.

Step 3: (2S,3R,4R,5S,6R)-2-(4-Chloro-3-((5-(thiophen-3-yl)thiazol-2-yl)methyl)phenyl)-6-(hydroxymethyl)-tetrahydro-2H-pyran-3,4,5-triol (48, Case A)

To a solution of the perbenzylated thiaozole compound 50 (308 mg, 0.378 mmol) in acetonitrile (5.0 mL) was added in TMSI (5.0 mL). The resulting mixture was heated at 50° C. for 24 h. After cooling to 0° C., the reaction was quenched with MeOH, and then evaporated under vacuum. The residue was redissolved in MeOH and further purified by prep HPLC (C18) to provide the titled compound 48 (103 mg, 60%) as a white solid.

$^1$H NMR (400 MHz, $CD_3OD_3$) δ 7.80 (s, 1H), 7.53-7.51 (m, 2H), 7.47-7.45 (m, 1H), 7.41-7.36 (m, 2H), 7.31-7.29 (m, 1H), 4.44 (d, J=2.0 Hz, 2H), 4.13 (d, J=9.2 Hz, 1H), 3.84 (d, J=12.0 Hz, 1H), 3.74-3.66 (m, 1H), 3.43-3.30 (m, 4H). MH+454.

Example 2

(2S,3R,4R,5S,6R)-2-(3-((5-(4-Fluorophenyl)thiazol-2-yl)methyl)-4-methoxynaphthalen-1-yl)-6-(hydroxymethyl)-tetrahydro-2H-pyran-3,4,5-triol (50, Case B)

The starting compound 49 was obtained in the same manner as in Example 1 (Step 1 and Step 2).

To a solution of 5-(4-fluorophenyl)-2-((1-methoxy-4-((2S,3S,4R,5R,6R)-3,4,5-tris(benzyloxy)-6-(benzyloxymethyl)-tetrahydro-2H-pyran-2-yl)naphthalen-2-yl)methyl)thiazole 49 (917 mg, 1.05 mmol) in $Ac_2O$ (10 mL) was added TMSOTf (1.53 mL, 8.41 mmol) in $Ac_2O$ (5 mL) at −30° C. The mixture was warmed-up to room temperature and stirred at room temperature for 15 h. After cooling to 0° C., the reaction was quenched by addition of saturated $NaHCO_3$ solution. The mixture was diluted with EtOAc and washed with saturated $NaHCO_3$ solution. The organic layer was dried over anhydrous $MgSO_4$, filtered and concentrated in vacuo. The residue was purified by silica column chromatography to provide the peracetylated compound (655 mg, 92%). MH+685.

To a solution of the peracetylated compound (655 mg, 0.96 mmol) in MeOH (7 mL) was added NaOMe (25 wt. % in MeOH, 0.5 mL). The reaction mixture was stirred at ambient temperature for 3 h. Acetic acid was added to neutralize the reaction mixture and concentrated in vacuo. The residue was redissolved in MeOH and further purified by prep HPLC (C18) to provide the titled compound 50 (278 mg, 0.54 mmol) as a white solid.

$^1$H NMR (400 MHz, DMSO-d$_6$) δ 8.24 (dd, J=7.6, 1.2 Hz, 1H), 8.06-8.02 (m, 2H), 7.62-7.57 (m, 2H), 7.55-7.48 (m, 3H), 7.20 (t, J=8.8 Hz, 2H), 4.99 (br, 2H), 4.79 (d, J=4.8 Hz, 1H), 4.68 (d, J=9.6 Hz, 1H), 4.49 (d, J=15.6 Hz, 1H), 4.44 (d, J=15.6 Hz, 1H), 4.38 (br, 1H), 3.86 (s, 3H), 3.70-3.65 (m, 1H), 3.58-3.50 (m, 1H), 3.48-3.32 (m, 3H), 3.29-3.22 (m, 1H); MH+512.

Example 3

(2S,3R,4R,5S,6R)-2-(4-Chloro-3-(1-(5-(furan-2-yl)thiazol-2-yl)cyclopropyl)phenyl)-6-(hydroxymethyl)-tetrahydro-2H-pyran-3,4,5-triol (52, Case C)

The starting compound 51 was obtained in the same manner as in Example 1 (Step 1 and Step 2).

To a solution of perbenzylated thiazole 51 (306 mg, 0.371 mmol) in CH$_2$Cl$_2$ (10 mL) was added BBr$_3$ (1.0 M in CH$_2$Cl$_2$, 3.0 mL, 2.97 mmol) at 0° C. The mixture was stirred at 0° C. for 20 min. MeOH was added to the mixture to quench the reaction. The mixture was diluted with EtOAc (50 mL), washed with aq. saturated NH$_4$Cl solution and aq. saturated NaHCO$_3$ solution successively. The aqueous layer was back-extracted with EtOAc. The combined organic layers were dried over anhydrous MgSO$_4$, filtered and concentrated in vacuo. The residue was purified by prep HPLC (C18) to provide the titled compound 52 (70 mg, 41%) as a white solid.

$^1$H NMR (400 MHz, CD$_3$OD) δ 7.69 (s, 1H), 7.63 (d, J=1.6 Hz, 1H), 7.48-7.41 (m, 3H), 6.51 (d, J=3.2 Hz, 1H), 6.47-6.41 (m, 1H), 4.84 (s, 4H), 4.17 (d, J=9.6 Hz, 1H), 3.88 (dd, J=12.0, 1.8 Hz, 1H), 3.75-3.67 (m, 1H), 3.53-3.39 (m, 3H), 3.33 (d, J=2.0 Hz, 1H), 1.83-1.77 (m, 2H), 1.58-1.47 (m, 2H); MH+464.

Example 4

(2S,3R,4R,5S,6R)-2-(3-((5-(Furan-2-yl)thiazol-2-yl)methyl)-4-(trifluoromethyl)phenyl)-6-(hydroxymethyl)-tetrahydro-2H-pyran-3,4,5-triol (54, Case D)

The starting compound 53 was obtained in the same manner as in Example 1 (Step 1 and Step 2).

To a solution of perbenzylated thiazole 53 (261 mg, 0.314 mmol) in CH$_2$Cl$_2$ (15 mL) was added BCl$_3$ (1.0 M in CH$_2$Cl$_2$, 2.5 mL, 2.51 mmol) at 0° C. The mixture was stirred at 0° C. for 10 min. MeOH was added to the mixture to quench the reaction. The mixture was concentrated in vacuo. After dilution with water, the residue was extracted with EtOAc/H$_2$O. The combined organic layers were dried over anhydrous MgSO$_4$, filtered and concentrated in vacuo. The residue was purified by prep HPLC (C18) to provide the titled compound 54 (68 mg, 46%) as a white solid.

$^1$H NMR (400 MHz, DMSO-d$_6$) δ 7.95 (s, 1H), 7.77-7.71 (m, 2H), 7.61 (s, 1H), 7.52 (d, J=8.0 Hz, 1H), 6.80 (d, J=2.0 Hz, 1H), 6.61-6.55 (m, 1H), 4.96 (br s, 3H), 4.51 (t, J=16.8 Hz, 3H), 4.14 (d, J=9.2 Hz, 1H), 3.72 (d, J=10.8 Hz, 1H), 3.48 (dd, J=11.6, 5.6 Hz, 1H), 3.32-3.15 (m, 4H); MH+472.

Example 5

(2S,3R,4R,5S,6R)-2-(4-Chloro-3-((5-(furan-2-yl)thiazol-2-yl)methyl)phenyl)-6-(hydroxymethyl)-tetrahydro-2H-pyran-3,4,5-triol (89)

The titled compound was obtained in the same manner as in Example 1.

$^1$H NMR (400 MHz, CD$_3$OD) δ 7.79 (s, 1H), 7.52-7.51 (m, 2H), 7.41-7.35 (m, 2H), 6.61 (d, J=3.2 Hz, 1H), 6.48-6.46 (m, 1H), 4.45 (d, J=2.4 Hz, 2H), 4.13 (d, J=9.2 Hz, 1H), 3.88-3.85 (m, 1H), 3.71-3.66 (m, 1H), 3.46-3.33 (m, 4H); MH+438.

Example 6

(2S,3R,4R,5S,6R)-2-(4-Chloro-3-((5-(furan-3-yl)thiazol-2-yl)methyl)phenyl)-6-(hydroxymethyl)-tetrahydro-2H-pyran-3,4,5-triol The titled compound was obtained in the same manner as in Example 1.

$^1$H NMR (400 MHz, CD$_3$OD) δ 7.77 (s, 1H), 7.71 (s, 1H), 7.55-7.51 (m, 2H), 7.41-7.35 (m, 2H), 6.67 (s, 1H), 4.43 (d, J=2.0 Hz, 2H), 4.13 (d, J=9.6 Hz, 1H), 3.86 (d, J=12.0 Hz, 1H), 3.73-3.66 (m, 1H), 3.43-3.32 (m, 4H): MH+438.

Example 7

(2S,3R,4R,5S,6R)-2-(4-Chloro-3-((5-(thiophen-2-yl)thiazol-2-yl)methyl)phenyl)-6-(hydroxymethyl)tetrahydro-2H-pyran-3,4,5-triol The titled compound was obtained in the same manner as in Example 1.

$^1$H NMR (400 MHz, DMSO-d$_6$) δ 7.72 (s, 1H), 7.52 (d, J=1.6 Hz, 1H), 7.43-7.35 (m, 3H), 7.18 (dd, J=4.0, 1.0 Hz, 1H), 7.05-6.98 (m, 1H), 4.81 (s, 4H), 4.45-4.31 (m, 2H), 4.13 (d, J=9.6 Hz, 1H), 3.88 (dd, J=12.0, 1.6 Hz, 1H), 3.69 (dd, J=12.0, 5.2 Hz, 1H), 3.48-3.25 (m, 4H); MH+454.

Example 8

(2S,3R,4R,5S,6R)-2-(4-Chloro-3-((5-(5-chlorothiophen-2-yl)thiazol-2-yl)methyl)phenyl)-6-(hydroxymethyl)tetrahydro-2H-pyran-3,4,5-triol The titled compound was obtained in the same manner as in Example 1.

$^1$H NMR (400 MHz, DMSO-d$_6$) δ 7.88 (s, 1H), 7.45 (d, J=2.4 Hz, 1H), 7.43-7.38 (m, 1H), 7.29 (dd, J=8.0, 2.0 Hz, 1H), 7.15 (d, J=3.6 Hz, 1H), 7.09 (d, J=4.0 Hz, 1H), 4.92 (br, 4H), 4.45-4.35 (m, 2H), 4.07-3.95 (m, 1H), 3.66 (dd, J=11.6, 1.6 Hz, 1H), 3.47-3.38 (m, 1H), 3.37-3.04 (m, 4H); MH+488.

Example 9

(2S,3R,4R,5S,6R)-2-(3-(2,5'-Bithiazol-2'-ylmethyl)-4-chlorophenyl)-6-(hydroxymethyl)-tetrahydro-2H-pyran-3,4,5-triol The titled compound was obtained in the same manner as in Example 1.

$^1$H NMR (400 MHz, CD$_3$OD) δ 8.12 (s, 1H), 7.76 (d, J=3.2 Hz, 1H), 7.57-7.55 (m, 2H), 7.42-7.37 (m, 2H), 4.49 (d, J=2.4 Hz, 2H), 4.14 (d, J=9.2 Hz, 1H), 3.87 (d, J=12.4 Hz, 1H), 3.73-3.67 (m, 1H), 3.48-3.36 (m, 4H); MH+455.

Example 10

(2S,3R,4R,5S,6R)-2-(4-Chloro-3-((5-(pyridin-2-yl)thiazol-2-yl)methyl)phenyl)-6-(hydroxymethyl)-tetrahydro-2H-pyran-3,4,5-triol The titled compound was obtained in the same manner as in Example 1.

$^1$H NMR (400 MHz, CD$_3$OD) δ 8.46 (d, J=4.8, 1H), 8.19 (s, 1H), 7.82-7.78 (m, 2H), 7.55 (s, 1H), 7.42-7.36 (m, 2H), 7.29-7.24 (m, 1H), 4.48 (d, J=2.8 Hz, 2H), 4.14 (d, J=9.6 Hz, 1H), 3.88-3.85 (m, 1H), 3.72-3.67 (m, 1H), 3.48-3.34 (m, 4H); MH+449.

Example 11

(2S,3R,4R,5S,6R)-2-(4-Chloro-3-((5-(4-fluorophenyl)thiazol-2-yl)methyl)phenyl)-6-(hydroxymethyl)-tetrahydro-2H-pyran-3,4,5-triol The titled compound was obtained in the same manner as in Example 1.
$^1$H NMR (400 MHz, DMSO-$d_6$) δ 8.01 (s, 1H), 7.64-7.59 (m, 2H), 7.47 (s, 1H), 7.41 (d, J=8.0 Hz, 1H), 7.30-7.27 (m, 1H), 7.23-7.18 (m, 2H), 4.40 (d, J=6.0 Hz, 2H), 4.01 (d, J=9.2 Hz, 1H), 3.67 (d, J=10.4 Hz, 1H), 3.44-3.33 (m, 1H), 3.25-3.06 (m, 4H); MH+466.

Example 12

(2S,3R,4R,5S,6R)-2-(4-chloro-3-((5-ethylthiazol-2-yl)methyl)phenyl)-6-(hydroxymethyl)-tetrahydro-2H-pyran-3,4,5-triol The titled compound was obtained in the same manner as in Example 1.
$^1$H NMR (400 MHz, CD$_3$OD) δ 7.47 (s, 1H), 7.39-7.35 (m, 2H), 7.33 (s, 1H), 4.38 (d, J=3.2 Hz, 2H), 4.11 (d, J=9.2 Hz, 1H), 3.88-3.85 (m, 1H), 3.71-3.66 (m, 1H), 3.48-3.33 (m, 4H), 2.79 (q, J=7.6 Hz, 2H), 1.25 (d, J=7.6 Hz, 3H); MH+400.

Example 13

(2S,3R,4R,5S,6R)-2-(3-((5-Butylthiazol-2-yl)methyl)-4-chlorophenyl)-6-(hydroxymethyl)-tetrahydro-2H-pyran-3,4,5-triol The titled compound was obtained in the same manner as in Example 1.
$^1$H NMR (400 MHz, CD$_3$OD) δ 7.48 (s, 1H), 7.39-7.34 (m, 2H), 7.33 (s, 1H), 4.39 (d, J=2.2 Hz, 2H), 4.12 (d, J=9.2 Hz, 1H), 3.89-3.84 (m, 1H), 3.72-3.66 (m, 1H), 3.48-3.33 (m, 4H), 2.77 (t, J=7.2 Hz, 2H), 1.62-1.54 (m, 2H), 1.39-1.30 (m, 2H), 0.91 (t, J=7.2 Hz, 3H); MH+428.

Example 14

(2S,3R,4R,5S,6R)-2-(4-Chloro-3-((5-pentylthiazol-2-yl)methyl)phenyl)-6-(hydroxymethyl)-tetrahydro-2H-pyran-3,4,5-triol The titled compound was obtained in the same manner as in Example 1.
$^1$H NMR (400 MHz, CD$_3$OD) δ 7.47 (s, 1H), 7.39-7.33 (m, 2H), 7.31 (s, 1H), 4.38 (d, J=4.2 Hz, 2H), 4.11 (d, J=9.6 Hz, 1H), 3.88-3.84 (m, 1H), 3.72-3.65 (m, 1H), 3.47-3.33 (m, 4H), 2.76 (t, J=7.2 Hz, 2H), 1.64-1.56 (m, 2H), 1.36-1.26 (m, 4H), 0.88 (t, J=7.2 Hz, 3H); MH+442.

Example 15

(2S,3R,4R,5S,6R)-2-(4-Chloro-3-((5-hexylthiazol-2-yl)methyl)phenyl)-6-(hydroxymethyl)-tetrahydro-2H-pyran-3,4,5-triol The titled compound was obtained in the same manner as in Example 1.
$^1$H NMR (400 MHz, CD$_3$OD) δ 7.48 (s, 1H), 7.39-7.34 (m, 2H), 7.33 (s, 1H), 4.39 (d, J=2.8 Hz, 2H), 4.12 (d, J=9.6 Hz, 1H), 3.88-3.84 (m, 1H), 3.74-3.64 (m, 1H), 3.47-3.32 (m, 4H), 2.77 (t, J=7.6 Hz, 2H), 1.63-1.55 (m, 2H), 1.36-1.25 (m, 6H), 0.87 (t, J=6.8 Hz, 3H); MH+456.

Example 16

(2S,3R,4R,5S,6R)-2-(4-Chloro-3-((5-isopropylthiazol-2-yl)methyl)phenyl)-6-(hydroxymethyl)-tetrahydro-2H-pyran-3,4,5-triol The titled compound was obtained in the same manner as in Example 1.
$^1$H NMR (400 MHz, CD$_3$OD) δ 7.48 (s, 1H), 7.39-7.35 (m, 2H), 7.33 (s, 1H), 4.38 (d, J=2.8 Hz, 2H), 4.12 (d, J=9.6 Hz, 1H), 3.89-3.85 (m, 1H), 3.71-3.66 (m, 1H), 3.48-3.33 (m, 4H), 3.18-3.12 (m, 1H), 1.27 (d, J=7.2 Hz, 6H); MH+414.

Example 17

(2S,3R,4R,5S,6R)-2-(3-((5-Allylthiazol-2-yl)methyl)-4-chlorophenyl)-6-(hydroxymethyl)-tetrahydro-2H-pyran-3,4,5-triol The titled compound was obtained in the same manner as in Example 1.
$^1$H NMR (400 MHz, CD$_3$OD) δ 7.48 (s, 1H), 7.39-7.34 (m, 3H), 6.52 (s, 1H), 6.48 (s, 1H), 6.02-5.94 (m, 1H), 4.38 (d, J=2.8 Hz, 2H), 4.12 (d, J=9.2 Hz, 1H), 3.88-3.84 (m, 1H), 3.71-3.66 (m, 1H), 3.48-3.33 (m, 4H), 1.81 (d, J=6.4 Hz, 2H); MH+412.

Example 18

(2S,3R,4R,5S,6R,E)-2-(3-((5-(but-2-en-2-yl)thiazol-2-yl)methyl)-4-chlorophenyl)-6-(hydroxymethyl)-tetrahydro-2H-pyran-3,4,5-triol The titled compound was obtained in the same manner as in Example 1.
$^1$H NMR (400 MHz, CD$_3$OD) δ 7.48 (s, 1H), 7.46 (s, 1H), 7.39-7.34 (m, 2H), 5.86 (q, J=6.8 Hz, 1H), 4.37 (d, J=2.8 Hz, 2H), 4.12 (d, J=9.2 Hz, 1H), 3.88-3.84 (m, 1H), 3.71-3.66 (m, 1H), 3.48-3.34 (m, 4H), 1.98 (s, 3H), 1.74 (d, J=7.2 Hz, 3H); MH+426.

Example 19

(2S,3R,4R,5S,6R)-2-(4-Chloro-3-((5-cyclopentylthiazol-2-yl)methyl)phenyl)-6-(hydroxymethyl)-tetrahydro-2H-pyran-3,4,5-triol The titled compound was obtained in the same manner as in Example 1.
$^1$H NMR (400 MHz, CD$_3$OD) δ 7.49 (s, 1H), 7.43 (s, 1H), 7.40-7.35 (m, 2H), 4.43 (d, J=1.6 Hz, 2H), 4.12 (d, J=9.2 Hz, 1H), 3.89-3.84 (m, 1H), 3.71-3.66 (m, 1H), 3.48-3.33 (m, 4H), 3.24-3.22 (m, 1H), 2.15-2.06 (m, 2H), 1.82-1.74 (m, 2H), 1.73-1.64 (m, 2H), 1.59-1.52 (m, 2H); MH+440.

Example 20

(2S,3R,4R,5S,6R)-2-(4-Chloro-3-((5-cyclohexylthiazol-2-yl)methyl)phenyl)-6-(hydroxymethyl)-tetrahydro-2H-pyran-3,4,5-triol The titled compound was obtained in the same manner as in Example 1.
$^1$H NMR (400 MHz, CD$_3$OD) δ 7.47 (s, 1H), 7.38-7.34 (m, 2H), 7.33 (s, 1H), 4.38 (d, J=3.2 Hz, 2H), 4.11 (d, J=9.6 Hz, 1H), 3.88-3.84 (m, 1H), 3.71-3.66 (m, 1H), 3.48-3.33 (m, 4H), 2.84-2.77 (m, 1H), 1.98-1.93 (m, 2H), 1.82-1.64 (m, 3H), 1.45-1.31 (m, 4H), 1.28-1.22 (m, 1H); MH+454.

Example 21

(2S,3R,4R,5S,6R)-2-(4-Chloro-3-((5-ethoxythiazol-2-yl)methyl)phenyl)-6-(hydroxymethyl)-tetrahydro-2H-pyran-3,4,5-triol The titled compound was obtained in the same manner as in Example 1.
$^1$H NMR (400 MHz, CD$_3$OD) δ 7.45 (s, 1H), 7.38-7.33 (m, 2H), 6.92 (s, 1H), 4.28 (d, J=2.4 Hz, 2H), 4.11 (d, J=9.6 Hz, 1H), 4.06 (q, J=6.8 Hz, 2H), 3.86 (d, J=12.0 Hz, 1H), 3.72-3.66 (m, 1H), 3.48-3.30 (m, 4H), 1.34 (t, J=6.8 Hz, 3H); MH+416.

Example 22

(2S,3R,4R,5S,6R)-2-(4-Chloro-3-((5-propoxythiazol-2-yl)methyl)phenyl)-6-(hydroxymethyl)-tetrahydro-2H-pyran-3,4,5-triol The titled compound was obtained in the same manner as in Example 1.
$^1$H NMR (400 MHz, CD$_3$OD) δ 7.45 (s, 1H), 7.38-7.32 (m, 2H), 6.92 (s, 1H), 4.28 (d, J=2.8 Hz, 2H), 4.11 (d, J=9.6 Hz, 1H), 3.97 (t, J=6.4 Hz, 2H), 3.88-3.84 (m, 1H), 3.72-3.66 (m, 1H), 3.48-3.30 (m, 4H), 1.79-1.70 (m, 2H), 0.98 (t, J=7.6 Hz, 3H); MH+430.

Example 23

(2S,3R,4R,5S,6R)-2-(4-Chloro-3-((5-(pentyloxy)thiazol-2-yl)methyl)phenyl)-6-(hydroxymethyl)-tetrahydro-2H-pyran-3,4,5-triol The titled compound was obtained in the same manner as in Example 1.
$^1$H NMR (400 MHz, CD$_3$OD) δ 7.45 (s, 1H), 7.39-7.33 (m, 2H), 6.92 (s, 1H), 4.28 (d, J=2.8 Hz, 2H), 4.11 (d, J=9.6 Hz, 1H), 4.00 (t, J=6.4 Hz, 2H), 3.88-3.84 (m, 1H), 3.71-3.66 (m, 1H), 3.47-3.30 (m, 4H), 1.76-1.69 (m, 2H), 1.41-1.32 (m, 4H), 0.91 (t, J=7.2 Hz, 3H); MH+458.

Example 24

(2S,3R,4R,5S,6R)-2-(4-Chloro-3-((5-(ethylthio)thiazol-2-yl)methyl)phenyl)-6-(hydroxymethyl)-tetrahydro-2H-pyran-3,4,5-triol The titled compound was obtained in the same manner as in Example 1.
$^1$H NMR (400 MHz, CD$_3$OD) δ 7.57 (s, 1H), 7.50 (s, 1H), 7.40-7.35 (m, 2H), 4.42 (d, J=2.4 Hz, 2H), 4.12 (d, J=9.6 Hz, 1H), 3.88-3.84 (m, 1H), 3.71-3.66 (m, 1H), 3.47-3.30 (m, 4H), 2.75 (q, J=7.6 Hz, 2H), 1.21 (t, J=7.6 Hz, 3H); MH+432.

Example 25

(2S,3R,4R,5S,6R)-2-(4-Chloro-3-((5-(propylthio)thiazol-2-yl)methyl)phenyl)-6-(hydroxymethyl)-tetrahydro-2H-pyran-3,4,5-triol The titled compound was obtained in the same manner as in Example 1.
$^1$H NMR (400 MHz, CD$_3$OD) δ 7.55 (s, 1H), 7.50 (s, 1H), 7.40-7.35 (m, 2H), 4.41 (d, J=2.4 Hz, 2H), 4.12 (d, J=9.2 Hz, 1H), 3.88-3.84 (m, 1H), 3.71-3.65 (m, 1H), 3.47-3.30 (m, 4H), 2.72 (t, J=7.2 Hz, 2H), 1.61-1.52 (m, 2H), 0.96 (t, J=7.2 Hz, 3H); MH+446.

Example 26

(2S,3R,4R,5S,6R)-2-(3-((5-(Butylthio)thiazol-2-yl)methyl)-4-chlorophenyl)-6-(hydroxymethyl)-tetrahydro-2H-pyran-3,4,5-triol The titled compound was obtained in the same manner as in Example 1.
$^1$H NMR (400 MHz, CD$_3$OD) δ 7.59 (s, 1H), 7.51 (s, 1H), 7.41-7.35 (m, 2H), 4.30 (d, J=2.0 Hz, 2H), 4.13 (d, J=9.2 Hz, 1H), 3.88-3.84 (m, 1H), 3.72-3.66 (m, 1H), 3.48-3.35 (m, 4H), 2.76 (t, J=7.2 Hz, 2H), 1.56-1.50 (m, 2H), 1.43-1.36 (m, 2H), 0.88 (t, J=7.6 Hz, 3H); MH+460.

Example 27

(2S,3R,4R,5S,6R)-2-(4-Chloro-3-((5-(pentylthio)thiazol-2-yl)methyl)phenyl)-6-(hydroxymethyl)-tetrahydro-2H-pyran-3,4,5-triol The titled compound was obtained in the same manner as in Example 1.
$^1$H NMR (400 MHz, CD$_3$OD) δ 7.55 (s, 1H), 7.50 (s, 1H), 7.40-7.35 (m, 2H), 4.41 (d, J=2.0 Hz, 2H), 4.12 (d, J=9.2 Hz, 1H), 3.88-3.85 (m, 1H), 3.71-3.67 (m, 1H), 3.48-3.30 (m, 4H), 2.74 (t, J=7.2 Hz, 2H), 1.58-1.51 (m, 2H), 1.38-1.26 (m, 4H), 0.87 (t, J=7.2 Hz, 3H); MH+474.

Example 28

(2S,3R,4R,5S,6R)-2-(4-Chloro-3-(1-(5-(furan-3-yl)thiazol-2-yl)cyclopropyl)phenyl)-6-(hydroxymethyl)tetrahydro-2H-pyran-3,4,5-triol The titled compound was obtained in the same manner as in Example 3.
$^1$H NMR (400 MHz, DMSO-d$_6$) δ 7.70 (s, 1H), 7.68-7.58 (m, 2H), 7.45 (d, J=1.6 Hz, 1H), 7.49-7.39 (m, 2H), 6.66-6.02 (m, 1H), 4.87 (s, 4H), 4.17 (d, J=9.2 Hz, 1H), 3.89 (dd, J=12.0, 2.0 Hz, 1H), 3.71 (dd, J=12.0, 5.6 Hz, 1H), 3.51-3.31 (m, 4H), 1.85-1.61 (m, 2H), 1.53-1.44 (m, 21-1); MH+464.

Example 29

(2S,3R,4R,5S,6R)-2-(4-Chloro-3-(1-(5-(thiophen-2-yl)thiazol-2-yl)cyclopropyl)phenyl)-6-(hydroxymethyl)tetrahydro-2H-pyran-3,4,5-triol The titled compound was obtained in the same manner as in Example 3.
$^1$H NMR (400 MHz, DMSO-d$_6$) δ 7.63 (s, 2H), 7.48-7.41 (m, 2H), 7.33 (dd, J=5.2, 1.2 Hz, 1H), 7.11 (dd, J=5.2, 1.2 Hz, 1H), 7.04-6.97 (m, 1H), 4.85 (s, 4H), 4.17 (d, J=9.2 Hz, 1H), 3.89 (dd, J=12.0, 1.8 Hz, 1H), 3.71 (dd, J=12.0, 5.6 Hz, 1H), 3.51-3.37 (m, 4H), 1.87-1.65 (m, 2H), 1.53-1.48 (m, 2H); MH+480.

Example 30

(2S,3R,4R,5S,6R)-2-(3-((5-(Furan-2-yl)thiazol-2-yl)methyl)-4-methylphenyl)-6-(hydroxymethyl)tetrahydro-2H-pyran-3,4,5-triol The titled compound was obtained in the same manner as in Example 1.

$^1$H NMR (400 MHz, DMSO-d$_6$) δ 7.89 (s, 1H), 7.68 (d, J=1.6 Hz, 1H), 7.25 (s, 1H), 7.17-7.08 (m, 2H), 6.73 (d, J=3.2 Hz, 1H), 6.57-6.51 (m, 1H), 4.90 (d, J=4.0 Hz, 2H), 4.72 (d, J=5.6 Hz, 1H), 4.41 (t, J=5.6 Hz, 1H), 4.33-4.25 (m, 2H), 3.84 (d, J=9.2 Hz, 1H), 3.71-3.63 (m, 1H), 3.45-3.36 (m, 1H), 3.27-3.08 (m, 4H), 2.21 (s, 3H), MH+418.

Example 31

(2S,3R,4R,5S,6R)-2-(4-Chloro-2-ethoxy-5-((5-(furan-3-yl)thiazol-2-yl)methyl)phenyl)-6-(hydroxymethyl)tetrahydro-2H-pyran-3,4,5-triol The titled compound was obtained in the same manner as in Example 1.

$^1$H NMR (400 MHz, DMSO-d$_6$) δ 8.00 (s, 1H), 7.83 (m, 1H), 7.70 (t, J=1.6 Hz, 1H), 7.24 (s, 1H), 7.17-7.08 (m, 2H), 6.85-6.80 (m, 1H), 4.74 (s, 4H), 4.31-4.19 (m, 2H), 3.94 (d, J=9.2 Hz, 1H), 3.66 (dd, J=12.0, 1.6 Hz, 1H), 3.38 (dd, J=12.0, 6.0 Hz, 1H), 3.25-3.07 (m, 4H), 2.21 (s, 3H); MH+418.

Example 32

(2R,3S,4R,5R,6S)-2-(Hydroxymethyl)-6-(4-methyl-3-((5-(thiophen-2-yl)thiazol-2-yl)methyl)phenyl)tetrahydro-2H-pyran-3,4,5-triol The titled compound was obtained in the same manner as in Example 1.

$^1$H NMR (400 MHz, CD$_3$OD) δ 7.72 (s, 1H), 7.38-7.34 (m, 2H), 7.27 (dd, J=8.0, 1.6 Hz, 1H), 7.23-7.16 (m, 2H), 7.05-6.98 (m, 1H), 4.84 (s, 4H), 4.32 (s, 2H), 4.10 (d, J=9.2 Hz, 1H), 3.86 (dd, J=12.0, 2.0 Hz, 1H), 3.70 (dd, J=12.0, 5.6 Hz, 1H), 3.48-3.32 (m, 4H); MH+434.

Example 33

(2R,3S,4R,5R,6S)-2-(Hydroxymethyl)-6-(4-methyl-3-((5-(thiophen-3-yl)thiazol-2-yl)methyl)phenyl)tetrahydro-2H-pyran-3,4,5-triol The titled compound was obtained in the same manner as in Example 1.

$^1$H NMR (400 MHz, DMSO-d$_6$) δ 7.88 (s, 1H), 7.54-7.49 (m, 2H), 7.39-7.33 (m, 1H), 7.31-7.25 (m, 2H), 7.18 (d, J=7.6 Hz, 1H), 4.84 (s, 4H), 4.34 (s, 2H), 4.10 (d, J=9.2 Hz, 1H), 3.86 (dd, J=12.0, 2.0 Hz, 1H), 3.68 (dd, J=12.0, 5.6 Hz, 1H), 3.48-3.31 (m, 4H), 2.20 (s, 3H); MH+434.

Example 34

(2S,3R,4R,5S,6R)-2-(3-(2,5'-Bithiazol-2'-ylmethyl)-4-methylphenyl)-6-(hydroxymethyl)tetrahydro-2H-pyran-3,4,5-triol The titled compound was obtained in the same manner as in Example 1.

$^1$H NMR (400 MHz, DMSO-d$_6$) δ 8.25 (s, 1H), 7.81 (d, J=2.0 Hz, 1H), 7.76 (d, J=2.4 Hz, 1H), 7.30 (s, 1H), 7.20-7.11 (m, 2H), 4.86 (s, 4H), 4.39-4.28 (m, 2H), 4.00 (d, J=9.2 Hz, 1H), 3.69 (dd, J=12.0, 1.2 Hz, 1H), 3.44 (dd, J=12.0, 5.6 Hz, 1H), 3.25-3.13 (m, 4H), 2.26 (s, 3H); MH+435.

Example 35

(2R,3S,4R,5R,6S)-2-(Hydroxymethyl)-6-(4-methyl-3-((5-phenylthiazol-2-yl)methyl)phenyl)tetrahydro-2H-pyran-3,4,5-triol The titled compound was obtained in the same manner as in Example 1.

$^1$H NMR (400 MHz, CD$_3$OD) δ 7.88 (s, 1H), 7.54-7.49 (m, 2H), 7.39-7.33 (m, 3H), 7.31-7.25 (m, 2H), 7.18 (d, J=7.6 Hz, 1H), 4.84 (s, 4H), 4.34 (s, 2H), 4.10 (d, J=9.2 Hz, 1H), 3.86 (dd, J=12.0, 2.0 Hz, 1H), 3.68 (dd, J=12.0, 5.6 Hz, 1H), 3.48-3.31 (m, 4H); MH+ 428.

Example 36

(2R,3S,4R,5R,6S)-2-(Hydroxymethyl)-6-(4-methyl-3-((5-p-tolylthiazol-2-yl)methyl)phenyl)tetrahydro-2H-pyran-3,4,5-triol The titled compound was obtained in the same manner as in Example 1.

$^1$H NMR (400 MHz, DMSO-d$_6$) δ 7.98 (s, 1H), 7.43 (d, J=8.0 Hz, 1H), 7.25 (s, 1H), 7.19-7.08 (m, 4H), 4.90 (br, 2H), 4.73 (br, 1H), 4.42 (s, 1H), 4.32-4.21 (m, 2H), 3.94 (d, J=8.8 Hz, 1H), 3.67 (d, J=10.4 Hz, 1H), 3.41 (dd, J=12.0, 5.6 Hz, 1H), 3.27-3.07 (m, 4H), 2.26 (s, 3H), 2.23 (s, 3H); MH+442.

Example 37

(2S,3R,4R,5S,6R)-2-(3-((5-(4-Fluorophenyl)thiazol-2-yl)methyl)-4-methylphenyl)-6-(hydroxymethyl)tetrahydro-2H-pyran-3,4,5-triol The titled compound was obtained in the same manner as in Example 1.

$^1$H NMR (400 MHz, DMSO-d$_6$) δ 8.01 (s, 1H), 7.65-7.56 (m, 2H), 7.25 (s, 1H), 7.23-7.18 (m, 2H), 7.15-7.07 (m, 2H), 4.84 (s, 4H), 4.32-4.22 (m, 2H), 3.94 (d, J=9.2 Hz, 1H), 3.66 (d, J=11.2 Hz, 1H), 3.45-3.31 (m, 1H), 3.27-3.06 (m, 4H), 2.23 (s, 3H); MH+446.

Example 38

(2S,3R,4R,5S,6R)-2-(3-((5-(4-Chlorophenyl)thiazol-2-yl)methyl)-4-methylphenyl)-6-(hydroxymethyl)tetrahydro-2H-pyran-3,4,5-triol The titled compound was obtained in the same manner as in Example 1.

$^1$H NMR (400 MHz, DMSO-d$_6$) δ 8.08 (s, 1H), 7.63-7.56 (m, 2H), 7.44-7.38 (m, 2H), 7.26 (s, 1H), 7.17-7.09 (m, 2H), 4.91 (br, 2H), 4.72 (br, 1H), 4.42 (t, J=5.6 Hz, 1H), 4.32-4.22

(m, 2H), 3.94 (d, J=9.6 Hz, 1H), 3.67 (dd, J=11.6, 3.6 Hz, 1H), 3.45-3.38 (m, 1H), 3.27-3.07 (m, 4H), 2.23 (s, 3H); MH+462.

Example 39

(2S,3R,4R,5S,6R)-2-(3-((5-Benzylthiazol-2-yl)methyl)-4-methylphenyl)-6-(hydroxymethyl)tetrahydro-2H-pyran-3,4,5-triol The titled compound was obtained in the same manner as in Example 1.

$^1$H NMR (400 MHz, DMSO-d$_6$) δ 7.41 (s, 1H), 7.28-7.22 (m, 2H), 7.19-7.05 (m, 6H), 4.90 (br, 2H), 4.68 (br, 1H), 4.40 (t, J=5.6 Hz, 1H), 4.32-4.22 (m, 2H), 4.05 (s, 2H), 3.90 (d, J=9.2 Hz, 1H), 3.65 (dd, J=11.6, 3.6 Hz, 1H), 3.44-3.36 (m, 1H), 3.27-3.04 (m, 4H), 2.17 (s, 3H); MH+442.

Example 40

(2S,3R,4R,5S,6R)-2-(4-Fluoro-3-((5-(furan-2-yl)thiazol-2-yl)methyl)phenyl)-6-(hydroxymethyl)tetrahydro-2H-pyran-3,4,5-triol The titled compound was obtained in the same manner as in Example 1.

$^1$H NMR (400 MHz, DMSO-d$_6$) δ 7.93 (s, 1H), 7.74 (d, J=2.0 Hz, 1H), 7.44 (dd, J=7.2, 2.0 Hz, 1H), 7.34-7.32 (m, 1H), 7.18 (t, J=9.2 Hz, 1H), 6.81 (d, J=3.6 Hz, 1H), 6.60 (dd, J=3.6, 2.0 Hz, 1H), 4.40 (d, J=16.0 Hz, 1H), 4.35 (d, J=16.0 Hz, 1H), 4.04 (d, J=9.6 Hz, 1H), 3.71 (dd, J=11.6, 1.2 Hz, 1H), 3.46 (dd, J=12.0, 5.6 Hz, 1H), 3.31-3.11 (m, 4H); MH+422.

Example 41

(2S,3R,4R,5S,6R)-2-(4-Fluoro-3-((5-(furan-3-yl)thiazol-2-yl)methyl)phenyl)-6-(hydroxymethyl)tetrahydro-2H-pyran-3,4,5-triol The titled compound was obtained in the same manner as in Example 1.

$^1$H NMR (400 MHz, DMSO-d$_6$) δ 8.09 (s, 1H), 7.90 (s, 1H), 7.78 (t, J=2.0 Hz, 1H), 7.46 (dd, J=7.6, 2.0 Hz, 1H), 7.38-7.34 (m, 1H), 7.20 (t, J=9.2 Hz, 1H), 6.90 (dd, J=2.0, 0.8 Hz, 1H), 4.40 (d, J=15.6 Hz, 2H), 4.35 (d, J=15.6 Hz, 1H), 4.06 (d, J=9.2 Hz, 1H), 3.74 (d, J=11.6 Hz, 1H), 3.49 (dd, J=12.0, 5.6 Hz, 1H), 3.33-3.14 (m, 4H); MH+422.

Example 42

(2S,3R,4R,5S,6R)-2-(4-Fluoro-3-((5-(thiophen-2-yl)thiazol-2-yl)methyl)phenyl)-6-(hydroxymethyl)tetrahydro-2H-pyran-3,4,5-triol The titled compound was obtained in the same manner as in Example 1.

$^1$H NMR (400 MHz, DMSO-d$_6$) δ 7.89 (s, 1H), 7.59 (dd, J=4.8, 1.2 Hz, 1H), 7.46 (dd, J=7.6, 2.0 Hz, 1H), 7.37-7.33 (m, 2H), 7.19 (t, J=9.2 Hz, 1H), 7.12 (dd, J=5.2, 3.6 Hz, 1H), 4.40 (d, J=16.0 Hz, 1H), 4.35 (d, J=16.0 Hz, 1H), 4.05 (d, J=9.2 Hz, 1H), 3.72 (dd, J=11.6, 1.6 Hz, 1H), 3.47 (dd, J=12.0, 5.6 Hz, 1H), 3.32-3.13 (m, 4H); MH+438.

Example 43

(2S,3R,4R,5S,6R)-2-(4-Fluoro-3-((5-(thiazol-3-yl)thiazol-2-yl)methyl)phenyl)-6-(hydroxymethyl)tetrahydro-2H-pyran-3,4,5-triol The titled compound was obtained in the same manner as in Example 1.

$^1$H NMR (400 MHz, DMSO-d$_6$) δ 7.96 (s, 1H), 7.73 (dd, J=2.8, 1.2 Hz, 1H), 7.64 (dd, J=5.2, 2.8 Hz, 1H), 7.43 (dd, J=5.2, 1.2 Hz, 2H), 7.34-7.30 (m, 1H), 7.17 (t, J=9.2 Hz, 1H), 4.37 (d, J=16.0 Hz, 1H), 4.32 (d, J=16.0 Hz, 1H), 4.03 (d, J=9.6 Hz, 1H), 3.70 (dd, J=11.6, 2.0 Hz, 1H), 3.45 (dd, J=12.0, 5.6 Hz, 1H), 3.29-3.11 (m, 4H); MH+438.

Example 44

(2S,3R,4R,5S,6R)-2-(4-Fluoro-3-((5-phenylthiazol-2-yl)methyl)phenyl)-6-(hydroxymethyl)tetralrydro-2H-pyran-3,4,5-triol The titled compound was obtained in the same manner as in Example 1.

$^1$H NMR (400 MHz, DMSO-d$_6$) δ 8.06 (s, 1H), 7.60 (d, J=7.2 Hz, 2H), 7.45-7.39 (m, 3H), 7.35-7.31 (m, 2H), 7.17 (t, J=9.2 Hz, 1H), 4.39 (d, J=16.0 Hz, 1H), 4.34 (d, J=16.0 Hz, 1H), 4.03 (d, J=9.6 Hz, 1H), 3.70 (d, J=10.4 Hz, 1H), 3.45 (dd, J=11.6, 5.6 Hz, 1H), 3.32-3.11 (m, 4H); MH+432.

Example 45

(2S,3R,4R,5S,6R)-2-(4-Fluoro-3-((5-(4-fluorophenyl)thiazol-2-yl)methyl)phenyl)-6-(hydroxymethyl)tetrahydro-2H-pyran-3,4,5-triol The titled compound was obtained in the same manner as in Example 1.

$^1$H NMR (400 MHz, DMSO-d$_6$) δ 8.03 (s, 1H), 7.67-7.63 (m, 2H), 7.43 (dd, J=7.6, 2.0 Hz, 1H), 7.34-7.30 (m, 1H), 7.27-7.21 (m, 2H), 7.16 (t, J=9.2 Hz, 1H), 4.38 (d, J=16.0 Hz, 1), 4.34 (d, J=16.0 Hz, 1H), 4.02 (d, J=9.2 Hz, 1H), 3.70 (dd, J=12.0, 1.6 Hz, 1H), 3.47-3.11 (m, 5H); MH+450.

Example 46

(2S,3R,4R,5S,6R)-2-(4-Bromo-3-((5-(furan-2-yl)thiazol-2-yl)methyl)phenyl)-6-(hydroxymethyl)-tetrahydro-2H-pyran-3,4,5-triol The titled compound was obtained in the same manner as in Example 1.

$^1$H NMR (400 MHz, DMSO-d$_6$) δ 7.96 (s, 1H), 7.75 (d, J=2.0 Hz, 1H), 7.63 (d, J=8.4 Hz, 1H), 7.53 (d, J=2.0 Hz, 1H), 7.27 (dd, J=8.4, 2.0 Hz, 1H), 6.82 (d, J=3.2 Hz, 1H), 6.61 (dd, J=3.2, 2.0 Hz, 1H), 4.90 (br, 4H), 4.49 (d, J=16.0 Hz, 1H), 4.45 (d, J=16.0 Hz, 1H), 4.06 (d, J=9.6 Hz, 1H), 7.73 (d, J=10.0 Hz, 1H), 3.48 (dd, J=11.6, 5.6 Hz, 1H), 3.32-3.11 (m, 4H); MH+482.

Example 47

(2S,3R,4R,5S,6R)-2-(4-Bromo-3-((5-(thiophen-3-yl)thiazol-2-yl)methyl)phenyl)-6-(hydroxymethyl)-tetrahydro-2H-pyran-3,4,5-triol The titled compound was obtained in the same manner as in Example 1.
$^1$H NMR (400 MHz, DMSO-d$_6$) δ 7.99 (s, 1H), 7.74-7.73 (m, 1H), 7.65-7.63 (m, 1H), 7.60 (d, J=8.4 Hz, 1H), 7.51 (d, J=1.6 Hz, 1H), 7.43 (dd, J=5.2, 4.6 Hz, 1H), 7.25 (dd, J=8.4, 2.0 Hz, 1H), 5.85 (br, 4H), 4.46 (d, J=16.0 Hz, 1H), 4.41 (d, J=16.0 Hz, 1H), 4.03 (d, J=9.2 Hz, 1H), 3.71 (d, J=10.0 Hz, 1H), 3.46 (dd, J=11.6, 5.6 Hz, 1H), 3.30-3.09 (m, 4H); MH+498.

Example 48

(2S,3R,4R,5S,6R)-2-(3-((5-(Furan-3-yl)thiazol-2-yl)methyl)-4-(trifluoromethyl)phenyl)-6-(hydroxymethyl)tetrahydro-2H-pyran-3,4,5-triol The titled compound was obtained in the same manner as in Example 4.
$^1$H NMR (400 MHz, DMSO-d$_6$) δ 8.05 (s, 1H), 7.88 (s, 1H), 7.77-7.72 (m, 1H), 7.71 (s, 1H), 7.59 (s, 1H), 7.51 (d, J=8.4 Hz, 1H), 6.88-6.84 (m, 1H), 5.05-4.94 (m, 3H), 4.52-4.47 (m, 2H), 4.12 (d, J=9.2 Hz, 1H), 3.71 (dd, J=12.0, 1.6 Hz, 1H), 3.51-3.44 (m, 1H), 3.35-3.05 (m, 4H); MH+472.

Example 49

(2R,3S,4R,5R,6S)-2-(Hydroxymethyl)-6-(3-((5-(thiophen-2-yl)thiazol-2-yl)methyl)-4-(trifluoromethyl)phenyl)tetrahydro-2H-pyran-3,4,5-triol The titled compound was obtained in the same manner as in Example 4.
$^1$H NMR (400 MHz, DMSO-d$_6$) δ 7.90 (s, 1H), 7.73 (d, J=8.0 Hz, 1H), 7.62 (s, 1H), 7.62 (d, J=8.4 Hz, 1H), 7.59-7.51 (m, 2H), 7.31 (dd, J=4.0, 0.8 Hz, 1H), 7.13-7.07 (m, 1H), 5.10-4.91 (m, 3H), 4.55-4.43 (m, 3H), 4.14 (d, J=9.2 Hz, 1H), 3.72 (d, J=10.8 Hz, 1H), 3.54-3.43 (m, 1H), 3.37-3.07 (m, 4H); MH+488.

Example 50

(2R,3S,4R,5R,6S)-2-(Hydroxymethyl)-6-(3-((5-(thiophen-3-yl)thiazol-2-yl)methyl)-4-(trifluoromethyl)phenyl)tetrahydro-2H-pyran-3,4,5-triol The titled compound was obtained in the same manner as in Example 4.
$^1$H NMR (400 MHz, DMSO-d$_6$) δ 7.99 (s, 1H), 7.76-7.72 (m, 2H), 7.67-7.62 (m, 1H), 7.61 (s, 1H), 7.52 (d, J=8.4 Hz, 1H), 7.43 (dd, J=5.2, 1.2 Hz, 1H), 5.05-4.94 (m, 3H), 4.54-4.42 (m, 2H), 4.13 (d, J=9.6 Hz, 1H), 3.77-3.64 (m, 1H), 3.53-3.42 (m, 1H), 3.31-3.07 (m, 5H); MH+488.

Example 51

(2R,3S,4R,5R,6S)-2-(Hydroxymethyl)-6-(3-((5-phenylthiazol-2-yl)methyl)-4-(trifluoromethyl)phenyl)tetrahydro-2H-pyran-3,4,5-triol The titled compound was obtained in the same manner as in Example 4.
$^1$H NMR (400 MHz, DMSO-d$_6$) δ 8.09 (s, 1H), 7.73 (d, J=8.0 Hz, 1H), 7.64-7.57 (m, 3H), 7.52 (d, J=8.4 Hz, 1H), 7.44-7.38 (m, 2H), 7.36-7.31 (m, 1H), 5.04-4.93 (m, 3H), 4.51 (s, 2H), 4.46 (t, J=5.6 Hz, 1H), 4.13 (d, J=9.2 Hz, 1H), 3.77-3.68 (m, 1H), 3.52-3.44 (m, 1H), 3.31-3.24 (m, 2H), 3.23-3.09 (m, 2H); MH+482.

Example 52

(2S,3R,4R,5S,6R)-2-(3-((5-(4-Fluorophenyl)thiazol-2-yl)methyl)-4-(trifluoromethyl)phenyl)-6-(hydroxymethyl)tetrahydro-2H-pyran-3,4,5-triol The titled compound was obtained in the same manner as in Example 4.
$^1$H NMR (400 MHz, DMSO-d$_6$) δ 8.06 (s, 1H), 7.72 (d, J=8.4 Hz, 1H), 7.68-7.59 (m, 3H), 7.52 (d, J=8.0 Hz, 1H), 7.30-7.21 (m, 2H), 5.07-4.91 (m, 3H), 4.50 (s, 2H), 4.46 (t, J=5.6 Hz, 1H), 4.13 (d, J=9.6 Hz, 1H), 3.71 (dd, J=11.2, 3.6 Hz, 1H), 3.52-3.43 (m, 1H), 3.31-3.23 (m, 2H), 3.24-3.09 (m, 2H); MH+500.

Example 53

(2S,3R,4R,5S,6R)-2-(4-Chloro-2-fluoro-5-((5-(furan-2-yl)thiazol-2-yl)methyl)phenyl)-6-(hydroxymethyl)tetrahydro-2H-pyran-3,4,5-triol The titled compound was obtained in the same manner as in Example 1.
$^1$H NMR (400 MHz, DMSO-d$_6$) δ 7.90 (s, 1H), 7.70 (m, 1H), 7.61 (d, J=7.6 Hz, 1H), 7.40 (d, J=9.6 Hz, 1H), 6.76 (d, J=3.2 Hz, 1H), 6.56-6.55 (m, 1H), 4.95 (td, J=10.8, 4.0 Hz, 3H), 4.43 (t, J=6.0 Hz, 1H), 4.41 (s, 2H), 4.28 (d, J=9.2 Hz, 1H), 3.67 (dd, J=10.4, 5.2 Hz, 1H), 3.43-3.37 (m, 1H), 3.27-3.20 (m, 3H), 3.17-3.13 (m, 1H); MH+456.

Example 54

(2S,3R,4R,5S,6R)-2-(4-Chloro-2-fluoro-5-((5-(furan-3-yl)thiazol-2-yl)methyl)phenyl)-6-(hydroxymethyl)tetrahydro-2H-pyran-3,4,5-triol The titled compound was obtained in the same manner as in Example 1.
$^1$H NMR (400 MHz, DMSO-d$_6$) δ 8.03 (s, 1H), 7.84 (m, 1H), 7.72-7.71 (m, 1H), 7.60 (d, J=7.2 Hz, 1H), 7.40 (d, J=9.6 Hz, 1H), 6.83 (m, 1H), 4.96 (br, 4H), 4.38 (s, 2H), 4.28 (d, J=9.2 Hz, 1H), 3.66 (d, J=10.4 Hz, 1H), 3.39 (dd, J=11.6, 5.6 Hz, 1H), 3.28-3.21 (m, 3H), 3.16-3.11 (m, 1H); MH+456.

Example 55

(2S,3R,4R,5S,6R)-2-(4-Chloro-2-fluoro-5-((5-(thiophen-2-yl)thiazol-2-yl)methyl)phenyl)-6-(hydroxymethyl)tetrahydro-2H-pyran-3,4,5-triol The titled compound was obtained in the same manner as in Example 1.
$^1$H NMR (400 MHz, DMSO-$d_6$) δ 7.85 (s, 1H), 7.62 (d, J=7.6 Hz, 1H), 7.53 (dd, J=5.2, 1.2 Hz, 1H), 7.41 (d, J=9.6 Hz, 1H), 7.28 (dd, J=3.6, 1.2 Hz, 1H), 7.06 (dd, J=5.2, 4.0 Hz, 1H), 5.01-4.95 (m, 3H), 4.46-4.44 (m, 1H), 4.40 (s, 2H), 4.28 (d, J=9.2 Hz, 1H), 3.66 (dd, J=11.6, 3.6 Hz, 1H), 3.43-3.38 (m, 1H), 3.25-3.21 (m, 3H), 3.17-3.13 (m, 1H); MH+ 472.

Example 56

(2S,3R,4R,5S,6R)-2-(4-Chloro-2-fluoro-5-((5-(thiophen-3-yl)thiazol-2-yl)methyl)phenyl)-6-(hydroxymethyl)tetrahydro-2H-pyran-3,4,5-triol The titled compound was obtained in the same manner as in Example 1.
$^1$H NMR (400 MHz, DMSO-$d_6$) δ 7.94 (s, 1H), 7.70 (dd, J=3.2, 1.2 Hz, 1H), 7.62-7.60 (m, 2H), 7.42-7.39 (m, 2H), 5.01-4.93 (m, 3H), 4.45 (t, J=5.6 Hz, 1H), 4.39 (s, 2H), 4.28 (d, J=8.8 Hz, 1H), 3.69-3.65 (m, 1H), 3.43-3.37 (m, 1H), 3.27-3.21 (m, 3H), 3.17-3.13 (m, 1H); MH+472.

Example 57

(2S,3R,4R,5S,6R)-2-(4-Chloro-2-fluoro-5-((5-phenylthiazol-2-yl)methyl)phenyl)-6-(hydroxymethyl)tetrahydro-2H-pyran-3,4,5-triol The titled compound was obtained in the same manner as in Example 1.
$^1$H NMR (400 MHz, DMSO-$d_6$) δ 8.05 (s, 1H), 7.62 (d, J=7.2 Hz, 1H), 7.58-7.56 (m, 2H), 7.42-7.36 (m, 3H), 7.32-7.28 (m, 1H), 4.94 (br, 4H), 4.41 (d, J=10.0 Hz, 1H), 3.67 (d, J=10.4 Hz, 1H), 3.40 (dd, J=12.0, 6.0 Hz, 1H), 3.28-3.21 (m, 3H), 3.16-3.12 (m, 1H); MH+ 466.

Example 58

(2S,3R,4R,5S,6R)-2-(4-Chloro-2-fluoro-5-((5-(4-fluorophenyl)thiazol-2-yl)methyl)phenyl)-6-(hydroxymethyl)tetrahydro-2H-pyran-3,4,5-triol The titled compound was obtained in the same manner as in Example 1.
$^1$H NMR (400 MHz, DMSO-$d_6$) δ 8.01 (s, 1H), 7.63-7.60 (m, 3H), 7.40 (d, J=9.2 Hz, 1H), 7.22 (t, J=8.4 Hz, 2H), 7.40 (d, J=9.6 Hz, 1H), 4.98-4.92 (m, 3H), 4.45-4.41 (m, 1H), 4.41 (s, 2H), 4.28 (d, J=8.8 Hz, 1H), 3.68-3.66 (m, 1H), 3.42-3.38 (m, 1H), 3.25-3.21 (m, 3H), 3.16-3.14 (m, 1H); MH+484.

Example 59

(2S,3R,4R,5S,6R)-2-(2,4-Dichloro-5-((5-(furan-2-yl)thiazol-2-yl)methyl)phenyl)-6-(hydroxymethyl)tetrahydro-2H-pyran-3,4,5-triol The titled compound was obtained in the same manner as in Example 1.
$^1$H NMR (400 MHz, DMSO-$d_6$) δ 7.89 (s, 1H), 7.69 (d, J=1.2 Hz, 1H), 7.65 (s, 1H), 7.61 (s, 1H), 6.76 (d, J=3.6 Hz, 1H), 6.59-6.51 (m, 1H), 4.91 (br, 4H), 4.49-4.39 (m, 3H), 3.66 (d, J=10.4 Hz, 1H), 3.37-3.14 (m, 5H); MH+472.

Example 60

(2S,3R,4R,5S,6R)-2-(2,4-Dichloro-5-((5-(furan-3-yl)thiazol-2-yl)methyl)phenyl)-6-(hydroxymethyl)tetrahydro-2H-pyran-3,4,5-triol The titled compound was obtained in the same manner as in Example 1.
$^1$H NMR (400 MHz, DMSO-$d_6$) δ 8.03 (s, 1H), 7.84 (s, 1H), 7.71 (t, J=1.6 Hz, 1H), 7.65 (s, 1H), 7.59 (s, 1H), 6.89-6.83 (m, 1H), 5.03 (br, 4H), 4.43 (d, J=9.2 Hz, 1H), 4.40 (s, 2H), 3.66 (dd, J=12.0, 1.6 Hz, 1H), 3.39 (dd, J=12.0, 5.6 Hz, 1H), 3.35-3.15 (m, 5H); MH+472.

Example 61

(2S,3R,4R,5S,6R)-2-(2,4-Dichloro-5-((5-(thiophen-2-yl)thiazol-2-yl)methyl)phenyl)-6-(hydroxymethyl)tetrahydro-2H-pyran-3,4,5-triol The titled compound was obtained in the same manner as in Example 1.
$^1$H NMR (400 MHz, DMSO-$d_6$) δ 7.86 (s, 1H), 7.67 (s, 1H), 7.61 (s, 1H), 7.54 (dd, J=5.2, 1.2 Hz, 1H), 7.29 (dd, J=3.6, 0.8 Hz, 1H), 7.09-7.04 (m, 1H), 4.71-4.49 (m, 5H), 3.67 (d, J=10.4 Hz, 1H), 3.41 (dd, J=12.0, 5.4 Hz, 1H), 3.38-3.17 (m, 6H); MH+488.

Example 62

(2S,3R,4R,5S,6R)-2-(2,4-Dichloro-5-((5-(thiophen-3-yl)thiazol-2-yl)methyl)phenyl)-6-(hydroxymethyl)tetrahydro-2H-pyran-3,4,5-triol The titled compound was obtained in the same manner as in Example 1.
$^1$H NMR (400 MHz, DMSO-$d_6$) δ 7.94 (s, 1H), 7.77-7.68 (m, 1H), 7.66 (s, 1H), 7.64-7.58 (m, 2H), 7.40 (dd, J=4.8, 1.6 Hz, 1H), 6.76 (d, J=3.6 Hz, 1H), 6.59-6.51 (m, 1H), 4.49-4.35 (m, 4H), 3.67 (dd, J=11.6, 1.6 Hz, 1H), 3.40 (dd, J=12.0, 5.6 Hz, 1H), 3.37-3.11 (m, 7H); MH+488.

Example 63

(2S,3R,4R,5S,6R)-2-(2,4-Dichloro-5-((5-methylthiazol-2-yl)methyl)phenyl)-6-(hydroxymethyl)tetrahydro-2H-pyran-3,4,5-triol The titled compound was obtained in the same manner as in Example 1.
$^1$H NMR (400 MHz, CD$_3$OD) δ 7.63 (s, 1H), 7.48 (s, 1H), 7.33 (d, J=1.2 Hz, 1H), 4.83 (s, 4H), 4.66 (d, J=8.8 Hz, 1H), 4.42-4.33 (m, 2H), 3.84 (dd, J=12.0, 1.8 Hz, 1H), 3.70-3.65 (m, 1H), 3.53-3.38 (m, 4H), 2.41 (s, 3H); MH+420.

Example 64

(2S,3R,4R,5S,6R)-2-(2,4-Dichloro-5-((5-ethylthiazol-2-yl)methyl)phenyl)-6-(hydroxymethyl)tetrahydro-2H-pyran-3,4,5-triol The titled compound was obtained in the same manner as in Example 1.
$^1$H NMR (400 MHz, CD$_3$OD) δ 7.64 (s, 1H), 7.48 (s, 1H), 7.33 (t, J=1.0 Hz, 1H), 4.83 (s, 4H), 4.66 (d, J=8.8 Hz, 1H), 4.42-4.33 (m, 2H), 3.83 (dd, J=12.0, 1.6 Hz, 1H), 3.66 (dd, J=12.0, 5.2 Hz, 1H), 3.53-3.38 (m, 4H), 2.80 (qd, J=7.6, 0.8 Hz, 2H), 1.25 (d, J=7.6 Hz, 3H); MH+434.

Example 65

(2S,3R,4R,5S,6R)-2-(2,4-Dichloro-5-((5-propylthiazol-2-yl)methyl)phenyl)-6-(hydroxymethyl)tetrahydro-2H-pyran-3,4,5-triol The titled compound was obtained in the same manner as in Example 1.
$^1$H NMR (400 MHz, CD$_3$OD) δ 7.63 (s, 1H), 7.48 (s, 1H), 7.35 (s, 1H), 4.83 (s, 4H), 4.66 (d, J=8.8 Hz, 1H), 4.43-4.32 (m, 2H), 3.85 (dd, J=12.0, 1.6 Hz, 1H), 3.70-3.62 (m, 1H), 3.52-3.38 (m, 4H), 2.75 (t, J=3.6 Hz, 2H), 1.64 (sext, J=3.6 Hz, 2H), 0.94 (t, J=3.6 Hz, 3H); MH+448.

Example 66

(2S,3R,4R,5S,6R)-2-(5-((5-Butylthiazol-2-yl)methyl)-2,4-dichlorophenyl)-6-(hydroxymethyl)tetrahydro-2H-pyran-3,4,5-triol The titled compound was obtained in the same manner as in Example 1.
$^1$H NMR (400 MHz, CD$_3$OD) δ 7.63 (s, 1H), 7.48 (s, 1H), 7.33 (s, 1H), 4.85 (s, 4H), 4.66 (d, J=7.2 Hz, 1H), 4.42-4.31 (m, 2H), 3.85-3.81 (m, 1H), 3.71-3.64 (m, 1H), 3.53-3.37 (m, 4H), 2.78 (t, J=7.6 Hz, 2H), 1.58 (quint, J=7.6 Hz, 2H), 1.35 (sext, J=7.6 Hz, 2H), 0.91 (t, J=7.6 Hz, 1H); MH+462.

Example 67

(2S,3R,4R,5S,6R)-2-(2,4-Dichloro-5-((5-hexylthiazol-2-yl)methyl)phenyl)-6-(hydroxymethyl)tetrahydro-2H-pyran-3,4,5-triol The titled compound was obtained in the same manner as in Example 1.
$^1$H NMR (400 MHz, CD$_3$OD) δ 7.64 (s, 1H), 7.49 (s, 1H), 7.35 (s, 1H), 4.84 (s, 4H), 4.66 (d, J=8.8 Hz, 1H), 4.45-4.31 (m, 2H), 3.86 (dd, J=12.0, 1.6 Hz, 1H), 3.66 (dd, J=12.0, 1.0 Hz, 1H), 3.52-3.35 (m, 4H), 2.78 (t, J=7.2 Hz, 2H), 1.61 (quint, J=7.2 Hz, 2H), 1.48-1.32 (m, 6H), 0.84 (t, J=6.8 Hz, 3H); MH+490.

Example 68

(2S,3R,4R,5S,6R)-2-(2,4-Dichloro-5-((5-cyclopentylthiazol-2-yl)methyl)phenyl)-6-(hydroxymethyl)tetrahydro-2H-pyran-3,4,5-triol The titled compound was obtained in the same manner as in Example 1.
$^1$H NMR (400 MHz, CD$_3$OD) δ 7.63 (s, 1H), 7.48 (s, 1H), 7.34 (s, 1H), 4.82 (s, 4H), 4.66 (d, J=8.8 Hz, 1H), 4.45-4.32 (m, 2H), 3.86 (dd, J=12.0, 1.6 Hz, 1H), 3.67 (dd, J=12.0, 1.0 Hz, 1H), 3.52-3.36 (m, 4H), 3.39-3.27 (m, 1H), 2.15-2.06 (m, 2H), 1.82-1.61 (m, 4H), 1.59-1.49 (m, 2H); MH+474.

Example 69

(2S,3R,4R,5S,6R)-2-(4-Chloro-5-((5-(furan-2-yl)thiazol-2-yl)methyl)-2-methoxyphenyl)-6-(hydroxymethyl)tetrahydro-2H-pyran-3,4,5-triol The titled compound was obtained in the same manner as in Example 1.
$^1$H NMR (400 MHz, DMSO-d$_6$) δ 7.89 (s, 1H), 7.69 (m, 1H), 7.44 (s, 1H), 7.07 (s, 1H), 6.74 (d, J=3.6 Hz, 1H), 6.55-6.54 (m, 1H), 4.90 (t, J=4.8 Hz, 2H), 4.65 (d, J=5.6 Hz, 1H), 4.43-4.37 (m, 3H), 4.34 (s, 2H), 3.76 (s, 3H), 3.62 (m, 1H), 3.38-3.30 (m, 1H), 3.28-3.22 (m, 1H), 3.15-3.12 (m, 2H); MH+468.

Example 70

(2S,3R,4R,5S,6R)-2-(4-Chloro-5-((5-(furan-3-yl)thiazol-2-yl)methyl)-2-methoxyphenyl)-6-(hydroxymethyl)tetrahydro-2H-pyran-3,4,5-triol The titled compound was obtained in the same manner as in Example 1.
$^1$H NMR (400 MHz, DMSO-d$_6$) δ 8.00 (s, 1H), 7.83 (s, 1H), 7.70 (t, J=1.6 Hz, 1H), 7.42 (s, 1H), 7.06 (s, 1H), 6.88-6.83 (m, 1H), 4.42 (d, J=9.2 Hz, 1H), 4.31 (s, 2H), 4.09 (br, 4H), 3.76 (s, 1H), 3.66 (d, J=10.4 Hz, 1H), 3.36 (dd, J=12.0, 5.2 Hz, 1H), 3.32-3.07 (m, 4H); MH+468.

Example 71

(2S,3R,4R,5S,6R)-2-(4-Chloro-3-((4-phenylthiazol-2-yl)methyl)phenyl)-6-(hydroxymethyl)tetrahydro-2H-pyran-3,4,5-triol The titled compound was obtained in the same manner as in Example 1.
$^1$H NMR (400 MHz, DMSO-d$_6$) δ 7.84 (s, 1H), 7.52 (dd, J=4.8, 1.2 Hz, 1H), 7.44 (m, 1H), 7.26 (dd, J=3.6, 1.2 Hz, 1H), 7.07-7.04 (m, 2H), 4.88 (t, J=4.0 Hz, 2H), 4.64 (d, J=5.2 Hz, 1H), 4.41 (d, J=9.2 Hz, 1H), 4.37 (t, J=6.0 Hz, 1H), 4.33 (s, 2H), 3.76 (s, 3H), 3.65 (dd, J=10.8, 5.6 Hz, 1H), 3.40-3.29 (m, 1H), 3.28-3.21 (m, 2H), 3.18-3.11 (m, 2H); MH+ 484.

Example 72

(2S,3R,4R,5S,6R)-2-(4-Chloro-2-methoxy-5-((5-(thiophen-3-yl)thiazol-2-yl)methyl)phenyl)-6-(hydroxymethyl)tetrahydro-2,1-pyran-3,4,5-triol The titled compound was obtained in the same manner as in Example 1.
$^1$H NMR (400 MHz, DMSO-d$_6$) δ 7.93 (s, 1H), 7.67 (dd, J=2.8, 1.2 Hz, 1H), 7.60 (dd, J=4.8, 2.8 Hz, 1H), 7.43 (s, 1H), 7.39 (dd, J=5.2, 1.2 Hz, 1H), 7.07 (s, 1H), 4.41 (d, J=9.6 Hz, 1H), 4.32 (s, 2H), 4.05 (br, 4H), 3.76 (s, 3H), 3.64 (d, J=10.4 Hz, 1H), 3.39-3.35 (m, 1H), 3.32-3.18 (m, 2H), 3.15-3.09 (m, 2H); MH+484.

Example 73

(2S,3R,4R,5S,6R)-2-(4-Chloro-2-methoxy-5-((5-phenylthiazol-2-yl)methyl)phenyl)-6-(hydroxymethyl)tetrahydro-2H-pyran-3,4,5-triol The titled compound was obtained in the same manner as in Example 1.
$^1$H NMR (400 MHz, DMSO-$d_6$) δ 8.03 (s, 1H), 7.58-7.52 (m, 2H), 7.44 (s, 1H), 7.39-7.34 (m, 2H), 7.31-7.25 (m, 1H), 7.07 (s, 1H), 4.52 (br, 4H), 4.43 (d, J=9.6 Hz, 1H), 4.34 (2H), 3.77 (s, 3H), 3.62 (d, J=10.4 Hz, 1H), 3.37 (dd, J=12.0, 5.6 Hz, 1H), 3.32-3.07 (m, 4H); MH+478.

Example 74

(2S,3R,4R,5S,6R)-2-(4-Chloro-5-((5-(4-fluorophenyl)thiazol-2-yl)methyl)-2-methoxyphenyl)-6-(hydroxymethyl)tetrahydro-2H-pyran-3,4,5-triol The titled compound was obtained in the same manner as in Example 1.
$^1$H NMR (400 MHz, DMSO-$d_6$) δ 8.00 (s, 1H), 7.65-7.57 (m, 2H), 7.44 (s, 1H), 7.25-7.18 (m, 2H), 7.06 (s, 1H), 4.57 (br s, 4H), 4.42 (d, J=9.2 Hz, 1H), 4.34 (s, 2H), 3.76 (s, 3H), 3.64 (d, J=10.4 Hz, 1H), 3.36 (dd, J=12.0, 5.6 Hz, 1H), 3.32-3.08 (m, 4H); MH+496.

Example 75

(2S,3R,4R,5S,6R)-2-(4-Chloro-5-((5-hexylthiazol-2-yl)methyl)-2-methoxyphenyl)-6-(hydroxymethyl)tetrahydro-2H-pyran-3,4,5-triol The titled compound was obtained in the same manner as in Example 1.
$^1$H NMR (400 MHz, DMSO-$d_6$) δ 7.49 (s, 1H), 7.38 (s, 2H), 7.04 (s, 1H), 4.82 (s, 4H), 4.63 (d, J=9.2 Hz, 1H), 4.39-4.29 (m, 2H), 3.84 (d, J=2.0 Hz, 1H), 3.81 (s, 3H), 3.64 (dd, J=12.0, 5.2 Hz, 1H), 3.59-3.31 (m, 5H), 2.77 (t, J=7.2 Hz, 2H), 1.60 (q, J=7.2 Hz, 2H), 1.40-1.22 (m, 5H), 0.87 (t, J=7.2 Hz, 3H); MH+486.

Example 76

(2S,3R,4R,5S,6R)-2-(4-Chloro-5-((5-cyclopentylthiazol-2-yl)methyl)-2-methoxyphenyl)-6-(hydroxymethyl)tetrahydro-2H-pyran-3,4,5-triol The titled compound was obtained in the same manner as in Example 1.
$^1$H NMR (400 MHz, DMSO-$d_6$) δ 7.48 (s, 1H), 7.32 (s, 1H), 7.03 (s, 1H), 4.82 (s, 4H), 4.63 (d, J=8.8 Hz, 1H), 4.35-4.32 (m, 2H), 3.84 (d, J=2.0 Hz, 1H), 3.81 (s, 3H), 3.67 (dd, J=12.0, 1.0 Hz, 1H), 3.49-3.31 (m, 4H), 3.29-3.15 (m, 1H), 2.13-2.06 (m, 2H), 1.82-1.61 (m, 4H), 1.59-1.49 (m, 2H); MH+470.

Example 77

(2S,3R,4R,5S,6R)-2-(4-Chloro-2-ethoxy-5-((5-(furan-2-yl)thiazol-2-yl)methyl)phenyl)-6-(hydroxymethyl)tetrahydro-2H-pyran-3,4,5-triol The titled compound was obtained in the same manner as in Example 1.
$^1$H NMR (400 MHz, CD$_3$OD) δ 7.79 (s, 1H), 7.55-7.46 (m, 2H), 7.03 (s, 3H), 6.60 (d, J=3.2 Hz, 1H), 7.03 (s, 1H), 6.50-6.44 (m, 1H), 4.84 (s, 4H), 4.64 (d, J=9.2 Hz, 1H), 4.43-4.32 (m, 2H), 4.10-4.01 (m, 2H), 3.82 (dd, J=12.0, 1.6 Hz, 1H), 3.66 (dd, J=12.0, 5.6 Hz, 1H), 3.57-3.32 (m, 4H), 1.40 (t, J=7.2 Hz, 3H); MH+482.

Example 78

(2S,3R,4R,5S,6R)-2-(4-Chloro-2-ethoxy-5-((5-(furan-3-yl)thiazol-2-yl)methyl)phenyl)-6-(hydroxymethyl)-tetrahydro-2H-pyran-3,4,5-triol The titled compound was obtained in the same manner as in Example 1.
$^1$H NMR (400 MHz, DMSO-$d_6$) δ 8.01 (s, 1H), 7.83 (s, 1H), 7.71 (t, J=1.6 Hz, 1H), 7.41 (s, 1H), 7.04 (s, 1H), 6.84-6.78 (m, 1H), 4.82 (s, 4H), 4.39 (d, J=9.6 Hz, 1H), 4.31 (s, 2H), 4.00 (q, J=1.2 Hz, 1H), 3.63 (d, J=1.04 Hz, 1H), 3.41-3.29 (m, 2H), 3.23 (t, J=8.4 Hz, 1H), 3.18-3.04 (m, 2H), 1.29 (t, J=7.2 Hz, 3H); MH+482.

Example 79

(2S,3R,4R,5S,6R)-2-(4-Chloro-2-ethoxy-5-((5-(thiophen-2-yl)thiazol-2-yl)methyl)phenyl)-6-(hydroxymethyl)tetralrydro-2H-pyran-3,4,5-triol The titled compound was obtained in the same manner as in Example 1.
$^1$H NMR (400 MHz, CD$_3$OD) δ 7.86 (s, 1H), 7.53 (s, 1H), 7.43 (dd, J=5.6, 0.8 Hz, 1H), 7.25 (dd, J=5.6, 0.8 Hz, 1H), 7.09-7.04 (m, 2H), 4.84 (s, 4H), 4.64 (d, J=9.2 Hz, 1H), 4.47-3.76 (m, 2H), 4.11-4.02 (m, 2H), 3.83 (dd, J=12.0, 1.6 Hz, 1H), 3.65 (dd, J=12.0, 1.2 Hz, 1H), 3.57-3.33 (m, 4H), 1.40 (t, J=7.2 Hz, 1H); MH+498

Example 80

(2S,3R,4R,5S,6R)-2-(4-Chloro-2-ethoxy-5-((5-(thiophen-3-yl)thiazol-2-yl)methyl)phenyl)-6-(hydroxymethyl)tetrahydro-2H-pyran-3,4,5-triol The titled compound was obtained in the same manner as in Example 1.
$^1$H NMR (400 MHz, DMSO-$d_6$) δ 7.79 (s, 1H), 7.55-7.46 (m, 1H), 7.03 (s, 1H), 6.60 (d, J=3.2 Hz, 1H), 7.03 (s, 1H), 6.51-6.45 (m, 1H), 4.84 (s, 4H), 4.64 (d, J=9.2 Hz, 1H), 4.43-4.32 (m, 2H), 4.10-4.01 (m, 2H), 3.82 (dd, J=12.0, 1.6 Hz, 1H), 3.66 (dd, J=12.0, 5.6 Hz, 1H), 3.57-3.32 (m, 4H), 1.40 (t, J=7.2 Hz, 3H); MH+482.

Example 81

(2S,3R,4R,5S,6R)-2-(4-Chloro-2-ethoxy-5-((5-phenylthiazol-2-yl)methyl)phenyl)-6-(hydroxymethyl)tetrahydro-2H-pyran-3,4,5-triol The titled compound was obtained in the same manner as in Example 1.
$^1$H NMR (400 MHz, CD$_3$OD) δ 7.87 (s, 1H), 7.56-7.51 (m, 3H), 7.39-7.34 (m, 2H), 7.32-7.26 (m, 1H), 7.03 (s, 1H), 4.84 (s, 4H), 4.64 (d, J=9.2 Hz, 1H), 4.43-4.33 (m, 2H), 4.09-4.01 (m, 2H), 3.82 (dd, J=12.0, 1.6 Hz, 1H), 3.64 (dd, J=12.0, 5.6 Hz, 1H), 3.56-3.37 (m, 4H), 1.40 (t, J=6.8 Hz, 3H); MH+492.

Example 82

(2S,3R,4R,5S,6R)-2-(4-Chloro-2-ethoxy-5-((5-(4-fluorophenyl)thiazol-2-yl)methyl)phenyl)-6-(hydroxymethyl)tetrahydro-2H-pyran-3,4,5-triol The titled compound was obtained in the same manner as in Example 1.

$^1$H NMR (400 MHz, CD$_3$OD) δ 7.84 (s, 1H), 7.58-7.52 (m, 2H), 7.51 (s, 3H), 7.15-7.08 (m, 2H), 7.03 (s, 1H), 4.84 (s, 4H), 4.64 (d, J=9.2 Hz, 1H), 4.43-4.32 (m, 2H), 4.10-4.02 (m, 2H), 3.83 (dd, J=12.0, 1.6 Hz, 1H), 3.65 (dd, J=12.0, 5.6 Hz, 1H), 3.57-3.34 (m, 4H), 1.40 (t, J=7.2 Hz, 3H); MH+510.

Example 83

(2S,3R,4R,5S,6R)-2-(2-(Allyloxy)-4-chloro-5-((5-(furan-2-yl)thiazol-2-yl)methyl)phenyl)-6-(hydroxymethyl)tetrahydro-2H-pyran-3,4,5-triol The titled compound was obtained in the same manner as in Example 1.

$^1$H NMR (400 MHz, DMSO-d$_6$) δ 7.89 (s, 1H), 7.71-7.62 (m, 1H), 7.44 (s, 1H), 7.06 (s, 1H), 6.74 (d, J=3.6 Hz, 1H), 6.69-6.63 (m, 1H), 6.06-5.93 (m, 1H), 5.41 (dd, J=17.2, 1.6 Hz, 1H), 5.22 (dd, J=10.4, 1.6 Hz, 1H), 4.91 (dd, J=18.8, 3.6 Hz, 2H), 4.68 (d, J=4.8 Hz, 1H), 4.59-4.52 (m, 2H), 4.47-4.29 (m, 4H), 3.69-3.59 (m, 1H), 3.41-3.06 (m, 5H); MH+494.

Example 84

(2S,3R,4R,5S,6R)-2-(2-(Allyloxy)-4-chloro-5-((5-(furan-3-yl)thiazol-2-yl)methyl)phenyl)-6-(hydroxymethyl)tetrahydro-2H-pyran-3,4,5-triol The titled compound was obtained in the same manner as in Example 1.

$^1$H NMR (400 MHz, DMSO-d$_6$) δ 8.01 (s, 1H), 7.83 (s, 1H), 7.71 (t, J=1.6 Hz, 1H), 7.43 (s, 1H), 7.05 (s, 1H), 6.85-6.79 (m, 1H), 6.06-5.95 (m, 1H), 5.40 (qd, J=17.2, 1.6 Hz, 1H), 5.22 (qd, J=10.4, 1.6 Hz, 1H), 4.90 (dd, J=18.8, 4.8 Hz, 2H), 4.66 (d, J=5.2 Hz, 1H), 4.59-4.53 (m, 2H), 4.42 (d, J=9.6 Hz, 1H), 4.38 (t, J=5.6 Hz, 1H), 4.31 (s, 2H), 3.64 (dd, J=12.0, 5.6 Hz, 1H), 3.43-3.31 (m, 2H), 3.27-3.20 (m, 1H), 3.19-3.09 (m, 2H); MH+ 494.

Example 85

(2S,3R,4R,5S,6R)-2-(2-(Allyloxy)-4-chloro-5-((5-(thiophen-2-yl)thiazol-2-yl)methyl)phenyl)-6-(hydroxymethyl)tetrahydro-2H-pyran-3,4,5-triol The titled compound was obtained in the same manner as in Example 1.

$^1$H NMR (400 MHz, DMSO-d$_6$) δ 7.84 (s, 1H), 7.52 (dd, J=5.2, 1.2 Hz, 1H), 7.44 (s, 1H), 7.27 (dd, J=3.6, 1.2 Hz, 1H), 7.08-7.02 (m, 2H), 6.06-5.95 (m, 1H), 5.41 (dd, J=17.6, 1.6 Hz, 1H), 5.22 (dd, J=11.2, 1.6 Hz, 1H), 4.90 (dd, J=18.8, 4.8 Hz, 2H), 4.68 (d, J=5.2 Hz, 1H), 4.59-4.53 (m, 2H), 4.42 (d, J=9.6 Hz, 1H), 4.38 (t, J=5.6 Hz, 1H), 4.32 (s, 2H), 3.64 (dd, J=12.0, 5.6 Hz, 1H), 3.42-3.31 (m, 2H), 3.29-3.20 (m, 1H), 3.19-3.09 (m, 2H); MH+510.

Example 86

(2S,3R,4R,5S,6R)-2-(2-(Allyloxy)-4-chloro-5-((5-(thiophen-3-yl)thiazol-2-yl)methyl)phenyl)-6-(hydroxymethyl)tetrahydro-2H-pyran-3,4,5-triol The titled compound was obtained in the same manner as in Example 1.

$^1$H NMR (400 MHz, DMSO-d$_6$) δ 7.93 (s, 1H), 7.71-7.65 (m, 1H), 7.67-7.58 (m, 1H), 7.42 (s, 1H), 7.39 (dd, J=1.6 Hz, 1H), 7.05 (s, 1H), 6.06-5.95 (m, 1H), 5.41 (dd, J=17.2, 1.6 Hz, 1H), 5.22 (dd, J=11.8, 1.6 Hz, 1H), 4.93 (dd, J=18.8, 4.4 Hz, 2H), 4.70 (d, J=5.2 Hz, 1H), 4.60-4.53 (m, 2H), 4.48-4.39 (m, 2H), 4.32 (s, 2H), 3.59-3.51 (m, 1H), 3.41-3.05 (m, 5H); MH+510.

Example 87

(2S,3R,4R,5S,6R)-2-(2-(Allyloxy)-4-chloro-5-((5-phenylthiazol-2-yl)methyl)phenyl)-6-(hydroxymethyl)tetrahydro-2H-pyran-3,4,5-triol The titled compound was obtained in the same manner as in Example 1.

$^1$H NMR (400 MHz, DMSO-d$_6$) δ 8.04 (s, 1H), 7.58-7.53 (m, 2H), 7.45 (s, 1H), 7.40-7.32 (m, 2H), 7.31-7.26 (m, 1H), 7.06 (s, 1H), 6.07-5.95 (m, 1H), 5.42 (dd, J=17.6, 1.6 Hz, 1H), 5.22 (dd, J=11.2, 1.6 Hz, 1H), 4.90 (dd, J=19.2, 4.8 Hz, 2H), 4.68 (d, J=5.2 Hz, 1H), 4.62-4.51 (m, 2H), 4.40 (d, J=11.2 Hz, 1H), 4.38 (t, J=5.6 Hz, 1H), 4.34 (s, 2H), 3.64 (d, J=10.4 Hz, 1H), 3.41-3.32 (m, 2H), 3.24 (t, J=8.0 Hz, 1H), 3.28-3.09 (m, 2H); MH+504.

Example 88

(2S,3R,4R,5S,6R)-2-(2-(Allyloxy)-4-chloro-5-((5-(4-fluorophenyl)thiazol-2-yl)methyl)phenyl)-6-(hydroxymethyl)tetrahydro-2H-pyran-3,4,5-triol The titled compound was obtained in the same manner as in Example 1.

$^1$H NMR (400 MHz, DMSO-d$_6$) δ 8.00 (s, 1H), 7.65-7.57 (m, 2H), 7.45 (s, 1H), 7.21 (t, J=1.2 Hz, 2H), 7.05 (s, 1H), 6.07-5.95 (m, 1H), 5.42 (dd, J=17.6, 1.6 Hz, 1H), 5.22 (dd, J=11.2, 1.6 Hz, 1H), 4.90 (dd, J=19.2, 4.8 Hz, 2H), 4.69 (d, J=5.2 Hz, 1H), 4.62-4.51 (m, 2H), 4.43 (d, J=9.6 Hz, 1H), 4.38 (t, J=5.6 Hz, 1H), 4.33 (s, 2H), 3.64 (dd, J=11.2, 5.2 Hz, 1H), 3.42-3.31 (m, 2H), 3.29-3.21 (m, 1H), 3.20-3.09 (m, 2H); MH+522.

Example 89

(2S,3R,4R,5S,6R)-2-(2-(Allyloxymethyl)-4-chloro-5-((5-(furan-2-yl)thiazol-2-yl)methyl)phenyl)-6-(hydroxymethyl)-tetrahydro-2H-pyran-3,4,5-triol The titled compound was obtained in the same manner as in Example 1.

$^1$H NMR (400 MHz, DMSO-d$_6$) δ 7.92 (s, 1H), 7.72 (d, J=1.6 Hz, 1H), 7.59 (s, 1H), 7.45 (s, 1H), 6.78 (d, J=3.2 Hz, 1H), 6.59-6.54 (m, 1H), 6.03-5.91 (m, 1H), 5.31 (qd, J=17.2, 1.6 Hz, 1H), 5.19 (qd, J=10.4, 2.0 Hz, 1H), 4.70 (d, J=12.8 Hz, 2H), 4.55 (d, J=12.8 Hz, 1H), 4.43 (s, 3H), 4.28 (d, J=8.8 Hz, 2H), 4.05 (td, J=5.6, 1.6 Hz, 2H), 3.69 (d, J=10.0 Hz, 1H), 3.45 (dd, J=11.6, 5.2 Hz, 1H), 3.32-3.16 (m, 4H); MH+508.

Example 90

(2S,3R,4R,5S,6R)-2-(2-(Allyloxymethyl)-4-chloro-5-((5-(furan-3-yl)thiazol-2-yl)methyl)phenyl)-6-(hydroxymethyl)-tetrahydro-2H-pyran-3,4,5-triol The titled compound was obtained in the same manner as in Example 1.

$^1$H NMR (400 MHz, DMSO-$d_6$) δ 8.05 (s, 1H), 7.87 (s, 1H), 7.74 (t, J=1.6 Hz, 1H), 7.58 (s, 1H), 7.45 (s, 1H), 6.86-6.82 (m, 1H), 6.03-5.91 (m, 1H), 5.32 (qd, J=18.0, 1.6 Hz, 1H), 5.19 (qd, J=10.4, 2.0 Hz, 1H), 4.70 (d, J=12.8 Hz, 2H), 4.55 (d, J=12.8 Hz, 2H), 4.41 (s, 3H), 4.28 (d, J=9.2 Hz, 2H), 4.05 (tdt, J=5.6, 1.6 Hz, 2H), 3.69 (d, J=10.4 Hz, 1H), 3.44 (dd, J=12.0, 5.6 Hz, 1H), 3.31-3.17 (m, 4H); MH+508.

Example 91

(2S,3R,4R,5S,6R)-2-(2-(Allyloxymethyl)-4-chloro-5-((5-(thiophen-2-yl)thiazol-2-yl)methyl)phenyl)-6-(hydroxymethyl)-tetrahydro-2H-pyran-3,4,5-triol The titled compound was obtained in the same manner as in Example 1.

$^1$H NMR (400 MHz, DMSO-$d_6$) δ 7.88 (s, 1H), 7.59 (s, 1H), 7.56 (dd, J=5.2, 1.2 Hz, 1H), 7.45 (s, 1H), 7.31 (dd, J=2.4, 1.2 Hz, 1H), 7.12-7.07 (m, 1H), 6.04-5.91 (m, 1H), 5.30 (qd, J=17.2, 1.6 Hz, 1H), 5.18 (qd, J=10.4, 2.0 Hz, 1H), 4.70 (d, J=12.8 Hz, 2H), 4.61 (d, J=12.8 Hz, 2H), 4.42 (s, 3H), 4.29 (d, J=9.2 Hz, 2H), 4.04 (td, J=5.6, 1.6 Hz, 2H), 3.70 (d, J=10.0 Hz, 1H), 3.45 (dd, J=12.0, 5.6 Hz, 1H), 3.32-3.15 (m, 4H); MH+524.

Example 92

(2S,3R,4R,5S,6R)-2-(2-(Allyloxymethyl)-4-chloro-5-((5-(thiophen-3-yl)thiazol-2-yl)methyl)phenyl)-6-(hydroxymethyl)-tetrahydro-2H-pyran-3,4,5-triol The titled compound was obtained in the same manner as in Example 1.

$^1$H NMR (400 MHz, DMSO-$d_6$) δ 7.97 (s, 1H), 7.74-7.70 (m, 1H), 7.15-7.11 (m, 1H), 7.57 (s, 1H), 7.45 (s, 1H), 7.43 (dd, J=5.2, 1.2 Hz, 1H), 6.04-5.91 (m, 1H), 5.32 (qd, J=18.0, 1.6 Hz, 1H), 5.18 (qd, J=10.4, 2.0 Hz, 1H), 4.70 (d, J=13.4 Hz, 2H), 4.55 (d, J=13.4 Hz, 2H), 4.46 (s, 3H), 4.28 (d, J=8.8 Hz, 2H), 4.05 (td, J=5.6, 1.6 Hz, 2H), 3.69 (d, J=10.0 Hz, 1H), 3.44 (dd, J=12.0, 5.6 Hz, 1H), 3.31-3.16 (m, 4H); MH+524.

Example 93

(2S,3R,4R,5S,6R)-2-(3-((5-(Furan-2-yl)thiazol-2-yl)methyl)naphthalen-1-yl)-6-(hydroxymethyl)tetrahydro-2H-pyran-3,4,5-triol The titled compound was obtained in the same manner as in Example 2.

$^1$H NMR (400 MHz, DMSO-$d_6$) δ 8.21-8.19 (m, 1H), 7.93 (s, 1H), 7.86-7.84 (m, 1H), 7.78 (s, 1H), 7.68 (d, J=1.2 Hz, 1H), 7.55 (d, J=1.2 Hz, 1H), 7.47-7.44 (m, 2H), 6.74 (d, J=3.6 Hz, 1H), 6.55-6.53 (m, 1H), 4.96-4.95 (m, 2H), 4.75-7.42 (m, 2H), 4.47 (s, 2H), 4.38 (t, J=5.2 Hz, 1H), 3.68 (dd, J=11.2, 3.2 Hz, 1H), 3.56-3.50 (m, 1H), 3.48-3.43 (m, 1H), 3.42-3.34 (m, 2H), 3.26-3.23 (m, 1H); MH+454.

Example 94

(2R,3S,4R,5R,6S)-2-(Hydroxymethyl)-6-(3-((5-(thiophen-2-yl)thiazol-2-yl)methyl)naphthalen-1-yl)tetrahydro-2H-pyran-3,4,5-triol The titled compound was obtained in the same manner as in Example 2.

$^1$H NMR (400 MHz, DMSO-$d_6$) δ 8.22-8.19 (m, 1H), 7.89 (s, 1H), 7.87-7.84 (m, 1H), 7.80 (s, 1H), 7.55 (d, J=1.6 Hz, 1H), 7.52 (dd, J=5.2, 1.2 Hz, 1H), 7.48-7.44 (m, 2H), 7.27 (dd, J=3.6, 1.2 Hz, 1H), 7.05 (dd, J=5.2, 3.6 Hz, 1H), 4.74 (d, J=9.2 Hz, 1H), 4.46 (s, 2H), 4.22 (br s, 4H), 3.68 (d, J=11.6 Hz, 1H), 3.54 (t, J=8.8 Hz, 1H), 3.47-3.41 (m, 1H), 3.39-3.34 (m, 2H), 3.29-3.26 (m, 1H); MH+470.

Example 95

(2S,3R,4R,5S,6R)-2-(3-((5-(Furan-2-yl)thiazol-2-yl)methyl)-4-methoxynaphthalen-1-yl)-6-(hydroxymethyl)-tetrahydro-2H-pyran-3,4,5-triol The titled compound was obtained in the same manner as in Example 2.

$^1$H NMR (400 MHz, DMSO-$d_6$) δ 8.23 (d, J=7.6 Hz, 1H), 8.05-8.03 (m, 1H), 7.90 (s, 1H), 7.68 (d, J=1.2 Hz, 1H), 7.56-7.48 (m, 3H), 6.73 (d, J=3.2 Hz, 1H), 6.53 (dd, J=3.6, 1.6 Hz, 1H), 4.97 (d, J=5.2 Hz, 2H), 4.79 (d, J=5.6 Hz, 1H), 4.68 (d, J=9.6 Hz, 1H), 4.49 (d, J=16.0 Hz, 1H), 4.44 (d, J=16.0 Hz, 1H), 4.38 (t, J=6.0 Hz, 1H), 3.84 (s, 3H), 3.67 (dd, J=10.0, 5.6 Hz, 1H), 3.56-3.50 (m, 1H), 3.46-3.21 (m, 4H); MH+484.

Example 96

(2R,3S,4R,5R,6S)-2-(Hydroxymethyl)-6-(4-methoxy-3-((5-(thiophen-2-yl)thiazol-2-yl)methyl)naphthalen-1-yl)-tetrahydro-2H-pyran-3,4,5-triol The titled compound was obtained in the same manner as in Example 2.

$^1$H NMR (400 MHz, DMSO-$d_6$) δ 8.24 (d, J=7.6 Hz, 1H), 8.06-8.03 (m, 1H), 7.85 (s, 1H), 7.55-7.48 (m, 4H), 7.25 (dd, J=3.6, 1.2 Hz, 1H), 7.04 (dd, J=5.2, 3.6 Hz, 1H), 4.99 (br, 2H), 4.80 (br, 1H), 4.68 (d, J=9.6 Hz, 1H), 4.47 (d, J=15.6 Hz, 1H), 4.43 (d, J=15.6 Hz, 1H), 4.39 (br, 1H), 3.85 (s, 3H), 3.70-3.66 (m, 1H), 3.57-3.50 (m, 1H), 3.48-3.22 (m, 4H); MH+500.

Example 97

(2R,3S,4R,5R,6S)-2-(Hydroxymethyl)-6-(4-methoxy-3-((5-phenylthiazol-2-yl)methyl)naphthalen-1-yl)-tetrahydro-2H-pyran-3,4,5-triol The titled compound was obtained in the same manner as in Example 2.

$^1$H NMR (400 MHz, DMSO-$d_6$) δ 8.24 (d, J=7.6 Hz, 1H), 8.06-8.04 (m, 2H), 7.56-7.48 (m, 5H), 7.36 (t, J=7.2 Hz, 2H), 7.28 (t, J=7.2 Hz, 1H), 4.99 (br, 2H), 4.80 (d, J=4.8 Hz, 1H), 4.69 (d, J=9.6 Hz, 1H), 4.49 (d, J=15.6 Hz, 1H), 4.45 (d,

J=15.6 Hz, 1H), 4.39 (br, 1H), 3.86 (s, 3H), 3.69-3.65 (m, 1H), 3.58-3.51 (m, 1H), 3.48-3.22 (m, 4H); MH+494.

Example 98

(2R,3S,4R,5R,6S)-2-(Hydroxymethyl)-6-(4-methoxy-3-((5-methylthiazol-2-yl)methyl)naphthalen-1-yl)-tetrahydro-2H-pyran-3,4,5-triol The titled compound was obtained in the same manner as in Example 2.
$^1$H NMR (400 MHz, DMSO-$d_6$) δ 8.22 (d, J=7.6 Hz, 1H), 8.04-8.02 (m, 1H), 7.54-7.46 (m, 3H), 7.31 (d, J=1.6 Hz, 1H), 4.96 (br, 2H), 4.75 (d, J=6.0 Hz, 1H), 4.66 (d, J=9.2 Hz, 1H), 4.39 (d, J=15.6 Hz, 1H), 4.39 (br, 1H), 4.34 (d, J=15.6 Hz, 1H), 3.83 (s, 3H), 3.69-3.65 (m, 1H), 3.55-3.49 (m, 1H), 3.46-3.21 (m, 4H), 2.32 (s, 3H); MH+432.

Example 99

(2R,3R,4R,5R,6S)-2-(Hydroxymethyl)-6-(4-methoxy-3-((5-propylthiazol-2-yl)methyl)naphthalen-1-yl)-tetrahydro-2H-pyran-3,4,5-triol The titled compound was obtained in the same manner as in Example 2.
$^1$H NMR (400 MHz, DMSO-$d_6$) δ 8.22 (d, J=7.6 Hz, 1H), 8.04-8.02 (m, 1H), 7.54-7.47 (m, 2H), 7.49 (s, 1H), 7.35 (m, 1H), 4.96 (br, 2H), 4.75 (d, J=6.0 Hz, 1H), 4.67 (d, J=9.6 Hz, 1H), 4.40 (d, J=16.0 Hz, 1H), 4.37 (br, 1H), 4.36 (d, J=16.0 Hz, 1H), 3.83 (s, 3H), 3.71-3.66 (m, 1H), 3.57-3.22 (m, 5H), 2.67 (t, J=7.2 Hz, 2H), 1.52 (sext, J=7.2 Hz, 2H), 0.84 (t, J=7.2 Hz, 3H); MH+460.

Example 100

(2S,3R,4R,5S,6R)-2-(3-((5-Heptylthiazol-2-yl)methyl)-4-methoxynaphthalen-1-yl)-6-(hydroxymethyl)-tetrahydro-2H-pyran-3,4,5-triol The titled compound was obtained in the same manner as in Example 2.
$^1$H NMR (400 MHz, DMSO-$d_6$) δ 8.22 (d, J=8.0 Hz, 1H), 8.04-8.02 (m, 1H), 7.54-7.47 (m, 2H), 7.49 (s, 1H), 7.34 (s, 1H), 4.96-4.95 (m, 1H), 4.75 (d, J=6.0 Hz, 1H), 4.67 (d, J=9.6 Hz, 1H), 4.40 (d, J=15.6 Hz, 1H), 4.67 (br, 1H), 4.36 (d, J=15.6 Hz, 1H), 3.83 (s, 3H), 3.72-3.66 (m, 1H), 3.56-3.50 (m, 1H), 3.47-3.22 (m, 4H), 2.69 (t, J=7.2 Hz, 2H), 1.49 (quint, J=7.2 Hz, 2H), 1.27-1.13 (m, 8H), 0.80 (t, J=7.2 Hz, 3H); MH+516.

Example 101

(2S,3R,4R,5S,6R)-2-(3-((5-Cyclopentylthiazol-2-yl)methyl)-4-methoxynaphthalen-1-yl)-6-(hydroxymethyl)-tetrahydro-2H-pyran-3,4,5-triol The titled compound was obtained in the same manner as in Example 2.
$^1$H NMR (400 MHz, DMSO-$d_6$) δ 8.22 (d, J=7.6 Hz, 1H), 8.03 (dd, J=7.6, 1.6 Hz, 1H), 7.53-7.46 (m, 3H), 7.36 (d, J=0.8 Hz, 1H), 4.99 (br, 2H), 4.78 (d, J=5.2 Hz, 1H), 4.66 (d, J=9.6 Hz, 1H), 4.39 (d, J=16.0 Hz, 1H), 4.37 (br, 1H), 4.34 (d, J=16.0 Hz, 1H), 3.83 (s, 3H), 3.70-3.65 (m, 1H), 3.56-3.49 (m, 1H), 3.48-3.22 (m, 4H), 3.15 (quint, J=8.0 Hz, 1H), 1.99-1.97 (m, 2H), 1.67-1.54 (m, 4H), 1.45-1.40 (m, 2H); MH+486.

Example 102

(2S,3R,4R,5S,6R)-2-(3-((5-Cyclohexylthiazol-2-yl)methyl)-4-methoxynaphthalen-1-yl)-6-(hydroxyethyl)-tetrahydro-2H-pyran-3,4,5-triol The titled compound was obtained in the same manner as in Example 2.
$^1$H NMR (400 MHz, DMSO-$d_6$) δ 8.22 (d, J=8.0 Hz, 1H), 8.04-8.02 (m, 1H), 7.54-7.47 (m, 3H), 7.36 (s, 1H), 4.67 (d, J=9.6 Hz, 1H), 4.50 (br, 4H), 4.39 (d, J=15.6 Hz, 1H), 4.35 (d, J=15.6 Hz, 1H), 3.83 (s, 3H), 3.67 (d, J=10.0 Hz, 1H), 3.52 (t, J=8.8 Hz, 1H), 3.45-3.33 (m, 3H), 3.24 (t, J=9.2 Hz, 1H), 2.77-2.72 (m, 1H), 1.90-1.82 (m, 2H), 1.70-1.56 (m, 3H), 1.34-1.20 (m, 4H), 1.17-1.08 (1H); MH+500.

Example 103

(2S,3R,4R,5S,6R)-2-(3-((5-Ethoxythiazol-2-yl)methyl)-4-methoxynaphthalen-1-yl)-6-(hydroxyethyl)-tetrahydro-2H-pyran-3,4,5-triol The titled compound was obtained in the same manner as in Example 2.
$^1$H NMR (400 MHz, DMSO-$d_6$) δ 8.22 (d, J=7.6 Hz, 1H), 8.04-8.01 (m, 1H), 7.54-7.47 (m, 2H), 7.46 (s, 1H), 6.98 (s, 1H), 4.99 (br, 2H), 4.77 (d, J=5.6 Hz, 1H), 4.67 (d, J=9.6 Hz, 1H), 4.38 (t, J=5.6 Hz, 1H), 4.30 (d, J=15.6 Hz, 1H), 4.25 (d, J=15.6 Hz, 1H), 4.04 (q, J=7.2 Hz, 2H), 3.82 (s, 3H), 3.69-3.65 (m, 1H), 3.54-3.48 (m, 1H), 3.46-3.21 (m, 4H), 1.24 (t, J=7.2 Hz, 3H); MH+462.

Example 104

(2S,3R,4R,5S,6R)-2-(4-((5-(Furan-2-yl)thiazol-2-yl)methyl)naphthalen-2-yl)-6-(hydroxymethyl)-tetrahydro-2H-pyran-3,4,5-triol The titled compound was obtained in the same manner as in Example 2.
$^1$H NMR (400 MHz, DMSO-$d_6$) δ 8.05-8.02 (m, 1H), 7.91-7.88 (m, 1H), 7.88 (s, 1H), 7.82 (s, 1H), 7.65 (d, J=1.2 Hz, 1H), 7.59 (s, 1H), 7.49-7.46 (m, 2H), 6.67 (d, J=3.2 Hz, 1H), 6.51 (dd, J=3.2, 2 Hz, 1H), 4.95 (br, 2H), 4.82-4.72 (m, 2H), 4.44 (t, J=5.6 Hz, 1H), 4.17 (d, J=8.8 Hz, 1H), 3.74-3.70 (m, 1H), 3.48 (quint, J=6.0 Hz, 1H), 3.32-3.20 (m, 5H); MH+454.

Example 105

(2S,3R,4R,5S,6R)-2-(4-((5-Ethylthiazol-2-yl)methyl)naphthalen-2-yl)-6-(hydroxymethyl)-tetrahydro-2H-pyran-3,4,5-triol The titled compound was obtained in the same manner as in Example 2.
$^1$H NMR (400 MHz, DMSO-$d_6$) δ 8.05-8.02 (m, 1H), 7.91-7.88 (m, 1H), 7.79 (s, 1H), 7.53 (s, 1H), 7.48-7.45 (m, 2H), 7.33 (s, 1H), 4.97-4.95 (m, 2H), 4.81 (d, J=5.6 Hz, 1H), 4.71 (d, J=15.6 Hz, 1H), 4.64 (d, J=15.6 Hz, 1H), 4.46 (t, J=5.6 Hz, 1H), 4.15 (d, J=9.2 Hz, 1H), 3.75-3.68 (m, 1H), 3.47 (quint, J=6.0 Hz, 1H), 3.42-3.20 (m, 4H), 2.67 (q, J=7.6 Hz, 2H), 1.10 (t, J=7.6 Hz, 3H); MH+416.

Example 106

Ethyl 2-(2-chloro-5-((2S,3R,4R,5S,6R)-3,4,5-trihydroxy-6-(hydroxymethyl)-tetrahydro-2H-pyran-2-yl)benzyl)thiazole-5-carboxylate Step 1: Ethyl 2-(2-chloro-5-((2S,3S,4R,5R,6R)-3,4,5-tris(benzyloxy)-6-(benzyloxymethyl)-tetrahydro-2H-pyran-2-yl)benzyl)thiazole-5-carboxylate (56)

To a solution of carboxylic acid 55 (2.5 g, 3.6 mmol) and DMF (0.1 mL) in $CH_2Cl_2$ (12 mL) under nitrogen atmosphere, was slowly added oxalyl chloride (1.28 mL, 7.2 mmol) at 0° C. After an additional stirring at 0° C. for 15 min, the reaction mixture was stirred at room temperature for 5 h. The mixture was evaporated under vacuum to provide acyl chloride (2.6 g).

The residue was dissolved in THF (25 mL) and to the solution of acyl chloride was added $NH_4OH$ (10 mL) at 0° C. The reaction mixture was warmed to room temperature and stirred for 5 h. The mixture was evaporated under vacuum to provide amide (2.6 g).

To a solution of the crude amide in anhydrous THF (40 mL) was added Lawesson's reagent (874 mg, 2.16 mmol). The reaction mixture was refluxed for 15 h. After cooling to room temperature, the reaction mixture was poured into a saturated $NaHCO_3$ solution, and extracted with EtOAc. The organic phase was dried over anhydrous $MgSO_4$, filtered and evaporated under vacuum to provide the crude thioamide.

To a solution of the thioamide residue and ethyl-2-chloro-2-formylacetate (1.35 g, 9.0 mmol) in EtOH (30 mL) was added pyridine (0.5 mL). The reaction mixture was stirred at 80° C. for 15 h. The reaction mixture was poured into a 1.0 M HCl solution, and extracted with $CH_2Cl_2$. The organic phase was dried over anhydrous $MgSO_4$, filtered and evaporated under vacuum. The residue was further purified by silica column chromatography to provide the ester intermediate 56 (1013 mg, 35%, 4 steps). MH+804.

Step 2: Ethyl 2-(2-chloro-5-((2S,3R,4R,5S,6R)-3,4,5-trihydroxy-6-(hydroxymethyl)-tetrahydro-2H-pyran-2-yl)benzyl)thiazole-5-carboxylate The titled compound was obtained in the same manner as in Example 4.
$^1H$ NMR (400 MHz, $CD_3OD$) δ 8.23 (s, 1H), 7.53 (s, 1H), 7.42-7.38 (m, 2H), 4.48 (d, J=2.4 Hz, 2H), 4.30 (q, J=7.2 Hz, 2H), 4.14 (d, J=9.6 Hz, 1H), 3.87 (d, J=12.4 Hz, 1H), 3.71-3.67 (m, 1H), 3.48-3.30 (m, 4H), 1.31 (t, J=7.2 Hz, 3H); MH+444.

Example 107

(2S,3R,4R,5S,6R)-2-(3-((5-(1,3,4-Thiadiazol-2-yl)thiazol-2-yl)methyl)-4-chlorophenyl)-6-(hydroxymethyl)-tetrahydro-2H-pyran-3,4,5-triol Step 1: 2-(2-(2-Chloro-5-((2S,3S,4R,5R,6R)-3,4,5-tris(benzyloxy)-6-(benzyloxymethyl)-tetrahydro-2H-pyran-2-yl)benzyl)thiazol-5-yl)-1,3,4-thiadiazole (57)

The mixture of the ester 56 (910 mg, 1.13 mmol) and KOH (254 mg, 4.52 mmol) in EtOH/THF (1:2, 30 mL) was refluxed for 2 h. After cooling to room temperature, the reaction mixture was poured into a 1.0 M HCl solution, and extracted with $CH_2Cl_2$. The organic phase was dried over anhydrous $MgSO_4$ and evaporated under vacuum to provide a carboxylic acid (769 mg, 0.99 mmol).

To a mixture of the carboxylic acid (769 mg, 0.99 mmol), EDCI (380 mg, 1.98 mmol), HOBt (268 mg, 1.98 mmol) and formylhydrazine (90 mg, 1.49 mmol) in DMF (10 mL) was added NMM (0.44 mL, 3.96 mmol). After stirring at room temperature for 15 h, the reaction mixture was poured into brine, and extracted with EtOAc. The organic phase was washed with a saturated $NaHCO_3$ solution and dried over anhydrous $MgSO_4$. The solution was evaporated under vacuum to provide a hydrazide intermediate (810 mg, 0.99 mmol).

To a solution of the hydrazide intermediate (810 mg, 0.99 mmol) in anhydrous THF (10 mL) was added Lawesson's reagent (1002 mg, 2.48 mmol). The reaction mixture was refluxed for 3 h. After cooling to room temperature, the reaction mixture was poured into a saturated $NaHCO_3$ solution, and extracted with EtOAc. The organic phase was dried over $MgSO_4$, filtered and evaporated under vacuum to provide the titled compound 57 (403 mg, 44%). MH+816.

Step 2: (2S,3R,4R,5S,6R)-2-(3-((5-(1,3,4-Thiadiazol-2-yl)thiazol-2-yl)methyl)-4-chlorophenyl)-6-(hydroxymethyl)-tetrahydro-2H-pyran-3,4,5-triol The titled compound was obtained in the same manner as in Example 4.
$^1H$ NMR (400 MHz, $CD_3OD$) δ 9.41 (s, 1H), 8.28 (s, 1H), 7.57 (m, 1H), 7.44-7.38 (m, 2H), 4.53 (d, J=2.0 Hz, 2H), 4.15 (d, J=9.6 Hz, 1H), 3.87 (d, J=12.4 Hz, 1H), 3.72-3.67 (m, 1H), 3.48-3.30 (m, 4H); MH+456.

Example 108

2-((5-(Furan-2-yl)thiazol-2-yl)methyl)-4-((2S,3R,4R,5S,6R)-3,4,5-trihydroxy-6-(hydroxymethyl)-tetrahydro-2H-pyran-2-yl)benzonitrile Step 1: (2R,3R,4R,5S,6S)-2-(Acetoxymethyl)-6-(4-bromo-3-((5-(furan-2-yl)thiazol-2-yl)methyl)phenyl)-tetrahydro-2H-pyran-3,4,5-triyl triacetate (58)

To a solution of (2S,3R,4R,5S,6R)-2-(4-bromo-3-((5-(furan-2-yl)thiazol-2-yl)methyl)phenyl)-6-(hydroxymethyl)-tetrahydro-2H-pyran-3,4,5-triol (750 mg, 1.55 mmol) and DMAP (19 mg, 0.16 mmol) in $CH_2Cl_2$ (16 mL) was slowly added acetic anhydride (1.18 mL, 12.4 mmol) and triethylamine (2.17 mL, 15.5 mmol) at 0° C. After an additional stirring at 0° C. for 15 min, the reaction mixture was stirred at room temperature for 3 h. The mixture was evaporated in vacuo to remove $CH_2Cl_2$. The residue was diluted with EtOAc and washed with water, 1.0 M HCl solution and brine. The organic layer was dried over anhydrous $MgSO_4$, filtered and concentrated in vacuo. The residue was purified by silica column chromatography to provide the intermediate 58 (974 mg, 97%) as a white solid. MH+650.

Step 2: (2R,3R,4R,5S,6S)-2-(Acetoxymethyl)-6-(4-cyano-3-((5-(furan-2-yl)thiazol-2-yl)methyl)phenyl)-tetrahydro-2H-pyran-3,4,5-triyl triacetate (59)

The bromide 58 (300 mg, 0.46 mmol) was added to a microwave reaction tube containing copper(I) cyanide (124 mg, 1.38 mmol) in NMP. The capped reaction tube was placed in a microwave reactor and the mixture irradiated at 230° C. for 30 min. After dilution with EtOAc, the organic layer was washed with 15% NH$_4$OH solution prior to drying over anhydrous MgSO$_4$. After filtration and concentration under reduced pressure, the residue was purified by silica column chromatography to provide the cyanide 59 (208 mg, 76%) as a white solid. MH+597.

Step 3: 2-((5-(Furan-2-yl)thiazol-2-yl)methyl)-4-((2S,3R,4R,5S,6R)-3,4,5-trihydroxy-6-(hydroxymethyl)-tetrahydro-2H-pyran-2-yl)benzonitrile To a solution of the peracetylate 59 (208 mg, 0.35 mmol) in MeOH (10 mL) was added NaOMe (25 wt. % in MeOH, 0.2 mL). The reaction mixture was stirred at ambient temperature for 3 h. Acetic acid was added to neutralize the reaction mixture and concentrated in vacuo. The residue was redissolved in MeOH and further purified by prep HPLC (C18) to provide the titled compound (106 mg, 71 mmol) as a white solid.

$^1$H NMR (400 MHz, DMSO-d$_6$) δ 7.96 (s, 1H), 7.83 (d, J=8.0 Hz, 1H), 7.75 (d, J=1.6 Hz, 1H), 7.63 (s, 1H), 7.49 (dd, J=8.0, 1.2 Hz, 1H), 6.83 (d, J=3.2 Hz, 1H), 6.61-6.59 (m, 1H), 5.01 (br, 3H), 4.49 (br, 1H), 4.14 (d, J=9.2 Hz, 1H), 4.10 (br, 1H), 3.72 (d, J=11.6 Hz, 1H), 3.52-3.45 (m, 1H), 3.33-3.18 (m, 4H), 3.10 (t, J=9.2 Hz, 1H)

Example 109

2-((5-(Thiophen-3-yl)thiazol-2-yl)methyl)-4-((2S,3R,4R,5S,6R)-3,4,5-trihydroxy-6-(hydroxymethyl)-tetrahydro-2H-pyran-2-yl)benzonitrile The titled compound was obtained in the same manner as in Example 108.

$^1$H NMR (400 MHz, DMSO-d$_6$) δ 7.99 (s, 1H), 7.82 (d, J=8.0 Hz, 1H), 7.76 (dd, J=2.8, 1.2 Hz, 1H), 7.65 (dd, J=4.8, 2.8 Hz, 1H), 7.62 (s, 1H), 7.49 (dd, J=8.0, 1.2 Hz, 1H), 7.44 (dd, J=4.8, 1.2 Hz, 1H), 5.03 (d, J=5.2 Hz, 1H), 5.00 (d, J=5.2 Hz, 1H), 4.98 (d, J=6.0 Hz, 1H), 4.54 (s, 2H), 4.48 (t, J=5.6 Hz, 1H), 4.11 (d, J=5.6 Hz, 1H), 3.71 (dd, J=10.0, 5.6 Hz, 1H), 3.47 (quint, J=6.0 Hz, 1H), 3.32-3.06 (m, 4H); MH+445.

Example 110

(2S,3R,4R,5S,6R)-2-(4-Cyclopropyl-3-((5-(furan-2-yl)thiazol-2-yl)methyl)phenyl)-6-(hydroxymethyl)-tetrahydro-2H-pyran-3,4,5-triol Step 1: (2R,3R,4R,5S,6S)-2-(Acetoxymethyl)-6-(4-cyclopropyl-3-((5-(furan-2-yl)thiazol-2-yl)methyl)phenyl)-tetrahydro-2H-pyran-3,4,5-triyl triacetate (60)

The bromide 58 (300 mg, 0.46 mmol) was added to a microwave reaction tube containing cyclopropylboronic acid (86.9 mg, 1.01 mmol), palladium(II) acetate (31 mg, 46 μmol), tricyclohexylphosphonium tetrafluoroborate (68 mg, 0.18 mmol) and cesium carbonate (601 mg, 1.84 mmol) in dioxaone (5 mL). The capped reaction tube was placed in a microwave reactor and the mixture irradiated at 150° C. for 25 min. After dilution with EtOAc, the organic layer was washed with water and brine prior to drying over anhydrous MgSO$_4$. After filtration and concentration under reduced pressure, the residue was purified by silica column chromatography to provide the cyclopropane 60 (56 mg, 20%) as a yellow oil. MH+612.

Step 2: (2S,3R,4R,5S,6R)-2-(4-Cyclopropyl-3-((5-(furan-2-yl)thiazol-2-yl)methyl)phenyl)-6-(hydroxymethyl)-tetrahydro-2H-pyran-3,4,5-triol The titled compound was obtained in the same manner as in Example 108 (Step 3). $^1$H NMR (400 MHz, DMSO-d$_6$) δ 7.95 (s, 1H), 7.44 (d, J=1.2 Hz, 1H), 7.32 (d, J=1.6 Hz, 1H), 7.22 (dd, J=8.4, 1.6 Hz, 1H), 6.99 (d, J=8.0 Hz, 1H), 6.80-6.79 (m, 1H), 6.61-6.59 (m, 1H), 4.52 (d, J=13.2 Hz, 2H), 4.00 (d, J=9.2 Hz, 1H), 3.72 (d, J=11.6 Hz, 1H), 3.49-3.44 (m, 1H), 3.32-3.27 (m, 1H), 3.21-3.16 (m, 3H), 1.99-1.95 (m, 1H), 0.89-0.85 (m, 2H), 0.63-0.59 (m, 2H); MH+444.

Example 111

(2S,3R,4R,5S,6R)-2-(3-((5-(Furan-2-yl)thiazol-2-yl)methyl)phenyl)-6-(hydroxymethyl)-tetrahydro-2H-pyran-3,4,5-triol The titled compound was obtained as a side product in Example 110.

$^1$H NMR (400 MHz, DMSO-d$_6$) δ 7.95 (s, 1H), 7.74 (d, J=1.6 Hz, 1H), 7.35-7.22 (m, 4H), 6.79 (d, J=3.2 Hz, 1H), 6.60 (dd, J=3.2, 1.6 Hz, 1H), 4.94 (d, J=4.8 Hz, 2H), 4.78 (d, J=6.0 Hz, 1H), 4.45 (t, J=6.0 Hz, 1H), 4.34 (s, 3H), 4.02 (d, J=9.2 Hz, 1H), 3.74-3.69 (m, 1H), 3.49-3.43 (m, 1H), 3.33-3.15 (m, 4H); MH+404.

Example 112

(2S,3R,4R,5S,6R)-2-(4-Chloro-5-((5-(furan-2-yl)thiazol-2-yl)methyl)-2-hydroxyphenyl)-6-(hydroxymethyl)-tetrahydro-2H-pyran-3,4,5-triol (63)

Step 1: 5-Chloro-4-((5-(furan-2-yl)thiazol-2-yl)methyl)-2-((2S,3S,4R,5R,6R)-3,4,5-tris(benzyloxy)-6-(benzyloxymethyl)-tetrahydro-2H-pyran-2-yl)phenol (62)

To a solution of allyl ether 61 (3.76 g, 4.40 mmol) in THF (50 mL) were added sodium borohydride (1.0 g, 26.4 mmol) and tetrakis(triphenylphosphine)-palladium(0) (0.25 g, 0.22 mmol) at 0° C. The mixture was stirred at 0° C. for 10 min and at room temperature for 15 h. Saturated NaHCO$_3$ solution was added slowly to the mixture to quench the reaction. The mixture was extracted with EtOAc. The organic layer was dried over MgSO$_4$, filtered and concentrated in vacuo. The residue was purified by silica column chromatography to provide the titled compound 62 (3.2 g, 83%).

$^1$H NMR (400 MHz, CDCl$_3$) δ 7.84 (s, 1H), 7.75 (s, 1H), 7.43-7.37 (m, 2H), 7.35-7.24 (m, 3H), 7.21-7.13 (m, 11H), 7.15-6.94 (m, 5H), 6.46-6.36 (m, 3H), 4.92-4.82 (m, 6H), 4.59-4.22 (m, 8H), 3.85-3.55 (m, 4H); MH+814.

Step 2: (2S,3R,4R,5S,6R)-2-(4-Chloro-5-((5-(furan-2-yl)thiazol-2-yl)methyl)-2-hydroxyphenyl)-6-(hydroxymethyl)-tetrahydro-2H-pyran-3,4,5-triol (63)

The titled compound was obtained in the same manner as in Example 4.

$^1$H NMR (400 MHz, DMSO-d$_6$) δ 7.93 (s, 1H), 7.73 (d, J=1.6 Hz, 1H), 7.48 (s, 1H), 7.11 (s, 1H), 6.78 (d, J=3.2 Hz, 1H), 6.65-6.57 (m, 1H), 5.10-4.92 (m, 2H), 4.55-4.46 (m, 3H), 4.15-4.09 (m, 2H), 3.78-3.60 (m, 2H), 3.51-3.12 (m, 11H); MH+512.

Example 113

(2S,3R,4R,5S,6R)-2-(4-Chloro-5-((5-(furan-2-yl)thiazol-2-yl)methyl)-2-(hydroxymethyl)phenyl)-6-(hydroxymethyl)-tetrahydro-2H-pyran-3,4,5-triol The titled compound was obtained in the same manner as in Example 112.

$^1$H NMR (400 MHz, DMSO-d$_6$) δ 7.92 (s, 1H), 7.72 (d, J=1.2 Hz, 1H), 7.55 (s, 1H), 7.49 (s, 1H), 6.77 (d, J=3.2 Hz, 1H), 6.60-6.54 (m, 1H), 4.95 (br, 1H), 4.63 (s, 4H), 4.42 (s, 3H), 4.27 (d, J=9.2 Hz, 2H), 3.69 (d, J=10.0 Hz, 1H), 3.43 (dd, J=11.6, 1.6 Hz, 1H), 3.32-3.14 (m, 4H); MH+468.

Example 114

(2S,3R,4R,5S,6R)-2-(4-Chloro-5-((5-(furan-3-yl)thiazol-2-yl)methyl)-2-(hydroxymethyl)phenyl)-6-(hydroxymethyl)-tetrahydro-2H-pyran-3,4,5-triol The titled compound was obtained in the same manner as in Example 112.

$^1$H NMR (400 MHz, DMSO-d$_6$) δ 8.04 (s, 1H), 7.86 (s, 1H), 7.74 (t, J=1.6 Hz, 1H), 7.55 (s, 1H), 7.49 (s, 1H), 6.88-6.83 (m, 1H), 5.05 (br s, 1H), 4.63 (s, 4H), 4.42 (s, 3H), 4.27 (d, J=9.2 Hz, 2H), 3.69 (d, J=10.0 Hz, 1H), 3.43 (dd, J=11.6, 1.6 Hz, 1H), 3.31-3.12 (m, 4H); MH+468.

Example 115

(2S,3R,4R,5S,6R)-2-(4-Chloro-2-(hydroxymethyl)-5-((5-(thiophen-2-yl)thiazol-2-yl)methyl)phenyl)-6-(hydroxymethyl)-tetrahydro-2H-pyran-3,4,5-triol The titled compound was obtained in the same manner as in Example 112.

$^1$H NMR (400 MHz, DMSO-d$_6$) δ 7.87 (s, 1H), 7.56 (s, 1H), 7.54 (d, J=0.8 Hz, 1H), 7.31 (dd, J=4.0, 0.8 Hz, 1H), 7.11-7.05 (m, 1H), 4.90 (br, 1H), 4.63 (s, 4H), 4.41 (s, 3H), 4.27 (d, J=9.2 Hz, 2H), 3.69 (d, J=10.0 Hz, 1H), 3.43 (dd, J=11.6, 1.6 Hz, 1H), 3.33-3.13 (m, 4H); MH+484.

Example 116

(2S,3R,4R,5S,6R)-2-(4-Chloro-2-(hydroxymethyl)-5-((5-(thiophen-3-yl)thiazol-2-yl)methyl)phenyl)-6-(hydroxymethyl)-tetrahydro-2H-pyran-3,4,5-triol The titled compound was obtained in the same manner as in Example 112.

$^1$H NMR (400 MHz, DMSO-d$_6$) δ 7.97 (s, 1H), 7.75-7.70 (m, 1H), 7.66-7.61 (m, 1H), 7.55 (s, 1H), 7.49 (s, 1H), 7.42 (dd, J=5.2, 1.2 Hz, 1H), 4.96 (br, 1H), 4.63 (s, 4H), 4.40 (s, 3H), 4.28 (d, J=9.2 Hz, 2H), 3.69 (d, J=10.4 Hz, 1H), 3.44 (dd, J=11.6, 1.6 Hz, 1H), 3.33-3.13 (m, 4H); MH+484.

Example 117

(2S,3R,4R,5S,6R)-2-(4-Chloro-5-((5-(furan-2-yl)thiazol-2-yl)methyl)-2-(2-methoxyethoxy)phenyl)-6-(hydroxymethyl)-tetrahydro-2H-pyran-3,4,5-triol
(64)

To a solution of phenol 63 (205 mg, 0.451 mmol) in acetone (10 mL) was added bromoethylmethyl ether (1.6 mL, 15.8 mmol) and K$_2$CO$_3$ (2.3 g, 15.8 mmol) at room temperature. The mixture was stirred at 50° C. for 15 h. The mixture was cooled to room temperature and filtered off through the celite. The filtrate was concentrated in vacuo. The residue was purified by prep HPLC (C18) to provide the titled compound 64 (42 mg, 19%).

$^1$H NMR (400 MHz, DMSO-d$_6$) δ 7.95 (s, UT), 7.73 (d, J=1.2 Hz, 1H), 7.40 (s, 1H), 6.90 (s, 1H), 6.78 (d, J=3.2 Hz, 1H), 6.62-6.55 (m, 1H), 4.94 (t, J=5.2 Hz, 2H), 4.49-4.39 (m, 2H), 4.33 (s, 2H), 3.75-3.66 (m, 1H), 3.47-3.15 (m, 7H); MH+512.

Example 118

(2S,3R,4R,5S,6R)-2-(4-Chloro-5-((5-(furan-2-yl)thiazol-2-yl)methyl)-2-propoxyphenyl)-6-(hydroxymethyl)tetrahydro-2H-pyran-3,4,5-triol The titled compound was obtained in the same manner as in Example 117.

$^1$H NMR (400 MHz, DMSO-d$_6$) δ 7.91 (s, 1H), 7.72 (d, J=1.6 Hz, 1H), 7.45 (s, 1H), 7.07 (s, 1H), 6.78 (d, J=3.2 Hz, 1H), 6.58 (q, J=1.6 Hz, 1H), 4.52 (br s, 4H), 4.43 (d, J=9.6 Hz, 1H), 4.36 (s, 1H), 3.95 (td, J=6.4, 1.6 Hz, 2H), 4.48-4.75 (m, 4H), 3.67 (d, J=10.8 Hz, 1H), 3.47-3.37 (m, 2H), 3.26 (t, J=8.0 Hz, 1H), 3.23-3.11 (m, 2H), 1.73 (sext, J=6.4 Hz, 2H), 0.99 (d, J=7.2 Hz, 3H); MH+496.

Example 119

(2S,3R,4R,5S,6R)-2-(2-(But-3-enyloxy)-4-chloro-5-((5-(furan-2-yl)thiazol-2-yl)methyl)phenyl)-6-(hydroxymethyl)tetrahydro-2H-pyran-3,4,5-triol The titled compound was obtained in the same manner as in Example 117.

$^1$H NMR (400 MHz, DMSO-d$_6$) δ 7.912 (s, 1H), 7.72 (d, J=1.2 Hz, 1H), 7.46 (s, 1H), 7.10 (s, 1H), 6.77 (d, J=3.2 Hz, 1H), 6.58 (q, J=2.0 Hz, 1H), 5.99-5.87 (m, 1H), 5.18 (dd, J=17.2, 1.6 Hz, 1H), 5.09 (d, J=9.2 Hz, 1H), 5.00 (br, 2H), 4.5269 (br, 2H), 4.42 (d, J=9.6 Hz, 2H), 4.36 (s, 2H), 4.04 (td, J=6.4, 1.2 Hz, 2H), 4.48-4.75 (m, 4H), 3.67 (d, J=11.2 Hz, 1H), 3.40 (t, J=8.8 Hz, 2H), 3.28-3.11 (m, 4H); MH+508.

Example 120

(2S,3R,4R,5S,6R)-2-(4-Chloro-5-((5-(furan-2-yl)thiazol-2-yl)methyl)-2-(prop-2-ynyloxy)phenyl)-6-(hydroxymethyl)-tetrahydro-2H-pyran-3,4,5-triol The titled compound was obtained in the same manner as in Example 117.

$^1$H NMR (400 MHz, DMSO-d$_6$) δ 7.91 (s, 1H), 7.72 (d, J=1.6 Hz, 1H), 7.51 (s, 1H), 7.17 (s, 1H), 6.79-6.74 (m, 1H), 6.57 (q, J=1.6 Hz, 1H), 4.92 (dd, J=11.2, 4.8 Hz, 2H), 4.85 (d, J=2.4 Hz, 2H), 4.71 (d, J=5.2 Hz, 1H), 4.48-4.75 (m, 4H), 3.68 (dd, J=10.4, 5.2 Hz, 1H), 3.62 (t, J=2.4 Hz, 1H), 3.45-3.11 (m, 5H); MH+492.

Example 121

(2S,3R,4R,5S,6R)-2-(4-Chloro-5-((5-(furan-2-yl)thiazol-2-yl)methyl)-2-(2-hydroxyethoxy)phenyl)-6-(hydroxymethyl)tetrahydro-2H-pyran-3,4,5-triol The titled compound was obtained in the same manner as in Example 117.

$^1$H NMR (400 MHz, DMSO-d$_6$) δ 7.92 (s, 1H), 7.74-7.71 (m, 1H), 7.47 (s, 1H), 7.12 (s, 1H), 6.77 (d, J=3.2 Hz, 1H), 6.59-6.53 (m, 1H), 4.97-4.91 (m, 2H), 4.81 (t, J=6.0 Hz, 1H), 4.70 (d, J=5.2 Hz, 1H), 4.51 (d, J=9.2 Hz, 1H), 4.44 (t, J=5.6 Hz, 1H), 4.37 (s, 2H), 4.03 (t, J=4.8 Hz, 2H), 3.76-3.63 (m, 3H), 3.48-3.39 (m, 1H), 3.31-3.13 (m, 4H); MH+498.

Example 122

(2S,3R,4R,5S,6R)-2-(2-(2-(1H-1,2,4-Triazol-1-yl)ethoxy)-4-chloro-5-((5-(furan-2-yl)thiazol-2-yl)methyl)phenyl)-6-(hydroxymethyl)-tetrahydro-2H-pyran-3,4,5-triol (65)

To a solution of phenol 63 (200 mg, 0.441 mmol) and cesium carbonate (158 mg, 0.485 mmol) in DMF (10 mL) was added 1,2-dibromoethane (96 µL, 1.11 mmol). The resulting mixture was stirred at room temperature for 60 h. After dilution with water, the mixture was extracted with EtOAc. The organic layer was dried over anhydrous $MgSO_4$, filtered and concentrated in vacuo. The residue was carried on to the next step without further purification.

To a solution of the crude bromide in DMF (10 mL) was added 1,2,4-triazole sodium derivative (122 mg, 1.34 mmol). The mixture was stirred at room temperature for 15 h. After dilution with water, the mixture was extracted with EtOAc. The organic layer was dried over anhydrous $MgSO_4$, filtered and concentrated in vacuo. The residue was purified by prep HPLC (C18) to provide the titled compound 65 (78 mg, 33%, 2 steps).

$^1$H NMR (400 MHz, DMSO-$d_6$) δ 8.59 (s, 1H), 8.02 (s, 1H), 7.95 (s, 1H), 7.77-7.71 (m, 1H), 7.47 (s, 1H), 7.13 (s, 1H), 6.78 (d, J=3.2 Hz, 1H), 6.62-6.58 (m, 1H), 5.02-4.92 (m, 2H), 4.71-4.35 (m, 8H), 3.71-3.61 (m, 3H), 3.49-3.41 (m, 1H), 3.38-3.15 (m, 5H); MH+549.

Example 123

(2S,3R,4R,5S,6R)-2-(3-((5-(4-Fluorophenyl)thiazol-2-yl)methyl)-4-hydroxynaphthalen-1-yl)-6-(hydroxymethyl)-tetrahydro-2H-pyran-3,4,5-triol (66)

To a solution of phenol 50 (166 mg, 0.32 mmol) in $CH_2Cl_2$ (10 mL) was added $BBr_3$ (1.0 M in $CH_2Cl_2$, 3.0 mL, 2.97 mmol) at 0° C. The reaction mixture was allowed to warm to room temperature and stirred for 2 h. After recooling to 0° C., the reaction was quenched by addition of MeOH and concentrated in vacuo. The redisue was purified by prep HPLC (C18) to provide the titled compound 66 (118 mg, 74%) as a white solid.

$^1$H NMR (400 MHz, DMSO-$d_6$) δ 9.69 (br, 1H), 8.24-8.22 (m, 1H), 8.15-8.12 (m, 1H), 8.01 (s, 1H), 7.61-7.55 (m, 2H), 7.46-7.41 (m, 3H), 7.18 (t, J=8.8 Hz, 2H), 4.94 (br, 2H), 4.69 (d, J=4.4 Hz, 1H), 4.62 (d, J=9.2 Hz, 1H), 4.47 (d, J=16.0 Hz, 1H), 4.43 (d, J=16.0 Hz, 1H), 4.37 (br, 1H), 3.67 (d, J=10.8 Hz, 1H), 3.58-3.52 (m, 1H), 3.44-3.13 (m, 4H); MH+498.

Example 124

(2S,3R,4R,5S,6R)-2-(4-Hydroxy-3-((5-(thiophen-2-yl)thiazol-2-yl)methyl)naphthalen-1-yl)-6-(hydroxymethyl)-tetrahydro-2H-pyran-3,4,5-triol The titled compound was obtained in the same manner as in Example 123.

$^1$H NMR (400 MHz, DMSO-$d_6$) δ 9.58 (br, 1H), 8.21-8.19 (m, 1H), 8.12-8.10 (m, 1H), 7.81 (s, 1H), 7.47-7.38 (m, 4H), 7.20 (dd, J=3.6, 1.2 Hz, 1H), 6.99 (dd, J=5.2, 3.6 Hz, 1H), 4.90 (br, 2H), 4.65 (d, J=6.0 Hz, 1H), 4.59 (d, J=9.6 Hz, 1H), 4.43 (d, J=16.0 Hz, 1H), 4.38 (d, J=16.0 Hz, 1H), 4.33 (t, J=5.6 Hz, 1H), 4.03 (q, J=5.2 Hz, 1H), 3.63 (dd, J=10.0, 5.2 Hz, 1H), 3.53-3.49 (m, 1H), 3.42-3.17 (m, 3H); MH+486.

Example 125

(2S,3R,4R,5S,6R)-2-(4-Hydroxy-3-((5-phenylthiazol-2-yl)methyl)naphthalen-1-yl)-6-(hydroxymethyl)-tetrahydro-2H-pyran-3,4,5-triol The titled compound was obtained in the same manner as in Example 123.

$^1$H NMR (400 MHz, DMSO-$d_6$) δ 9.70 (br, 1H), 8.25-8.22 (m, 1H), 8.15-8.11 (m, 1H), 8.04 (s, 1H), 7.54-7.52 (m, 2H), 7.45-7.42 (m, 3H), 7.36-7.32 (m, 2H), 7.28-7.25 (m, 1H), 4.94 (br, 2H), 4.69 (br, 1H), 4.62 (d, J=9.6 Hz, 1H), 4.48 (d, J=15.6 Hz, 1H), 4.43 (d, J=15.6 Hz, 1H), 4.36 (br, 1H), 3.67 (d, J=11.2 Hz, 1H), 3.55 (t, J=8.8 Hz, 1H), 3.45-3.21 (m, 4H); MH+480.

Example 126

(2S,3R,4R,5S,6R)-2-(4-Hydroxy-3-((5-propylthiazol-2-yl)methyl)naphthalen-1-yl)-6-(hydroxymethyl)-tetrahydro-2H-pyran-3,4,5-triol The titled compound was obtained in the same manner as in Example 123.

$^1$H NMR (400 MHz, DMSO-$d_6$) δ 9.70 (br, 1H), 8.22-8.20 (m, 1H), 8.13-8.11 (m, 1H), 7.45-7.35 (m, 4H), 4.94 (d, J=4.4 Hz, 1H), 4.67 (d, J=5.6 Hz, 1H), 4.60 (d, J=9.6 Hz, 1H), 4.41-4.33 (m, 3H), 3.66 (dd, J=10.4, 5.6 Hz, 1H), 3.56-3.50 (m, 1H), 3.42 (quint, J=6.0 Hz, 1H), 3.37-3.19 (m, 4H), 2.65 (t, J=7.6 Hz, 2H), 1.50 (sext, J=7.6 Hz, 2H), 0.83 (t, J=7.6 Hz, 3H); MH+446.

Example 127

(2S,3R,4R,5S,6R)-2-(3-((5-Heptylthiazol-2-yl)methyl)-4-hydroxynaphthalen-1-yl)-6-(hydroxymethyl)-tetrahydro-2H-pyran-3,4,5-triol The titled compound was obtained in the same manner as in Example 123.

$^1$H NMR (400 MHz, DMSO-$d_6$) δ 9.75 (br, 1H), 8.23-8.20 (m, 1H), 8.12-8.09 (m, 1H), 7.44-7.33 (m, 4H), 4.96 (br, 2H), 4.67 (br, 1H), 4.59 (d, J=9.6 Hz, 1H), 4.36 (s, 3H), 3.66 (d, J=11.2 Hz, 1H), 3.54 (t, J=8.4 Hz, 1H), 3.43-3.13 (m, 4H), 2.67 (t, J=7.2 Hz, 2H), 1.47 (quint, J=7.2 Hz, 2H), 1.25-1.12 (m, 8H), 0.80 (t, J=7.2 Hz, 3H); MH+501.

Example 128

(2S,3R,4R,5S,6R)-2-(3-((5-Ethoxythiazol-2-yl)methyl)-4-hydroxynaphthalen-1-yl)-6-(hydroxymethyl)-tetrahydro-2H-pyran-3,4,5-triol The titled compound was obtained in the same manner as in Example 123.

$^1$H NMR (400 MHz, DMSO-$d_6$) δ 9.62 (br, 1H), 8.22-8.20 (m, 1H), 8.13-8.10 (m, 1H), 7.43-7.40 (m, 2H), 7.35 (s, 1H), 6.98 (s, 1H), 4.95 (br, 2H), 4.68 (br, 1H), 4.60 (d, J=9.2 Hz, 1H), 4.37 (br, 1H), 4.29 (d, J=16.0 Hz, 1H), 4.25 (d, J=16.0 Hz, 1H), 4.00 (q, J=6.8 Hz, 2H), 3.70-3.63 (m, 1H), 3.57-3.50 (m, 1H), 3.43-3.0 (m, 5H), 1.23 (t, J=6.8 Hz, 3H); MH+448.

Example 129

(1S,3'R,4'S,5'S,6'R)-5-Chloro-6'-(hydroxymethyl)-6-(1-(5-(thiophen-2-yl)thiazol-2-yl)cyclopropyl)-3',4',5',6'-tetrahydro-3H-spiro[isobenzofuran-1,2'-pyran]-3',4',5'-triol (72)

Step 1: 2-(5-Bromo-2-chloro-4-((triisopropylsilyloxy)methyl)phenyl)-acetonitrile (68)

To a solution of compound 67 (15 g, 38 mmol) in THF (150 mL) was added N-bromosuccinimide (10 g, 57 mmol) and AIBN (630 mg, 3.8 mmol). The reaction mixture was stirred at 120° C. for 1 d. After the mixture was cooled to room temperature and evaporated volatile materials under reduced pressure. The crude compound was dried with anhydrous $MgSO_4$ and used next step without further purification.

To a solution of intermediate (17 g, crude) in EtOH (100 ml) was added NaCN (9 g, 190 mmol). The mixture was stirred at refluxed temperature for 15 h. The mixture was cooled to room temperature and evaporated in vacuo to remove solvent. The residue was purified with silica gel column to obtain the titled compound (10 g, 64%, 2 steps).

$^1$H NMR (400 MHz, $CDCl_3$) δ 7.78 (s, 1H), 7.44 (s, 1H), 4.83 (s, 2H), 4.53 (s, 2H), 1.25-1.16 (m, 3H), 1.10 (d, J=7.2 Hz, 18H).

Step 2: 1-(5-Bromo-2-chloro-4-((triisopropylsilyloxy)methyl)phenyl)-cyclopropanecarboxylic acid (69)

To a solution of acetonitrile 68 (5 g, 12 mmol) in toluene (100 ml) and NaOH (1.9 g, 48 mmol) dissolved in water (100 ml) was added tetrabutylammonium bromide (100 mg) and 1,2-dibromoethane (4 ml). The reaction mixture was stirred at room temperature for 15 h. The resulting organic solution was separated with methylene chloride and dried with anhydrous $MgSO_4$. After evaporation under reduced pressure, the crude product was used without further purification.

To a solution of intermediate in aqueous EtOH (100 ml) was added NaOH (1.9 g, 48 mmol). The reaction mixture was refluxed for 40 h. After reaction completion, the resulting solution was acidified with 4.0 M HCl until pH<1. The title compound was purified with work-up with $CH_2Cl_2$, anhydrous $MgSO_4$ and used next step without further purification (5.5 g, 62%, 2 steps).

Step 3: 2-(1-(5-Bromo-2-chloro-4-((triisopropylsilyloxy)methyl)phenyl)-cyclopropyl)-5—(thiophen-2-yl)thiazole (70)

To a mixture of the carboxylic acid 69 (1.4 g, 3.0 mmol), 2-amino-1-(thiophen-3-yl)ethanone hydrochloride (1.1 g, 6.0 mmol), EDCI (1.1 g, 6.0 mmol), and HOBt (1.0 g, 7.5 mmol) in DMF (10 mL) was added NMM (1.6 mL, 15 mmol). The resulting mixture was stirred at room temperature for 15 h. The reaction mixture was poured into 1.0 M HCl solution, and extracted with EtOAc. The organic phase was dried over anhydrous $MgSO_4$, filtered and evaporated under vacuum. The residue was further purified by silica column chromatography to provide the titled amide compound.

To a solution of the amide from Step 1 in anhydrous THF (10 mL) was added Lawesson's reagent (1.0 g, 2.60 mmol). The reaction mixture was refluxed overnight. After cooling to room temperature, the reaction mixture was poured into a saturated $NaHCO_3$ solution, and extracted with EtOAc. The organic phase was dried over anhydrous MgSO4, filtered and evaporated under vacuum. The residue was further purified by silica column chromatography to provide the titled thiazole compound 70 (972 mg, 55%, 2 steps).

$^1$H NMR (400 MHz, $CDCl_3$) δ 8.41-8.20 (m, 3H), 7.77 (s, 1H), 7.49 (s, 1H), 7.21 (s, 1H), 4.87 (s, 2H), 1.25-1.16 (m, 3H), 1.10 (d, J=7.2 Hz, 18H), 0.99-0.96 (m, 2H), 0.91-0.87 (m, 2H).

Step 4: (1S,3'R,4'S,5'S,6'R)-5-Chloro-6'-(hydroxymethyl)-6-(1-(5-(thiophen-2-yl)thiazol-2-yl)cyclopropyl)-3',4',5',6'-tetrahydro-3H-spiro[isobenzofuran-1,2'-pyran]-3',4',5'-triol (72)

To a solution of compound 70 (972 mg, 1.67 mmol) in THF (40 mL) at −78° C. was added n-butyllithium (2.5 M in hexanes, 0.67 mL) dropwisely not to increase the temperature of reaction mixture. The reaction mixture stirred at −78° C. for 30 min, then a solution of lactone (1 g, 1.67 mmol) in THF (40 mL) was added dropwise, and the mixture was stirred for 3 h at −78° C. and then reaction solution warmed up to room temperature. The reaction was quenched by addition of saturated $NH_4Cl$ solution. The organic layer was separated and the aqueous layer was extracted with EtOAc. The combined organic layers were washed with brine, dried over anhydrous $MgSO_4$, filtered and concentrated in vacuo to yield the intermediate compound 71 as sticky yellow solid.

To a solution of crude intermediate 71 in MeOH (50 mL) was added 4.0 M HCl (5 mL). The reaction mixture was stirred at refluxed temperature for 1 d. After reaction complete, the resulting solution was evaporated under reduced pressure. The residue was purified with prep HPLC (C18) to provide the titled compound 72 (229 mg, 27%) as a white solid.

$^1$H NMR (400 MHz, $CDCl_3$) δ 8.42-8.31 (m, 3H), 7.79 (s, 1H), 7.45 (s, 1H), 7.20 (s, 1H), 4.87 (dd, J=12.0, 9.2 Hz, 2H), 4.43 (d, J=2.4 Hz, 2H), 4.12 (d, J=9.2 Hz, 1H), 3.77 (d, J=12.0 Hz, 1H), 3.77-3.73 (m, 1H), 3.39-3.29 (m, 4H), 0.99-0.96 (m, 2H), 0.91-0.87 (m, 2H).

Example 130

(2R,3R,4S,5S,6R)-2-(3-((5-(Furan-2-yl)thiazol-2-yl)methyl)-1H-indol-1-yl)-6-(hydroxymethyl)-tetrahydro-2H-pyran-3,4,5-triol Step 1: Methyl 2-(1H-indol-3-yl)acetate (74)

To a solution of carboxylic acid 73 (10 g, 57.1 mmol) in MeOH (500 mL) was added dropwise thionyl chloride (21 mL, 285 mmol) at 0° C. The mixture was stirred at room temperature for 2 h and concentrated in vacuo to remove solvent. The residue was diluted with EtOAc and washed with aq. saturated $NH_4Cl$ solution, aq. saturated $NaHCO_3$ solution and brine successively. The organic layer was dried over anhydrous $MgSO_4$, filtered and concentrated in vacuo. The crude titled compound 74 (10.9 g, quantitative) was used without further purification. MH+190.

Step 2: Methyl 2-(indolin-3-yl)acetate (75)

To a solution of indole 74 (10.9 g, 57.4 mmol) in trifluoroacetic acid (200 mL) was added triethylsilane (20 mL, 121 mmol) at room temperature. The mixture was stirred at 60° C. for 3 h, cooled to room temperature and concentrated in vacuo to remove solvent. The residue was diluted with EtOAc and washed with aq. saturated $Cs_2CO_3$ solution. The organic layer was dried over anhydrous $MgSO_4$, filtered and concentrated in vacuo. The residue was purified by silica column chromatography to provide the titled compound 75 (8.5 g, 77%). MH+192.

Step 3: Methyl 2-(1-((2R,3R,4S,5S,6R)-3,4,5-trihydroxy-6-(hydroxymethyl)-tetrahydro-2H-pyran-2-yl)indolin-3-yl)acetate (76)

To a solution of indoline 75 (8.5 g, 44.2 mmol) in MeOH (150 mL) was added α-D-glucose (27 g, 146 mmol) at room temperature. The mixture was stirred at 70° C. for 60 h, cooled to room temperature and concentrated in vacuo to remove solvent. The residue was purified by silica column chromatography to provide the titled compound 76 (13.7 g, 88%). MH+354.

Step 4: (2R,3R,4S,5R,6R)-2-(Acetoxymethyl)-6-(3-(2-methoxy-2-oxoethyl)-1H-indol-1-yl)-tetrahydro-2H-pyran-3,4,5-triyl triacetate (77)

To a solution of indoline 76 (13.7 g, 38.9 mmol) in $CH_2Cl_2$ (150 mL) were added acetic anhydride (20 mL, 195 mmol), triethylamine (38 mL, 272 mmol) and catalytic amount (0.1 g) of DMAP room temperature. The mixture was stirred at room temperature for 1 h. The mixture was concentrated in vacuo. The residue was diluted with EtOAc, washed with aq. saturated $NaHCO_3$ solution, $H_2O$ and brine successively. The organic layer was dried over anhydrous $MgSO_4$, filtered, and concentrated in vacuo. The residue was purified by silica column chromatography to provide intermediate (18.0 g).
To a solution of intermediate (2.0 g, 3.84 mmol) in 1,4-dioxane (25 mL) was added DDQ (0.96 g, 4.22 mmol) at room temperature. The mixture was stirred at 70° C. for 15 h. The mixture was cooled to room temperature and concentrated in vacuo. The residue was diluted with EtOAc and washed with aq. saturated $NaHCO_3$ solution. The organic layer was dried over anhydrous $MgSO_4$, filtered, and concentrated in vacuo. The residue was purified by silica column chromatography to provide the titled compound 77 (0.91 g, 40%, 2 steps). MH+520.

Step 5: 2-(1-((2R,3R,4S,5R,6R)-3,4,5-Triacetoxy-6-(acetoxymethyl)-tetrahydro-2H-pyran-2-yl)-1H-indol-3-yl)acetic acid (78)

To a solution of ester 77 (0.91 g, 1.75 mmol) in EtOH (20 mL) was added aq. 1.0 M KOH solution (20 mL) at room temperature. The mixture was stirred at 100° C. for 15 h. The mixture was cooled to room temperature and concentrated in vacuo to remove solvents. The residue was dried under vacuum to obtain the intermediate and used without further purification.
To a solution of intermediate in pyridine (25 mL) was added excess amount of acetic anhydride (3 mL) at room temperature. The mixture was stirred at room temperature for 1 h. The mixture was concentrated in vacuo and the residue was diluted with $H_2O$ and acidified with c-HCl. The mixture was extracted with EtOAc. The combined organic layer was dried over anhydrous $MgSO_4$, filtered and concentrated in vacuo. The residue was purified by prep HPLC (C18) to provide the titled compound 78 (273 mg, 31%, 2-steps). MH+506.

Step 6: (2R,3R,4S,5R,6R)-2-(Acetoxymethyl)-6-(3-((5-(furan-2-yl)thiazol-2-yl)methyl)-1H-indol-1-yl)-tetrahydro-2H-pyran-3,4,5-triyl triacetate (79)

To a solution of carboxylic acid 78 (273 mg, 0.541 mmol) in DMF (10 mL) were added aminoketone (200 mg, 0.810 mmol), EDCI (207 mg, 1.08 mmol), HOBt (182 mg, 1.35 mmol) and NMM (0.3 mL, 2.71 mmol). The mixture was stirred at room temperature for 15 h. The mixture was diluted with EtOAc and washed with aq. saturated $NaHCO_3$ solution. The organic layer was dried over anhydrous $MgSO_4$, filtered and concentrated in vacuo. The residue was purified by silica column chromatography to provide the intermediate (236 mg).
To a solution of intermediate (236 mg) in THF (10 mL) was added Lawesson's reagent (312 mg, 0.771 mmol) at room temperature. The mixture was stirred at 75° C. for 1 h. The mixture was cooled to room temperature, diluted with EtOAc and washed with aq. saturated $NaHCO_3$ solution. The organic layer was dried over anhydrous $MgSO_4$, filtered, and concentrated in vacuo. The residue was purified by silica column chromatography to provide the titled compound 79 (195 mg, 59%, 2-steps).
$^1$H NMR (400 MHz, $CDCl_3$) δ 7.81 (s, 1H), 7.53 (d, J=8.0 Hz, 1H), 7.41 (d, J=8.4 Hz, 1H), 7.36 (s, 1H), 7.29-7.25 (m, 2H), 7.15 (t, J=7.2 Hz, 1H), 6.98 (s, 1H), 6.43-6.37 (m, 1H), 5.62 (d, J=9.2 Hz, 1H), 5.55 (t, J=9.2 Hz, 1H), 5.45 (t, J=9.2 Hz, 1H), 5.30 (t, J=9.6 Hz, 1H), 4.43 (s, 2H), 4.30 (dd, J=12.8, 4.8 Hz, 1H), 4.17 (dd, J=12.4, 2.0 Hz, 1H), 4.04-3.96 (m, 1H), 2.08 (s, 6H), 1.43 (s, 6H); MH+611.

Step 7: (2R,3R,4S,5S,6R)-2-(3-((5-(Furan-2-yl)thiazol-2-yl)methyl)-1H-indol-1-yl)-6-(hydroxymethyl)-tetrahydro-2H-pyran-3,4,5-triol (80)

To a solution of acetate 79 (195 mg, 0.32 mmol) in MeOH (15 mL) were added sodium methoxide (25 wt. % in MeOH, 1 mL) at room temperature. The mixture was stirred at room temperature for 1 hours. The amberlite IR-120H resin was added to the mixture to acidify the mixture. The mixture was filtered off and the filtrate was concentrated in vacuo. The residue was purified by prep HPLC (C18) to provide the titled compound 80 (25 mg, 18%).
$^1$H NMR (400 MHz, DMSO-$d_6$) δ 7.88 (s, 1H), 7.66 (d, J=1.2 Hz, 1H), 7.52 (d, J=8.4 Hz, 1H), 7.45 (d, J=8.8 Hz, 2H), 7.12 (t, J=8.0 Hz, 1H), 7.01 (t, J=8.0 Hz, 1H), 6.70 (d, J=3.6 Hz, 1H), 6.53-6.47 (m, 1H), 5.37 (d, J=9.2 Hz, 1H), 5.14 (dd, J=10.4, 5.6 Hz, 2H), 4.50 (t, J=5.6 Hz, 1H), 4.40 (s, 2H), 3.74-3.62 (m, 2H), 3.48-3.33 (m, 3H), 3.27-3.19 (m, 1H); MH+443.

Example 131

(2R,3S,4S,5R,6R)-2-(Hydroxymethyl)-6-(3-((5-(thiophen-2-yl)thiazol-2-yl)methyl)-1H-indol-1-yl)tetrahydro-2H-pyran-3,4,5-triol The titled compound was obtained in the same manner as in Example 130.
$^1$H NMR (400 MHz, DMSO-$d_6$) δ 7.84 (s, 1H), 7.54-7.44 (m, 4H), 7.23 (dd, J=3.6, 1.2 Hz, 1H), 7.12 (t, J=7.2 Hz, 1H), 7.07-6.97 (m, 2H), 5.37 (d, J=9.2 Hz, 2H), 5.15 (d, J=6.0 Hz, 1H), 5.12 (d, J=5.2 Hz, 1H), 4.49 (t, J=5.6 Hz, 1H), 4.38 (s, 2H), 3.73-3.64 (m, 2H), 3.47-3.36 (m, 3H), 3.28-3.19 (m, 1H); MH+459.

Example 132

(2R,3S,4S,5R,6R)-2-(Hydroxymethyl)-6-(3-((5-methylthiazol-2-yl)methyl)-1H-indol-1-yl)tetrahydro-2H-pyran-3,4,5-triol The titled compound was obtained in the same manner as in Example 130.

¹H NMR (400 MHz, DMSO-d₆) δ 7.49 (d, J=8.0 Hz, 1H), 7.43 (d, J=7.6 Hz, 1H), 7.38 (s, 1H), 7.30 (d, J=1.2 Hz, 1H), 7.11 (t, J=7.2 Hz, 1H), 6.99 (t, J=7.2 Hz, 1H), 5.36 (d, J=8.8 Hz, 1H), 5.23-5.03 (m, 3H), 4.50 (t, J=5.2 Hz, 1H), 4.30 (s, 2H), 3.71-3.59 (m, 2H), 3.47-3.31 (m, 3H), 3.25-3.19 (m, 1H), 2.30 (s, 3H); MH+391

Example 133

(2R,3R,4S,5S,6R)-2-(3-((5-Ethylthiazol-2-yl)methyl)-1H-indol-1-yl)-6-(hydroxymethyl)tetrahydro-2H-pyran-3,4,5-triol The titled compound was obtained in the same manner as in Example 130.
¹H NMR (400 MHz, CD₃OD) δ 7.51 (d, J=8.4 Hz, 1H), 7.40 (d, J=7.6 Hz, 1H), 7.38 (s, 1H), 7.30 (d, J=2.0 Hz, 1H), 7.16 (t, J=7.2 Hz, 1H), 7.01 (t, J=7.2 Hz, 1H), 5.42 (d, J=9.2 Hz, 1H), 4.83 (s, 4H), 4.37 (s, 1H), 3.92-3.83 (m, 2H), 3.71-3.65 (m, 1H), 3.62-3.53 (m, 2H), 3.51-3.44 (m, 1H), 2.77 (q, J=7.6 Hz, 2H), 1.21 (t, J=7.6 Hz, 1H); MH+405.

Example 134

(2R,3S,4S,5R,6R)-2-(Hydroxymethyl)-6-(3((5-propylthiazol-2-yl)methyl)-1H-indol-1-yl)tetrahydro-2H-pyran-3,4,5-triol The titled compound was obtained in the same manner as in Example 130.
¹H NMR (400 MHz, CD₃OD) δ 7.51 (d, J=8.0 Hz, 1H), 7.39 (d, J=8.0 Hz, 1H), 7.38 (s, 1H), 7.15 (t, J=7.2 Hz, 1H), 7.02 (t, J=7.2 Hz, 1H), 5.42 (d, J=9.2 Hz, 1H), 4.83 (s, 4H), 4.38 (s, 2H), 3.93-3.82 (m, 2H), 3.68 (dd, J=12.0, 5.6 Hz, 1H), 3.61-3.52 (m, 2H), 3.49-3.43 (m, 1H), 2.71 (t, J=7.2 Hz, 2H), 1.58 (sext, J=7.2 Hz, 2H), 0.90 (t, J=7.2 Hz, 1H); MH+419.

Example 135

(2R,3R,4S,5S,6R)-2-(3((5-Butylthiazol-2-yl)methyl)-1H-indol-1-yl)-6-(hydroxymethyl)tetrahydro-2H-pyran-3,4,5-triol The titled compound was obtained in the same manner as in Example 130.
¹H NMR (400 MHz, CD₃OD) δ 7.51 (d, J=8.4 Hz, 1H), 7.41-7.33 (m, 2H), 7.29 (s, 1H), 7.15 (t, J=7.2 Hz, 1H), 7.02 (t, J=7.2 Hz, 1H), 5.42 (d, J=9.2 Hz, 1H), 4.84 (s, 4H), 4.38 (s, 2H), 3.92-3.81 (m, 2H), 3.68 (dd, J=12.0, 5.6 Hz, 1H), 3.61-3.52 (m, 2H), 3.51-3.45 (m, 1H), 2.73 (t, J=7.6 Hz, 2H), 1.54 (quint, J=7.6 Hz, 2H), 1.31 (sext, J=7.6 Hz, 2H), 0.89 (t, J=7.6 Hz, 1H); MH+433.

Example 136

(2R,3S,4S,5R,6R)-2-(Hydroxymethyl)-6-(3-((5-pentylthiazol-2-yl)methyl)-1H-indol-1-yl)tetrahydro-2H-pyran-3,4,5-triol The titled compound was obtained in the same manner as in Example 130.
¹H NMR (400 MHz, CD₃OD) δ 7.52 (d, J=8.4 Hz, 1H), 7.43-7.36 (m, 2H), 7.17 (s, 1H), 7.15 (t, J=8.0 Hz, 1H), 7.02 (t, J=8.0 Hz, 1H), 5.42 (d, J=9.2 Hz, 1H), 4.83 (s, 4H), 4.38 (s, 2H), 3.97-3.83 (m, 2H), 3.68 (dd, J=12.0, 5.6 Hz, 1H), 3.61-3.52 (m, 2H), 3.51-3.45 (m, 1H), 2.74 (t, J=7.6 Hz, 2H), 1.57 (quint, J=7.2 Hz, 2H), 1.37-1.21 (m, 4H), 0.85 (t, J=3.2 Hz, 3H); MH+447.

Example 137

(2R,3S,4R,5R,6S)-2-(Hydroxymethyl)-6-(1-((5-phenylthiazol-2-yl)methyl)-1H-indol-3-yl)-tetrahydro-2H-pyran-3,4,5-triol (88)

Step 1: 1-Tosyl-1H-indole (82)

To a solution of indole 81 (10 g, 85 mmol) in DMF (50 mL) at 0° C. was added NaH (60% dispersion in mineral oil 4 g) and tosylchloride (24 g, 128 mmol) portionwisely. And the reaction mixture was stirred at room temperature for 2 h. The resulting solution was acidified with 2.0 M HCl, and organic layer was extracted with Et₂O. After evaporating the volatile material with reduced pressure, the residue was purified by silica column chromatography to obtain titled compound 82 (19 g, 84%).
¹H NMR (400 MHz, CDCl₃) δ 7.98 (dd, J=8.0, 0.4 Hz, 1H), 7.75 (d, J=8.8 Hz, 2H), 7.55 (d, J=3.6 Hz, 1H), 7.51 (d, J=7.2 Hz, 1H), 7.30 (td, J=8.4, 1.2 Hz, 1H), 7.25-7.19 (m, 3H), 6.64 (dd, J=3.6, 0.8 Hz, 1H), 2.31 (s, 3H). MH+272.

Step 2: 3-Bromo-1-tosyl-1H-indole (83)

To a solution of compound 82 (13 g, 47.9 mmol) in methylene chloride (100 mL) at 0° C. was added bromine (2.7 mL, 52.7 mmol) dropwise. After reaction complete, the resulting solution was evaporated under reduced pressure. The residue was quenched with saturated Na₂S₂O₄ solution, work-up with Et₂O. After evaporation of volatile solvent, the title compound was obtained by trituration with hexane.
¹H NMR (400 MHz, CDCl₃) δ 7.98 (d, J=8.4 Hz, 1H), 7.76 (d, J=8.0 Hz, 2H), 7.62 (s, 1H), 7.47 (d, J=8.0 Hz, 1H), 7.36 (td, J=8.4, 1.2 Hz, 1H), 7.32-7.25 (m, 1H), 7.21 (d, J=8.0 Hz, 2H), 2.32 (S, 3H). MH+272.

Step 3: 1-Tosyl-3-((2S,3S,4R,5R,6R)-3,4,5-tris(benzyloxy)-6-(benzyloxymethyl)-tetrahydro-2H-pyran-2-yl)-1H-indole (84)

To a solution of bromide 83 (3.9 g, 11 mmol) in THF (40 mL) at −78° C. was added n-butyllithium (2.5 M in hexanes, 4.3 mL) was added dropwisely. After the reaction mixture was stirring for 30 min at the same temperature, perbenzylated lactone 1 (5 g, 9.3 mmol) in THF (10 mL) wad added at −78° C. The resulting solution was stirring for 10 min, and then warmed up to 0° C. and stirred further 1 h more. Saturated aqueous NH₄Cl was added to quench the reaction mixture, and then work-up with Et₂O. The organic solution was dried with anhydrous MgSO₄, evaporated under reduced pressure. The crude product was used to next step without further purification.

To a stirred −15° C. solution of the lactols 84 in dichloromethane (50 mL) was added triethylsilane (2.14 mL, 13.5 mmol) followed by boron trifluoride diethyl etherate (0.92 mL, 13.5 mmol) at a rate such that the reaction temperature was maintained −15° C. The solution was allowed to warm to room temperature over 1 h prior to quenching with saturated potassium carbonate. After removal of organic volatiles under reduced pressure, the residue was partitioned between EtOAc and water. Following extraction of the aqueous layer with EtOAc, the combined organic layers were washed with water prior to drying over anhydrous MgSO₄. The residue was purified by silica column chromatography to obtain titled compound 84 (6.5 g, 74%) as light yellow solid.

$^1$H NMR (400 MHz, CDCl$_3$) δ 7.85 (d, J=8.0 Hz, 1H), 7.71 (s, 1H), 7.38-7.20 (m, 15H), 7.19-7.04 (m, 3H), 6.91-6.89 (m, 1H), 5.52 (s, 2H), 4.94-4.86 (m, 3H), 4.66 (dd, J=12.0, 11.2 Hz, 1H), 4.58 (dd, J=17.6, 12.0 Hz, 2H), 4.33 (d, J=10.2 Hz, 1H), 3.92-3.79 (m, 6H), 2.33 (s, 3H). MH+794.

Step 4: 3-((2S,3S,4R,5R,6R)-3,4,5-Tris(benzyloxy)-6-(benzyloxymethyl)-tetrahydro-2H-pyran-2-yl)-1H-indole (85)

To a solution of compound 84 (740 mg, 0.93 mmol) in a mixture of EtOH (20 mL) and THF (10 ml) was added KOH (250 mg). The reaction mixture was stirred at 50° C. for 1 d. After reaction complete, the resulting solution was quenched with 1.0 M HCl and organic layer was extracted with EtOAc. After evaporating volatile material under reduced pressure, the residue was purified with normal phase column chromatography to afford titled compound 85 (370 mg, 62%) as off-white solid.

$^1$H NMR (400 MHz, CDCl$_3$) δ 7.83 (d, J=8.4 Hz, 1H), 7.37-7.20 (m, 16H), 7.18-7.06 (m, 2H), 5.52 (d, J=3.2 Hz, 2H), 4.93-4.86 (m, 3H), 4.68 (dd, J=12.0, 11.2 Hz, 1H), 4.58 (dd, J=17.6, 12.0 Hz, 2H), 4.33 (d, J=10.2 Hz, 1H), 3.92-3.79 (m, 6H). MH+639.

Step 5: 2-(3-((2S,3S,4R,5R,6R)-3,4,5-Tris(benzyloxy)-6-(benzyloxymethyl)-tetrahydro-2H-pyran-2-yl)-1H-indol-1-yl)acetic acid (86)

To a solution of compound 85 (500 mg, 0.78 mmol) in DMF (10 mL) was added NaH (63 mg, 0.94 mmol) and ethyl bromoacetate (195 mg, 1.17 mmol) at room temperature. The reaction mixture was stirred at room temperature for 4 h, and then it was quenched with saturated NH$_4$Cl solution. The organic layer was extract with Et$_2$O, and dried through anhydrous MgSO$_4$. After evaporation the volatile material under reduced pressure, the crude product was used without further purification.

To a solution of intermediate in aq. THF was added NaOH (200 mg) at room temperature. The reaction mixture was stirred at 50° C. for 1 h with TLC monitoring. After reaction complete, the reaction mixture was cooled down to rt and then quenched with 1.0 M HCl. Organic layer was extracted with EtOAc and dried with anhydrous MgSO$_4$. The crude title compound was dried in vacuo and used without further purification. MH+698.

Step 6: (2R,3S,4R,5R,6S)-2-(Hydroxymethyl)-6-(1-((5-phenylthiazol-2-yl)methyl)-1H-indol-3-yl)-tetrahydro-2H-pyran-3,4,5-triol (88)

The titled compound was obtained in the same manner as in Example 1 (Step 1 and 2) and Example 2.

$^1$H NMR (400 MHz, CD$_3$OD) δ 7.82 (d, J=8.0 Hz, 1H), 7.39-7.32 (m, 7H), 7.31-7.24 (m, 8H), 6.94 (dd, J=12.0, 11.6 Hz, 1H), 5.64 (d, J=12.4 Hz, 1H), 4.91-4.84 (dd, J=16.4, 12.0 Hz, 2H), 4.70 (s, 1H), 4.57-4.46 (m, 6H), 3.72 (dd, J=9.2, 4.0 Hz, 1H), 3.65 (dd, J=9.2, 4.0 Hz, 1H). MH+453.

Example 138

((2R,3S,4R,5R,6S)-6-(4-Chloro-3-((5-(furan-2-yl)thiazol-2-yl)methyl)phenyl)-3,4,5-trihydroxy-tetrahydro-2H-pyran-2-yl)methyl 4-methylbenzenesulfonate (90)

The solution of alcohol 89 (1.0 g, 2.28 mmol) and p-toluenesulfonyl chloride (2.3 g, 11.8 mmol) in 2,6-lutidine (22.8 mL) was stirred at room temperature for 15 h. H$_2$O (150 mL) was added to the reaction mixture and then extracted with EtOAc. The organic layer was dried over anhydrous MgSO$_4$, filtered and concentrated in vacuo. Purification by silica gel column chromatography provided desired toluenesulfonate 90 (1.03 g, 78%) as a solid.

$^1$H NMR (400 MHz, CD$_3$OD) δ 7.80 (s, 1H), 7.69 (d, J=8.4 Hz, 2H), 7.51 (d, J=1.2 Hz, 1H), 7.40 (d, J=8.4 Hz, 2H), 7.23 (d, J=8.0 Hz, 2H), 7.21 (d, J=2.0 Hz, 1H), 6.61 (d, J=3.2 Hz, 1H), 6.48-6.47 (m, 1H), 4.45 (d, J=2.0 Hz, 2H), 4.33 (dd, J=11.0, 2.0 Hz, 1H), 4.18 (dd, J=10.8, 6.0 Hz, 1H), 4.03 (d, J=9.6 Hz, 1H), 3.53-3.48 (m, 1H), 3.41-3.32 (m, 2H), 3.23-3.19 (m, 1H). MH+592.

Example 139

(2S,3R,4R,5S,6R)-2-(4-Chloro-3-((5-(furan-2-yl)thiazol-2-yl)methyl)phenyl)-6-(methoxymethyl)-tetrahydro-2H-pyran-3,4,5-triol (91)

The solution of toluenesulfonate 90 (104 mg, 0.18 mmol) and NaOMe (25 wt. % in MeOH, 5 mL) in methanol (3.5 mL) was stirred at room temperature for 15 h. After reaction complete, the resulting solution was quenched with H$_2$O. Reaction mixture was evaporated under reduced pressure. The residue was purified by prep HPLC (C18) to afford the titled compound 91 (12 mg, 56%) as a solid.

$^1$H NMR (400 MHz, CD$_3$OD) δ 7.82 (s, 1H), 7.54 (d, J=1.6 Hz, 1H), 7.50 (d, J=1.2 Hz, 1H), 7.42 (d, J=6.4 Hz, 1H), 7.37 (dd, J=7.6, 1.6 Hz, 1H), 6.64 (d, J=2.8 Hz, 1H), 6.51-6.50 (m, 1H), 4.47 (d, J=2.0 Hz, 2H), 4.13 (d, J=7.6 Hz, 1H), 3.73 (dd, J=8.8, 1.6 Hz, 1H), 3.62 (dd, J=8.8, 4.4 Hz, 1H), 3.51-3.49 (m, 1H), 3.48-3.42 (m, 2H), 3.37 (s, 3H), 3.30-3.28 (m, 1H). MH+452.

Example 140

(2S,3R,4R,5S,6R)-2-(4-Chloro-3-((5-(furan-2-yl)thiazol-2-yl)methyl)phenyl)-6-(ethoxymethyl)tetrahydro-2H-pyran-3,4,5-triol The titled compound was obtained in the same manner as in Example 139.

$^1$H NMR (400 MHz, DMSO-d$_6$) δ 7.88 (s, 1H), 7.69 (d, J=1.6 Hz, 1H), 7.42-7.38 (m, 2H), 7.25 (dd, J=8.4, 2.0 Hz, 1H), 6.75 (d, J=3.6 Hz, 1H), 6.55-6.54 (m, 1H), 4.41 (d, J=2.4 Hz, 2H), 4.00 (d, J=9.6 Hz, 1H), 3.62 (d, J=10.0 Hz, 1H), 3.41-3.35 (m, 4H), 3.33-3.31 (m, 2H), 3.25-3.21 (m, 1H), 3.17-3.05 (m, 3H), 1.02 (t, J=6.3 Hz, 3H). MH+ 466.

Example 141

(2S,3R,4R,5S,6R)-2-(4-Chloro-3-((5-(furan-2-yl)thiazol-2-yl)methyl)phenyl)-6-((2-hydroxyethoxy)methyl)tetrahydro-2H-pyran-3,4,5-triol The titled compound was obtained in the same manner as in Example 139.

$^1$H NMR (400 MHz, CD$_3$OD) δ 7.80 (s, 1H), 7.51 (d, J=1.6 Hz, 1H), 7.47 (d, J=2.0 Hz, 1H), 7.42-7.38 (m, 1H), 7.34 (dd, J=8.4, 2.0 Hz, 1H), 6.61 (d, J=3.2 Hz, 1H), 6.48-6.47 (m, 1H), 4.45 (d, J=1.6 Hz, 2H), 4.11 (d, J=9.2 Hz, 1H), 3.73 (dd, J=11.2, 2.0 Hz, 1H), 3.62 (dd, J=11.2, 5.6 Hz, 1H), 3.62-3.60 (m, 3H), 3.58-3.50 (m, 2H), 3.49-3.45 (m, 1H), 3.44-3.42 (m, 2H). MH+482.

Example 142

(2S,3R,4R,5S,6S)-2-(4-Chloro-3-((5-(furan-2-yl)thiazol-2-yl)methyl)phenyl)-6-(methylthiomethyl)-tetrahydro-2H-pyran-3,4,5-triol (92)

The solution of toluenesulfonate 90 (500 mg, 0.84 mmol) and NaSMe (296 mg 4.22 mmol) in DMF (4.2 mL) was stirred at room temperature for 4 h. After reaction complete, the resulting solution was quenched with MeOH. Reaction mixture was evaporated under reduced pressure. The residue was purified by prep HPLC (C18) to afford the titled compound methyl sulfide 92 (175 mg, 45%) as a solid.
$^1$H NMR (400 MHz, $CD_3OD$) δ 7.80 (s, 1H), 7.52 (d, J=1.6 Hz, 1H), 7.45 (d, J=2.0 Hz, 1H), 7.40 (d, J=8.4 Hz, 1H), 7.32 (dd, J=8.0, 2.0 Hz, 1H), 6.62 (d, J=3.2 Hz, 1H), 6.49-6.48 (m, 1H), 4.45 (s, 2H), 4.12 (d, J=9.2 Hz, 1H), 3.54-3.50 (m, 1H), 3.44-3.42 (m, 2H), 3.26-3.24 (m, 1H), 2.93 (dd, J=14.4, 2.4 Hz, 1H), 2.68 (dd, J=14.4, 6.8 Hz, 1H), 2.08 (s, 3H). MH+468.

Example 143

(2S,3R,4R,5S,6S)-2-(4-Chloro-3-((5-(furan-2-yl)thiazol-2-yl)methyl)phenyl)-6-(ethylthiomethyl)tetrahydro-2H-pyran-3,4,5-triol The titled compound was obtained in the same manner as in Example 142.
$^1$H NMR (400 MHz, $CD_3OD$) δ 7.80 (s, 1H), 7.51 (d, J=1.6 Hz, 1H), 7.45 (d, J=2.0 Hz, 1H), 7.40 (d, J=8.4 Hz, 1H), 7.32 (dd, J=8.4, 2.0 Hz, 1H), 6.61 (d, J=3.6 Hz, 1H), 6.49-6.47 (m, 1H), 4.45 (s, 2H), 4.11 (d, J=9.2 Hz, 1H), 3.51-3.44 (m, 1H), 3.43-3.40 (m, 2H), 3.26-3.24 (m, 1H), 2.97 (dd, J=14.4, 2.4 Hz, 1H), 2.70 (dd, J=14.4, 6.8 Hz, 1H), 2.58-2.51 (m, 2H), 1.14 (t, J=7.2 Hz, 3H). MH+482.

Example 144

(2S,3R,4R,5S,6S)-2-(4-Chloro-3-((5-(furan-2-yl)thiazol-2-yl)methyl)phenyl)-6-(methylsulfonylmethyl)-tetrahydro-2H-pyran-3,4,5-triol (93)

The solution of methyl sulfide 92 (175 mg, 0.37 mmol) and meta-chloroperoxybenzoic acid (210 mg 0.93 mmol) in $CH_2Cl_2$ (3.7 mL) was stirred at 0° C. for 1 h. To the reaction solution was added to sodium thiosulfate solution, and the resulting mixture was extracted with $CH_2Cl_2$. The organic layer was washed with a saturated sodium bicarbonate aqueous solution and brine, and dried with anhydrous $MgSO_4$. The drying agent was filtered off, and evaporated under reduced pressure. The residue was purified by prep HPLC (C18) to afford the titled compound methylsulfone 93 (121 mg, 66%) as a solid.
$^1$H NMR (400 MHz, $CD_3OD$) δ 7.80 (s, 1H), 7.51 (d, J=2.0 Hz, 1H), 7.49 (d, J=2.0 Hz, 1H), 7.41 (d, J=8.0 Hz, 1H), 7.34 (dd, J=8.4, 2.0 Hz, 1H), 6.62 (d, J=3.2 Hz, 1H), 6.49-6.47 (m, 1H), 4.45 (d, J=2.8 Hz, 2H), 4.21 (d, J=9.2 Hz, 1H), 3.86 (td, J=9.6, 2.4 Hz, 1H), 3.49-3.37 (m, 3H), 3.33-3.31 (m, 2H), 2.83 (s, 3H). MH+500.

Example 145

(2S,3R,4R,5S,6S)-2-(4-Chloro-3-((5-(furan-2-yl)thiazol-2-yl)methyl)phenyl)-6-(fluoromethyl)-tetrahydro-2H-pyran-3,4,5-triol (94)

The solution of toluenesulfonate 90 (200 mg, 0.34 mmol) and potassium fluoride (23.5 mg 0.41 mmol) in ethylene glycol (3.5 mL) was stirred at 100° C. for 20 h. $H_2O$ was added to the reaction mixture and then extracted with $CH_2Cl_2$. The organic layer was dried over anhydrous $MgSO_4$, filtered and concentrated in vacuo. The residue was purified by prep HPLC (C18) to afford the titled compound 94 (16 mg, 11%) as a solid.
$^1$H NMR (400 MHz, DMSO-$d_6$) δ 7.89 (s, 1H), 7.69 (d, J=1.2 Hz, 1H), 7.43-7.41 (m, 2H), 7.26 (dd, J=8.4, 2.0 Hz, 1H), 6.76 (d, J=3.2 Hz, 1H), 6.55-6.54 (m, 1H), 4.64-4.41 (m, 4H), 4.10-4.08 (m, 2H), 3.52-3.41 (m, 2H), 3.39-3.11 (m, 4H). MH+440.

Example 146

(2S,3R,4S,5S,6R)-2-(4-Chloro-3-((5-(furan-2-yl)thiazol-2-yl)methyl)phenyl)-6-methyl-tetrahydro-2H-pyran-3,4,5-triol (96)

Step 1: (2S,3R,4R,5S,6S)-2-(4-Chloro-3-((5-(furan-2-yl)thiazol-2-yl)methyl)phenyl)-6-(iodomethyl)-tetrahydro-2H-pyran-3,4,5-triol (95)

The solution of toluenesulfonate 90 (100 mg, 0.17 mmol) and sodium iodide (38 mg 0.25 mmol) in 2-butanone (1.7 mL) was stirred at 80° C. for 2 h. $H_2O$ was added to the reaction mixture and then extracted with $CH_2Cl_2$. The organic layer was dried over anhydrous $MgSO_4$, filtered and concentrated in vacuo. The residue was purified by prep HPLC (C18) to afford the titled compound 95 (45 mg, 48%) as a solid. MH+547

Step 2: (2S,3R,4S,5S,6R)-2-(4-Chloro-3-((5-(furan-2-yl)thiazol-2-yl)methyl)phenyl)-6-methyl-tetrahydro-2H-pyran-3,4,5-triol (96)

To the solution of iodide 95 (85 mg, 0.16 mmol) in methanol (1.6 mL) was added $Et_2NH$ (0.03 mL, 0.31 mmol) and Raney nickel (20 mg). The reaction mixture was stirred 1 d under $H_2$ (1 atm), filtered on Celite and evaporated under reduced pressure. The residue was purified by prep HPLC (C18) to afford title compound 96 (21 mg, 31%) as a solid.
$^1$H NMR (400 MHz, DMSO-$d_6$) δ 7.95 (s, 1H), 7.74 (d, J=1.6 Hz, 1H), 7.47-7.44 (m, 2H), 7.30 (dd, J=10.2, 2.0 Hz, 1H), 6.81 (d, J=3.6 Hz, 1H), 6.61-6.59 (m, 1H), 5.01 (dd, J=14.8, 4.4 Hz, 2H), 4.89 (d, J=5.6 Hz, 1H), 4.46 (d, J=2.8 Hz, 2H), 4.06 (d, J=9.2 Hz, 1H), 3.38-3.30 (m, 1H), 3.38-3.23 (m, 1H), 3.19-3.13 (m, 1H), 2.99-2.93 (m, 1H), 1.19 (d, J=6.0 Hz, 3H). MH+422.

Example 147

(2R,3S,4R,5S,6S)-2-((1H-1,2,4-Triazol-1-yl)methyl)-6-(4-chloro-3-((5-(furan-2-yl)thiazol-2-yl)methyl)phenyl)-tetrahydro-2H-pyran-3,4,5-triol (97)

Cesium carbonate (660 mg, 2.02 mmol) was added to the solution of 1,2,4-triazole (140 mg, 2.02 mmol) in DMF (2.0 mL) at 0° C. The reaction mixture was stirred at 0° C. for 1 h. The solution of toluenesulfonate 90 (240 mg, 0.41 mmol) in DMF (1.0 mL) was added to the reaction mixture. The reaction mixture was warmed up to room temperature, stirred at room temperature for 3 d. $H_2O$ was added to the reaction mixture and then extracted with EtOAc. The organic extract was dried over anhydrous $MgSO_4$, filtered and concentrated in vacuo. Purification by prep HPLC (C18) provided desired triazole 97 (28 mg, 14%) as a solid.

$^1$H NMR (400 MHz, DMSO-d$_6$) δ 8.34 (s, 1H), 7.39 (s, 1H), 7.91 (s, 1H), 7.73 (d, J=1.2 Hz, 1H), 7.43-7.41 (m, 2H), 7.23 (dd, J=8.4, 2.0 Hz, 1H), 6.80 (d, J=3.2 Hz, 1H), 6.59-6.57 (m, 1H), 4.53 (dd, J=14.2, 2.4 Hz, 2H), 4.27 (s, 2H), 4.32 (dd, J=14.4, 8.4 Hz, 1H), 4.05 (d, J=9.2 Hz, 1H), 3.64-3.59 (m, 1H), 3.34-3.29 (m, 2H), 3.17-3.03 (m, 4H). MH+489.

Example 148

(2R,3S,4R,5R,6S)-2-((2H-Tetrazol-2-yl)methyl)-6-(4-chloro-3-((5-(furan-2-yl)thiazol-2-yl)methyl)phenyl)-tetrahydro-2H-pyran-3,4,5-triol (98)

The solution of toluenesulfonate 90 (612 mg, 1.03 mmol), tetrazole (0.45 M in acetonitrile) (11.5 mL 5.17 mmol) and triethyl amine (0.72 mL 5.17 mmol) in DMF (2.0 mL) was stirred at 80° C. for 3 d. Reaction mixture was evaporated under reduced pressure. The residue was purified by prep HPLC (C18) to afford the titled compound 98 (120 mg, 24%) as a solid.

$^1$H NMR (400 MHz, DMSO-d$_6$) δ 8.89 (s, 1H), 7.92 (s, 1H), 7.73 (d, J=1.2 Hz, 1H), 7.40 (d, J=8.4 Hz, 1H), 7.33 (d, J=2.4 Hz, 1H), 7.18 (dd, J=8.4, 2.0 Hz, 1H), 6.80 (d, J=3.6 Hz, 1H), 6.59-6.58 (m, 1H), 5.50 (br s, 1H), 5.18 (br s, 1H), 5.02-4.98 (m, 2H), 4.32 (dd, J=14.2, 8.0 Hz, 1H), 4.39 (d, J=5.6 Hz, 2H), 4.03 (d, J=9.6 Hz, 1H), 3.86 (td, J=8.6, 2.8 Hz, 1H), 3.35-3.25 (m, 2H), 3.17-3.06 (m, 1H). MH+490.

Example 149

(2R,3S,4R,5R,6S)-2-((1H-Tetrazol-1-yl)methyl)-6-(4-chloro-3-((5-(furan-2-yl)thiazol-2-yl)methyl)phenyl)tetrahydro-2H-pyran-3,4,5-triol The titled compound was obtained in the same manner as in Example 148.

$^1$H NMR (400 MHz, DMSO-d$_6$) δ 9.21 (s, 1H), 7.93 (s, 1H), 7.73 (d, J=1.2 Hz, 1H), 7.44-7.42 (m, 2H), 7.22 (dd, J=8.4, 2.0 Hz, 1H), 6.80 (d, J=3.2 Hz, 1H), 6.59-6.58 (m, 1H), 5.49 (d, J=5.6 Hz, 1H), 5.13 (d, J=4.8 Hz, 1H), 5.02 (d, J=6.0 Hz, 1H), 4.82 (dd, J=14.4, 2.4 Hz, 1H), 4.39 (dd, J=14.6, 8.0 Hz, 1H), 4.43 (s, 2H), 4.09 (d, J=9.6 Hz, 1H), 3.86 (td, J=8.4, 2.4 Hz, 1H), 3.35-3.31 (m, 1H), 3.10-3.02 (m, 2H). MH+490.

Example 150

(2S,3R,4R,5S,6S)-2-(4-Chloro-3-((5-(furan-2-yl)thiazol-2-yl)methyl)phenyl)-6-(difluoromethyl)-tetrahydro-2H-pyran-3,4,5-triol Step 1: ((2R,3R,4R,5S,6S)-3,4,5-Tris(benzyloxy)-6-(4-chloro-3-((5-(furan-2-yl)thiazol-2-yl)methyl)phenyl)-tetrahydro-2H-pyran-2-yl)methanol (100)

To the solution of 99 (7.3 g 9.16 mmol) in acetic anhydride (30 mL) and CH$_2$Cl$_2$ (30 mL) was added dropwise a solution of TMSOTf (7.5 mL, 41.2 mmol) in CH$_2$Cl$_2$ (10 mL) at −55° C. After stirring at −55° C. for 1 h, the reaction was quenched with saturated NaHCO$_3$. The reaction mixture was diluted with CH$_2$Cl$_2$, washed with water. The organic layer was dried over anhydrous MgSO$_4$, filtered and concentrated in vacuo. The resulting crude mono-acetate was carried on to the next step without further purification.

To a solution of the crude product in MeOH (100 mL) was added NaOMe (25 wt. % in MeOH, 1 mL). The reaction mixture was stirred at ambient temperature for 3 h. Acetic acid was added to neutralize the reaction mixture and concentrated in vacuo. H$_2$O was added to the reaction mixture and then extracted with CH$_2$Cl$_2$. The organic layer was dried over anhydrous MgSO$_4$, filtered and concentrated in vacuo. Purification by silica column chromatography provided desired alcohol 100 (5.75 g, 89%, 2 steps) as a solid.

MH+709.

Step 2: (2S,3S,4R,5S,6S)-3,4,5-Tris(benzyloxy)-6-(4-chloro-3-((5-(furan-2-yl)thiazol-2-yl)methyl)phenyl)-tetrahydro-2H-pyran-2-carbaldehyde (101)

The solution of alcohol 100 (600 mg, 0.85 mmol) and Dess-Martin periodinane (540 mg, 1.27 mmol) in CH$_2$Cl$_2$ (4.2 mL) was stirred at room temperature for 2 h. The reaction mixture was filtered off the white solid. The filtrate was diluted with CH$_2$Cl$_2$ and washed with brine. The organic layer was dried over anhydrous MgSO$_4$, filtered and concentrated in vacuo. Purification by silica gel column chromatography provided the desired aldehyde 101 (395 mg, 65%) as a solid.

MH+706.

Step 3: 2-(2-Chloro-5-((2S,3S,4R,5S,6S)-3,4,5-Tris(benzyloxy)-6-(difluoromethyl)-tetrahydro-2H-pyran-2-yl)benzyl)-5-(furan-2-yl)thiazole (102)

To the solution of aldehyde 101 (500 mg, 0.71 mmol) in CH$_2$Cl$_2$(2.5 mL) in Falcon tube was added DAST (0.28 mL, 2.12 mmol). The reaction mixture was stirred for 15 h at room temperature. Saturated NaHCO$_3$ was added to the reaction mixture. After 1 h, the organic extract was dried over anhydrous MgSO$_4$, filtered and concentrated in vacuo. Purification by silica gel column chromatography provided the desired difluoride 102 (210 mg, 41%) as a solid.

MH+728.

Step 4: (2S,3R,4R,5S,6S)-2-(4-Chloro-3-((5-(furan-2-yl)thiazol-2-yl)methyl)phenyl)-6-(difluoromethyl)-tetrahydro-2H-pyran-3,4,5-triol The titled compound was obtained in the same manner as in Example 4.

$^1$H NMR (400 MHz, DMSO-d$_6$) δ 7.93 (s, 1H), 7.72 (s, 1H), 7.48-7.46 (m, 2H), 7.29 (dd, J=8.2, 1.6 Hz, 1H), 6.79 (d, J=2.8 Hz, 1H), 6.59-6.57 (m, 1H), 6.14 (t, J=53.6 Hz, 1H), 4.46 (d, J=3.6 Hz, 2H), 4.19 (d, J=9.6 Hz, 1H), 3.65-3.60 (m, 1H), 3.37-3.33 (m, 2H), 3.19-3.14 (m, 1H). MH+458.

Example 151

(2S,3R,4R,5S,6R)-2-(4-Chloro-3-((5-(furan-2-yl)thiazol-2-yl)methyl)phenyl)-6-(1-hydroxyethyl)-tetrahydro-2H-pyran-3,4,5-triol Step 1: 1-((2R,3S,4R,5S,6S)-3,4,5-Tris(benzyloxy)-6-(4-chloro-3-((5-(furan-2-yl)thiazol-2-yl)methyl)phenyl)-tetrahydro-2H-pyran-2-yl)ethanol (103)

To the solution of aldehyde 101 (390 mg, 0.55 mmol) in THF (5.5 mL) was added methyl magnesiumbromide (3.0 M in ether, 0.28 mL) at 0° C. The reaction mixture was allowed to warm to room temperature and stirred for 3 h. The mixture was poured into a saturated NH$_4$Cl solution and then extracted with CH$_2$Cl$_2$. The organic layer was dried over anhydrous MgSO$_4$, filtered and concentrated in vacuo. Purification by silica gel column chromatography provided the desired secondary alcohol 103 (300 mg, 75%) as a solid. MH+723.

Step 2: (2S,3R,4R,5S,6R)-2-(4-Chloro-3-((5-(furan-2-yl)thiazol-2-yl)methyl)phenyl)-6-(1-hydroxyethyl)-tetrahydro-2H-pyran-3,4,5-triol The titled compound was obtained in the same manner as in Example 4.

$^1$H NMR (400 MHz, DMSO-$d_6$) one isomer at C-6: δ 7.93 (s, 1H), 7.73-7.72 (m, 1H), 7.45-7.43 (m, 2H), 7.29 (dd, J=8.2, 2.0 Hz, 1H), 6.79 (d, J=3.2 Hz, 1H), 6.59-6.57 (m, 1H), 5.04-4.87 (m, 3H), 4.52-4.44 (m, 3H), 4.03-3.94 (m, 2H), 3.31-3.04 (m, 4H), 1.06 (d, J=6.4 Hz, 3H); the other isomer at C-6: δ 7.93 (s, 1H), 7.73-7.72 (m, 1H), 7.55 (d, J=2.0 Hz, 1H), 7.45-7.42 (m, 1H), 7.36 (dd, J=8.2, 2.0 Hz, 1H), 6.78 (d, J=3.2 Hz, 1H), 6.59-6.57 (m, 1H), 4.92-4.84 (m, 3H), 4.43 (d, J=5.6 Hz, 2H), 4.13-3.92 (m, 2H), 3.46-3.44 (m, 1H), 3.32-3.01 (m, 4H), 1.10 (d, J=6.8 Hz, 3H). MH+452.

Example 152

(2S,3R,4R,5S,6R)-2-(4-Chloro-3-((5-(furan-2-yl)thiazol-2-yl)methyl)phenyl)-6-(1-hydroxyallyl)-tetrahydro-2H-pyran-3,4,5-triol The titled compound was obtained in the same manner as in Example 151.

$^1$H NMR (400 MHz, DMSO-$d_6$) one isomer at C-6: δ 7.94 (s, 1H), 7.73 (d, J=1.2 Hz, 1H), 7.45-7.41 (m, 2H), 7.27 (dd, J=8.2, 2.0 Hz, 1H), 6.79 (d, J=3.2 Hz, 1H), 6.59-6.58 (m, 1H), 5.94-5.85 (m, 1H), 5.16 (dd, J=17.2, 1.2 Hz, 1H), 5.08-4.98 (m, 3H), 4.89-4.86 (m, 2H), 4.44 (d, J=3.6 Hz, 2H), 4.27-4.24 (m, 1H), 4.09 (d, J=5.2 Hz, 1H), 3.26-2.96 (m, 4H); the other isomer at C-6: δ 7.93 (s, 1H), 7.73 (d, J=1.2 Hz, 1H), 7.52 (d, J=2.0 Hz, 1H), 7.45-7.43 (m, 1H), 7.34 (dd, J=8.2, 2.0 Hz, 1H), 6.79 (d, J=3.2 Hz, 1H), 6.59-6.58 (m, 1H), 5.96-5.87 (m, 1H), 5.21-5.16 (m, 1H), 5.04-4.98 (m, 2H), 4.91-4.86 (m, 1H), 4.53 (d, J=8.0 Hz, 1H), 4.47-4.38 (m, 2H), 4.27-4.24 (m, 1H), 4.03-4.00 (m, 1H), 3.49-3.46 (m, 1H), 3.29-3.02 (m, 4H). MH+464.

Example 153

(2S,3R,4R,5S,6R)-2-(4-Chloro-3-((5-(furan-2-yl)thiazol-2-yl)methyl)phenyl)-6-(1-hydroxybut-3-enyl)-tetrahydro-2H-pyran-3,4,5-triol The titled compound was obtained in the same manner as in Example 151.

$^1$H NMR (400 MHz, DMSO-$d_6$) δ 7.93 (s, 1H), 7.73 (d, J=1.2 Hz, 1H), 7.56-7.35 (m, 3H), 7.30 (dd, J=8.2, 2.0 Hz, 1H), 6.78 (d, J=3.2 Hz, 1H), 6.59-6.57 (m, 1H), 5.89-5.80 (m, 1H), 5.03-4.95 (m, 2H), 4.48 (d, J=2.8 Hz, 1H), 4.44 (br s, 2H), 4.40 (d, J=2.8 Hz, 1H), 4.01 (d, J=9.6 Hz, 1H), 3.82-3.75 (m, 1H), 3.50-3.04 (m, 4H), 2.26-2.18 (m, 2H). MH+478.

Example 154

(2S,3R,4R,5S,6R)-2-(4-chloro-3-((5-(thiophen-3-yl)thiazol-2-yl)methyl)phenyl)-6-(1-hydroxyethyl)tetrahydro-2H-pyran-3,4,5-triol The titled compound was obtained in the same manner as in Example 151.

$^1$H NMR (400 MHz, DMSO-$d_6$) non-separated: δ 7.97 (s, 1H), 7.73-7.71 (m, 1H), 7.64 (dd, J=4.8, 2.8 Hz, 1H), 7.55 (d, J=2.0 Hz, 1H), 7.46-7.42 (m, 2H), 7.36 (dd, J=8.0, 2.0 Hz, 1H), 4.89 (s, 3H), 4.42 (d, J=6.0 Hz, 2H), 4.04 (d, J=9.6 Hz, 1H), 3.448 (t, J=9.2 Hz, 1H), 3.32 (s, 5H), 3.27 (d, J=8.8 Hz, 1H), 3.17 (s, 1H), 3.04 (t, J=9.6 Hz, 2H), 1.10 (d, J=6.4 Hz, 2H); MH+648.

Example 155

(2S,3S,4R,5R,6S)-Methyl 6-(4-chloro-3-((5-(furan-2-yl)thiazol-2-yl)methyl)phenyl)-3,4,5-trihydroxy-tetrahydro-2H-pyran-2-carboxylate Step 1: (2S,3S,4R,5S,6S)-3,4,5-Tris(benzyloxy)-6-(4-chloro-3-((5-(furan-2-yl)thiazol-2-yl)methyl)phenyl)-tetrahydro-2H-pyran-2-carboxylic acid (104)

To the solution of aldehyde 101 (830 mg, 1.17 mmol) in t-BuOH (34 mL) was added 2-methyl-2-butene (5.9 mL, 55.2 mmol), $KH_2PO_4$ (1.1 g, 8.3 mmol) and $NaClO_2$ (960 mg, 10.6 mmol in $H_2O$ (20 mL)). The reaction mixture was stirred for 15 h at room temperature. The reaction mixture was acidified with AcOH and extracted with EtOAc. The organic layer was dried over anhydrous $MgSO_4$, filtered and concentrated in vacuo to provide the desired acid 104 (815 mg, 96%) as a solid. The obtained acid was used without further purification. MH+722.

Step 2: (2S,3S,4R,5S,6S)-Methyl 3,4,5-tris(benzyloxy)-6-(4-chloro-3-((5-(furan-2-yl)thiazol-2-yl)methyl)phenyl)-tetrahydro-2H-pyran-2-carboxylate (105)

To the solution of acid 104 (1.7 g, 2.35 mmol) in $CH_2Cl_2$ (7.8 mL) was added $TMSCHN_2$ (1.4 mL, 2.82 mmol) at 0° C. The reaction mixture was allowed to warm to room temperature and stirred for 15 h. $H_2O$ was added to the reaction mixture and then extracted with $CH_2Cl_2$. The organic layer was dried over anhydrous $MgSO_4$, filtered and concentrated in vacuo. Purification by silica gel column chromatography provided the desired methyl ester 105 (560 mg, 32%) as a solid. MH+737.

Step 3: (2S,3S,4R,5R,6S)-Methyl 6-(4-chloro-3-((5-(furan-2-yl)thiazol-2-yl)methyl)phenyl)-3,4,5-trihydroxy-tetrahydro-2H-pyran-2-carboxylate The titled compound was obtained in the same manner as in Example 4.

$^1$H NMR (400 MHz, DMSO-$d_6$) δ 7.93 (s, 1H), 7.73 (d, J=1.2 Hz, 1H), 7.47-7.44 (m, 2H), 7.29 (dd, J=8.0, 2.0 Hz, 1H), 6.79 (d, J=3.2 Hz, 1H), 6.59-6.57 (m, 1H), 4.45 (d, J=2.4 Hz, 2H), 4.20 (d, J=9.6 Hz, 2H), 3.88 (d, J=9.6 Hz, 1H), 3.65 (s, 3H), 3.47-3.45 (m, 1H), 3.35-3.21 (m, 2H). MH+466.

Example 156

(2S,3R,4R,5S,6S)-2-(4-Chloro-3-((5-(furan-2-yl) thiazol-2-yl)methyl)phenyl)-6-(2-hydroxypropan-2-yl)-tetrahydro-2H-pyran-3,4,5-triol Step 1: 2-((2S,3S,4R,5S,6S)-3,4,5-Tris(benzyloxy)-6-(4-chloro-3-((5-(furan-2-yl)thiazol-2-yl)methyl) phenyl)-tetrahydro-2H-pyran-2-yl)propan-2-ol (106)

To the solution of methyl ester 105 (370 mg, 0.50 mmol) in THF (2.5 mL) was added methyl magnesiumchloride (3.0 M in THF, 1.6 mL). The reaction mixture was stirred at room temperature for 15 h. The reaction mixture was poured into a saturated $NH_4Cl$ solution and extracted with $CH_2Cl_2$. The organic layer was dried over anhydrous $MgSO_4$, filtered and concentrated in vacuo. Purification by silica column chromatography provided the desired tertiary alcohol 106 (203 mg, 55%) as a solid. MH+ 736.

Step 2: 2S,3R,4R,5S,6S)-2-(4-Chloro-3-((5-(furan-2-yl)thiazol-2-yl)methyl)phenyl)-6-(2-hydroxypropan-2-yl)-tetrahydro-2H-pyran-3,4,5-triol The titled compound was obtained in the same manner as in Example 4.
$^1$H NMR (400 MHz, DMSO-$d_6$) δ 7.93 (s, 1H), 7.73 (d, J=1.2 Hz, 1H), 7.47-7.42 (m, 2H), 7.29 (dd, J=8.2, 2.4 Hz, 1H), 6.78 (d, J=3.2 Hz, 1H), 6.59-6.58 (m, 1H), 4.44 (d, J=1.2 Hz, 2H), 4.08 (d, J=9.2 Hz, 2H), 3.46-3.42 (m, 1H), 3.34-3.30 (m, 5H), 3.10-3.01 (m, 2H), 1.14 (s, 3H), 1.10 (s, 3H). MH+466.

Example 157

(2S,3R,4R,5S,6S)-2-(4-Chloro-3-((5-(furan-2-yl) thiazol-2-yl)methyl)phenyl)-6-(1-hydroxycyclopropyl)-tetrahydro-2H-pyran-3,4,5-triol Step 1: 1-((2S,3S,4R,5S,6S)-3,4,5-Tris(benzyloxy)-6-(4-chloro-3-((5-(furan-2-yl)thiazol-2-yl)methyl) phenyl)-tetrahydro-2H-pyran-2-yl)cyclopropanol (107)

To the solution of methyl ester 105 (350 mg, 0.47 mmol) in THF (2.5 mL) was added ethyl magnesiumchloride (1.2 mL, 2.0M solution in THF) and Ti(Oi-Pr)$_4$ (0.15 mL 0.52 mmol) at 0° C. The reaction mixture was allowed to warm to room temperature and stirred for 18 h. The reaction mixture was poured into a saturated $NH_4Cl$ solution and extracted with ethyl acetate. The organic layer was dried over anhydrous $MgSO_4$, filtere, and concentrated in vacuo. Purification by silica gel column chromatography provided of desired tertiary alcohol 107 (98 mg, 28%) as a solid. MH+734.

Step 2: (2S,3R,4R,5S,6S)-2-(4-Chloro-3-((5-(furan-2-yl)thiazol-2-yl)methyl)phenyl)-6-(1-hydroxycyclopropyl)-tetrahydro-2H-pyran-3,4,5-triol The titled compound was obtained in the same manner as in Example 4.
$^1$H NMR (400 MHz, DMSO-$d_6$) δ 7.79 (s, 1H), 7.53-7.49 (m, 2H), 7.42-7.36 (m, 2H), 6.60 (d, J=3.6 Hz, 1H), 6.48-6.46 (m, 1H), 4.44 (d, J=3.2 Hz, 2H), 4.09 (d, J=9.6 Hz, 1H), 3.80-3.76 (m, 1H), 3.49-3.44 (m, 1H), 2.66 (d, J=7.2 Hz, 1H) 0.79-0.75 (m, 2H), 0.66-0.60 (m, 1H), 0.56-0.50 (m, 1H). MH+464.

Example 158

1-((2S,3R,4R,5R,6S)-6-(4-Chloro-3-((5-(furan-2-yl) thiazol-2-yl)methyl)phenyl)-3,4,5-trihydroxytetrahydro-2H-pyran-2-yl)propan-1-one The titled compound was obtained as a side product in Example 157.
$^1$H NMR (400 MHz, CD$_3$OD) δ 7.79 (s, 1H), 7.51-7.30 (m, 4H), 6.60 (d, J=3.2 Hz, 1H), 6.48-6.47 (m, 1H), 4.45 (s, 2H), 4.19 (d, J=9.6 Hz, 1H), 3.87 (d, J=9.6 Hz, 1H) 3.57-3.45 (m, 2H), 3.31-3.29 (m, 1H), 2.68-2.62 (m, 2H) 0.98 (t, J=7.2 Hz, 3H). MH+ 464.

Example 159

Butyl ((2R,3S,4R,5R,6S)-6-(4-chloro-3-((5-(thiophen-3-yl)thiazol-2-yl)methyl)phenyl)-3,4,5-trihydroxy-tetrahydro-2H-pyran-2-yl)methyl carbonate To a solution of 48 (200 mg, 0.44 mmol) in 2,6-lutidine (2.0 ml) was added butyl chloroformate (73 µl, 0.57 mmol) at 0° C. and stirred at room temperature for 2 h. The crude product was purified by prep HPLC (C18) to provide the titled compound (123 mg, 50%).
$^1$H NMR (400 MHz, CD$_3$OD) δ 7.79 (s, 1H), 7.52-7.51 (m, 1H), 7.49-7.44 (m, 2H), 7.40 (d, J=8.4 Hz, 1H), 7.34-7.29 (m, 3H), 4.45 (d, J=8.4 Hz, 1H), 4.29 (dd, J=11.6, 6.0 Hz, 2H), 4.14 (d, J=9.6 Hz, 1H), 4.05 (t, J=6.4 Hz, 2H), 3.56 (t, J=7.2 Hz, 1H), 3.43 (quint, J=8.8 Hz, 2H), 1.55 (quint, J=8.0 Hz, 2H), 1.30 (sext, J=7.6 Hz, 2H), 0.86 (t, J=7.6 Hz, 3H); MH+526.

Example 160

((2R,3S,4R,5R,6S)-6-(4-Chloro-3-((5-(furan-2-yl) thiazol-2-yl)methyl)phenyl)-3,4,5-trihydroxytetrahydro-2H-pyran-2-yl)methyl ethyl carbonate The titled compound was obtained in the same manner as in Example 159.
$^1$H NMR (400 MHz, DMSO-$d_6$) δ 7.89 (s, 1H), 7.69 (d, J=1.2 Hz, 1H), 7.42-7.40 (m, 2H), 7.24 (dd, J=8.4, 2.0 Hz, 1H), 6.75 (d, J=3.2 Hz, 1H), 6.55-6.54 (m, 1H), 4.45-4.33 (m, 4H), 4.10-4.01 (m, 4H), 3.78-3.72 (m, 1H), 3.58-3.44 (m, 2H), 3.28-3.06 (m, 3H), 1.15 (t, J=7.2 Hz, 3H). MH+510.

Example 161

Butyl ((2R,3S,4R,5R,6S)-6-(4-chloro-3-((5-(furan-2-yl) thiazol-2-yl)methyl)phenyl)-3,4,5-trihydroxytetrahydro-2H-pyran-2-yl)methyl carbonate The titled compound was obtained in the same manner as in Example 159.
$^1$H NMR (400 MHz, DMSO-$d_6$) δ 7.89 (s, 1H), 7.69-7.68 (m, 1H), 7.42-7.40 (m, 2H), 7.25 (dd, J=8.4, 2.0 Hz, 1H), 6.75 (d, J=3.6 Hz, 1H), 6.55-6.54 (m, 1H), 4.45-4.33 (m, 5H), 4.11-4.08 (m, 2H), 4.06-3.96 (m, 2H), 3.81-3.70 (m, 1H), 3.48-3.44 (m, 1H), 3.28-3.07 (m, 3H), 1.52-1.45 (m, 2H), 1.28-1.19 (m, 2H), 0.80 (t, J=7.2 Hz, 3H). MH+538.

Example 162 tert-Butyl ((2R,3S,4R,5R,6S)-6-(4-chloro-3-((5-(furan-2-yl)thiazol-2-yl)methyl)phenyl)-3,4,5-trihydroxytetrahydro-2H-pyran-2-yl)methyl carbonate The titled compound was obtained in the same manner as in Example 159.
$^1$H NMR (400 MHz, DMSO-$d_6$) δ 7.89 (s, 1H), 7.69 (d, J=1.2 Hz, 1H), 7.42-7.40 (m, 2H), 7.25 (dd, J=8.2, 2.0 Hz, 1H), 6.75 (d, J=3.2 Hz, 1H), 6.55-6.54 (m, 1H), 5.02-4.91 (m, 3H), 4.44-4.35 (m, 2H), 4.09-3.97 (m, 2H), 3.81-3.69 (m, 1H), 3.57-3.41 (m, 1H), 3.28-3.08 (m, 3H), 1.33 (s, 9H). MH+538.

Example 163

Allyl ((2R,3S,4R,5R,6S)-6-(4-chloro-3-((5-(furan-2-yl)thiazol-2-yl)methyl)phenyl)-3,4,5-trihydroxytetrahydro-2H-pyran-2-yl)methyl carbonate The titled compound was obtained in the same manner as in Example 159.
$^1$H NMR (400 MHz, DMSO-d$_6$) δ 7.89 (s, 1H), 7.69-7.68 (m, 1H), 7.42-7.40 (m, 2H), 7.25 (dd, J=8.4, 2.0 Hz, 1H), 6.75 (d, J=3.2 Hz, 1H), 6.55-6.54 (m, 1H), 5.86-5.81 (m, 1H), 5.27-5.14 (m, 4H), 5.06-4.92 (m, 2H), 4.53-4.51 (m, 2H), 4.40-4.36 (m, 2H), 4.13-4.06 (m, 2H), 3.48-3.46 (m, 1H), 3.28-3.06 (m, 3H). MH+522.

Example 164

Benzyl ((2R,3S,4R,5R,6S)-6-(4-chloro-3-((5-(furan-2-yl)thiazol-2-yl)methyl)phenyl)-3,4,5-trihydroxytetrahydro-2H-pyran-2-yl)methyl carbonate The titled compound was obtained in the same manner as in Example 159.
$^1$H NMR (400 MHz, DMSO-d$_6$) δ 7.88 (s, 1H), 7.68-7.67 (m, 1H), 7.41-7.39 (m, 2H), 7.30-7.24 (m, 6H), 6.74 (d, J=3.2 Hz, 1H), 6.55-6.54 (m, 1H), 5.24-4.91 (m, 3H), 4.44-4.34 (m, 4H), 4.15-4.05 (m, 2H), 3.78-3.72 (m, 1H), 3.50-3.49 (m, 1H), 3.28-3.06 (m, 3H). MH+572.

Example 165

((2R,3S,4R,5R,6S)-6-(4-Chloro-3-((5-(thiophen-3-yl)thiazol-2-yl)methyl)phenyl)-3,4,5-trihydroxytetrahydro-2H-pyran-2-yl)methyl ethyl carbonate The titled compound was obtained in the same manner as in Example 159.
$^1$H NMR (400 MHz, DMSO-d$_6$) δ 7.96 (s, 1H), 7.71 (t, J=1.6 Hz, 1H), 7.63 (q, J=2.8 Hz, 1H) 7.45-7.41 (m, 3H), 7.26 (d, J=8.4 Hz, 1H), 5.25 (d, J=5.6 Hz, 1H), 5.06 (d, J=4.8 Hz, 1H), 4.94 (d, J=5.6 Hz, 1H), 4.41 (d, J=4.4 Hz, 2H), 4.37 (d, J=9.6 Hz, 1H), 4.13-4.01 (m, 4H), 1.22 (s, 3H), 1.15 (t, J=7.2 Hz, 3H); MH+526.

Example 166

Allyl (((2R,3S,4R,5R,6S)-6-(4-chloro-3-((5-(thiophen-3-yl)thiazol-2-yl)methyl)phenyl)-3,4,5-trihydroxytetrahydro-2H-pyran-2-yl)methyl) carbonate The titled compound was obtained in the same manner as in Example 159.
$^1$H NMR (400 MHz, CD$_3$OD) δ 7.79 (s, 1H), 7.52 (dd, J=2.8, 1.2 Hz, 1H), 7.47-7.45 (m, 2H), 7.40 (d, J=8.4 Hz, 1H), 7.33 (dd, J=8.4, 2.0 Hz 1H), 7.30 (dd, J=5.2, 1.6 Hz, 1H), 5.87 (m, 1H), 5.28 (d, J=1.6 Hz, 0.5H), 5.24 (d, J=1.6 Hz, 0.5H), 5.15 (d, J=10.4 Hz, 1H), 4.54 (td, J=5.6, 1.2 Hz, 2H), 4.45 (s, 3H), 4.32 (dd, J=12.0, 6.0 Hz, 1H), 4.14 (d, J=9.2 Hz, 1H), 3.59-3.55 (m, 1H), 3.44 (quint, J=8.8 Hz, 2H), 1.27 (s, 1H); MH+538.

Example 167

Benzyl (((2R,3S,4R,5R,6S)-6-(4-chloro-3-((5-(thiophen-3-yl)thiazol-2-yl)methyl)phenyl)-3,4,5-trihydroxytetrahydro-2H-pyran-2-yl)methyl) carbonate The titled compound was obtained in the same manner as in Example 159.
$^1$H NMR (400 MHz, CD$_3$OD) δ 8.17 (s, 1H), 7.91 (m, 1H), 7.84 (dd, J=5.2, 3.2 Hz, 1H), 7.66-7.62 (m, 3H), 7.56 (s, 4H), 7.48 (dd, J=8.4. 1.6 Hz, 1H), 5.48 (d, J=5.6 Hz, 1H), 5.31 (s, 2H), 5.29 (d, J=5.2 Hz, 1H), 5.16 (d, J=6.0 Hz, 1H), 4.64-4.61 (m, 3H), 3.52 (s, 6H), 3.43 (dd, J=8.8, 5.2 Hz, 1H), 3.34 (dd, J=9.2, 6.0 Hz, 1H), 2.71 (s, 4H), 1.96 (quint, J=3.2 Hz, 1H); MH+588.

Example 168

((2R,3S,4R,5R,6S)-6-(4-Chloro-3-((2-(thiophen-3-yl)thiazol-5-yl)methyl)phenyl)-3,4,5-trihydroxytetrahydro-2H-pyran-2-yl)methyl ethyl carbonate The titled compound was obtained in the same manner as in Example 159.
$^1$H NMR (400 MHz, DMSO-d$_6$) δ 8.00 (s, 1H), 7.64-7.62 (m, 1H), 7.58 (s, 1H), 7.47 (d, J=5.28 Hz, 1H), 7.40 (d, J=8.4 Hz, 1H), 7.37 (s, 1H), 7.21 (d, J=8.4 Hz, 1H), 4.35 (d, J=11.6 Hz, 1H), 4.22 (m, 2H), 4.11-4.01 (m, 4H), 3.48-3.43 (m, 1H), 3.26 (t, J=8.8 Hz, 1H), 3.17 (t, J=9.2 Hz, 1H), 3.10 (t, J=9.2 Hz, 1H), 1.13 (t, J=6.8 Hz, 3H); MH+ 526.

Example 169

((2R,3S,4R,5R,6S)-6-(4-Chloro-3-((5-(furan-2-yl)thiazol-2-yl)methyl)phenyl)-3,4,5-trihydroxytetrahydro-2H-pyran-2-yl)methyl isobutyrate The titled compound was obtained in the same manner as in Example 159.
$^1$H NMR (400 MHz, DMSO-d$_6$) δ 7.92 (s, 1H), 7.72 (d, J=1.2 Hz, 1H), 7.45-7.43 (m, 2H), 7.28 (dd, J=8.4, 2.0 Hz, 1H), 6.78 (d, J=3.6 Hz, 1H), 6.59-6.58 (m, 1H), 5.24-4.96 (m, 3H), 4.43-4.34 (m, 4H), 4.14-4.03 (m, 2H), 3.52-3.48 (m, 1H), 3.28-3.08 (m, 3H), 1.05-1.01 (m, 6H). MH+508.

Example 170

((2R,3S,4R,5R,6S)-6-(4-Chloro-3-((5-(furan-2-yl)thiazol-2-yl)methyl)phenyl)-3,4,5-trihydroxytetrahydro-2H-pyran-2-yl)methyl pivalate The titled compound was obtained in the same manner as in Example 159.
$^1$H NMR (400 MHz, DMSO-d$_6$) δ 7.92 (s, 1H), 7.73-7.72 (m, 1H), 7.46-7.42 (m, 2H), 7.27 (dd, J=8.4, 2.0 Hz, 1H), 6.78 (d, J=3.6 Hz, 1H), 6.59-6.58 (m, 1H), 5.21-4.95 (m, 3H), 4.42-4.30 (m, 3H), 4.10-4.06 (m, 2H), 3.49-3.46 (m, 1H), 3.31-3.23 (m, 2H), 3.13-3.07 (m, 1H), 1.10 (s, 9H). MH+522.

Example 171

((2R,3S,4R,5R,6S)-6-(4-Chloro-3-((5-(thiophen-3-yl)thiazol-2-yl)methyl)phenyl)-3,4,5-trihydroxytetrahydro-2H-pyran-2-yl)methyl pivalate To a solution of 48 (150 mg, 0.33 mmol) and DMAP (4 mg, 0.033 mmol) in pyridine (1.0 ml) was added pivaloyl chloride (57 µl, 0.46 mmol) as dropwise at room temperature and stirred for 10 h. The crude product was purified by prep HPLC (C18) to provide the titled compound (83 mg, 47%).

$^1$H NMR (400 MHz, CD$_3$OD) δ 7.80 (s, 1H), 7.51 (dd, J=3.2, 1.2 Hz, 1H), 7.47-7.44 (m, 2H), 7.40 (d, J=8.0 Hz, 1H), 7.32-7.29 (m, 2H), 4.43 (s, 2H), 4.40 (dd, J=12.0, 2.4 Hz, 1H), 4.24 (dd, J=11.6, 5.2 Hz, 1H), 4.14 (d, J=9.2 Hz, 1H), 3.55 (m, 1H), 3.45 (m, 2H), 3.29 (m, 1H), 1.24 (s, 9H); MH+558.

Example 172

((2R,3S,4R,5R,6S)-6-(4-Chloro-3-((5-(thiophen-3-yl)thiazol-2-yl)methyl)phenyl)-3,4,5-trihydroxytetrahydro-2H-pyran-2-yl)methyl isobutyrate The titled compound was obtained in the same manner as in Example 171.

$^1$H NMR (400 MHz, CD$_3$OD) δ 7.80 (s, 1H), 7.52 (dd, J=2.8, 1.2 Hz, 1H), 7.47-7.44 (m, 2H), 7.40 (d, J=8.4 Hz, 1H), 7.33-7.29 (m, 2H), 4.44 (s, 2H), 4.21 (dd, J=12, 2.4 Hz, 1H), 4.23 (dd, J=11.6, 5.6 Hz, 1H), 4.13 (d, J=9.6 Hz, 1H), 3.58-3.54 (m, 1H), 3.43 (quint, J=8.8 Hz, 2H), 3.29 (s, 1H), 2.52 (quint, J=6.8 Hz, 1H), 1.08 (t, J=6.8 Hz, 3H); MH+524.

Example 173

((2R,3S,4R,5R,6S)-6-(4-Chloro-3-((5-(thiophen-3-yl)thiazol-2-yl)methyl)phenyl)-3,4,5-trihydroxy-tetrahydro-2H-pyran-2-yl)methyl 3,4-dimethoxybenzoate To a solution of 48 (150 mg, 0.33 mmol), EDCI (130 mg, 0.66 mmol) and DMAP (20 mg, 0.16 mmol) and pyridine (0.13 ml, 1.65 mmol) in CH$_2$Cl$_2$ (4 ml) was added 3,4-dimethoxybenzoic acid (120 mg, 0.66 mmol) at room temperature and stirred for 16 hours. The reaction mixture was diluted with CH$_2$Cl$_2$ (8 ml), and washed with brine (8 ml). The organic phase was dried over anhydrous MgSO$_4$, filtered and concentrated in vacuo. The crude product was purified by prep HPLC (C18) to provide the titled compound (55 mg, 27%).

$^1$H NMR (400 MHz, CD$_3$OD) δ 7.98 (s, 1H), 7.94 (s, 1H), 7.73-7.62 (m, 4H), 7.46-7.42 (m, 5H), 7.05 (t, J=9.2 Hz, 2H), 5.32 (m, 2H), 5.14 (m, 1H), 4.96 (d, J=3.6 Hz 1H), 4.50 (d, J=2.4 Hz, 2H), 4.25 (d, J=8.6 Hz, 1H), 3.83 (s, 3H), 3.80 (s, 3H), 3.76 (s, 1H); MH+618.

Example 174

((2R,3S,4R,5R,6S)-6-(4-Chloro-3-((5-(furan-2-yl)thiazol-2-yl)methyl)phenyl)-3,4,5-trihydroxytetrahydro-2H-pyran-2-yl)methyl 3,4-dimethoxybenzoate The titled compound was obtained in the same manner as in Example 173.

$^1$H NMR (400 MHz, DMSO-d$_6$) δ 7.90 (s, 1H), 7.72-7.71 (m, 1H), 7.57 (dd, J=8.4, 2.0 Hz, 1H), 7.45-7.42 (m, 3H), 7.29 (dd, J=8.4, 2.0 Hz, 1H), 7.04 (d, J=8.4 Hz, 1H), 6.75 (d, J=3.2 Hz, 1H), 6.58-6.57 (m, 1H), 5.20-4.97 (m, 3H), 4.56-4.30 (m, 4H), 4.16-4.14 (m, 1H), 3.80 (s, 3H), 3.76 (s, 3H), 3.65-3.63 (m, 1H), 3.35-3.22 (m, 2H), 3.17-3.13 (m, 1H). MH+510.

Example 175

((2R,3S,4R,5R,6S)-6-(4-Chloro-3-((5-(furan-2-yl)thiazol-2-yl)methyl)phenyl)-3,4,5-trihydroxytetrahydro-2H-pyran-2-yl)methyl 3,4,5-trimethoxybenzoate The titled compound was obtained in the same manner as in Example 173.

$^1$H NMR (400 MHz, DMSO-d$_6$) δ 7.89 (s, 1H), 7.72-7.71 (m, 1H), 7.45-7.42 (m, 2H), 7.31-7.29 (m, 1H), 7.23-7.21 (m, 2H), 6.75 (d, J=3.2 Hz, 1H), 6.58-6.57 (m, 1H), 5.31-4.98 (m, 3H), 4.57-4.35 (m, 4H), 4.17-4.15 (m, 1H), 3.79 (s, 6H), 3.71 (s, 3H), 3.66-3.64 (m, 1H), 3.35-3.33 (m, 2H), 3.17-3.16 (m, 1H). MH+632.

Example 176

(2S,3S)-((2R,3S,4R,5R,6S)-6-(4-Chloro-3-((5-(furan-2-yl)thiazol-2-yl)methyl)phenyl)-3,4,5-trihydroxy-tetrahydro-2H-pyran-2-yl)methyl 2-amino-3-methylpentanoate Step 1: (2S,3S)-((2R,3S,4R,5R,6S)-6-(4-Chloro-3-((5-(furan-2-yl)thiazol-2-yl)methyl)phenyl)-3,4,5-trihydroxy-tetrahydro-2H-pyran-2-yl)methyl 2-(tert-butoxycarbonylamino)-3-methylpentanoate A mixture of parent compound 89 (438 mg, 1.0 mmol), N-Boc-Ile (463 mg, 2.0 mmol), EDCI (384 mg, 2.0 mmol) and DMAP (162 mg, 1.3 mmol) in DMF (0.9 mL) was stirred at room temperature for 15 h. The reaction mixture was poured into 1.0 M HCl solution, and extracted with EtOAc. The organic phase was dried over anhydrous MgSO$_4$ and evaporated under vacuum. The residue was further purified by silica column chromatography to provide the titled intermediate (157 mg, 24%). MH+651.

Step 2: (2S,3S)-((2R,3S,4R,5R,6S)-6-(4-Chloro-3-((5-(furan-2-yl)thiazol-2-yl)methyl)phenyl)-3,4,5-trihydroxy-tetrahydro-2H-pyran-2-yl)methyl 2-amino-3-methylpentanoate To a solution of the intermediate (100 mg, 0.15 mmol) in CH$_2$Cl$_2$ (1.0 mL) was added a HCl solution (2.0 M in ether, 2 mL) at 0° C. The reaction mixture was allowed warmed up to room temperature and stirred for 2 h. The mixture was evaporated under vacuum and the residue was further purified by prep HPLC (C18, 0.1% TFA in eluent) to provide the titled compound (47 mg, 53%) as TFA salt.

$^1$H NMR (400 MHz, DMSO-d$_6$) δ 8.26 (br, 2H), 7.93 (s, 1H), 7.73 (s, 1H), 7.46-7.42 (m, 2H), 7.27 (d, J=8.4 Hz, 1H), 6.78 (d, J=3.2 Hz, 1H), 6.60-6.58 (m, 1H), 4.43 (d, J=8.0 Hz, 2H), 4.37 (d, J=4.8 Hz, 2H), 4.09 (d, J=9.6 Hz, 1H), 4.0-3.94 (m, 1H), 3.57-3.52 (m, 1H), 3.33 (t, J=8.8 Hz, 1H), 3.22 (t, J=9.2 Hz, 1H), 3.15 (t, J=8.8 Hz, 1H), 1.79-1.72 (m, 1H), 1.40-1.33 (m, 1H), 1.20-1.10 (m, 1H), 0.74 (d, J=6.8 Hz, 3H), 0.69 (t, J=7.2 Hz, 3H); MH+.

Example 177

(S)-((2R,3S,4R,5R,6S)-6-(4-Chloro-3-((5-(furan-2-yl)thiazol-2-yl)methyl)phenyl)-3,4,5-trihydroxytetrahydro-2H-pyran-2-yl)methyl 2-aminopropanoate The titled compound was obtained in the same manner as in Example 176.

$^1$H NMR (400 MHz, DMSO-d$_6$) δ 8.27 (br, 2H), 7.93 (s, 1H), 7.73 (s, 1H), 7.49-7.44 (m, 2H), 7.30 (d, J=8.0 Hz, 1H), 6.79 (d, J=3.2 Hz, 1H), 6.59-6.58 (m, 1H), 4.72-4.66 (m, 1H), 4.44 (d, J=4.8 Hz, 2H), 4.29-4.24 (m, 1H), 4.11 (d, J=9.2 Hz, 1H), 3.56-3.53 (m, 2H), 3.33 (t, J=8.8 Hz, 1H), 3.26 (t, J=9.6 Hz, 1H), 3.17 (t, J=8.8 Hz, 1H), 1.35 (t, J=7.6 Hz, 3H); MH+509.

Example 178

(S)-((2R,3S,4R,5R,6S)-6-(4-Chloro-3-((5-(furan-2-yl)thiazol-2-yl)methyl)phenyl)-3,4,5-trihydroxytetrahydro-2H-pyran-2-yl)methyl 2-amino-3-methylbutanoate The titled compound was obtained in the same manner as in Example 176.

$^1$H NMR (400 MHz, DMSO-$d_6$) δ 8.26 (br, 2H), 7.93 (s, 1H), 7.73 (s, 1H), 7.45-7.42 (m, 2H), 7.28 (d, J=8.4 Hz, 1H), 6.78 (d, J=3.6 Hz, 1H), 6.60-6.58 (m, 1H), 4.43 (d, J=6.4 Hz, 2H), 4.40-4.33 (m, 2H), 4.09 (d, J=9.6 Hz, 1H), 3.93-3.90 (m, 1H), 3.58-3.53 (m, 1H), 3.33 (t, J=8.8 Hz, 1H), 3.24 (t, J=9.2 Hz, 1H), 3.17 (t, J=9.2 Hz, 1H), 2.05-2.01 (m, 1H), 0.86 (d, J=7.2 Hz, 3H), 0.80 (d, J=6.8 Hz, 3H); MH+537.

Example 179

(S)-((2R,3S,4R,5R,6S)-6-(4-Chloro-3-((5-(furan-2-yl)thiazol-2-yl)methyl)phenyl)-3,4,5-trihydroxytetrahydro-2H-pyran-2-yl)methyl 2-amino-4-methylpentanoate The titled compound was obtained in the same manner as in Example 176.

$^1$H NMR (400 MHz, DMSO-$d_6$) δ 8.29 (br, 2H), 7.93 (s, 1H), 7.73 (s, 1H), 7.46-7.42 (m, 2H), 7.28 (d, J=8.4 Hz, 1H), 6.78 (d, J=3.2 Hz, 1H), 6.60-6.58 (m, 1H), 4.43 (d, J=8.0 Hz, 2H), 4.38-4.31 (m, 2H), 4.09 (d, J=9.2 Hz, 1H), 4.00-3.94 (m, 1H), 3.59-3.53 (m, 1H), 3.33 (t, J=8.8 Hz, 1H), 3.22 (t, J=9.6 Hz, 1H), 3.14 (t, J=9.2 Hz, 1H), 1.66-1.52 (m, 2H), 1.49-1.42 (m, 1H), 0.75 (d, J=6.4 Hz, 3H), 0.69 (d, J=6.4 Hz, 3H). MH+551/MH2+276.

Example 180

(S)-((2R,3S,4R,5R,6S)-6-(4-Chloro-3-((5-(furan-2-yl)thiazol-2-yl)methyl)phenyl)-3,4,5-trihydroxytetrahydro-2H-pyran-2-yl)methyl 2-amino-3-phenylpropanoate The titled compound was obtained in the same manner as in Example 176.

$^1$H NMR (400 MHz, DMSO-$d_6$) δ 8.36 (br, 2H), 7.93 (s, 1H), 7.72 (s, 1H), 7.48-7.45 (m, 2H), 7.31 (d, J=8.0 Hz, 3H), 7.20-7.16 (m, 3H), 7.15-7.13 (m, 2H), 6.75 (d, J=3.2 Hz, 1H), 6.59-6.57 (m, 1H), 4.43 (d, J=4.4 Hz, 2H), 4.41-4.36 (m, 2H), 4.24-4.19 (m, 1H), 4.10 (d, J=9.2 Hz, 1H), 3.52-3.47 (m, 1H), 3.13 (t, J=8.8 Hz, 1H), 3.25-3.22 (m, 2H), 3.06-3.01 (m, 2H); MH+585.

Example 181

(2S,3S)-((2R,3S,4R,5R,6S)-6-(4-Chloro-3-((5-(thiophen-3-yl)thiazol-2-yl)methyl)phenyl)-3,4,5-trihydroxytetrahydro-2H-pyran-2-yl)methyl 2-amino-3-methylpentanoate The titled compound was obtained in the same manner as in Example 176.

$^1$H NMR (400 MHz, DMSO-$d_6$) δ 8.24 (br, 2H), 8.03-8.02 (m, 1H), 7.68-7.66 (m, 1H), 7.60 (s, 1H), 7.50 (d, J=4.8 Hz, 1H), 7.43 (d, J=8.0 Hz, 1H), 7.37 (s, 1H), 7.23 (d, J=8.4 Hz, 1H), 4.41-4.34 (m, 2H), 4.29 (d, J=5.2 Hz, 2H), 4.06 (d, J=9.2 Hz, 1H), 3.98-3.96 (m, 1H), 3.56-3.51 (m, 1H), 3.32 (t, J=8.8 Hz, 1H), 3.22 (t, J=9.2 Hz, 1H), 3.14 (t, J=8.8 Hz, 1H), 1.78-1.71 (m, 1H), 1.38-1.30 (m, 1H), 1.18-1.08 (m, 1H), 0.71 (d, J=7.2 Hz, 3H), 0.66 (t, J=7.2 Hz, 3H); MH+567.

Example 182

(2R,3R,4R,5S,6S)-2-((2-Aminoacetoxy)methyl)-6-(4-chloro-3-((5-(furan-2-yl)thiazol-2-yl)methyl)phenyl)-tetrahydro-2H-pyran-3,4,5-triyl tris(2-aminoacetate)

Step 1: (2R,3R,4R,5S,6S)-2-((2-(tert-Butoxycarbonylamino)acetoxy)methyl)-6-(4-chloro-3-((5-(furan-2-yl)thiazol-2-yl)methyl)phenyl)-tetrahydro-2H-pyran-3,4,5-triyl tris(2-(tert-butoxycarbonylamino)acetate)

A mixture of parent compound 89 (219 mg, 0.5 mmol), N-Boc-Gly (701 mg, 4.0 mmol), EDCI (767 mg, 4.0 mmol), and DMAP (244 mg, 2.0 mmol) in DMF (1.0 mL) was stirred at room temperature for 15 h. The reaction mixture was poured into 1.0 M HCl solution and extracted with EtOAc. The organic phase was dried over anhydrous MgSO$_4$ and evaporated under vacuum. The residue was further purified by silica column chromatography to provide the intermediate (412 mg, 77%); MH+1066.

Step 2: (2R,3R,4R,5S,6S)-2-((2-Aminoacetoxy)methyl)-6-(4-chloro-3-((5-(furan-2-yl)thiazol-2-yl)methyl)phenyl)-tetrahydro-2H-pyran-3,4,5-triyl tris(2-aminoacetate)

To a solution of the intermediate (412 mg, 0.15 mmol) in CH$_2$Cl$_2$ (1.5 mL) was added TFA (3.0 mL) at room temperature. The reaction mixture was stirred for 2 hours and evaporated under vacuum. The residue was further purified by prep HPLC (C18, 0.1% TFA in eluent) to provide the titled compound (220 mg, 50%) as TFA salt.

$^1$H NMR (400 MHz, DMSO-$d_6$) δ 8.58-8.26 (br, 8H), 7.96 (s, 1H), 7.75 (s, 1H), 7.50-7.42 (m, 3H), 6.80 (d, J=3.0 Hz, 1H), 6.62-6.60 (m, 1H), 5.66-5.61 (m, 1H), 5.46-5.41 (m, 1H), 5.26-5.21 (m, 1H), 4.88-4.83 (m, 1H), 4.47 (d, J=8.4 Hz, 2H), 4.31-4.26 (m, 2H), 4.02-3.63 (m, 9H); MH+666.

Example 183

(2S,3R,4R,5S,6R)-2-(4-Chloro-3-((2-phenylthiazol-5-yl)methyl)phenyl)-6-(hydroxymethyl)-tetrahydro-2H-pyran-3,4,5-triol Step 1: N-(3-(2-chloro-5-((2S,3S,4R,5R,6R)-3,4,5-Tris(benzyloxy)-6-(benzyloxymethyl)-tetrahydro-2H-pyran-2-yl)phenyl)-2-oxopropyl)benzamide To a mixture of 1-amino-3-(2-chloro-5-((2S,3S,4R,5R,6R)-3,4,5-tris(benzyloxy)-6-(benzyloxymethyl)-tetrahydro-2H-pyran-2-yl)phenyl)propan-2-one hydrochloride (1.75 g, 2.35 mmol), benzoic acid (430 mg, 3.53 mmol), EDCI (901 mg, 4.70 mmol) and HOBt (699 mg, 5.17 mmol) in DMF (15 mL) was added NMM (1.29 mL, 11.8 mmol). The resulting mixture was stirred at room temperature for 16 hours. The reaction mixture was poured into 1.0 M HCl solution, and extracted with EtOAc. The organic phase was dried over anhydrous MgSO$_4$ and evaporated under vacuum. The residue was further purified by silica column chromatography to provide the titled amide intermediate (980 mg, 51%). MH+706.

Step 2: 5-(2-Chloro-5-((2S,3S,4R,5R,6R)-3,4,5-Tris(benzyloxy)-6-(benzyloxymethyl)-tetrahydro-2H-pyran-2-yl)benzyl)-2-phenylthiazole The titled compound was obtained in the same manner as in Example 1 (Step 2). MH+808.

Step 3: (2S,3R,4R,5S,6R)-2-(4-Chloro-3-((2-phenylthiazol-5-yl)methyl)phenyl)-6-(hydroxymethyl)-tetrahydro-2H-pyran-3,4,5-triol The titled compound was obtained in the same manner as in Example 4.
$^1$H NMR (400 MHz, CD$_3$OD) δ 7.84-7.81 (m, 2H), 7.57 (s, 1H), 7.48 (d, J=2.0 Hz, 1H), 7.43-7.37 (m, 1H), 7.35-7.32 (m, 1H), 4.33 (d, J=2.4 Hz, 2H), 4.12 (d, J=9.2 Hz, 1H), 3.86 (d, J=11.2 Hz, 1H), 3.72-3.66 (m, 1H), 3.47-3.32 (m, 4H); MH+448.

Example 184

(2S,3R,4R,5S,6R)-2-(4-Chloro-3-((2-(furan-2-yl)thiazol-5-yl)methyl)phenyl)-6-(hydroxymethyl)tetrahydro-2H-pyran-3,4,5-triol The titled compound was obtained in the same manner as in Example 183.
$^1$H NMR (400 MHz, DMSO-d$_6$) δ 7.79 (s, 1H), 7.62 (s, 1H), 7.42 (d, J=2.0 Hz, 1H), 7.38 (d, J=8.4 Hz, 1H), 7.25 (dd, J=8.0, 2.0 Hz, 1H), 6.98 (d, J=3.2 Hz, 1H), 6.63-6.61 (m, 1H), 4.99 (br s, 2H), 4.86 (br s, 1H), 4.44 (br s, 2H), 4.27 (d, J=3.6 Hz, 2H), 3.98 (d, J=9.2 Hz, 1H), 3.66 (d, J=11.2 Hz, 1H), 3.43-3.31 (m, 1H), 3.23-3.11 (m, 3H), 3.06 (t, J=8.8 Hz, 1H); MH+438.

Example 185

(2S,3R,4R,5S,6R)-2-(3-((2-(Benzofuran-2-yl)thiazol-5-yl)methyl)-4-chlorophenyl)-6-(hydroxymethyl)tetrahydro-2H-pyran-3,4,5-triol The titled compound was obtained in the same manner as in Example 183.
$^1$H NMR (400 MHz, DMSO-d$_6$) δ 7.78 (s, 1H), 7.68 (d, J=7.2 Hz, 1H), 7.63 (d, J=8.0 Hz, 1H), 7.46 (s, 2H), 7.41-7.35 (m, 2H), 7.30-7.25 (m, 2H), 4.80 (br, 3H), 4.34 (d, J=3.2 Hz, 2H), 3.99 (d, J=9.6 Hz, 1H), 3.68-3.65 (m, 1H), 3.42 (dd, J=12.0, 5.6 Hz, 1H), 3.26-3.06 (m, 4H); MH+488.

Example 186

(2S,3R,4R,5S,6R)-2-(4-Chloro-3-((2-(furan-3-yl)thiazol-5-yl)methyl)phenyl)-6-(hydroxymethyl)tetrahydro-2H-pyran-3,4,5-triol The titled compound was obtained in the same manner as in Example 183.
$^1$H NMR (400 MHz, DMSO-d$_6$) δ 8.30 (s, 1H), 7.78 (s, 1H), 7.60 (s, 1H), 7.44 (d, J=0.8 Hz, 1H), 7.41 (d, J=6.4 Hz, 1H), 7.28 (dd, J=6.4, 1.2 Hz, 1H), 6.87 (s, 1H), 4.99 (br s, 2H), 4.86 (br s, 1H), 4.44 (br s, 1H), 4.28 (d, J=6.0 Hz, 2H), 4.00 (d, J=7.6 Hz, 1H), 3.69 (d, J=9.2 Hz, 1H), 3.44-3.42 (m, 1H), 3.25-3.20 (m, 2H), 3.17-3.14 (m, 1H), 3.09 (t, J=7.2 Hz, 1H); MH+438.

Example 187

(2S,3R,4R,5S,6R)-2-(4-Chloro-3-((2-(thiophen-2-yl)thiazol-5-yl)methyl)phenyl)-6-(hydroxymethyl)tetrahydro-2H-pyran-3,4,5-triol The titled compound was obtained in the same manner as in Example 183.
$^1$H NMR (400 MHz, CD$_3$OD) δ 7.51-7.46 (m, 4H), 7.39-7.32 (m, 2H), 7.08-7.06 (m, 1H), 4.30 (d, J=2.8 Hz, 2H), 4.12 (d, J=9.2 Hz, 1H), 3.86 (d, J=12.0 Hz, 1H), 3.71-3.66 (m, 1H), 3.47-3.30 (m, 4H); MH+454.

Example 188

(2S,3R,4R,5S,6R)-2-(4-Chloro-3-((2-(5-methylthiophen-2-yl)thiazol-5-yl)methyl)phenyl)-6-(hydroxymethyl)tetrahydro-2H-pyran-3,4,5-triol The titled compound was obtained in the same manner as in Example 183.
$^1$H NMR (400 MHz, DMSO-d$_6$) δ 7.51 (s, 1H), 7.41-7.37 (m, 2H), 7.32 (d, J=3.2 Hz, 1H), 7.24 (dd, J=8.0, 1.6 Hz, 1H), 6.78 (dd, J=4.0, 1.2 Hz, 1H), 4.93 (t, J=5.2 Hz, 2H), 4.82 (d, J=5.6 Hz, 2H), 4.41 (t, J=5.6 Hz, 1H), 4.24 (d, J=4.0 Hz, 1H), 3.68-3.64 (m, 1H), 3.44-3.39 (m, 1H), 3.27-3.08 (m, 3H), 3.07-3.04 (m, 1H), 2.42 (s, 3H); MH+468.

Example 189

(2S,3R,4R,5S,6R)-2-(4-Chloro-3-((2-(5-chlorothiophen-2-yl)thiazol-5-yl)methyl)phenyl)-6-(hydroxymethyl)tetrahydro-2H-pyran-3,4,5-triol The titled compound was obtained in the same manner as in Example 183.
$^1$H NMR (400 MHz, DMSO-d$_6$) δ 7.57 (s, 1H), 7.44 (d, J=4.0 Hz, 1H), 7.42 (d, J=2.0 Hz, 1H), 7.38 (d, J=8.4 Hz, 1H), 7.25 (dd, J=8.4, 2.4 Hz, 1H), 7.13 (d, J=4.0 Hz, 1H), 4.94 (dd, J=6.4, 4.8 Hz, 2H), 4.83 (d, J=5.6 Hz, 1H), 4.42 (t, J=5.6 Hz, 1H), 4.27 (d, J=3.6 Hz, 1H), 3.98 (d, J=9.2 Hz, 1H), 3.69-3.64 (m, 1H), 3.43-3.40 (m, 1H), 3.23-3.17 (m, 2H), 3.15-3.13 (m, 1H), 3.09-3.03 (m, 1H); MH+488.

Example 190

(2S,3R,4R,5S,6R)-2-(4-Chloro-3-((2-(thiophen-3-yl)thiazol-5-yl)methyl)phenyl)-6-(hydroxymethyl)tetrahydro-2H-pyran-3,4,5-triol The titled compound was obtained in the same manner as in Example 183.
$^1$H NMR (400 MHz, CD$_3$OD) δ 7.60 (s, 1H), 7.51-7.46 (m, 4H), 7.39-7.32 (m, 2H), 4.31 (d, J=2.0 Hz, 2H), 4.12 (d, J=9.6 Hz, 1H), 3.86 (d, J=11.2 Hz, 1H), 3.72-3.66 (m, 1H), 3.47-3.32 (m, 4H); MH+454.

Example 191

(2S,3R,4R,5S,6R)-2-(4-Chloro-3-((2-(oxazol-4-yl)thiazol-5-yl)methyl)phenyl)-6-(hydroxymethyl)tetrahydro-2H-pyran-3,4,5-triol The titled compound was obtained in the same manner as in Example 183.
$^1$H NMR (400 MHz, CD$_3$OD$_3$) δ 8.38 (s, 1H), 8.23 (s, 1H), 7.57 (s, 1H), 7.48 (s, 1H), 7.39-7.31 (m, 2H), 4.33 (d, J=3.2 Hz, 2H), 4.12 (d, J=9.6 Hz, 1H), 3.88-3.84 (m, 1H), 3.71-3.66 (m, 1H), 3.47-3.30 (m, 4H); MH+439.

Example 192

(2S,3R,4R,5S,6R)-2-(4-Chloro-3-((2-(isoxazol-5-yl)thiazol-5-yl)methyl)phenyl)-6-(hydroxymethyl)tetrahydro-2H-pyran-3,4,5-triol The titled compound was obtained in the same manner as in Example 183.
$^1$H NMR (400 MHz, DMSO-d$_6$) δ 8.73 (d, J=2.0 Hz, 1H), 7.86 (s, 1H), 7.45 (d, J=2.0 Hz, 1H), 7.39 (d, J=8.4 Hz, 1H), 7.26 (dd, J=8.4, 2.4 Hz, 1H), 7.05 (d, J=2.4 Hz, 1H), 4.97-4.94 (m, 2H), 4.85 (d, J=5.6 Hz, 1H), 4.43 (t, J=6.0 Hz, 1H), 4.36 (d, J=2.4 Hz, 2H), 4.00 (d, J=9.6 Hz, 1H), 3.68-3.65 (m, 1H), 3.44-3.38 (m, 1H), 3.26-3.18 (m, 2H), 3.18-3.12 (m, 1H), 3.10-3.04 (m, 1H); MH+439.

Example 193

(2S,3R,4R,5S,6R)-2-(3-(2,4'-Bithiazol-5-ylmethyl)-4-chlorophenyl)-6-(hydroxymethyl)tetrahydro-2H-pyran-3,4,5-triol The titled compound was obtained in the same manner as in Example 183.
$^1$H NMR (400 MHz, CD$_3$OD) δ 9.00 (s, 1H), 8.07 (s, 1H), 7.58 (s, 1H), 7.49 (s, 1H), 7.40-7.32 (m, 2H), 4.34 (d, J=3.6 Hz, 2H), 4.12 (d, J=9.6 Hz, 1H), 3.89-3.84 (m, 1H), 3.71-3.66 (m, 1H), 3.47-3.30 (m, 4H); MH+455.

Example 194

(2S,3R,4R,5S,6R)-2-(4-Chloro-3-((2-(4-fluorophenyl)thiazol-5-yl)methyl)phenyl)-6-(hydroxymethyl)tetrahydro-2H-pyran-3,4,5-triol The titled compound was obtained in the same manner as in Example 183.
$^1$H NMR (400 MHz, DMSO-d$_6$) δ 7.90-7.86 (m, 2H), 7.65 (s, 1H), 7.42 (d, J=2.0 Hz, 1H), 7.38 (d, J=8.4 Hz, 1H), 7.29-7.24 (m, 3H), 5.09 (br s, 1H), 5.02 (br s, 1H), 4.91 (br s, 1H), 4.44 (br s, 1H), 4.28 (d, J=4.0 Hz, 2H), 3.98 (d, J=9.6 Hz, 1H), 3.66 (dd, J=11.6, 4.0 Hz, 1H), 3.43-3.40 (m, 1H), 3.25-3.06 (m, 4H); MH+466.

Example 195

(2S,3R,4R,5S,6R)-2-(4-Chloro-3-O-(pyrazin-2-yl)thiazol-5-yl)methyl)phenyl)-6-(hydroxymethyl)tetrahydro-2H-pyran-3,4,5-triol The titled compound was obtained in the same manner as in Example 183.
$^1$H NMR (400 MHz, DMSO-d$_6$) δ 9.22 (d, J=1.6 Hz, 1H), 8.67 (d, J=2.4 Hz, 1H), 8.63-8.62 (m, 1H), 7.83 (s, 1H), 7.45 (d, J=1.6 Hz, 1H), 7.39 (d, J=8.4 Hz, 1H), 7.25 (dd, J=8.4, 2.0 Hz, 1H), 4.93 (t, J=4.8 Hz, 2H), 4.82 (d, J=6.0 Hz, 1H), 4.41 (t, J=6.0 Hz, 1H), 4.33 (d, J=3.6 Hz, 2H), 3.99 (d, J=9.2 Hz, 1H), 3.66-3.64 (m, 1H), 3.43-3.40 (m, 1H), 3.24-3.15 (m, 2H), 3.10-3.07 (m, 1H); MH+450.

Example 196

(2S,3R,4R,5S,6R)-2-(4-Chloro-3-((2-(cyclopent-3-enyl)thiazol-5-yl)methyl)phenyl)-6-(hydroxymethyl)tetrahydro-2H-pyran-3,4,5-triol The titled compound was obtained in the same manner as in Example 183.
$^1$H NMR (400 MHz, CD$_3$OD) δ 7.46-7.43 (m, 2H), 7.40-7.32 (m, 2H), 4.28 (d, J=2.0 Hz, 2H), 4.12 (d, J=9.6 Hz, 1H), 3.94-3.79 (m, 3H), 3.76-3.67 (m, 2H), 3.48-3.30 (m, 4H), 2.93-2.86 (m, 2H), 2.63-2.54 (m, 2H); MH+438.

Example 197

(2S,3R,4R,5S,6R)-2-(4-Chloro-3-((2-(methylthio)thiazol-5-yl)methyl)phenyl)-6-(hydroxymethyl)tetrahydro-2H-pyran-3,4,5-triol The titled compound was obtained in the same manner as in Example 183.
$^1$H NMR (400 MHz, CD$_3$OD) δ 7.43 (s, 1H), 7.39-7.32 (m, 3H), 4.25 (d, J=2.0 Hz, 2H), 3.93-3.85 (m, 1H), 3.72-3.67 (m, 1H), 3.49-3.32 (m, 4H), 2.63 (s, 3H); MH+418.

Example 198

(2S,3R,4R,5S,6R)-2-(4-Chloro-3-((2-(propylthio)thiazol-5-yl)methyl)phenyl)-6-(hydroxymethyl)tetrahydro-2H-pyran-3,4,5-triol The titled compound was obtained in the same manner as in Example 183.
$^1$H NMR (400 MHz, CD$_3$OD) δ 7.44 (s, 1H), 7.40-7.35 (m, 3H), 4.25 (s, 2H), 4.12 (d, J=9.6 Hz, 1H), 3.89-3.85 (m, 1H), 3.72-3.66 (m, 1H), 3.48-3.30 (m, 4H), 3.11 (t, J=7.2 Hz, 2H), 1.78-1.68 (m, 2H), 1.01 (t, J=7.6 Hz, 3H); MH+446.

Example 199

(2S,3R,4R,5S,6R)-2-(3-((2-(Furan-2-yl)thiazol-5-yl)methyl)-4-methylphenyl)-6-(hydroxymethyl)tetrahydro-2H-pyran-3,4,5-triol The titled compound was obtained in the same manner as in Example 183.
$^1$H NMR (400 MHz, CD$_3$OD) δ 7.60 (s, 1H), 7.45 (s, 1H), 7.30 (s, 1H), 7.25 (d, J=7.6 Hz, 1H), 7.17 (d, J=8.0 Hz, 1H), 6.96 (d, J=3.6 Hz, 1H), 6.58-6.56 (m, 1H), 4.20 (s, 2H), 4.10 (d, J=9.6 Hz, 1H), 3.86 (d, J=11.6 Hz, 1H), 3.71-3.66 (m, 1H), 3.48-3.34 (m, 4H), 2.29 (s, 3H); MH+418.

Example 200

(2R,3S,4R,5R,6S)-2-(Hydroxymethyl)-6-(4-methyl-3-((2-(thiophen-3-yl)thiazol-5-yl)methyl)phenyl)tetrahydro-2H-pyran-3,4,5-triol The titled compound was obtained in the same manner as in Example 183.

$^{1}$H NMR (400 MHz, CD$_{3}$OD) δ 7.88 (s, 1H), 7.52-7.45 (m, 2H), 7.44 (s, 1H), 7.31 (s, 1H), 7.26-7.24 (m, 1H), 7.16 (d, J=7.6 Hz, 1H), 4.20 (s, 2H), 4.10 (d, J=9.6 Hz, 1H), 3.87 (d, J=12.0 Hz, 1H), 3.71-3.66 (m, 1H), 3.46-3.33 (m, 4H), 2.30 (s, 3H); MH+434.

Example 201

(2S,3R,4R,5S,6R)-2-(4-Chloro-2-fluoro-5-((2-(furan-2-yl)thiazol-5-yl)methyl)phenyl)-6-(hydroxymethyl)tetrahydro-2H-pyran-3,4,5-triol The titled compound was obtained in the same manner as in Example 183.

$^{1}$H NMR (400 MHz, CD$_{3}$OD) δ 7.96 (s, 1H), 7.61 (s, 1H), 7.52 (s, 1H), 7.21 (d, J=9.6 Hz, 1H), 6.97-6.95 (m, 1H), 6.58-6.56 (m, 1H), 4.46 (d, J=9.2 Hz, 1H), 4.32-4.28 (m, 2H), 3.87-3.83 (m, 1H), 3.69-3.65 (m, 1H), 3.49-3.37 (m, 4H); MH+456.

Example 202

(2S,3R,4R,5S,6R)-2-(4-Chloro-2-fluoro-5-((2-(thiophen-2-yl)thiazol-5-yl)methyl)phenyl)-6-(hydroxymethyl)tetrahydro-2H-pyran-3,4,5-triol The titled compound was obtained in the same manner as in Example 183.

$^{1}$H NMR (400 MHz, CD$_{3}$OD) δ 7.61 (s, 1H), 7.59 (s, 1H), 7.52 (s, 1H), 7.21 (d, J=9.6 Hz, 1H), 6.97-6.95 (m, 1H), 6.58-6.56 (m, 1H), 4.46 (d, J=9.2 Hz, 1H), 4.30 (d, J=3.6 Hz, 1H), 3.85 (dd, J=12.0, 1.6 Hz, 1H), 3.69-3.65 (m, 1H), 3.49-3.42 (m, 1H), 3.40-3.37 (m, 3H); MH+472.

Example 203

(2S,3R,4R,5S,6R)-2-(4-Chloro-2-fluoro-5-((2-(thiophen-3-yl)thiazol-5-yl)methyl)phenyl)-6-(hydroxymethyl)tetrahydro-2H-pyran-3,4,5-triol The titled compound was obtained in the same manner as in Example 183.

$^{1}$H NMR (400 MHz, DMSO-d$_{6}$) δ 8.14-8.13 (m, 1H), 7.76-7.74 (m, 1H), 7.69 (s, 2H), 7.59 (dd, J=5.2, 1.2 Hz, 1H), 7.50 (d, J=9.6 Hz, 1H), 5.12 (br, 4H), 4.38 (s, 2H), 3.79 (dd, J=11.6, 6.0 Hz, 1H), 3.39-3.31 (m, 2H), 3.27-3.23 (m, 1H); MH+472.

Example 204

(2S,3R,4R,5S,6R)-2-(4-bromo-3-((5-(thiophen-3-yl)thiazol-2-yl)methyl)phenyl)-6-(hydroxymethyl)tetrahydro-2H-pyran-3,4,5-triol The titled compound was obtained in the same manner as in Example 1.

$^{1}$H NMR (400 MHz, DMSO-d$_{6}$) δ 7.99 (s, 1H), 7.73 (m, 1H), 7.64 (dd, J=3.0, 1.8 Hz, 1H), 7.62 (d, J=7.6 Hz, 1H), 7.51 (d, J=1.6 Hz, 1H), 7.43 (dd, J=5.0, 1.4 Hz, 1H), 7.25 (dd, J=8.4, 2.0 Hz, 1H), 4.43 (ABq, Δv$_{AB}$=12.0 Hz, J$_{AB}$=16.0 Hz, 2H), 4.03 (d, J=9.2 Hz, 1H), 3.71 (dd, J=11.6, 1.6 Hz, 1H), 3.46 (dd, J=11.6, 5.6 Hz, 1H), 3.30-3.16 (m, 3H), 3.11 (t, J=9.0 Hz, 1H); MH+$^{+}$500.

Example 205

((2R,3S,4R,5R,6S)-6-(4-chloro-3-((2-(thiophen-3-yl)thiazol-5-yl)methyl)phenyl)-3,4,5-trihydroxytetrahydro-2H-pyran-2-yl)methyl ethyl carbonate The titled compound was obtained in the same manner as in Example 159.

$^{1}$H NMR (400 MHz, DMSO-d$_{6}$) δ 8.00 (s, 1H), 7.63 (dd, J=5.0, 3.0 Hz, 1H), 7.58 (s, 1H), 7.47 (dd, J=5.2, 1.2 Hz, 1H), 7.40 (d, J=8.4 Hz, 1H), 7.36 (d, J=2.0 Hz, 1H), 7.21 (dd, J=8.4, 2.0 Hz, 1H), 4.35 (d, J=11.6 Hz, 1H), 4.26 (s, 2H), 4.10-4.01 (m, 4H), 3.48-3.43 (m, 1H), 3.25 (t, J=8.8 Hz, 1H), 3.16 (t, J=9.2 Hz, 1H), 3.08 (t, J=9.0 Hz, 1H), 1.13 (t, J=7.0 Hz, 3H); MH+526.

In Vitro Assay

Cloning and Cell Line Construction for Human SGLT2

Human SGLT2 (hSGLT2) gene was amplified by PCR from cDNA-Human Adult Normal Tissue Kidney (Invitrogen). The hSGLT2 sequence was cloned into pcDNA3.1(+) for mammalian expression and were stably transfected into chinese hamster ovary (CHO) cells. SGLT2-expressing clones were selected based on resistance to G418 antibiotic (Geneticin) and activity in the $^{14}$C-α-methyl-D-glucopyranoside ($^{14}$C-AMG) uptake assay.

Inhibitory Effects on Human SGLT2 Activities

For sodium-dependent glucose transport assay, cells expressing hSGLT2 were seeded into a 96-well culture plate at a density of 5×10$^{4}$ cells/well in RPMI medium 1640 containing 10% fetal bovine serum. The cells were used 1 day after plating. They were incubated in pretreatment buffer (10 mM HEPES, 5 mM Tris, 140 mM choline chloride, 2 mM KCl, 1 mM CaCl$_{2}$, and 1 mM MgCl$_{2}$, pH 7.4) at 37° C. for 10 min. They were then incubated in uptake buffer (10 mM HEPES, 5 mM Tris, 140 mM NaCl, 2 mM KCl, 1 mM CaCl$_{2}$, 1 mM MgCl$_{2}$, and 1 mM $^{14}$C-nonlabeled AMG, pH 7.4) containing $^{14}$C-labeled (8 μM) and inhibitor or dimethylsulfoxide (DMSO) vehicle at 37° C. for 2 h. Cells were washed twice with washing buffer (pretreatment buffer containing 10 mM AMG at room temperature) and then the radioactivity was measured using a liquid scintillation counter. IC$_{50}$ was determined by nonlinear regression analysis using GraphPad PRISM [Katsuno, K. et al. *J. Pharmacol. Exp. Ther.* 2007, 320, 323-330; Han, S. et al. *Deabetes*, 2008, 57, 1723-1729].

TABLE 1

| hSGLT2 Inhibitory Activity | |
|---|---|
| Example | IC$_{50}$ (nM) |
| 1 | 2.00 |
| 2 | 12.0 |
| 3 | 47.1 |
| 4 | 9.73 |
| 5 | 1.75 |
| 6 | 6.25 |
| 7 | 3.20 |
| 8 | 13.3 |
| 9 | 7.48 |
| 10 | 6.86 |
| 11 | 21.2 |
| 12 | 16.7 |
| 13 | 119 |
| 14 | 13.3 |
| 15 | 5.00 |

TABLE 1-continued hSGLT2 Inhibitory Activity

| Example | IC$_{50}$ (nM) |
|---|---|
| 16 | 51.4 |
| 17 | 11.5 |
| 18 | 4.69 |
| 19 | 9.71 |
| 20 | 25.4 |
| 21 | 18.8 |
| 22 | 12.4 |
| 23 | 8.21 |
| 24 | 30.9 |
| 25 | 56.4 |
| 26 | 58.7 |
| 27 | 18.9 |
| 28 | 110 |
| 29 | 38.6 |
| 30 | 1.43 |
| 31 | 3.66 |
| 32 | 3.80 |
| 33 | 1.28 |
| 34 | 5.69 |
| 35 | 4.17 |
| 36 | 21.5 |
| 37 | 9.80 |
| 38 | 25.6 |
| 39 | 176 |
| 40 | 6.11 |
| 41 | 30.5 |
| 42 | 25.4 |
| 43 | 7.36 |
| 44 | 30.8 |
| 45 | 47.7 |
| 46 | 1.89 |
| 49 | 16.9 |
| 50 | 14.6 |
| 51 | 20.8 |
| 52 | 87.2 |
| 53 | 3.49 |
| 54 | 5.35 |
| 55 | 3.88 |
| 56 | 2.12 |
| 57 | 4.57 |
| 59 | 5.43 |
| 60 | 13.3 |
| 61 | 4.77 |
| 62 | 2.31 |
| 63 | 49.1 |
| 64 | 26.3 |
| 65 | 43.7 |
| 66 | 60.5 |
| 67 | 38.7 |
| 68 | 33.0 |
| 69 | 2.24 |
| 70 | 7.37 |
| 71 | 1.59 |
| 72 | 1.29 |
| 73 | 2.01 |
| 74 | 6.08 |
| 75 | 4.48 |
| 76 | 9.35 |
| 77 | 3.98 |
| 78 | 4.35 |
| 79 | 4.29 |
| 80 | 1.18 |
| 81 | 2.87 |
| 82 | 7.55 |
| 83 | 1.24 |
| 84 | 1.54 |
| 85 | 1.69 |
| 86 | 0.934 |
| 87 | 3.38 |
| 88 | 4.22 |
| 93 | 14.3 |
| 94 | 5.98 |
| 95 | 2.94 |
| 96 | 4.94 |
| 97 | 6.77 |
| 98 | 29.9 |
| 99 | 19.2 |
| 100 | 7.30 |
| 101 | 26.8 |
| 102 | 50.3 |
| 103 | 51.8 |
| 104 | 100 |
| 105 | 243 |
| 106 | 50.3 |
| 107 | 14.0 |
| 108 | 36.7 |
| 110 | 54.8 |
| 111 | 22.6 |
| 112 | 0.797 |
| 117 | 5.55 |
| 121 | 1.51 |
| 122 | 131 |
| 123 | 58.2 |
| 124 | 7.97 |
| 125 | 30.6 |
| 126 | 67.3 |
| 127 | 32.8 |
| 128 | 116 |
| 129 | 160 |
| 130 | 8.75 |
| 131 | 13.8 |
| 132 | 162 |
| 133 | 180 |
| 134 | 108 |
| 135 | 123 |
| 136 | 210 |
| 137 | 124 |
| 138 | 156 |
| 139 | 23.5 |
| 140 | 68.7 |
| 141 | 30.9 |
| 145 | 10.6 |
| 146 | 7.01 |
| 160 | 24.0 |
| 161 | 5.08 |
| 162 | 79.9 |
| 163 | 11.4 |
| 164 | 2.44 |
| 165 | 7.39 |
| 183 | 5.76 |
| 184 | 1.42 |
| 185 | 76.6 |
| 186 | 4.47 |
| 187 | 2.79 |
| 188 | 10.4 |
| 189 | 8.64 |
| 190 | 0.901 |
| 191 | 45.4 |
| 192 | 20.2 |
| 193 | 17.7 |
| 194 | 6.39 |
| 195 | 4.35 |
| 197 | 9.48 |
| 198 | 15.4 |
| 203 | 1.39 |

\* Reference compound dapagliflozin IC$_{50}$ = 0.49 ± 0.04 nM (in-house assay).
\*\* These data were obtained by single determinations.

Urinary Glucose Excretion in Normal Animals
Animals

Male Sprague-Dawley (SD) rats were purchased by Charles River Laboratory. All animals were housed at 23±2° C. under a 12-h light/dark cycle (light on 7:00) and were fed a standard feed and water ad libitum.

Urinary Glucose Excretion in Normal Animal

For glucosuria assessment, overnight-fasted SD rats (5 weeks of ages) were placed into metabolism cages for baseline urine collection over 24 h. Rats were weighed, randomized into experimental groups (n=4) and orally administered with 50% aqueous glucose solution (2 g/kg) and drugs. Rats were returned to metabolism cages for 24 h urine collection. After the urine volume had been measured, the glucose concentration in the urine was determined using a LabAssay™ (Wako Pure Chemicals). These data were normalized per 200 g body weight [Katsuno, K. et al. *J. Pharmacol. Exp. Ther.* 2007, 320, 323-330; Han, S. et al. *Deabetes,* 2008, 57, 1723-1729].

Figure 2:
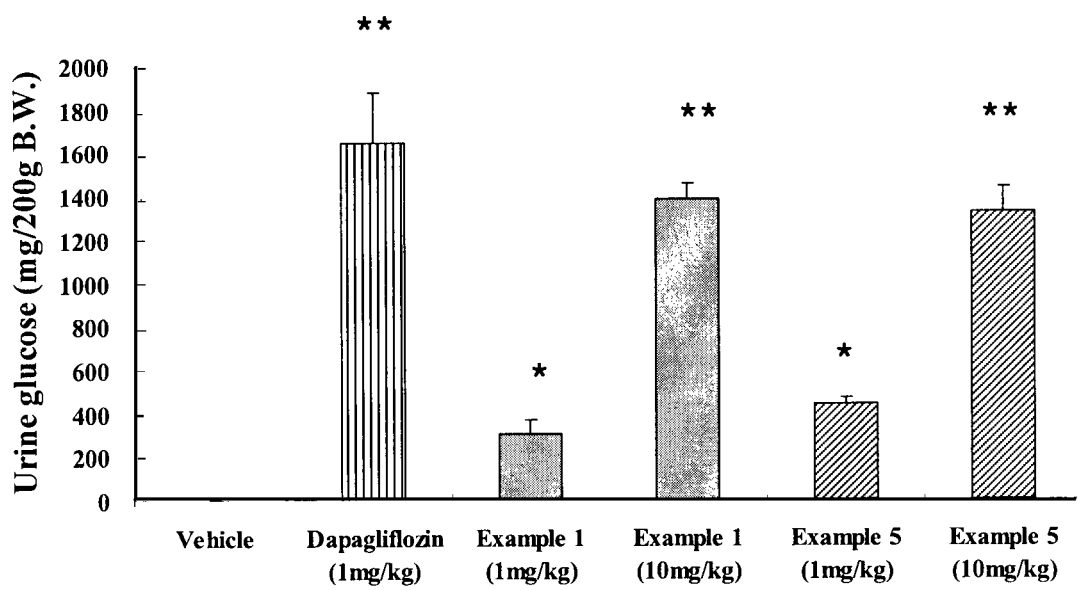
FIGS. 2 and 3 show effects of single oral administration of dapagliflozin, and the compounds of Examples 1 and 5 on urinary glucose excretion (FIG. 2) and urine volume (FIG. 3), respectively, in normal SD rats. All results are expressed as means±S.E.M. The statistical analysis was performed using a one-way ANOVA followed by Dunnett's post hoc test. *P<0.05, **P<0.01 versus vehicle.
Figure 3:
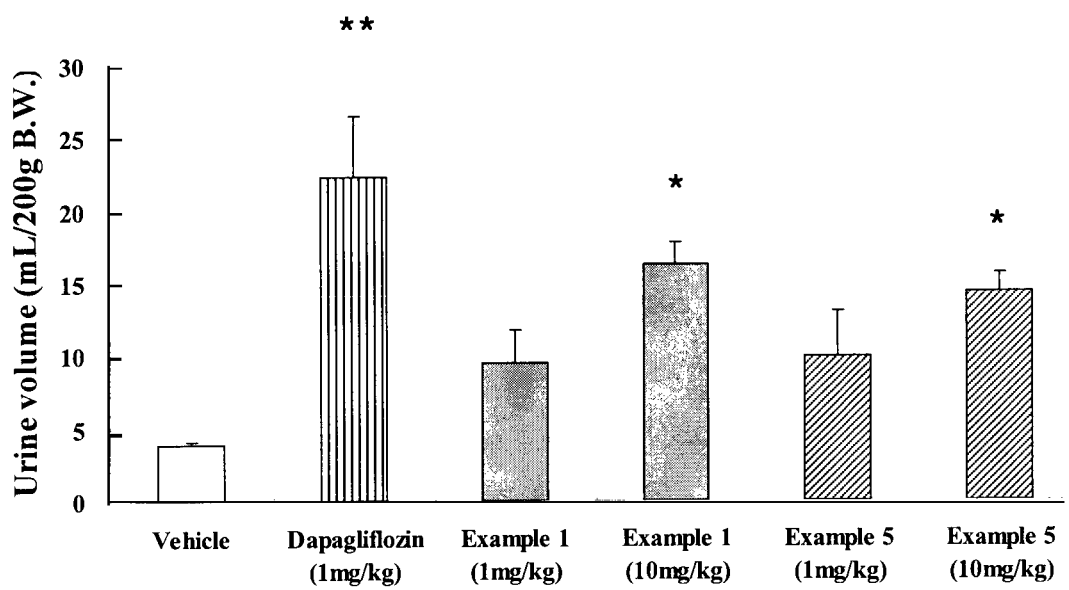

FIGS. 2 and 3 show effects of single oral administration of dapagliflozin, or the compounds of Examples 1 and 5, respectively, on urinary glucose excretion (FIG. 2) and urine volume (FIG. 3) in normal SD rats. All results are expressed as means±S.E.M. The statistical analysis was performed using a one-way ANOVA followed by Dunnett's post hoc test. (*P<0.05, **P<0.01 versus vehicle)

As shown in Table 1, and FIGS. 2 and 3, the inventive compounds exhibit an inhibitory activity against sodium-dependent glucose cotransporter 2 (SGLT2) and are effective as SGLT2 inhibitors.

While the invention has been described with respect to the above specific embodiments, it should be recognized that various modifications and changes may be made to the invention by those skilled in the art which also fall within the scope of the invention as defined by the appended claims.

What is claimed is:
1. A compound of formula I, or a pharmaceutically acceptable salt or a carboxylate or aminoacetate prodrug thereof:

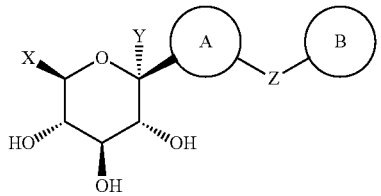

I wherein,
ring A is benzene, naphthalene, or indole;
ring B is thiazole;
X is methyl or cyclopropyl;
Y is H, $C_{1-4}$ alkoxy, or fused with a substituent of ring A to form 3 to 7-membered heterocyclic alkyl or 5 to 14-membered heteroaryl; and
Z is methylene or cyclopropane, and
optionally, said ring A, ring B, X, Y, and Z are each independently substituted with at least one substituent selected from the group consisting of halogen, hydroxy, cyano, nitro, amino, mercapto, carboxyl, carbamoyl, tosyl, —$CF_3$, $C_{1-7}$ alkyl, $C_{2-7}$ alkenyl, $C_{2-7}$ alkynyl, $C_{1-4}$ alkoxy-$C_{1-4}$ alkyl, $C_{1-7}$ alkoxy, $C_{1-7}$ alkenyloxy, $C_{1-7}$ alkynyloxy, $C_{3-7}$ cycloalkyloxy, phenyl-$C_{1-4}$ alkoxy, $C_{1-4}$ alkenyloxy-$C_{1-4}$ alkyl, $C_{1-4}$ alkoxy-$C_{1-4}$ alkoxy, $C_{6-10}$ aryloxy, 5 to 14-membered heteroaryl-$C_{1-4}$ alkoxy, $C_{3-7}$ cycloalkyl, $C_{3-7}$ cycloalkenyl, 3 to 7-membered heterocyclic alkyl, $C_{6-10}$ aryl, 5 to 14-membered heteroaryl, $C_{1-4}$ alkylsulfanyl, $C_{1-4}$ alkylsulfinyl, $C_{1-4}$ alkylsulfonyl, $C_{6-10}$ arylsulfanyl, $C_{6-10}$ arylsulfinyl, $C_{6-10}$ arylsulfonyl, mono- or di-$C_{1-4}$ alkylamino, $C_{1-4}$ alkanoylamino, $C_{1-4}$ alkoxycarbonyl, mono- or di-$C_{1-4}$ alkylcarbamoyl, $C_{1-4}$ alkanoyl, $C_{1-4}$ alkylsulfonylamino, and $C_{6-10}$ arylsulfonylamino; and
said alkyl, alkenyl, or alkoxy is optionally substituted with a substituent selected from the group consisting of halogen, hydroxy, cyano, nitro, amino, and mercapto; and said cycloalkyl, heterocyclic alkyl, aryl, or heteroaryl is optionally substituted with a substituent selected from the group consisting of halogen, hydroxy, cyano, nitro, amino, mercapto, $C_{1-4}$ alkyl, and $C_{1-4}$ alkoxy; and
said heterocyclic alkyl and heteroaryl each independently contains at least one heteroatom selected from N, O and S; and
when X, Y, Z and ring A are respectively hydroxymethyl, H, methylene and chlorobenzene, ring B is neither 2-thiazolyl nor 5-phenylthiazol-2-yl.

2. The compound of claim 1, wherein,
ring A is selected from the group consisting of:

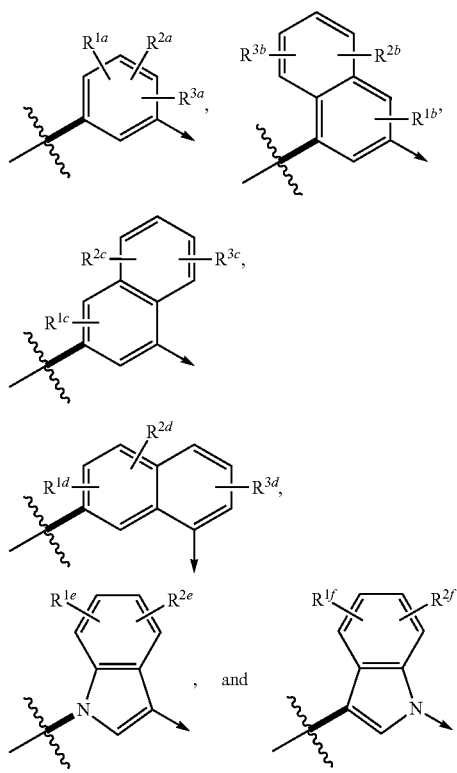

wherein, $R^{1a}$, $R^{2a}$, $R^{3a}$, $R^{1b}$, $R^{2b}$, $R^{3b}$, $R^{1c}$, $R^{2c}$, $R^{3c}$, $R^{1d}$, $R^{2d}$, $R^{3d}$, $R^{1e}$, $R^{2e}$, $R^{1f}$, and $R^{2f}$ are each independently H, halogen, hydroxy, cyano, —$CF_3$, $C_{1-7}$ alkyl, $C_{3-7}$ cycloalkyl, $C_{1-7}$ alkoxy, $C_{1-7}$ alkenyloxy, $C_{1-7}$ alkynyloxy, $C_{1-4}$ alkenyloxy-$C_{1-4}$ alkyl, $C_{1-4}$ alkoxy-$C_{1-4}$-alkoxy, or 5 to 14-membered heteroaryl-$C_{1-4}$alkoxy;

ring B is

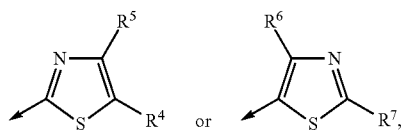

wherein, $R^4$, $R^5$, $R^6$ and $R^7$ are each independently H, $C_{1-7}$ alkyl, $C_{2-7}$ alkenyl, $C_{2-7}$ alkynyl, $C_{1-7}$ alkoxy, $C_{6-10}$ aryloxy, $C_{1-7}$ alkoxycarbonyl, $C_{3-7}$ cycloalkyl, $C_{1-4}$ alkylsulfanyl, $C_{6-10}$ aryl, or 5 to 14-membered heteroaryl;

X is

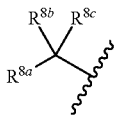

wherein, $R^{8a}$, $R^{8b}$ and $R^{8c}$ are each independently H, halogen, hydroxy, $C_{1-7}$alkyl, $C_{2-7}$ alkenyl, $C_{1-7}$ alkoxy, $C_{1-4}$ alkylsulfanyl, $C_{1-4}$ alkylsulfonyl, $C_{6-10}$ arylsulfonyl, $C_{6-10}$ aryl, $C_{6-10}$ aryloxy, and 5 to 14-membered heteroaryl;

Y is H or $C_{1-2}$ alkoxy, or fused with $R^{1a}$, $R^{2a}$ or $R^{3a}$ to form 3 to 7-membered heterocyclic alkyl or 5 to 14-membered heteroaryl; and Z is methylene or

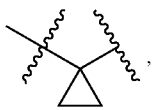 [SMILES: *C1(*)CC1]

and said alkyl, alkenyl, or alkoxy being optionally substituted with a substituent selected from the group consisting of halogen, hydroxy, cyano, nitro, amino, and mercapto; and said cycloalkyl, heterocyclic alkyl, aryl, or heteroaryl being optionally substituted with a substituent selected from the group consisting of halogen, hydroxy, cyano, nitro, amino, mercapto, $C_{1-4}$ alkyl, and $C_{1-4}$ alkoxy and said heterocyclic alkyl and heteroaryl each independently contains at least one heteroatom selected from N, O and S; and when X, Y, Z and ring A are respectively hydroxymethyl, H, methylene and chlorobenzene, ring B is neither 2-thiazolyl nor 5-phenylthiazol-2-yl.

3. The compound of claim 2, wherein $R^{1a}$, $R^{2a}$, $R^{3a}$, $R^{1b}$, $R^{2b}$, $R^{3b}$, $R^{1c}$, $R^{2c}$, $R^{3c}$, $R^{1d}$, $R^{2d}$, $R^{3d}$, $R^{1e}$, $R^{2e}$, $R^{1f}$, and $R^{2f}$ are each independently H, Cl, F, Br, trifluoromethyl, cyano, hydroxy, methyl, hydroxymethyl, methoxy, ethoxy, hydroxyethoxy, propoxy, allyloxy, butenyloxy, propynyloxy, triazolylethoxy, tetrahydrofuranylmethoxy, allyloxymethyl, or methoxyethoxy;

$R^4$ and $R^7$ are each independently H, methyl, ethyl, n-propyl, i-propyl, n-butyl, n-pentyl, n-hexyl, n-heptyl, allyl, butenyl, ethoxy, propoxy, pentoxy, cyclopentyl, cyclohexyl, cyclopentenyl, methylsulfanyl, ethylsulfanyl, propylsulfanyl, butylsulfanyl, pentylsulfanyl, phenyl, benzyl, thiophenyl, furanyl, thiazolyl, pyridinyl, thiadiazolyl, benzofuranyl, oxazolyl, i-oxazolyl, or pyrazinyl, wherein phenyl or thiophenyl is optionally substituted with halogen or methyl;

$R^5$ and $R^6$ are H;

$R^{8a}$, $R^{8b}$ and $R^{8c}$ are each independently H, fluoro, hydroxy, methyl, allyl, butenyl, mesyl, tosyloxy, methoxy, ethoxy, hydroxyethoxy, methylsulfanyl, ethylsulfanyl, triazolyl, or tetrazolyl;

Y is H, or fused with $R^{1a}$, $R^{2a}$ or $R^{3a}$ to form tetrahydrofuran; and Z is methylene or

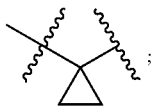

and when X, Y, Z and ring A are respectively hydroxymethyl, H, methylene and chlorobenzene, ring B is neither 2-thiazolyl nor 5-phenylthiazol-2-yl.

4. The compound of claim 1, wherein the prodrug is carboxylate or aminoacetate of the compound of formula I, the carboxylate or aminoacetate being substituted with at least one substituent selected from the group consisting of $C_{1-7}$ alkyl, $C_{1-7}$ alkoxy, $C_{2-7}$ alkenyl, $C_{2-7}$ alkenyloxy, $C_{6-10}$ aryl, $C_{6-10}$ aryloxy, $C_{6-10}$ $C_{6-10}$ aryl-$C_{1-4}$alkoxy, and $C_{6-10}$ aryl substituted with at least one $C_{1-4}$ alkoxy.

5. A compound of claim 1, which is selected from the group consisting of:

(1) (2S,3R,4R,5S,6R)-2-(4-Chloro-3-((5-(thiophen-3-yl)thiazol-2-yl)methyl)phenyl)-6-(hydroxymethyl)-tetrahydro-2H-pyran-3,4,5-triol;

(2) (2S,3R,4R,5S,6R)-2-(3-((5-(4-Fluorophenyl)thiazol-2-yl)methyl)-4-methoxynaphthalen-1-yl)-6-(hydroxymethyl)-tetrahydro-2H-pyran-3,4,5-triol;

(3) (2S,3R,4R,5S,6R)-2-(4-Chloro-3-(1-(5-(furan-2-yl)thiazol-2-yl)cyclopropyl)phenyl)-6-(hydroxymethyl)-tetrahydro-2H-pyran-3,4,5-triol;

(4) (2S,3R,4R,5S,6R)-2-(3-((5-(Furan-2-yl)thiazol-2-yl)methyl)-4-(trifluoromethyl)phenyl)-6-(hydroxymethyl)-tetrahydro-2H-pyran-3,4,5-triol;

(5) (2S,3R,4R,5S,6R)-2-(4-Chloro-3-((5-(furan-2-yl)thiazol-2-yl)methyl)phenyl)-6-(hydroxymethyl)-tetrahydro-2H-pyran-3,4,5-triol;

(6) (2S,3R,4R,5S,6R)-2-(4-Chloro-3-((5-(furan-3-yl)thiazol-2-yl)methyl)phenyl)-6-(hydroxymethyl)-tetrahydro-2H-pyran-3,4,5-triol;

(7) (2S,3R,4R,5S,6R)-2-(4-Chloro-3-((5-(thiophen-2-yl)thiazol-2-yl)methyl)phenyl)-6-(hydroxymethyl)tetrahydro-2H-pyran-3,4,5-triol;

(8) (2S,3R,4R,5S,6R)-2-(4-Chloro-3-((5-(5-chlorothiophen-2-yl)thiazol-2-yl)methyl)phenyl)-6-(hydroxymethyl)tetrahydro-2H-pyran-3,4,5-triol;

(9) (2S,3R,4R,5S,6R)-2-(3-(2,5'-Bithiazol-2'-ylmethyl)-4-chlorophenyl)-6-(hydroxymethyl)-tetrahydro-2H-pyran-3,4,5-triol;

(10) (2S,3R,4R,5S,6R)-2-(4-Chloro-3-((5-(pyridin-2-yl)thiazol-2-yl)methyl)phenyl)-6-(hydroxymethyl)-tetrahydro-2H-pyran-3,4,5-triol;

(11) (2S,3R,4R,5S,6R)-2-(4-Chloro-3-((5-(4-fluorophenyl)thiazol-2-yl)methyl)phenyl)-6-(hydroxymethyl)-tetrahydro-2H-pyran-3,4,5-triol;

(12) (2S,3R,4R,5S,6R)-2-(4-chloro-3-((5-ethylthiazol-2-yl)methyl)phenyl)-6-(hydroxymethyl)-tetrahydro-2H-pyran-3,4,5-triol;

(13) (2S,3R,4R,5S,6R)-2-(3-((5-Butylthiazol-2-yl)methyl)-4-chlorophenyl)-6-(hydroxymethyl)-tetrahydro-2H-pyran-3,4,5-triol;

(14) (2S,3R,4R,5S,6R)-2-(4-Chloro-3-((5-pentylthiazol-2-yl)methyl)phenyl)-6-(hydroxymethyl)-tetrahydro-2H-pyran-3,4,5-triol;

(15) (2S,3R,4R,5S,6R)-2-(4-Chloro-3-((5-hexylthiazol-2-yl)methyl)phenyl)-6-(hydroxymethyl)-tetrahydro-2H-pyran-3,4,5-triol;

(16) (2S,3R,4R,5S,6R)-2-(4-Chloro-3-((5-isopropylthiazol-2-yl)methyl)phenyl)-6-(hydroxymethyl)-tetrahydro-2H-pyran-3,4,5-triol;

(17) (2S,3R,4R,5S,6R)-2-(3-((5-Allylthiazol-2-yl)methyl)-4-chlorophenyl)-6-(hydroxymethyl)-tetrahydro-2H-pyran-3,4,5-triol;

(18) 2S,3R,4R,5S,6R,E)-2-(3-((5-(but-2-en-2-yl)thiazol-2-yl)methyl)-4-chlorophenyl)-6-(hydroxymethyl)-tetrahydro-2H-pyran-3,4,5-triol;

(19) (2S,3R,4R,5S,6R)-2-(4-Chloro-3-((5-cyclopentylthiazol-2-yl)methyl)phenyl)-6-(hydroxymethyl)-tetrahydro-2H-pyran-3,4,5-triol;

(20) (2S,3R,4R,5S,6R)-2-(4-Chloro-3-((5-cyclohexylthiazol-2-yl)methyl)phenyl)-6-(hydroxymethyl)-tetrahydro-2H-pyran-3,4,5-triol;

(21) (2S,3R,4R,5S,6R)-2-(4-Chloro-3-((5-ethoxythiazol-2-yl)methyl)phenyl)-6-(hydroxymethyl)-tetrahydro-2H-pyran-3,4,5-triol;

(22) (2S,3R,4R,5S,6R)-2-(4-Chloro-3-((5-propoxythiazol-2-yl)methyl)phenyl)-6-(hydroxymethyl)-tetrahydro-2H-pyran-3,4,5-triol;

(23) (2S,3R,4R,5S,6R)-2-(4-Chloro-3-((5-(pentyloxy)thiazol-2-yl)methyl)phenyl)-6-(hydroxymethyl)-tetrahydro-2H-pyran-3,4,5-triol;

(24) (2S,3R,4R,5S,6R)-2-(4-Chloro-3-((5-(ethylthio)thiazol-2-yl)methyl)phenyl)-6-(hydroxymethyl)-tetrahydro-2H-pyran-3,4,5-triol;

(25) (2S,3R,4R,5S,6R)-2-(4-Chloro-3-((5-(propylthio)thiazol-2-yl)methyl)phenyl)-6-(hydroxymethyl)-tetrahydro-2H-pyran-3,4,5-triol;

(26) (2S,3R,4R,5S,6R)-2-(3-((5-(Butylthio)thiazol-2-yl)methyl)-4-chlorophenyl)-6-(hydroxymethyl)-tetrahydro-2H-pyran-3,4,5-triol;

(27) (2S,3R,4R,5S,6R)-2-(3-((5-(Butylthio)thiazol-2-yl)methyl)-4-chlorophenyl)-6-(hydroxymethyl)-tetrahydro-2H-pyran-3,4,5-triol;

(28) (2S,3R,4R,5S,6R)-2-(4-Chloro-3-(1-(5-(furan-3-yl)thiazol-2-yl)cyclopropyl)phenyl)-6-(hydroxymethyl)tetrahydro-2H-pyran-3,4,5-triol;

(29) (2S,3R,4R,5S,6R)-2-(4-Chloro-3-(1-(5-(thiophen-2-yl)thiazol-2-yl)cyclopropyl)phenyl)-6-(hydroxymethyl)tetrahydro-2H-pyran-3,4,5-triol;

(30) (2S,3R,4R,5S,6R)-2-(3-((5-(Furan-2-yl)thiazol-2-yl)methyl)-4-methylphenyl)-6-(hydroxymethyl)tetrahydro-2H-pyran-3,4,5-triol;

(31) (2S,3R,4R,5S,6R)-2-(4-Chloro-2-ethoxy-5-((5-(furan-3-yl)thiazol-2-yl)methyl)phenyl)-6-(hydroxymethyl)tetrahydro-2H-pyran-3,4,5-triol;

(32) (2R,3S,4R,5R,6S)-2-(Hydroxymethyl)-6-(4-methyl-3-((5-(thiophen-2-yl)thiazol-2-yl)methyl)phenyl)tetrahydro-2H-pyran-3,4,5-triol;

(33) (2R,3S,4R,5R,6S)-2-(Hydroxymethyl)-6-(4-methyl-3-((5-(thiophen-3-yl)thiazol-2-yl)methyl)phenyl)tetrahydro-2H-pyran-3,4,5-triol;

(34) (2S,3R,4R,5S,6R)-2-(3-(2,5'-Bithiazol-2'-ylmethyl)-4-methylphenyl)-6-(hydroxymethyl)tetrahydro-2H-pyran-3,4,5-triol;

(35) (2R,3S,4R,5R,6S)-2-(Hydroxymethyl)-6-(4-methyl-3-((5-phenylthiazol-2-yl)methyl)phenyl)tetrahydro-2H-pyran-3,4,5-triol;

(36) (2R,3S,4R,5R,6S)-2-(Hydroxymethyl)-6-(4-methyl-3-((5-p-tolylthiazol-2-yl)methyl)phenyl)tetrahydro-2H-pyran-3,4,5-triol;

(37) (2S,3R,4R,5S,6R)-2-(3-((5-(4-Fluorophenyl)thiazol-2-yl)methyl)-4-methylphenyl)-6-(hydroxymethyl)tetrahydro-2H-pyran-3,4,5-triol;

(38) (2S,3R,4R,5S,6R)-2-(3-((5-(4-Chlorophenyl)thiazol-2-yl)methyl)-4-methylphenyl)-6-(hydroxymethyl)tetrahydro-2H-pyran-3,4,5-triol;

(39) (2S,3R,4R,5S,6R)-2-(3-((5-Benzylthiazol-2-yl)methyl)-4-methylphenyl)-6-(hydroxymethyl)tetrahydro-2H-pyran-3,4,5-triol;

(40) (2S,3R,4R,5S,6R)-2-(4-Fluoro-3-((5-(furan-2-yl)thiazol-2-yl)methyl)phenyl)-6-(hydroxymethyl)tetrahydro-2H-pyran-3,4,5-triol;

(41) (2S,3R,4R,5S,6R)-2-(4-Fluoro-3-((5-(furan-3-yl)thiazol-2-yl)methyl)phenyl)-6-(hydroxymethyl)tetrahydro-2H-pyran-3,4,5-triol;

(42) (2S,3R,4R,5S,6R)-2-(4-Fluoro-3-((5-(thiophen-2-yl)thiazol-2-yl)methyl)phenyl)-6-(hydroxymethyl)tetrahydro-2H-pyran-3,4,5-triol;

(43) (2S,3R,4R,5S,6R)-2-(4-Fluoro-3-((5-(thiazol-3-yl)thiazol-2-yl)methyl)phenyl)-6-(hydroxymethyl)tetrahydro-2H-pyran-3,4,5-triol;

(44) (2S,3R,4R,5S,6R)-2-(4-Fluoro-3-((5-phenylthiazol-2-yl)methyl)phenyl)-6-(hydroxymethyl)tetrahydro-2H-pyran-3,4,5-triol;

(45) (2S,3R,4R,5S,6R)-2-(4-Fluoro-3-((5-(4-fluorophenyl)thiazol-2-yl)methyl)phenyl)-6-(hydroxymethyl)tetrahydro-2H-pyran-3,4,5-triol;

(46) (2S,3R,4R,5S,6R)-2-(4-Bromo-3-((5-(furan-2-yl)thiazol-2-yl)methyl)phenyl)-6-(hydroxymethyl)-tetrahydro-2H-pyran-3,4,5-triol;

(47) (2S,3R,4R,5S,6R)-2-(4-Bromo-3-((5-(thiophen-3-yl)thiazol-2-yl)methyl)phenyl)-6-(hydroxymethyl)-tetrahydro-2H-pyran-3,4,5-triol;

(48) (2S,3R,4R,5S,6R)-2-(3-((5-(Furan-3-yl)thiazol-2-yl)methyl)-4-(trifluoromethyl)phenyl)-6-(hydroxymethyl)tetrahydro-2H-pyran-3,4,5-triol;

(49) (2R,3S,4R,5R,6S)-2-(Hydroxymethyl)-6-(3-((5-(thiophen-2-yl)thiazol-2-yl)methyl)-4-(trifluoromethyl)phenyl)tetrahydro-2H-pyran-3,4,5-triol;

(50) (2R,3S,4R,5R,6S)-2-(Hydroxymethyl)-6-(3-((5-(thiophen-3-yl)thiazol-2-yl)methyl)-4-(trifluoromethyl)phenyl)tetrahydro-2H-pyran-3,4,5-triol;

(51) (2R,3S,4R,5R,6S)-2-(Hydroxymethyl)-6-(3-((5-phenylthiazol-2-yl)methyl)-4-(trifluoromethyl)phenyl)tetrahydro-2H-pyran-3,4,5-triol;

(52) (2S,3R,4R,5S,6R)-2-(3-((5-(4-Fluorophenyl)thiazol-2-yl)methyl)-4-(trifluoromethyl)phenyl)-6-(hydroxymethyl)tetrahydro-2H-pyran-3,4,5-triol;

(53) (2S,3R,4R,5S,6R)-2-(4-Chloro-2-fluoro-5-((5-(furan-2-yl)thiazol-2-yl)methyl)phenyl)-6-(hydroxymethyl)tetrahydro-2H-pyran-3,4,5-triol;

(54) (2S,3R,4R,5S,6R)-2-(4-Chloro-2-fluoro-5-((5-(furan-3-yl)thiazol-2-yl)methyl)phenyl)-6-(hydroxymethyl)tetrahydro-2H-pyran-3,4,5-triol;

(55) (2S,3R,4R,5S,6R)-2-(4-Chloro-2-fluoro-5-((5-(thiophen-2-yl)thiazol-2-yl)methyl)phenyl)-6-(hydroxymethyl)tetrahydro-2H-pyran-3,4,5-triol;

(56) (2S,3R,4R,5S,6R)-2-(4-Chloro-2-fluoro-5-((5-(thiophen-3-yl)thiazol-2-yl)methyl)phenyl)-6-(hydroxymethyl)tetrahydro-2H-pyran-3,4,5-triol;

(57) (2S,3R,4R,5S,6R)-2-(4-Chloro-2-fluoro-5-((5-phenylthiazol-2-yl)methyl)phenyl)-6-(hydroxymethyl)tetrahydro-2H-pyran-3,4,5-triol;

(58) (2S,3R,4R,5S,6R)-2-(4-Chloro-fluoro-5-((5-(4-fluorophenyl)thiazol-2-yl)methyl)phenyl)-6-(hydroxymethyl)tetrahydro-2H-pyran-3,4,5-triol;

(59) (2S,3R,4R,5S,6R)-2-(2,4-Dichloro-5-((5-(furan-2-yl)thiazol-2-yl)methyl)phenyl)-6-(hydroxymethyl)tetrahydro-2H-pyran-3,4,5-triol;

(61) (2S,3R,4R,5S,6R)-2-(2,4-Dichloro-5-((5-(thiophen-2-yl)thiazol-2-yl)methyl)phenyl)-6-(hydroxymethyl)tetrahydro-2H-pyran-3,4,5-triol;
(62) (2S,3R,4R,5S,6R)-2-(2,4-Dichloro-5-((5-(thiophen-3-yl)thiazol-2-yl)methyl)phenyl)-6-(hydroxymethyl)tetrahydro-2H-pyran-3,4,5-triol;
(63) (2S,3R,4R,5S,6R)-2-(2,4-Dichloro-5-((5-methylthiazol-2-yl)methyl)phenyl)-6-(hydroxymethyl)tetrahydro-2H-pyran-3,4,5-triol;
(64) (2S,3R,4R,5S,6R)-2-(2,4-Dichloro-5-((5-ethylthiazol-2-yl)methyl)phenyl)-6-(hydroxymethyl)tetrahydro-2H-pyran-3,4,5-triol;
(65) (2S,3R,4R,5S,6R)-2-(2,4-Dichloro-5-((5-propylthiazol-2-yl)methyl)phenyl)-6-(hydroxymethyl)tetrahydro-2H-pyran-3,4,5-triol;
(66) (2S,3R,4R,5S,6R)-2-(5-((5-Butylthiazol-2-yl)methyl)-2,4-dichlorophenyl)-6-(hydroxymethyl)tetrahydro-2H-pyran-3,4,5-triol;
(67) (2S,3R,4R,5S,6R)-2-(2,4-Dichloro-5-((5-hexylthiazol-2-yl)methyl)phenyl)-6-(hydroxymethyl)tetrahydro-2H-pyran-3,4,5-triol;
(68) (2S,3R,4R,5S,6R)-2-(2,4-Dichloro-5-((5-cyclopentylthiazol-2-yl)methyl)phenyl)-6-(hydroxymethyl)tetrahydro-2H-pyran-3,4,5-triol;
(69) (2S,3R,4R,5S,6R)-2-(4-Chloro-5-((5-(furan-2-yl)thiazol-2-yl)methyl)-2-methoxyphenyl)-6-(hydroxymethyl)tetrahydro-2H-pyran-3,4,5-triol;
(70) (2S,3R,4R,5S,6R)-2-(4-Chloro-5-((5-(furan-3-yl)thiazol-2-yl)methyl)-2-methoxyphenyl)-6-(hydroxymethyl)tetrahydro-2H-pyran-3,4,5-triol;
(71) (2S,3R,4R,5S,6R)-2-(4-Chloro-3-((4-phenylthiazol-2-yl)methyl)phenyl)-6-(hydroxymethyl)tetrahydro-2H-pyran-3,4,5-triol;
(72) (2S,3R,4R,5S,6R)-2-(4-Chloro-2-methoxy-5-((5-(thiophen-3-yl)thiazol-2-yl)methyl)phenyl)-6-(hydroxymethyl)tetrahydro-2H-pyran-3,4,5-triol;
(73) (2S,3R,4R,5S,6R)-2-(4-Chloro-2-methoxy-5-((5-phenylthiazol-2-yl)methyl)phenyl)-6-(hydroxymethyl)tetrahydro-2H-pyran-3,4,5-triol;
(74) (2S,3R,4R,5S,6R)-2-(4-Chloro-5-((5-(4-fluorophenyl)thiazol-2-yl)methyl)-2-methoxyphenyl)-6-(hydroxymethyl)tetrahydro-2H-pyran-3,4,5-triol;
(75) (2S,3R,4R,5S,6R)-2-(4-Chloro-5-((5-hexylthiazol-2-yl)methyl)-2-methoxyphenyl)-6-(hydroxymethyl)tetrahydro-2H-pyran-3,4,5-triol;
(76) (2S,3R,4R,5S,6R)-2-(4-Chloro-5-((5-cyclopentylthiazol-2-yl)methyl)-2-methoxyphenyl)-6-(hydroxymethyl)tetrahydro-2H-pyran-3,4,5-triol;
(77) (2S,3R,4R,5S,6R)-2-(4-Chloro-2-ethoxy-5-((5-(furan-2-yl)thiazol-2-yl)methyl)phenyl)-6-(hydroxymethyl)tetrahydro-2H-pyran-3,4,5-triol;
(78) (2S,3R,4R,5S,6R)-2-(4-Chloro-2-ethoxy-5-((5-(furan-3-yl)thiazol-2-yl)methyl)phenyl)-6-(hydroxymethyl)-tetrahydro-2H-pyran-3,4,5-triol;
(79) (2S,3R,4R,5S,6R)-2-(4-Chloro-2-ethoxy-5-((5-(thiophen-2-yl)thiazol-2-yl)methyl)phenyl)-6-(hydroxymethyl)tetrahydro-2H-pyran-3,4,5-triol;
(80) (2S,3R,4R,5S,6R)-2-(4-Chloro-2-ethoxy-5-((5-(thiophen-3-yl)thiazol-2-yl)methyl)phenyl)-6-(hydroxymethyl)tetrahydro-2H-pyran-3,4,5-triol;
(81) (2S,3R,4R,5S,6R)-2-(4-Chloro-2-ethoxy-5-((5-phenylthiazol-2-yl)methyl)phenyl)-6-(hydroxymethyl)tetrahydro-2H-pyran-3,4,5-triol;
(82) (2S,3R,4R,5S,6R)-2-(4-Chloro-2-ethoxy-5-((5-(4-fluorophenyl)thiazol-2-yl)methyl)phenyl)-6-(hydroxymethyl)tetrahydro-2H-pyran-3,4,5-triol;
(83) (2S,3R,4R,5S,6R)-2-(2-(Allyloxy)-4-chloro-5-((5-(furan-2-yl)thiazol-2-yl)methyl)phenyl)-6-(hydroxymethyl)tetrahydro-2H-pyran-3,4,5-triol;
(84) (2S,3R,4R,5S,6R)-2-(2-(Allyloxy)-4-chloro-5-((5-(furan-3-yl)thiazol-2-yl)methyl)phenyl)-6-(hydroxymethyl)tetrahydro-2H-pyran-3,4,5-triol;
(85) (2S,3R,4R,5S,6R)-2-(2-(Allyloxy)-4-chloro-5-((5-(thiophen-2-yl)thiazol-2-yl)methyl)phenyl)-6-(hydroxymethyl)tetrahydro-2H-pyran-3,4,5-triol;
(86) (2S,3R,4R,5S,6R)-2-(2-(Allyloxy)-4-chloro-5-((5-(thiophen-3-yl)thiazol-2-yl)methyl)phenyl)-6-(hydroxymethyl)tetrahydro-2H-pyran-3,4,5-triol;
(87) (2S,3R,4R,5S,6R)-2-(2-(Allyloxy)-4-chloro-5-((5-phenylthiazol-2-yl)methyl)phenyl)-6-(hydroxymethyl)tetrahydro-2H-pyran-3,4,5-triol;
(88) (2S,3R,4R,5S,6R)-2-(2-(Allyloxy)-4-chloro-5-((5-(4-fluorophenyl)thiazol-2-yl)methyl)phenyl)-6-(hydroxymethyl)tetrahydro-2H-pyran-3,4,5-triol;
(89) (2S,3R,4R,5S,6R)-2-(2-(Allyloxymethyl)-4-chloro-5-((5-(furan-2-yl)thiazol-2-yl)methyl)phenyl)-6-(hydroxymethyl)-tetrahydro-2H-pyran-3,4,5-triol;
(90) (2S,3R,4R,5S,6R)-2-(2-(Allyloxymethyl)-4-chloro-5-((5-(furan-3-yl)thiazol-2-yl)methyl)phenyl)-6-(hydroxymethyl)-tetrahydro-2H-pyran-3,4,5-triol;
(91) (2S,3R,4R,5S,6R)-2-(2-(Allyloxymethyl)-4-chloro-5-((5-(thiophen-2-yl)thiazol-2-yl)methyl)phenyl)-6-(hydroxymethyl)-tetrahydro-2H-pyran-3,4,5-triol;
(92) (2S,3R,4R,5S,6R)-2-(2-(Allyloxymethyl)-4-chloro-5-((5-(thiophen-3-yl)thiazol-2-yl)methyl)phenyl)-6-(hydroxymethyl)-tetrahydro-2H-pyran-3,4,5-triol;
(93) (2S,3R,4R,5S,6R)-2-(3-((5-(Furan-2-yl)thiazol-2-yl)methyl)naphthalen-1-yl)-6-(hydroxymethyl)tetrahydro-2H-pyran-3,4,5-triol;
(94) (2R,3S,4R,5R,6S)-2-(Hydroxymethyl)-6-(3-((5-(thiophen-2-yl)thiazol-2-yl)methyl)naphthalen-1-yl)tetrahydro-2H-pyran-3,4,5-triol;
(95) (2S,3R,4R,5S,6R)-2-(3-((5-(Furan-2-yl)thiazol-2-yl)methyl)-4-methoxynaphthalen-1-yl)-6-(hydroxymethyl)-tetrahydro-2H-pyran-3,4,5-triol;
(96) (2R,3S,4R,5R,6S)-2-(Hydroxymethyl)-6-(4-methoxy-3-((5-(thiophen-2-yl)thiazol-2-yl)methyl)naphthalen-1-yl)-tetrahydro-2H-pyran-3,4,5-triol;
(97) (2R,3S,4R,5R,6S)-2-(Hydroxymethyl)-6-(4-methoxy-3-((5-phenylthiazol-2-yl)methyl)naphthalen-1-yl)tetrahydro-2H-pyran-3,4,5-triol;
(98) (2R,3S,4R,5R,6S)-2-(Hydroxymethyl)-6-(4-methoxy-3-((5-methylthiazol-2-yl)methyl)naphthalen-1-yl)-tetrahydro-2H-pyran-3,4,5-triol;
(99) (2R,3S,4R,5R,6S)-2-(Hydroxymethyl)-6-(4-methoxy-3-((5-propylthiazol-2-yl)methyl)naphthalen-1-yl)-tetrahydro-2H-pyran-3,4,5-triol;
(100) (2S,3R,4R,5S,6R)-2-(3-((5-Heptylthiazol-2-yl)methyl)-4-methoxynaphthalen-1-yl)-6-(hydroxymethyl)-tetrahydro-2H-pyran-3,4,5-triol;
(101) (2S,3R,4R,5S,6R)-2-(3-((5-Cyclopentylthiazol-2-yl)methyl)-4-methoxynaphthalen-1-yl)-6-(hydroxymethyl)-tetrahydro-2H-pyran-3,4,5-triol;
(102) (2S,3R,4R,5S,6R)-2-(4-Cyclopropyl-3-((5-(furan-2-yl)thiazol-2-yl)methyl)phenyl)-6-(hydroxymethyl)-tetrahydro-2H-pyran-3,4,5-triol;
(103) (2S,3R,4R,5S,6R)-2-(3-((5-Ethoxythiazol-2-yl)methyl)-4-methoxynaphthalen-1-yl)-6-(hydroxymethyl)-tetrahydro-2H-pyran-3,4,5-triol;
(104) (2S,3R,4R,5S,6R)-2-(4-((5-(Furan-2-yl)thiazol-2-yl)methyl)naphthalen-2-yl)-6-(hydroxymethyl)-tetrahydro-2H-pyran-3,4,5-triol;

(105) (2S,3R,4R,5S,6R)-2-(4-((5-Ethylthiazol-2-yl)methyl)naphthalen-2-yl)-6-(hydroxymethyl)-tetrahydro-2H-pyran-3,4,5-triol;
(106) Ethyl 2-(2-chloro-5-((2S,3R,4R,5S,6R)-3,4,5-trihydroxy-6-(hydroxymethyl)-tetrahydro-2H-pyran-2-yl)benzyl)thiazole-5-carboxylate;
(107) (2S,3R,4R,5S,6R)-2-(3-((5-(1,3,4-Thiadiazol-2-yl)thiazol-2-yl)methyl)-4-chlorophenyl)-6-(hydroxymethyl)-tetrahydro-2H-pyran-3,4,5-triol;
(108) (2S,3R,4R,5S,6R)-2-(3-((5-(1,3,4-Thiadiazol-2-yl)thiazol-2-yl)methyl)-4-chlorophenyl)-6-(hydroxymethyl)-tetrahydro-2H-pyran-3,4,5-triol;
(109) 2-45-(Thiophen-3-yl)thiazol-2-yl)methyl)-4-((2S,3R,4R,5S,6R)-3,4,5-trihydroxy-6-(hydroxymethyl)-tetrahydro-2H-pyran-2-yl)benzonitrile;
(110) (2S,3R,4R,5S,6R)-2-(4-Cyclopropyl-3-((5-(furan-2-yl)thiazol-2-yl)methyl)phenyl)-6-(hydroxymethyl)-tetrahydro-2H-pyran-3,4,5-triol;
(111) (2S,3R,4R,5S,6R)-2-(3-((5-(Furan-2-yl)thiazol-2-yl)methyl)phenyl)-6-(hydroxymethyl)-tetrahydro-2H-pyran-3,4,5-triol;
(112) (2S,3R,4R,5S,6R)-2-(4-Chloro-5-((5-(furan-2-yl)thiazol-2-yl)methyl)-2-hydroxyphenyl)-6-(hydroxymethyl)-tetrahydro-2H-pyran-3,4,5-triol;
(113) (2S,3R,4R,5S,6R)-2-(4-Chloro-5-((5-(furan-2-yl)thiazol-2-yl)methyl)-2-(hydroxymethyl)phenyl)-6-(hydroxymethyl)-tetrahydro-2H-pyran-3,4,5-triol;
(114) (2S,3R,4R,5S,6R)-2-(4-Chloro-5-((5-(furan-3-yl)thiazol-2-yl)methyl)-2-(hydroxymethyl)phenyl)-6-(hydroxymethyl)-tetrahydro-2H-pyran-3,4,5-triol;
(115) (2S,3R,4R,5S,6R)-2-(4-Chloro-2-(hydroxymethyl)-5-((5-(thiophen-2-yl)thiazol-2-yl)methyl)phenyl)-6-(hydroxymethyl)-tetrahydro-2H-pyran-3,4,5-triol;
(116) (2S,3R,4R,5S,6R)-2-(4-Chloro-2-(hydroxymethyl)-5-((5-(thiophen-3-yl)thiazol-2-yl)methyl)phenyl)-6-(hydroxymethyl)-tetrahydro-2H-pyran-3,4,5-triol;
(117) (2S,3R,4R,5S,6R)-2-(4-Chloro-5-05-(furan-2-yl)thiazol-2-yl)methyl)-2-(2-methoxyethoxy)phenyl)-6-(hydroxymethyl)-tetrahydro-2H-pyran-3,4,5-triol;
(118) (2S,3R,4R,5S,6R)-2-(4-Chloro-5-((5-(furan-2-yl)thiazol-2-yl)methyl)-2-propoxyphenyl)-6-(hydroxymethyl)tetrahydro-2H-pyran-3,4,5-triol;
(119) (2S,3R,4R,5S,6R)-2-(2-(But-3-enyloxy)-4-chloro-5-((5-(furan-2-yl)thiazol-2-yl)methyl)phenyl)-6-(hydroxymethyl)tetrahydro-2H-pyran-3,4,5-triol;
(120) (2S,3R,4R,5S,6R)-2-(4-Chloro-5-((5-(furan-2-yl)thiazol-2-yl)methyl)-2-(prop-2-ynyloxy)phenyl)-6-(hydroxymethyl)-tetrahydro-2H-pyran-3,4,5-triol;
(121) (2S,3R,4R,5S,6R)-2-(4-Chloro-5-((5-(furan-2-yl)thiazol-2-yl)methyl)-2-(2-hydroxyethoxy)phenyl)-6-(hydroxymethyl)tetrahydro-2H-pyran-3,4,5-triol;
(122) (2S,3R,4R,5S,6R)-2-(2-(2-(1H-1,2,4-Triazol-1-yl)ethoxy)-4-chloro-5-((5-(furan-2-yl)thiazol-2-yl)methyl)phenyl)-6-(hydroxymethyl)-tetrahydro-2H-pyran-3,4,5-triol;
(123) (2S,3R,4R,5S,6R)-2-(3-((5-(4-Fluorophenyl)thiazol-2-yl)methyl)-4-hydroxynaphthalen-1-yl)-6-(hydroxymethyl)-tetrahydro-2H-pyran-3,4,5-triol;
(124) (2S,3R,4R,5S,6R)-2-(4-Hydroxy-3-((5-(thiophen-2-yl)thiazol-2-yl)methyl)naphthalen-1-yl)-6-(hydroxymethyl)-tetrahydro-2H-pyran-3,4,5-triol;
(125) (2S,3R,4R,5S,6R)-2-(4-Hydroxy-3-((5-phenylthiazol-2-yl)methyl)naphthalen-1-yl)-6-(hydroxymethyl)-tetrahydro-2H-pyran-3,4,5-triol;
(126) (2S,3R,4R,5S,6R)-2-(4-Hydroxy-3-((5-propylthiazol-2-yl)methyl)naphthalen-1-yl)-6-(hydroxymethyl)-tetrahydro-2H-pyran-3,4,5-triol;
(127) (2S,3R,4R,5S,6R)-2-(3-((5-Heptylthiazol-2-yl)methyl)-4-hydroxynaphthalen-1-yl)-6-(hydroxymethyl)-tetrahydro-2H-pyran-3,4,5-triol;
(128) (2S,3R,4R,5S,6R)-2-(3-((5-Ethoxythiazol-2-yl)methyl)-4-hydroxynaphthalen-1-yl)-6-(hydroxymethyl)-tetrahydro-2H-pyran-3,4,5-triol;
(129) (1S,3'R,4'S,5' S,6'R)-5-Chloro-6'-(hydroxymethyl)-6-(1-(5-(thiophen-2-yl)thiazole-2-yl)cyclopropyl)-3',4',5',6'-tetrahydro-3H-spiro[isobenzofuran-1,2'-pyran]-3',4',5'-triol;
(130) (2R,3R,4S,5S,6R)-2-(3-((5-(Furan-2-yl)thiazol-2-yl)methyl)-1H-indol-1-yl)-6-(hydroxymethyl)-tetrahydro-2H-pyran-3,4,5-triol;
(131) (2R,3S,4S,5R,6R)-2-(Hydroxymethyl)-6-(3-((5-(thiophen-2-yl)thiazol-2-yl)methyl)-1H-indol-1-yl)tetrahydro-2H-pyran-3,4,5-triol;
(132) (2R,3S,4S,5R,6R)-2-(Hydroxymethyl)-6-(3-((5-methylthiazol-2-yl)methyl)-1H-indol-1-yl)tetrahydro-2H-pyran-3,4,5-triol;
(133) (2R,3R,4S,5S,6R)-2-(3-((5-Ethylthiazol-2-yl)methyl)-1H-indol-1-yl)-6-(hydroxymethyl)tetrahydro-2H-pyran-3,4,5-triol;
(134) (2R,3S,4S,5R,6R)-2-(Hydroxymethyl)-6-(3-((5-propylthiazol-2-yl)methyl)-1H-indol-1-yl)tetrahydro-2H-pyran-3,4,5-triol;
(135) (2R,3R,4S,5S,6R)-2-(3-((5-Butylthiazol-2-yl)methyl)-1H-indol-1-yl)-6-(hydroxymethyl)tetrahydro-2H-pyran-3,4,5-triol;
(136) (2R,3S,4S,5R,6R)-2-(Hydroxymethyl)-6-(3-((5-pentylthiazol-2-yl)methyl)-1H-indol-1-yl)tetrahydro-2H-pyran-3,4,5-triol;
(137) (2R,3S,4R,5R,6S)-2-(Hydroxymethyl)-6-(1-((5-phenylthiazol-2-yl)methyl)-1H-indol-3-yl)-tetrahydro-2H-pyran-3,4,5-triol;
(138) ((2R,3S,4R,5R,6S)-6-(4-Chloro-3-((5-(furan-2-yl)thiazol-2-yl)methyl)phenyl)-3,4,5-trihydroxy-tetrahydro-2H-pyran-2-yl)methyl 4-methylbenzenesulfonate;
(139) (2S,3R,4R,5S,6R)-2-(4-Chloro-3-((5-(furan-2-yl)thiazol-2-yl)methyl)phenyl)-6-(methoxymethyl)-tetrahydro-2H-pyran-3,4,5-triol;
(140) (2S,3R,4R,5S,6R)-2-(4-Chloro-3-((5-(furan-2-yl)thiazol-2-yl)methyl)phenyl)-6-(ethoxymethyl)tetrahydro-2H-pyran-3,4,5-triol;
(141) (2S,3R,4R,5S,6R)-2-(4-Chloro-3-((5-(furan-2-yl)thiazol-2-yl)methyl)phenyl)-6-((2-hydroxyethoxy)methyl)tetrahydro-2H-pyran-3,4,5-triol;
(142) (2S,3R,4R,5S,6S)-2-(4-Chloro-3-((5-(furan-2-yl)thiazol-2-yl)methyl)phenyl)-6-(methylthiomethyl)-tetrahydro-2H-pyran-3,4,5-triol;
(143) (2S,3R,4R,5S,6S)-2-(4-Chloro-3-((5-(furan-2-yl)thiazol-2-yl)methyl)phenyl)-6-(ethylthiomethyl)tetrahydro-2H-pyran-3,4,5-triol;
(144) (2S,3R,4R,5S,6S)-2-(4-Chloro-3-((5-(furan-2-yl)thiazol-2-yl)methyl)phenyl)-6-(methylsulfonylmethyl)-tetrahydro-2H-pyran-3,4,5-triol;
(145) (2S,3R,4R,5S,6S)-2-(4-Chloro-3-((5-(furan-2-yl)thiazol-2-yl)methyl)phenyl)-6-(fluoromethyl)-tetrahydro-2H-pyran-3,4,5-triol;
(146) (2S,3R,4S,5S,6R)-2-(4-Chloro-3-((5-(furan-2-yl)thiazol-2-yl)methyl)phenyl)-6-methyl-tetrahydro-2H-pyran-3,4,5-triol;
(147) (2R,3S,4R,5R,6S)-2-((1H-1,2,4-Triazol-1-yl)methyl)-6-(4-chloro-3-((5-(furan-2-yl)thiazol-2-yl)methyl)phenyl)-tetrahydro-2H-pyran-3,4,5-triol;
(148) (2R,3S,4R,5R,6S)-2-((2H-Tetrazol-2-yl)methyl)-6-(4-chloro-3-((5-(furan-2-yl)thiazol-2-yl)methyl)phenyl)-tetrahydro-2H-pyran-3,4,5-triol;

(149) (2R,3S,4R,5R,6S)-2-((1H-Tetrazol-1-yl)methyl)-6-(4-chloro-3-((5-(furan-2-yl)thiazol-2-yl)methyl)phenyl)tetrahydro-2H-pyran-3,4,5-triol;
(150) (2S,3R,4R,5S,6S)-2-(4-Chloro-3-((5-(furan-2-yl)thiazol-2-yl)methyl)phenyl)-6-(difluoromethyl)-tetrahydro-2H-pyran-3,4,5-triol;
(151) (2S,3R,4R,5S,6R)-2-(4-Chloro-3-((5-(furan-2-yl)thiazol-2-yl)methyl)phenyl)-6-(1-hydroxyethyl)-tetrahydro-2H-pyran-3,4,5-triol;
(152) (2S,3R,4R,5S,6R)-2-(4-Chloro-3-((5-(furan-2-yl)thiazol-2-yl)methyl)phenyl)-6-(1-hydroxyallyl)-tetrahydro-2H-pyran-3,4,5-triol;
(153) (2S,3R,4R,5S,6R)-2-(4-Chloro-3-((5-(furan-2-yl)thiazol-2-yl)methyl)phenyl)-6-(1-hydroxybut-3-enyl)-tetrahydro-2H-pyran-3,4,5-triol;
(154) (2S,3R,4R,5S,6R)-2-(4-chloro-3-((5-(thiophen-3-yl)thiazol-2-yl)methyl)phenyl)-6-(1-hydroxyethyl)tetrahydro-2H-pyran-3,4,5-triol;
(156) (2S,3R,4R,5S,6S)-2-(4-Chloro-3-((5-(furan-2-yl)thiazol-2-yl)methyl)phenyl)-6-(2-hydroxypropan-2-yl)-tetrahydro-2H-pyran-3,4,5-triol;
(157) (2S,3R,4R,5S,6S)-2-(4-Chloro-3-((5-(furan-2-yl)thiazol-2-yl)methyl)phenyl)-6-(1-hydroxycyclopropyl)-tetrahydro-2H-pyran-3,4,5-triol;
(159) Butyl ((2R,3S,4R,5R,6S)-6-(4-chloro-3-((5-(thiophen-3-yl)thiazol-2-yl)methyl)phenyl)-3,4,5-trihydroxy-tetrahydro-2H-pyran-2-yl)methyl carbonate;
(160) ((2R,3S,4R,5R,6S)-6-(4-Chloro-3-((5-(furan-2-yl)thiazol-2-yl)methyl)phenyl)-3,4,5-trihydroxytetrahydro-2H-pyran-2-yl)methyl ethyl carbonate;
(161) Butyl ((2R,3S,4R,5R,6S)-6-(4-chloro-3-((5-(furan-2-yl)thiazol-2-yl)methyl)phenyl)-3,4,5-trihydroxytetrahydro-2H-pyran-2-yl)methyl carbonate;
(162) tert-Butyl ((2R,3S,4R,5R,6S)-6-(4-chloro-3-((5-(furan-2-yl)thiazol-2-yl)methyl)phenyl)-3,4,5-trihydroxytetrahydro-2H-pyran-2-yl)methyl carbonate;
(163) Allyl ((2R,3S,4R,5R,6S)-6-(4-chloro-3-((5-(furan-2-yl)thiazol-2-yl)methyl)phenyl)-3,4,5-trihydroxytetrahydro-2H-pyran-2-yl)methyl carbonate;
(164) Benzyl ((2R,3S,4R,5R,6S)-6-(4-chloro-3-((5-(furan-2-yl)thiazol-2-yl)methyl)phenyl)-3,4,5-trihydroxytetrahydro-2H-pyran-2-yl)methyl carbonate;
(165) ((2R,3S,4R,5R,6S)-6-(4-Chloro-3-((5-(thiophen-3-yl)thiazol-2-yl)methyl)phenyl)-3,4,5-trihydroxytetrahydro-2H-pyran-2-yl)methyl ethyl carbonate;
(166) Allyl (((2R,3S,4R,5R,6S)-6-(4-chloro-3-((5-(thiophen-3-yl)thiazol-2-yl)methyl)phenyl)-3,4,5-trihydroxytetrahydro-2H-pyran-2-yl)methyl) carbonate;
(167) Benzyl (((2R,3S,4R,5R,6S)-6-(4-chloro-3-((5-(thiophen-3-yl)thiazol-2-yl)methyl)phenyl)-3,4,5-trihydroxytetrahydro-2H-pyran-2-yl)methyl) carbonate;
(168) ((2R,3S,4R,5R,6S)-6-(4-Chloro-3-((2-(thiophen-3-yl)thiazol-5-yl)methyl)phenyl)-3,4,5-trihydroxy-tetrahydro-2H-pyran-2-yl)methyl ethyl carbonate;
(169) ((2R,3S,4R,5R,6S)-6-(4-Chloro-3-((5-(furan-2-yl)thiazol-2-yl)methyl)phenyl)-3,4,5-trihydroxytetrahydro-2H-pyran-2-yl)methyl isobutyrate;
(170) ((2R,3S,4R,5R,6S)-6-(4-Chloro-3-((5-(furan-2-yl)thiazol-2-yl)methyl)phenyl)-3,4,5-trihydroxytetrahydro-2H-pyran-2-yl)methyl pivalate;
(171) ((2R,3S,4R,5R,6S)-6-(4-Chloro-3-((5-(thiophen-3-yl)thiazol-2-yl)methyl)phenyl)-3,4,5-trihydroxy-tetrahydro-2H-pyran-2-yl)methyl pivalate;
(172) ((2R,3S,4R,5R,6S)-6-(4-Chloro-3-((5-(thiophen-3-yl)thiazol-2-yl)methyl)phenyl)-3,4,5-trihydroxytetrahydro-2H-pyran-2-yl)methyl isobutyrate;
(173) ((2R,3S,4R,5R,6S)-6-(4-Chloro-3-((5-(thiophen-3-yl)thiazol-2-yl)methyl)phenyl)-3,4,5-trihydroxy-tetrahydro-2H-pyran-2-yl)methyl 3,4-dimethoxybenzoate;
(174) ((2R,3S,4R,5R,6S)-6-(4-Chloro-3-((5-(furan-2-yl)thiazol-2-yl)methyl)phenyl)-3,4,5-trihydroxytetrahydro-2H-pyran-2-yl)methyl 3,4-dimethoxybenzoate;
(175) ((2R,3S,4R,5R,6S)-6-(4-Chloro-3-((5-(furan-2-yl)thiazol-2-yl)methyl)phenyl)-3,4,5-trihydroxytetrahydro-2H-pyran-2-yl)methyl 3,4,5-trimethoxybenzoate;
(176) (2S,3S)-((2R,3S,4R,5R,6S)-6-(4-Chloro-3-((5-(furan-2-yl)thiazol-2-yl)methyl)phenyl)-3,4,5-trihydroxytetrahydro-2H-pyran-2-yl)methyl 2-amino-3-methylpentanoate;
(177) (S)-((2R,3S,4R,5R,6S)-6-(4-Chloro-3-((5-(furan-2-yl)thiazol-2-yl)methyl)phenyl)-3,4,5-trihydroxytetrahydro-2H-pyran-2-yl)methyl 2-aminopropanoate;
(178) (S)-((2R,3S,4R,5R,6S)-6-(4-Chloro-3-((5-(furan-2-yl)thiazol-2-yl)methyl)phenyl)-3,4,5-trihydroxytetrahydro-2H-pyran-2-yl)methyl 2-amino-3-methylbutanoate;
(179) (S)-((2R,3S,4R,5R,6S)-6-(4-Chloro-3-((5-(furan-2-yl)thiazol-2-yl)methyl)phenyl)-3,4,5-trihydroxytetrahydro-2H-pyran-2-yl)methyl 2-amino-4-methylpentanoate;
(180) (S)-((2R,3S,4R,5R,6S)-6-(4-Chloro-3-((5-(furan-2-yl)thiazol-2-yl)methyl)phenyl)-3,4,5-trihydroxytetrahydro-2H-pyran-2-yl)methyl 2-amino-3-phenylpropanoate;
(181) (2S,3S)-((2R,3S,4R,5R,6S)-6-(4-Chloro-3-((5-(thiophen-3-yl)thiazol-2-yl)methyl)phenyl)-3,4,5-trihydroxytetrahydro-2H-pyran-2-yl)methyl 2-amino-3-methylpentanoate;
(182) (2R,3R,4R,5S,6S)-2-((2-Aminoacetoxy)methyl)-6-(4-chloro-3-((5-(furan-2-yl)thiazol-2-yl)methyl)phenyl)-tetrahydro-2H-pyran-3,4,5-triyl tris(2-aminoacetate);
(183) (2S,3R,4R,5S,6R)-2-(4-Chloro-3-((2-phenylthiazol-5-yl)methyl)phenyl)-6-(hydroxymethyl)-tetrahydro-2H-pyran-3,4,5-triol;
(184) (2S,3R,4R,5S,6R)-2-(4-Chloro-3-((2-(furan-2-yl)thiazol-5-yl)methyl)phenyl)-6-(hydroxymethyl)tetrahydro-2H-pyran-3,4,5-triol;
(185) (2S,3R,4R,5S,6R)-2-(3-((2-(Benzofuran-2-yl)thiazol-5-yl)methyl)-4-chlorophenyl)-6-(hydroxymethyl)tetrahydro-2H-pyran-3,4,5-triol;
(186) (2S,3R,4R,5S,6R)-2-(4-Chloro-3-((2-(furan-3-yl)thiazol-5-yl)methyl)phenyl)-6-(hydroxymethyl)tetrahydro-2H-pyran-3,4,5-triol;
(187) (2S,3R,4R,5S,6R)-2-(4-Chloro-3-((2-(thiophen-2-yl)thiazol-5-yl)methyl)phenyl)-6-(hydroxymethyl)tetrahydro-2H-pyran-3,4,5-triol;
(188) (2S,3R,4R,5S,6R)-2-(4-Chloro-42-(5-methylthiophen-2-yl)thiazol-5-yl)methyl)phenyl)-6-(hydroxymethyl)tetrahydro-2H-pyran-3,4,5-triol;
(189) (2S,3R,4R,5S,6R)-2-(4-Chloro-3-((2-(5-chlorothiophen-2-yl)thiazol-5-yl)methyl)phenyl)-6-(hydroxymethyl)tetrahydro-2H-pyran-3,4,5-triol;
(190) (2S,3R,4R,5S,6R)-2-(4-Chloro-3-((2-(thiophen-3-yl)thiazol-5-yl)methyl)phenyl)-6-(hydroxymethyl)tetrahydro-2H-pyran-3,4,5-triol;
(191) (2S,3R,4R,5S,6R)-2-(4-Chloro-3-((2-(oxazol-4-yl)thiazol-5-yl)methyl)phenyl)-6-(hydroxymethyl)tetrahydro-2H-pyran-3,4,5-triol;
(192) (2S,3R,4R,5S,6R)-2-(4-Chloro-3-02-(isoxazol-5-yl)thiazol-5-yl)methyl)phenyl)-6-(hydroxymethyl)tetrahydro-2H-pyran-3,4,5-triol;

(193) (2S,3R,4R,5S,6R)-2-(3-(2,4'-Bithiazol-5-ylmethyl)-4-chlorophenyl)-6-(hydroxymethyl)tetrahydro-2H-pyran-3,4,5-triol;

(194) (2S,3R,4R,5S,6R)-2-(4-Chloro-3-((2-(4-fluorophenyl)thiazol-5-yl)methyl)phenyl)-6-(hydroxymethyl)tetrahydro-2H-pyran-3,4,5-triol;

(195) (2S,3R,4R,5S,6R)-2-(4-Chloro-3-((2-(pyrazin-2-yl)thiazol-5-yl)methyl)phenyl)-6-(hydroxymethyl)tetrahydro-2H-pyran-3,4,5-triol;

(196) (2S,3R,4R,5S,6R)-2-(4-Chloro-3-((2-(cyclopent-3-enyl)thiazol-5-yl)methyl)phenyl)-6-(hydroxymethyl)tetrahydro-2H-pyran-3,4,5-triol;

(197) (2S,3R,4R,5S,6R)-2-(4-Chloro-3-((2-(methylthio)thiazol-5-yl)methyl)phenyl)-6-(hydroxymethyl)tetrahydro-2H-pyran-3,4,5-triol;

(198) (2S,3R,4R,5S,6R)-2-(4-Chloro-3-((2-(propylthio)thiazol-5-yl)methyl)phenyl)-6-(hydroxymethyl)tetrahydro-2H-pyran-3,4,5-triol;

(199) (2S,3R,4R,5S,6R)-2-(3-((2-(Furan-2-yl)thiazol-5-yl)methyl)-4-methylphenyl)-6-(hydroxymethyl)tetrahydro-2H-pyran-3,4,5-triol;

(200) (2R,3S,4R,5R,6S)-2-(Hydroxymethyl)-6-(4-methyl-3-((2-(thiophen-3-yl)thiazol-5-yl)methyl)phenyl)tetrahydro-2H-pyran-3,4,5-triol;

(201) (2S,3R,4R,5S,6R)-2-(4-Chloro-2-fluoro-5-((2-(furan-2-yl)thiazol-5-yl)methyl)phenyl)-6-(hydroxymethyl)tetrahydro-2H-pyran-3,4,5-triol;

(202) (2S,3R,4R,5S,6R)-2-(4-Chloro-2-fluoro-5-((2-(thiophen-2-yl)thiazol-5-yl)methyl)phenyl)-6-(hydroxymethyl)tetrahydro-2H-pyran-3,4,5-triol;

(203) (2S,3R,4R,5S,6R)-2-(4-Chloro-2-fluoro-5-((2-(thiophen-3-yl)thiazol-5-yl)methyl)phenyl)-6-(hydroxymethyl)tetrahydro-2H-pyran-3,4,5-triol;

(204) (2S,3R,4R,5S,6R)-2-(4-bromo-3-((5-(thiophen-3-yl)thiazol-2-yl)methyl)phenyl)-6-(hydroxymethyl)tetrahydro-2H-pyran-3,4,5-triol; and (205) ((2R,3S,4R,5R,6S)-6-(4-chloro-3-((2-(thiophen-3-yl)thiazol-5-yl)methyl)phenyl)-3,4,5-trihydroxytetrahydro-2H-pyran-2-yl)methyl ethyl carbonate.

6. A method for preparing the compound of formula XV, comprising
  (a) reacting the compound of formula II sequentially with an organometallic compound and the compound of formula 1, followed by reduction, cyanization and hydrolysis to obtain the compound of formula XI; and
  (b) reacting the compound of formula XI with the compound of formula XII, followed by thionation-cyclization of the resulting product and deprotection of the four benzyl groups:

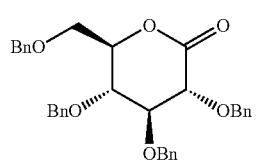

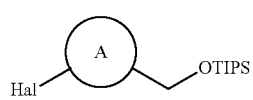

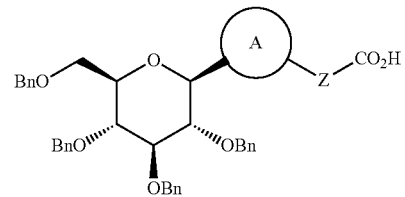

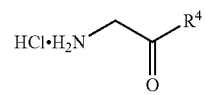

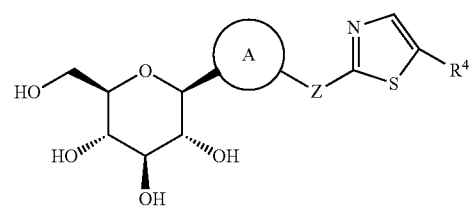

wherein, Hal is halogen, Bn is benzyl, TIPS is triisopropylsilyl, Z is methylene, and ring A and $R^4$ are as defined in claim 2.

7. A method for preparing the compound of formula XXIX, comprising
  (a) reacting the compound of formula II sequentially with an organometallic compound and the compound of formula 1, followed by reduction, cyanization and hydrolysis to obtain the compound of formula XI;
  (b) (b-1) reacting the compound of formula XI sequentially with (trimethylsilyl)diazomethane, HBr, and hexamethylenetetramine, or (b-2) reacting the compound of formula XI with nitromethane followed by reduction, to obtain the compound of formula XXV; and
  (c) reacting the compound of formula XXV with $HO_2C$—$R^7$, followed by thionation-cyclization of the resulting product and deprotection of the four benzyl groups:

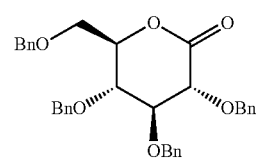

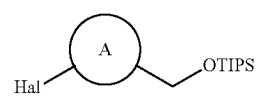

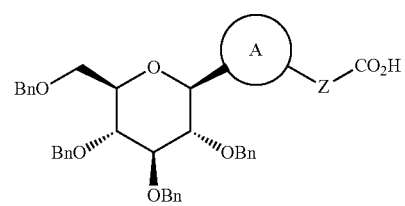

-continued

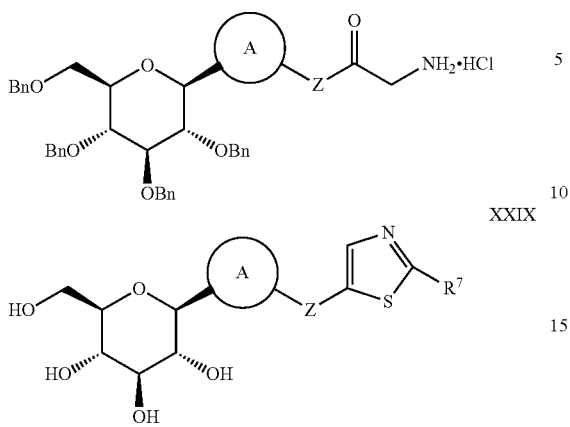

XXV

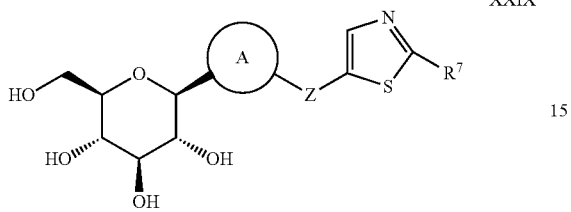

XXIX wherein, Hal is halogen, Bn is benzyl, TIPS is triisopropylsilyl, Z is methylene, and ring A and $R^7$ are as defined in claim 2.

8. A pharmaceutical composition for treating diabetes, comprising the compound of claim 1 as an active ingredient and a pharmaceutically acceptable carrier.

9. A method for treating diabetes in a mammal, which comprises administering the compound of claim 1 to the mammal.

10. A method for inhibiting sodium-dependent glucose cotransporter 2 (SGLT2) in a mammal, which comprises administering the compound of claim 1 to the mammal.

* * * * *

UNITED STATES PATENT AND TRADEMARK OFFICE
CERTIFICATE OF CORRECTION

PATENT NO. : 8,586,550 B2  Page 1 of 1
APPLICATION NO. : 13/704081
DATED : November 19, 2013
INVENTOR(S) : Lee et al.

It is certified that error appears in the above-identified patent and that said Letters Patent is hereby corrected as shown below:

In the claims:

Column 140,
Line 19, should read --$C_{6-10}$ aryloxy, $C_{6-10}$ aryl-$C_{1-4}$alkyl, $C_{6-10}$ aryl-$C_{1-4}$alkoxy, and $C_{6-10}$ aryl sub- --.

Column 145,
Line 37, "(4-Chloro-5-05" should read --(4-Chloro-5-((5--.

Column 148,
Line 53, "(4-Chloro-3-42" should read --(4-Chloro-3-((2--;
Line 65, "(4-Chloro-3-02" should read --(4-Chloro-3-((2--.

Signed and Sealed this
Eleventh Day of March, 2014

Michelle K. Lee
*Deputy Director of the United States Patent and Trademark Office*